US011312909B2

(12) United States Patent
Tong et al.

(10) Patent No.: US 11,312,909 B2
(45) Date of Patent: *Apr. 26, 2022

(54) POLYMERIZABLE COMPOUNDS AND THE USE THEREOF IN LIQUID-CRYSTAL DISPLAYS

(71) Applicant: MERCK PATENT GMBH, Darmstadt (DE)

(72) Inventors: Qiong Tong, Darmstadt (DE); Helga Haas, Lampertheim (DE); Alexander Hahn, Biebesheim (DE); Kaja Christina Deing, Darmstadt (DE); Christoph Marten, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 165 days.

This patent is subject to a terminal disclaimer.

(21) Appl. No.: 15/337,456

(22) Filed: Oct. 28, 2016

(65) Prior Publication Data

US 2017/0121606 A1 May 4, 2017

(30) Foreign Application Priority Data

Oct. 30, 2015 (EP) .................................... 15003124

(51) Int. Cl.
| | | |
|---|---|---|
| C09K 19/54 | (2006.01) | |
| C09K 19/34 | (2006.01) | |
| C09K 19/12 | (2006.01) | |
| C09K 19/04 | (2006.01) | |
| C07C 69/017 | (2006.01) | |
| C07C 69/54 | (2006.01) | |
| C09K 19/06 | (2006.01) | |
| C09K 19/32 | (2006.01) | |
| G02F 1/1343 | (2006.01) | |

(52) U.S. Cl.
CPC .......... *C09K 19/542* (2013.01); *C07C 69/017* (2013.01); *C07C 69/54* (2013.01); *C09K 19/0403* (2013.01); *C09K 19/062* (2013.01); *C09K 19/12* (2013.01); *C09K 19/32* (2013.01); *C09K 19/322* (2013.01); *C09K 19/3402* (2013.01); *C09K 19/3491* (2013.01); *G02F 1/134309* (2013.01); *C09K 2019/0448* (2013.01); *C09K 2019/122* (2013.01); *C09K 2019/123* (2013.01); *C09K 2019/3408* (2013.01); *C09K 2019/3425* (2013.01); *C09K 2019/548* (2013.01)

(58) Field of Classification Search
CPC ....... C07C 69/017; C07C 69/54; C07C 35/21; C07C 39/21; C07C 39/23; C07C 39/367; C07C 15/12; C07C 15/14; C07C 33/24; C08F 16/10; C09K 19/54; C09K 19/542
See application file for complete search history.

(56) References Cited

U.S. PATENT DOCUMENTS

| | | | | |
|---|---|---|---|---|
| 9,594,283 B2* | 3/2017 | Tong | ................... | G02F 1/137 |
| 9,663,718 B2* | 5/2017 | Smith | ................ | C09K 19/3852 |
| 9,809,748 B2* | 11/2017 | Archetti | ............ | C09K 19/3402 |
| 2005/0116200 A1 | 6/2005 | Nakanishi et al. | | |
| 2006/0149045 A1* | 7/2006 | Braekman | ............... | A61K 31/57 536/6.1 |
| 2010/0216967 A1* | 8/2010 | Allen | ................... | B01D 61/025 528/310 |
| 2010/0309423 A1* | 12/2010 | Bernatz | ............. | C09K 19/0403 349/183 |
| 2013/0210768 A1* | 8/2013 | Arrington | ............ | C07D 471/04 514/63 |
| 2014/0100342 A1* | 4/2014 | Nakatsuji | ................ | C07C 49/83 525/437 |
| 2016/0166571 A1* | 6/2016 | Janes | ..................... | A61K 31/00 424/133.1 |
| 2016/0202608 A1* | 7/2016 | Namai | .................. | C08F 220/26 430/270.1 |
| 2016/0213653 A1* | 7/2016 | Jacobsen | ............. | C07D 471/04 |
| 2016/0362606 A1* | 12/2016 | Tong | .................... | C09K 19/542 |
| 2017/0059990 A1* | 3/2017 | Tsuchimura | .......... | C08F 212/14 |

FOREIGN PATENT DOCUMENTS

| | | | | | |
|---|---|---|---|---|---|
| JP | 2012102017 A | * | 5/2012 | .......... | C07D 209/42 |
| JP | 2014129457 A | * | 7/2014 | | |
| JP | 2015102820 A | * | 6/2015 | | |
| WO | WO-2015046021 A | * | 4/2015 | .......... | G03F 7/0397 |

OTHER PUBLICATIONS

English translation of JP2015102820. (Year: 2015).*
English translation of JP2014129457. (Year: 2014).*
English translation of JP2012102017. (Year: 2012).*
Jarubek et al., "Strategies for High Transparency Acrylate Resists for 157 nm Lithography", 2003, Journal of Photopolymer Science and Technology, vol. 16, No. 4, 573-580. (Year: 2003).*
Manniche et al., "Karnatakafurans A and B: Two Dibenzofurans Isolated from the Fungus *Aspergillus karnatakaensis*", 2004, Journal or Natural Products, 67, 2111-2112. (Year: 2004).*
Siridechakorn et al., "Biphenyl and xanthone derivatives from the twigs of a *Garcinia* sp. (*Clusiaceae*)", Feb. 26, 2014, Phytochemistry Letters, 8, 77-80. (Year: 2014).*
European Search Report for EP16002128 dated Feb. 13, 2017.

* cited by examiner

*Primary Examiner* — Chanceity N Robinson
*Assistant Examiner* — Anna Malloy
(74) *Attorney, Agent, or Firm* — Millen, White, Zelano and Branigan, P.C.; Harry B. Shubin

(57) ABSTRACT

Polymerizable compounds, to processes and intermediates for the preparation thereof, liquid-crystal (LC) media comprising them, and the use of the polymerizable compounds and LC media for optical, electro-optical and electronic purposes, in particular in LC displays, especially in LC displays of the polymer sustained alignment type, or a stabilizers in LC media and LC displays.

23 Claims, No Drawings

POLYMERIZABLE COMPOUNDS AND THE USE THEREOF IN LIQUID-CRYSTAL DISPLAYS

The present invention relates to polymerizable compounds, to processes and intermediates for the preparation thereof, to liquid-crystal (LC) media comprising them, and to the use of the polymerizable compounds and LC media for optical, electro-optical and electronic purposes, in particular in LC displays, especially in LC displays of the polymer sustained alignment type or as stabilizers in LC media and LC displays.

BACKGROUND OF THE INVENTION

One of the liquid-crystal display (LCD) modes used at present is the TN ("twisted nematic") mode. However, TN LCDs have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative dielectric anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Furthermore, OCB ("optically compensated bend") displays are known which are based on a birefringence effect and have an LC layer with a so-called "bend" alignment and usually positive dielectric anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane.

Furthermore, so-called FFS ("fringe-field switching") displays have been reported (see, inter alia, S. H. Jung et al., Jpn. J. Appl. Phys., Volume 43, No. 3, 2004, 1028), which contain two electrodes on the same substrate, one of which structured in a comb-shaped manner and the other is unstructured. A strong, so-called "fringe field" is thereby generated, i.e. a strong electric field close to the edge of the electrodes, and, throughout the cell, an electric field which has both a strong vertical component and also a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

FFS displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

Furthermore, FFS displays have been disclosed (see S. H. Lee et al., Appl. Phys. Lett. 73(20), 1998, 2882-2883 and S. H. Lee et al., Liquid Crystals 39(9), 2012, 1141-1148), which have similar electrode design and layer thickness as FFS displays, but comprise a layer of an LC medium with negative dielectric anisotropy instead of an LC medium with positive dielectric anisotropy. The LC medium with negative dielectric ansiotropy shows a more favorable director orientation that has less tilt and more twist orientation compared to the LC medium with positive dielectric anisotropy, as a result of which these displays have a higher transmission. The displays further comprise an alignment layer, preferably of polyimide provided on at least one of the substrates that is in contact with the LC medium and induces planar alignment of the LC molecules of the LC medium. These displays are also known as "Ultra Brightness FFS (UB-FFS)" mode displays. These displays require an LC medium with high reliability.

The term "reliability" as used hereinafter means the quality of the performance of the display during time and with different stress loads, such as light load, temperature, humidity, voltage, and comprises display effects such as image sticking (area and line image sticking), mura (i.e., clouding), yogore (i.e., stains) etc. which are known to the skilled person in the field of LC displays. As a standard parameter for categorizing the reliability usually the voltage holding ration (VHR) value is used, which is a measure for maintaining a constant electrical voltage in a test display. The higher the VHR value, the better the reliability of the LC medium.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In so-called PVA ("patterned VA") displays, protrusions are rendered completely superfluous in that both electrodes are structured by means of slits on the opposite sides, which results in increased contrast and improved transparency to light, but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are displays of the so-called PS ("polymer sustained") or PSA ("polymer sustained alignment") type, for which the term "polymer stabilized" is also occasionally used. In these, a small amount (for example 0.3% by weight, typically <1% by weight) of one or more polymerizable, compound(s), preferably polymerizable monomeric compound(s), is added to the LC medium and, after filling the LC medium into the display, is polymerized or crosslinked in situ, usually by UV photopolymerization, optionally while a voltage is applied to the electrodes of the display. The polymerization is carried out at a temperature where the LC medium exhibits a liquid crystal phase, usually at room temperature. The addition of polymerizable mesogenic or liquid-crystalline compounds, also known as reactive mesogens or "RMs", to the LC mixture has proven particularly suitable.

Unless indicated otherwise, the term "PSA" is used hereinafter when referring to displays of the polymer sustained alignment type in general, and the term "PS" is used when referring to specific display modes, like PS-VA, PS-TN and the like.

Also, unless indicated otherwise, the term "RM" is used hereinafter when referring to a polymerizable mesogenic or liquid-crystalline compound.

In the meantime, the PS(A) principle is being used in various conventional LC display modes. Thus, for example, PS-VA, PS-OCB, PS-IPS, PS-FFS, PS-UB-FFS and PS-TN displays are known. The polymerization of the RMs preferably takes place with an applied voltage in the case of PS-VA and PS-OCB displays, and with or without, preferably without, an applied voltage in the case of PS-IPS displays. As can be demonstrated in test cells, the PS(A) method results in a pretilt in the cell. In the case of PS-OCB displays, for example, it is possible for the bend structure to be stabilized so that an offset voltage is unnecessary or can be reduced. In the case of PS-VA displays, the pretilt has a positive effect on response times. For PS-VA displays, a standard MVA or PVA pixel and electrode layout can be used. In addition, however, it is also possible, for example, to manage with only one structured electrode side and no protrusions, which significantly simplifies production and at the same time results in very good contrast at the same time as very good transparency to light.

Furthermore, the so-called posi-VA displays ("positive VA") have proven to be a particularly suitable mode. Like in classical VA displays, the initial orientation of the LC molecules in posi-VA displays is homeotropic, i.e. substantially perpendicular to the substrates, in the initial state when no voltage is applied. However, in contrast to classical VA displays, in posi-VA displays LC media with positive dielectric anisotropy are used. Like in the usually used IPS displays, the two electrodes in posi-VA displays are arranged on only one of the two substrates, and preferably exhibit intermeshed and comb-shaped (interdigital) structures. By application of a voltage to the interdigital electrodes, which create an electrical field that is substantially parallel to the layer of the LC medium, the LC molecules are transferred into an orientation that is substantially parallel to the substrates. In posi-VA displays polymer stabilization, by addition of RMs to the LC medium which are polymerized in the display, has also proven to be advantageous, as a significant reduction of the switching times could thereby be realized.

PS-VA displays are described, for example, in EP 1 170 626 A2, U.S. Pat. Nos. 6,861,107, 7,169,449, US 2004/0191428 A1, US 2006/0066793 A1 and US 2006/0103804 A1. PS-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

The PSA display may also comprise an alignment layer on one or both of the substrates forming the display cell. The alignment layer is usually applied on the electrodes (where such electrodes are present) such that it is in contact with the LC medium and induces initial alignment of the LC molecules. The alignment layer may comprise or consist of, for example, a polyimide, which may also be rubbed, or may be prepared by a photoalignment method.

In particular for monitor and especially TV applications, optimisation of the response times, but also of the contrast and luminance (thus also transmission) of the LC display continues to be demanded. The PSA method can provide significant advantages here. In particular in the case of PS-VA, PS-IPS, PS-FFS and PS-posi-VA displays, a shortening of the response times, which correlate with a measurable pretilt in test cells, can be achieved without significant adverse effects on other parameters.

Prior art has suggested biphenyl diacrylates or dimethacrylates, which are optionally fluorinated as RMs for use in PSA displays However, the problem arises that not all combinations consisting of an LC mixture and one or more RMs are suitable for use in PSA displays because, for example, an inadequate tilt or none at all becomes established or since, for example, the so-called "voltage holding ratio" (VHR or HR) is inadequate for TFT display applications. In addition, it has been found that, on use in PSA displays, the LC mixtures and RMs known from the prior art do still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerization by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce a particularly small pretilt angle. Preferred materials here are those which produce a lower pretilt angle during polymerization for the same exposure time than the materials known to date, and/or through the use of which the (higher) pretilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerized RMs, in particular after the polymerization step for production of the pretilt angle in the display. For example, unreacted RMs of this type may adversely affect the properties of the display by, for example, polymerizing in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they may reduce the effective applied voltage. This effect can also be observed in conventional LC displays without a polymer component.

In addition, an additional "image sticking" effect caused by the presence of unpolymerized RMs is often observed in PSA displays. Uncontrolled polymerization of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerization of the RMs to proceed as completely as possible during production of the PSA display and for the presence of unpolymerized RMs in the display to be excluded as far as possible or reduced to a minimum. Thus, RMs and LC mixtures are required which enable or support highly effective and complete polymerization of the RMs. In addition, controlled reaction of the residual RM amounts would be desirable. This would be simpler if the RM polymerized more rapidly and effectively than the compounds known to date.

A further problem that has been observed in the operation of PSA displays is the stability of the pretilt angle. Thus, it was observed that the pretilt angle, which was generated during display manufacture by polymerizing the RM as described above, does not remain constant but can deteriorate after the display was subjected to voltage stress during its operation. This can negatively affect the display performance, e.g. by increasing the black state transmission and hence lowering the contrast.

Another problem to be solved is that the RMs of prior art do often have high melting points, and do only show limited solubility in many currently common LC mixtures, and therefore frequently tend to spontaneously crystallize out of the mixture. In addition, the risk of spontaneous polymerization prevents the LC host mixture being warmed in order to dissolve the polymerizable component, meaning that the best possible solubility even at room temperature is necessary. In addition, there is a risk of separation, for example on introduction of the LC medium into the LC display (chromatography effect), which may greatly impair the homogeneity of the display. This is further increased by the fact that the LC media are usually introduced at low temperatures in order to reduce the risk of spontaneous polymerization (see above), which in turn has an adverse effect on the solubility.

Another problem observed in prior art is that the use of conventional LC media in LC displays, including but not limited to displays of the PSA type, often leads to the occurrence of mura in the display, especially when the LC medium is filled in the display cell manufactured using the one drop filling (ODF) method. This phenomenon is also known as "ODF mura". It is therefore desirable to provide LC media which lead to reduced ODF mura.

Another problem observed in prior art is that LC media for use in PSA displays, including but not limited to displays of the PSA type, do often exhibit high viscosities and, as a consequence, high switching times. In order to reduce the viscosity and switching time of the LC medium, it has been suggested in prior art to add LC compounds with an alkenyl group. However, it was observed that LC media containing alkenyl compounds often show a decrease of the reliability and stability, and a decrease of the VHR especially after exposure to UV radiation. Especially for use in PSA displays this is a considerable disadvantage, because the photopolymerization of the RMs in the PSA display is usually carried out by exposure to UV radiation, which may cause a VHR drop in the LC medium.

There is thus still a great demand for PSA displays and LC media and polymerizable compounds for use in such displays, which do not show the drawbacks as described above, or only do so to a small extent, and have improved properties.

In particular, there is a great demand for PSA displays, and LC media and polymerizable compounds for use in such PSA displays, which enable a high specific resistance at the same time as a large working-temperature range, short response times, even at low temperatures, and a low threshold voltage, a low pretilt angle, a multiplicity of grey shades, high contrast and a broad viewing angle, have high reliability and high values for the "voltage holding ratio" (VHR) after UV exposure, and, in case of the polymerizable compounds, have low melting points and a high solubility in the LC host mixtures. In PSA displays for mobile applications, it is especially desired to have available LC media that show low threshold voltage and high birefringence.

The invention provides novel suitable materials, in particular RMs and LC media comprising the same, for use in PSA displays, which do not have the disadvantages indicated above or do so to a reduced extent.

In particular, the invention provides RMs, and LC media comprising them, for use in PSA displays, which enable very high specific resistance values, high VHR values, high reliability, low threshold voltages, short response times, high birefringence, show good UV absorption especially at longer wavelengths, enable quick and complete polymerization of the RMs, allow the generation of a low pretilt angle as quickly as possible, enable a high stability of the pretilt even after longer time and/or after UV exposure, reduce or prevent the occurrence of "image sticking" and "ODF mura" in the display, and in case of the RMs polymerize as rapidly and completely as possible and show a high solubility in the LC media which are typically used as host mixtures in PSA displays.

The invention further provides novel RMs, in particular for optical, electro-optical and electronic applications, and of suitable processes and intermediates for the preparation thereof.

In particular, it has been found, surprisingly, that the use of compounds of formula I as described and claimed hereinafter in LC media allows achieving the advantageous effects as mentioned above. These compounds are characterized in that they contain a mesogenic core with one or more polymerizable reactive groups and one or more tertiary hydroxy substituents attached thereto.

It was surprisingly found that the use of these compounds, and of LC media comprising them, in PSA displays facilitates a quick and complete UV-photopolymerization reaction in particular at longer UV wavelengths in the range from 300-380 nm, preferably from 320 to 360 nm, even without the addition of photoinitiator, leads to a fast generation of a large and stable pretilt angle, reduces image sticking and ODF mura in the display, leads to a high reliability and a high VHR value after UV photopolymerization, especially in case of LC host mixtures containing LC compounds with an alkenyl group, and enables to achieve fast response times, a low threshold voltage and a high birefringence.

In addition, the compounds of formula I have low melting points, good solubility in a wide range of LC media, especially in commercially available LC host mixtures for PSA use, and a low tendency to crystallization. Besides, they show good absorption at longer UV wavelengths, in particular in the range from 300-380 nm, preferably from 320 to 360 nm, and enable a quick and complete polymerization with small amounts of residual, unreacted monomers in the cell.

The compounds of formula I have not been disclosed in prior art so far. Other compounds with tertiary hydroxy groups have been described in prior art for use as radical scavengers, for example in P. M. Cullis, S. Langman, I. D. Podmore and M. C. R. Symons, *J. Chem. Sci. Trans.* 1990, 86, 3267. Therefore, it was surprising that compounds comprising a tertiary hydroxy group as as disclosed and claimed hereinafter can be used as Polymerizable monomers for quick and complete UV photopolymerization in LC media and generation of a pretilt angle in PSA displays.

Another aspect of the present invention is related to the use of the compounds of formula I as disclosed and claimed hereinafter as stabilizers for LC media and LC displays. Thus, it was observed that in LC media as used in prior art, often do not have a sufficiently high reliability.

The term "reliability" as used hereinafter means the quality of the performance of the display during time and with different stress loads, such as light load, temperature, humidity, or voltage which cause display defects such as image sticking (area and line image sticking), mura, yogore etc. and which are known to the skilled person in the field of LC displays. As a standard parameter for categorizing the reliability usually the voltage holding ration (VHR) value is used, which is a measure for maintaining a constant electrical voltage in a test display. The higher the VHR value, the better the reliability of the medium.

For example, in case of UB-FFS displays using LC media with negative dielectric anisotropy, the reduced reliability can be explained by an interaction of the LC molecules with the polyimide of the alignment layer, as a result of which ions are extracted from the polyimide alignment layer, and wherein LC molecules with negative dielectric anisotropy do more effectively extract such ions.

This results in new requirements for LC media to be used in UB-FFS displays. In particular, the LC medium has to show a high reliability and a high VHR value after UV exposure. Further requirements are a high specific resistance, a large working-temperature range, short response times even at low temperatures, a low threshold voltage, a multiplicity of grey levels, high contrast and a broad viewing angle, and reduced image sticking.

Another problem observed in prior art is that LC media for use in displays, including but not limited to UB-FFS displays, do often exhibit high viscosities and, as a consequence, high switching times. In order to reduce the viscosity and switching time of the LC medium, it has been suggested in prior art to add LC compounds with an alkenyl group. However, it was observed that LC media containing alkenyl compounds often show a decrease of the reliability and stability, and a decrease of the VHR especially after exposure to UV radiation but also to visible light from the backlight of a display, that usually does not emit UV light.

In order to reduce the decrease of the reliability and stability, the use of stabilizers was proposed, such as for example compounds of the HALS-(hindered amine light stabilizer) type, as disclosed in e.g. EP 2 514 800 B1 and WO 2009/129911 A1. A typical example is Tinuvin 770, a compound of the formula

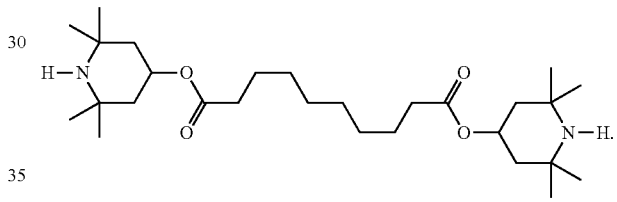

Nevertheless, these LC mixtures can still exhibit insufficient reliability during the operation of a display, e.g. upon irradiation with the typical CCFL-(Cold Cathode Fluorescent Lamp) backlight.

A different class of compound used for the stabilization of liquid crystals are antioxidants derived from phenol, such as for example the compound

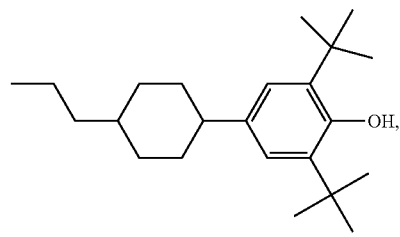 [SMILES: CCCC1CCC(c2cc(C(C)(C)C)c(O)c(C(C)(C)C)c2)CC1]

as described in DE 19539141 A1. Such stabilizers can be used to stabilize LC mixtures against heat or the influence of oxygen but typically do not show advantages under light stress.

Because of the complex modes of action of the different kinds of stabilizers and minute effects in a display, where the liquid crystal, a complex mixture of many different types of compounds itself, interacts with different kinds of species, including the polyimide, it is a challenging task also for the skilled person to choose the right stabilizer in order to identify the best material combination. Hence, there is still great demand for new types of stabilizers with different properties in order to broaden the range of applicable materials.

The present invention therefore also provides a process for providing improved LC media for use in LC displays, in particular in VA-, IPS- or UB-FFS displays, which do not exhibit the disadvantages described above or only do so to a small extent and have improved properties. A further object of the invention is to provide LC displays with good transmission, high reliability, high VHR value especially after backlight exposure, a high specific resistance, a large working-temperature range, short response times even at low temperatures, a low threshold voltage, a multiplicity of grey levels, high contrast and a broad viewing angle, and reduced image sticking.

The present invention provides a process for the stabilization of LC mixtures for the use in LC displays, in particular in VA-, IPS- or UB-FFS displays comprising an LC medium with negative dielectric anisotropy as described and claimed hereinafter. In particular, the inventors of the present invention have found that the above objects can be achieved by using an LC medium comprising one or more compounds of formula I as disclosed and claimed hereinafter as stabilizer, and preferably comprising one or more alkenyl compounds, in a VA-, IPS or UB-FFS display. It has also been found that when using such stabilizers in an LC medium for use in an UB-FFS display, surprisingly the reliability and the VHR value after backlight load are higher, compared to an LC medium without a stabilizer according to the present invention.

As described above, the compounds according to the present invention are also suitable for use as RMs in PSA display modes like for example PS-VA. Surprisingly it was found that such compounds, which contain one or more polymerizable groups, are, quite contrary to being harmful in terms of reliability of the LC, also suitable to stabilize LC mixtures under light stress.

Also, the use of an LC medium comprising a stabilizer as described hereinafter allows to exploit the known advantages of alkenyl-containing LC media, like reduced viscosity and faster switching time, and at the same time leads to improved reliability and high VHR value especially after backlight exposure.

SUMMARY OF THE INVENTION

The invention relates to compounds of formula I $$\text{P-Sp-A}^1\text{-}(Z^1\text{-}A^2)_z\text{-R} \qquad \text{I}$$

wherein the individual radicals, independently of each other and on each occurrence identically or differently, have the following meanings P a polymerizable group,
Sp a spacer group that is optionally substituted by one or more groups P or $L^a$, or a single bond,
$A^1$, $A^2$ an alicyclic, heterocyclic, aromatic or heteroaromatic group with 4 to 30 ring atoms, which may also contain fused rings, and is optionally substituted by one or more groups L or R,
$Z^1$ —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —CH=CF—, —CF=CH—, —CC—, —CH=CH— CO—O—, —O—CO—CH=CH—, —CH$_2$—CH$_2$— CO—O—, —O—CO—CH$_2$—CH$_2$—, —C(R$^0$)(R$^{00}$)—, or a single bond,
$R^0$, $R^{00}$ H or alkyl having 1 to 12 C atoms,
R H, L, P-Sp- or $L^a$-Sp-,
L F, Cl, —CN, P-Sp-, $L^a$, $L^a$-Sp-, or straight chain, branched or cyclic alkyl having 1 to 25 C atoms, wherein one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by P, F, Cl or $L^a$,
$L^a$ —C(R$^{aa}$)(R$^{bb}$)OH,
$R^{aa}$, $R^{bb}$ straight-chain alkyl with 1 to 20 C atoms, branched alkyl with 3 to 20 C atoms, or cyclic alkyl with 3 to 12, preferably 4 to 6, C atoms, or $R^{aa}$ and $R^{bb}$ together with the C atom to which they are attached form a cyclic alkyl group with 3 to 12, preferably 4 to 6, C atoms, wherein in all aforementioned groups one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl,
z 0, 1, 2 or 3,
n1 1, 2, 3 or 4,
characterized in that the compounds contain at least one group $L^a$ or $L^a$-Sp-.

The invention further relates to the use of compounds of formula I as polymerizable compounds or RMs in LC media and LC displays, especially in the LC medium, active layer or alignment layer of an LC display, wherein the LC displays are preferably PSA displays.

The invention further relates to the use of compounds of formula I as stabilizers in LC media and LC displays, especially in the LC medium, active layer or alignment layer of an LC display.

The invention further relates to methods for preparing compounds of formula I, and to novel intermediates used or obtained in these methods.

The invention furthermore relates to an LC medium comprising one or more compounds of formula I.

The invention furthermore relates to an LC medium comprising one or more stabilizers, at least one of which is a compound of formula I.

The invention furthermore relates to an LC medium comprising one or more polymerizable compounds, at least one of which is a compound of formula I.

The invention furthermore relates to an LC medium comprising
  a polymerizable component A) comprising, preferably consisting of, one or more polymerizable compounds, at least one of which is a compound of formula I, and
  a liquid-crystalline component B), hereinafter also referred to as "LC host mixture", comprising, preferably consisting of, one or more mesogenic or liquid-crystalline compounds.

The liquid-crystalline component B) of an LC medium according to the present invention is hereinafter also referred to as "LC host mixture", and preferably comprises one or more, preferably at least two mesogenic or LC compounds selected from low-molecular-weight compounds which are unpolymerizable.

The invention furthermore relates to an LC medium as described above and below, wherein the LC host mixture or component B) comprises at least one mesogenic or LC compound comprising an alkenyl group.

The invention furthermore relates to an LC medium or LC display as described above, wherein the compounds of formula I, or the polymerizable compounds of component A), are polymerized.

The invention furthermore relates to a process for preparing an LC medium as described above and below, comprising the steps of mixing one or more mesogenic or LC compounds, or an LC host mixture or LC component B) as described above and below, with one or more compounds of formula I, and optionally with further LC compounds and/or additives.

The invention furthermore relates to the use of compounds of formula I and LC media according to the invention in PSA displays, in particular the use in PSA displays containing an LC medium, for the production of a tilt angle in the LC medium by in-situ polymerization of the compound(s) of the formula I in the PSA display, preferably in an electric or magnetic field.

The invention furthermore relates to an LC display comprising one or more compounds of formula I or an LC medium according to the invention, in particular a PSA display, particularly preferably a PS-VA, PS-OCB, PS-IPS, PS-FFS, PS-UB-FFS, PS-posi-VA or PS-TN display.

The invention furthermore relates to an LC display comprising a polymer obtainable by polymerization of one or more compounds of formula I or of a polymerizable component A) as described above, or comprising an LC medium according to the invention, which is preferably a PSA display, very preferably a PS-VA, PS-OCB, PS-IPS, PS-FFS, PS-UB-FFS, PS-posi-VA or PS-TN display.

The invention furthermore relates to an LC display of the PSA type comprising two substrates, at least one which is transparent to light, an electrode provided on each substrate or two electrodes provided on only one of the substrates, and located between the substrates a layer of an LC medium that comprises one or more polymerizable compounds and an LC component as described above and below, wherein the polymerizable compounds are polymerized between the substrates of the display.

The invention furthermore relates to a process for manufacturing an LC display as described above and below, comprising the steps of filling or otherwise providing an LC medium, which comprises one or more polymerizable compounds as described above and below, between the substrates of the display, and polymerizing the polymerizable compounds.

The PSA displays according to the invention have two electrodes, preferably in the form of transparent layers, which are applied to one or both of the substrates. In some displays, for example in PS-VA, PS-OCB or PS-TN displays, one electrode is applied to each of the two substrates. In other displays, for example in PS-posi-VA, PS-IPS or PS-FFS or PS-UB-FFS displays, both electrodes are applied to only one of the two substrates.

In a preferred embodiment the polymerizable component is polymerized in the LC display while a voltage is applied to the electrodes of the display.

The polymerizable compounds of the polymerizable component are preferably polymerized by photo-polymerization, very preferably by UV photo-polymerization.

The invention furthermore relates to the use of compounds of formula I and LC media according to the invention as stabilizer in LC displays, in particular the use in LC displays containing an LC medium, for stabilising the LC medium against unwanted chemical reactions or degradation caused by ionic impurities and/or oxygen and/or humidity.

The invention furthermore relates to an LC display comprising one or more compounds of formula I as stabilizer, or an LC medium according to the invention, in particular a VA, IPS or UB-FFS display, or a TN, OCB, FFS or posi-VA display.

DETAILED DESCRIPTION OF THE INVENTION

Unless stated otherwise, the term "ultraviolet (UV) light" means light in the wavelength region of 310-400 nm of the electromagnetic spectrum.

Unless stated otherwise, the compounds of formula I are preferably selected from achiral compounds.

As used herein, the terms "active layer" and "switchable layer" mean a layer in an electrooptical display, for example an LC display, that comprises one or more molecules having structural and optical anisotropy, like for example LC molecules, which change their orientation upon an external stimulus like an electric or magnetic field, resulting in a change of the transmission of the layer for polarized or unpolarized light.

As used herein, the terms "tilt" and "tilt angle" will be understood to mean a tilted alignment of the LC molecules of an LC medium relative to the surfaces of the cell in an LC display (here preferably a PSA display). The tilt angle here denotes the average angle ($<90°$) between the longitudinal molecular axes of the LC molecules (LC director) and the surface of the plane-parallel outer plates which form the LC cell. A low value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

As used herein, the terms "reactive mesogen" and "RM" will be understood to mean a compound containing a mesogenic or liquid crystalline skeleton, and one or more functional groups attached thereto which are suitable for polymerization and are also referred to as "polymerizable group" or "P".

Unless stated otherwise, the term "polymerizable compound" as used herein will be understood to mean a polymerizable monomeric compound.

As used herein, the term "low-molecular-weight compound" will be understood to mean to a compound that is monomeric and/or is not prepared by a polymerization reaction, as opposed to a "polymeric compound" or a "polymer".

As used herein, the term "unpolymerizable compound" will be understood to mean a compound that does not contain a functional group that is suitable for polymerization under the conditions usually applied for the polymerization of the RMs.

The term "mesogenic group" as used herein is known to the person skilled in the art and described in the literature, and means a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerization. Typical mesogenic groups are, for example, rigid rod- or disc-shaped units. An overview of the terms and definitions used in connection with mesogenic or LC compounds is given in *Pure Appl. Chem.* 2001, 73(5), 888 and C. Tschierske, G. Pelzl, S. Diele, *Angew. Chem.* 2004, 116, 6340-6368.

The term "spacer group", hereinafter also referred to as "Sp", as used herein is known to the person skilled in the art and is described in the literature, see, for example, *Pure Appl. Chem.* 2001, 73(5), 888 and C. Tschierske, G. Pelzl, S. Diele, *Angew. Chem.* 2004, 116, 6340-6368. As used herein, the terms "spacer group" or "spacer" mean a flexible group, for example an alkylene group, which connects the mesogenic group and the polymerizable group(s) in a polymerizable mesogenic compound.

Above and below,

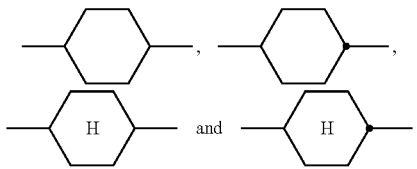

denote a trans-1,4-cyclohexylene ring, and

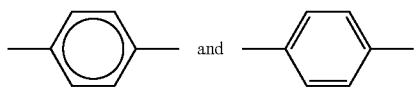

denote a 1,4-phenylene ring.

In a group

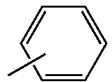

the single bond shown between the two ring atoms can be attached to any free position of the benzene ring.

Above and below "organic group" denotes a carbon or hydrocarbon group.

"Carbon group" denotes a mono- or polyvalent organic group containing at least one carbon atom, where this either contains no further atoms (such as, for example, —C≡C—) or optionally contains one or more further atoms, such as, for example, N, O, S, B, P, Si, Se, As, Te or Ge (for example carbonyl, etc.). The term "hydrocarbon group" denotes a carbon group which additionally contains one or more H atoms and optionally one or more heteroatoms, such as, for example, N, O, S, B, P, Si, Se, As, Te or Ge.

"Halogen" denotes F, Cl, Br or I.

—CO—, —C(=O)— and —C(O)— denote a carbonyl group, i.e.

"O." denotes an oxygen free radical.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms, preferably selected from N, O, S, Se, Te, Si and Ge.

Preferred carbon and hydrocarbon groups are optionally substituted, straight-chain, branched or cyclic, alkyl, alkenyl, alkynyl, alkoxy, alkylcarbonyl, alkoxycarbonyl, alkylcarbonyloxy and alkoxycarbonyloxy having 1 to 40, preferably 1 to 20, very preferably 1 to 12, C atoms, optionally substituted aryl or aryloxy having 5 to 30, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 5 to 30, preferably 6 to 25, C atoms, wherein one or more C atoms may also be replaced by hetero atoms, preferably selected from N, O, S, Se, Te, Si and Ge.

Further preferred carbon and hydrocarbon groups are $C_1$-$C_{20}$ alkyl, $C_2$-$C_{20}$ alkenyl, $C_2$-$C_{20}$ alkynyl, $C_3$-$C_{20}$ allyl, $C_4$-$C_{20}$ alkyldienyl, $C_4$-$C_{20}$ polyenyl, $C_6$-$C_{20}$ cycloalkyl, $C_4$-$C_{15}$ cycloalkenyl, $C_6$-$C_{30}$ aryl, $C_6$-$C_{30}$ alkylaryl, $C_6$-$C_{30}$ arylalkyl, $C_6$-$C_{30}$ alkylaryloxy, $C_6$-$C_{30}$ arylalkyloxy, $C_2$-$C_{30}$ heteroaryl, $C_2$-$C_{30}$ heteroaryloxy.

Particular preference is given to $C_1$-$C_{12}$ alkyl, $C_2$-$C_{12}$ alkenyl, $C_2$-$C_{12}$ alkynyl, $C_6$-$C_{25}$ aryl and $C_2$-$C_{25}$ heteroaryl.

Further preferred carbon and hydrocarbon groups are straight-chain, branched or cyclic alkyl having 1 to 20, preferably 1 to 12, C atoms, which are unsubstituted or mono- or polysubstituted by F, Cl, Br, I or CN and in which one or more non-adjacent $CH_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that O and/or S atoms are not linked directly to one another.

$R^x$ preferably denotes H, F, Cl, CN, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O— and in which one or more H atoms may be replaced by F or Cl, or denotes an optionally substituted aryl or aryloxy group with 6 to 30 C atoms, or an optionally substituted heteroaryl or heteroaryloxy group with 2 to 30 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 5 to 25 ring atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, 9,10-dihydro-phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquin-oline, acridine, phenothiazine, phenoxazine, benzopyridazine, benzopyrimi-dine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazo-thiophene, or combinations of these groups.

The aryl and heteroaryl groups mentioned above and below may also be substituted by alkyl, alkoxy, thioalkyl, fluorine, nitro, nitrile, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds.

Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent CH$_2$ groups may be replaced by —O— and/or —S—.

Preferred alicyclic and heterocyclic groups are, for example, 5-membered groups, such as cyclopentane, tetrahydrofuran, tetrahydrothiofuran, pyrroli-dine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents for the abovementioned aryl and heteroaryl groups are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents are, for example, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, straight-chain or branched alkyl, alkoxy, alkylcarbonyl, alkoxycarbonyl, alkylcarbonyloxy or alkoxycarbonyloxy each having 1 to 25 C atoms, in which one or more H atoms may optionally be replaced by F or Cl, optionally substituted silyl having 1 to 20 Si atoms, or optionally substituted aryl having 6 to 25, preferably 6 to 15, C atoms, wherein R$^x$ denotes H, F, Cl, CN, or straight chain, branched or cyclic alkyl having 1 to 25 C atoms, wherein one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl, P— or P-Sp-, and Y$^1$ denotes halogen.

"Substituted silyl or aryl" preferably means substituted by halogen, —CN, R$^0$, —OR$^0$, —CO—R$^0$, —CO—O—R$^0$, —O—CO—R$^0$ or —O—CO—O—R$^0$, wherein R$^0$ denotes H or alkyl with 1 to 20 C atoms.

Particularly preferred substituents are, for example, F, Cl, CN, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, furthermore phenyl.

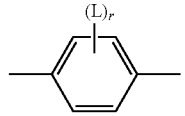

is preferably

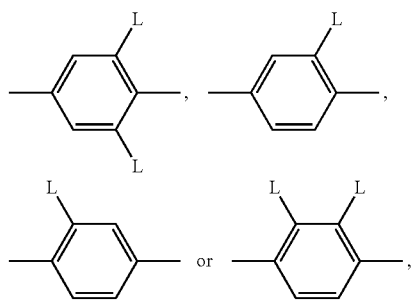

in which L has one of the meanings indicated above.

The polymerizable group P is a group which is suitable for a polymerization reaction, such as, for example, free-radical or ionic chain polymerization, polyaddition or polycondensation, or for a polymer-analogous reaction, for example addition or condensation onto a main polymer chain. Particular preference is given to groups for chain polymerization, in particular those containing a C=C double bond or —C≡C— triple bond, and groups which are suitable for polymerization with ring opening, such as, for example, oxetane or epoxide groups.

Preferred groups P are selected from the group consisting of $CH_2$=$CW^1$—CO—O—, $CH_2$=$CW^1$—CO—,

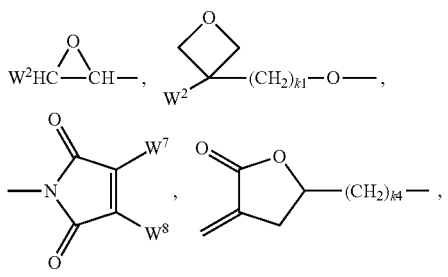

$CH_2$=$CW^2$—(O)$_{k3}$—, $CW^1$=CH—CO—(O)$_{k3}$—, $CW^1$=CH—CO—NH—, $CH_2$=$CW^1$—CO—NH—, $CH_3$—CH=CH—O—, $(CH_2$=$CH)_2$CH—OCO—, $(CH_2$=$CH$—$CH_2)_2$CH—OCO—, $(CH_2$=$CH)_2$CH—O—, $(CH_2$=$CH$—$CH_2)_2$N—, $(CH_2$=$CH$—$CH_2)_2$N—CO—, HO—$CW^2W^3$—, HS—$CW^2W^3$—, H$W^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Very preferred groups P are selected from the group consisting of $CH_2$=$CW^1$—CO—O—, $CH_2$=$CW^1$—CO—,

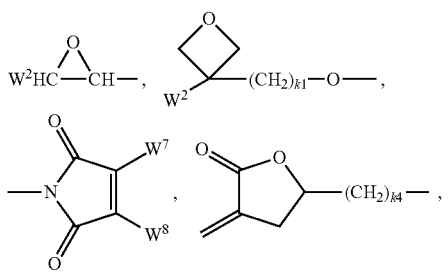

$CH_2$=$CW^2$—O—, $CH_2$=$CW^2$—, $CW^1$=CH—CO—(O)$_{k3}$—, $CW^1$=CH—CO—NH—, $CH_2$=$CW^1$—CO—NH—, $(CH_2$=$CH)_2$CH—OCO—, $(CH_2$=$CH$—$CH_2)_2$CH—OCO—, $(CH_2$=$CH)_2$CH—O—, $(CH_2$=$CH$—$CH_2)_2$N—, $(CH_2$=$CH$—$CH_2)_2$N—CO—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P are selected from the group consisting of $CH_2$=$CW^1$—CO—O—, in particular $CH_2$=CH—CO—O—, $CH_2$=C($CH_3$)—CO—O— and $CH_2$=CF—CO—O—, furthermore $CH_2$=CH—O—, $(CH_2$=$CH)_2$CH—O—CO—, $(CH_2$=$CH)_2$CH—O—,

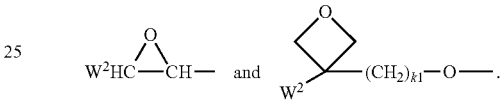

Further preferred polymerizable groups P are selected from the group consisting of vinyloxy, acrylate, methacrylate, fluoroacrylate, chloroacrylate, oxetane and epoxide, most preferably from acrylate and methacrylate.

If the spacer group Sp is different from a single bond, it is preferably of the formula Sp"-X", so that the respective radical P-Sp- conforms to the formula P-Sp"-X"—, wherein Sp" denotes linear or branched alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N($R^0$)—, —Si($R^0R^{00}$)—, —CO—, —CO—O—, —O—CO—, —O—CO—O—, —S—CO—, —CO—S—, —N($R^{00}$)—CO—O—, —O—CO—N($R^0$)—, —N($R^0$)—CO—N($R^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N($R^0$)—, —N($R^0$)—CO—, —N($R^0$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^2$=CY$^3$—, —C≡C—, —CH=CH—CO—O—, —O—CO—CH=CH— or a single bond, $R^0$ and $R^{00}$ each, independently of one another, denote H or alkyl having 1 to 20 C atoms, and $Y^2$ and $Y^3$ each, independently of one another, denote H, F, Cl or CN.

X" is preferably —O—, —S—, —CO—, —COO—, —OCO—, —O—COO—, —CO—NR$^0$—, —NR$^0$—CO—, —NR$^0$—CO—NR$^{00}$— or a single bond.

Typical spacer groups Sp and -Sp"-X"— are, for example, —(CH$_2$)$_{p1}$—, —(CH$_2$)$_{p1}$—O—, —(CH$_2$)$_{p1}$—O—CO—, —(CH$_2$)$_{p1}$—CO—O—, —(CH$_2$)$_{p1}$—O—CO—O—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^o$R$^{oo}$—O)$_{p1}$—, in which p1 is an integer from 1 to 12, q1 is an integer from 1 to 3, and R$^o$ and R$^{oo}$ have the meanings indicated above.

Particularly preferred groups Sp and -Sp"-X"— are —(CH$_2$)$_{p1}$—, —(CH$_2$)$_{p1}$—O—, —(CH$_2$)$_{p1}$—O—CO—, —(CH$_2$)$_{p1}$—CO—O—, —(CH$_2$)$_{p1}$—O—CO—O—, in which p1 and q1 have the meanings indicated above.

Particularly preferred groups Sp" are, in each case straight-chain, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methylimino-ethylene, 1-methylalkylene, ethenylene, propenylene and butenylene.

In a preferred embodiment of the invention the compounds of formula I and its subformulae contain a spacer group Sp that is substituted by one or more polymerizable groups P, so that the group Sp-P corresponds to Sp(P)$_s$, with s being (branched polymerizable groups).

Preferred compounds of formula I according to this preferred embodiment are those wherein s is 2, i.e. compounds which contain a group Sp(P)$_2$. Very preferred compounds of formula I according to this preferred embodiment contain a group selected from the following formulae:

| | |
|---|---|
| —X-alkyl-CHPP | S1 |
| —X-alkyl-CH((CH$_2$)$_{aa}$P)((CH$_2$)$_{bb}$P) | S2 |
| —X—N((CH$_2$)$_{aa}$P)((CH$_2$)$_{bb}$P) | S3 |
| —X-alkyl-CH P—CH$_2$—CH$_2$P | S4 |
| —X-alkyl-C(CH$_2$P)(CH$_2$P)—C$_{aa}$H$_{2aa+1}$ | S5 |
| —X-alkyl-CHP—CH$_2$P | S6 |
| —X-alkyl-CPP—C$_{aa}$H$_{2aa+1}$ | S7 |
| —X-alkyl-CHPCHP—C$_{aa}$H$_{2aa+1}$ | S8 | in which P is as defined in formula I, alkyl denotes a single bond or straight-chain or branched alkylene having 1 to 12 C atoms which is unsubstituted or mono- or polysubstituted by F, Cl or CN and in which one or more non-adjacent CH$_2$ groups may each, independently of one another, be replaced by —C(R$^o$)=C(R$^o$)—, —C≡C—, —N(R$^o$)—, —O—, —S—, —CO—, —CO—O—, —O—CO—, —O—CO—O— in such a way that O and/or S atoms are not linked directly to one another, where R$^o$ has the meaning indicated above, aa and bb each, independently of one another, denote 0, 1, 2, 3, 4, 5 or 6, X has one of the meanings indicated for X", and is preferably O, CO, SO$_2$, O—CO—, CO—O or a single bond.

Preferred spacer groups Sp(P)$_2$ are selected from formulae S1, S2 and S3.

Very preferred spacer groups Sp(P)$_2$ are selected from the following subformulae:

| | |
|---|---|
| —CHPP | S1a |
| —O—CHPP | S1b |
| —CH$_2$—CHPP | S1c |
| —OCH$_2$—CHPP | S1d |
| —CH(CH$_2$—P)(CH$_2$—P) | S2a |
| —OCH(CH$_2$—P)(CH$_2$—P) | S2b |
| —CH$_2$—CH(CH$_2$—P)(CH$_2$—P) | S2c |
| —OCH$_2$—CH(CH$_2$—P)(CH$_2$—P) | S2d |
| —CO—NH((CH$_2$)$_2$P)((CH$_2$P) | S3a |

In the compounds of formula I and its subformulae as described above and below, P is preferably selected from the group consisting of vinyloxy, acrylate, methacrylate, fluoroacrylate, chloroacrylate, oxetane and epoxide, most preferably from acrylate and methacrylate.

Further preferred are compounds of formula I and its subformulae as described above and below, wherein all polymerizable groups P that are present in the compound have the same meaning, and very preferably denote acrylate or methacrylate, most preferably methacrylate.

In the compounds of formula I and its subformulae as described above and below, R$^{aa}$ and R$^{bb}$ preferably denote straight chain alkyl with 1 to 12 C atoms or branched alkyl with 3 to 12 C atoms. More preferably R$^{aa}$ and R$^{bb}$ denote, independently of each other, methyl, ethyl, propyl and butyl, very preferably methyl or ethyl, most preferably methyl.

Further preferred are compounds of formula I and its subformulae as described above and below, wherein R$^{aa}$ and R$^{bb}$ together with the C atom to which they are attached form a cyclic alkyl group with 3 to 12 C atoms, very preferably a cyclopropyl, cyclobutyl, cyclopentyl or cyclohexyl group.

Very preferably the compounds of formula I contain a group L$^a$ or -Sp-L$^a$ selected from the following formulae

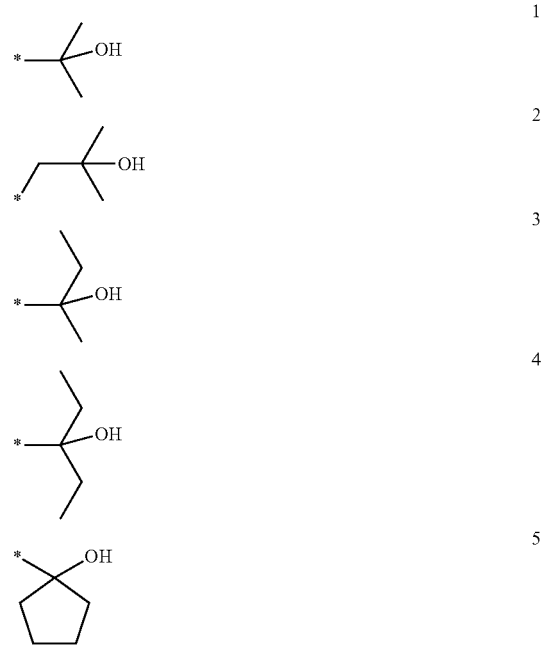

wherein the asterisk denotes the linkage to the adjacent group in the compound of formula I.

In another preferred embodiment of the invention the compounds of formula I and its subformulae contain a linear or branched alkylene spacer group Sp that is substituted by one or more groups L$^a$. Preferred compounds of formula I according to this preferred embodiment contain a group P-Sp- selected from the following formulae:

| | |
|---|---|
| P—CHL$^a$- | SL1 |
| P—(CH$_2$)$_{cc}$—O-CHL$^a$- | SL2 |

P—(CH$_2$)$_{cc}$—CO—O-CHL$^a$-      SL3

P—(CH$_2$)$_{cc}$—CHL$^a$-      SL4 in which P and L$^a$ are as defined in formula I or have one of the meanings given above and below, and cc is 1, 2, 3, 4, 5 or 6, preferably 1, 2 or 3.

Preferred compounds of formula I contain one or more groups P-Sp- selected from formulae SL1, SL2 and SL3, very preferably of formula SL1.

In the compounds of formula I, Z$^1$ is preferably a single bond.

In the compounds of formula I, A$^1$ and A$^2$ preferably denote benzene, naphthalene, phenanthrene or anthracene, which is optionally substituted by one or more groups L, P-Sp-, L$^a$ or L$^a$-Sp-.

Preferably -A$^1$-(Z$^1$-A$^2$)$_z$- in formula I denotes benzene, biphenylene, p-terphenylene (1,4-diphenylbenzene), m-terphenylene (1,3-diphenylbenzene), naphthylene, 2-phenylnaphthylene, phenanthrene, anthracene, dibenzofuran or dibenzothiophene, all of which are optionally substituted by one or more groups L, P-Sp-, L$^a$ or L$^a$-Sp-.

Very preferred groups -A$^1$-(Z$^1$-A$^2$)$_z$-, in formula I are selected from the following formulae

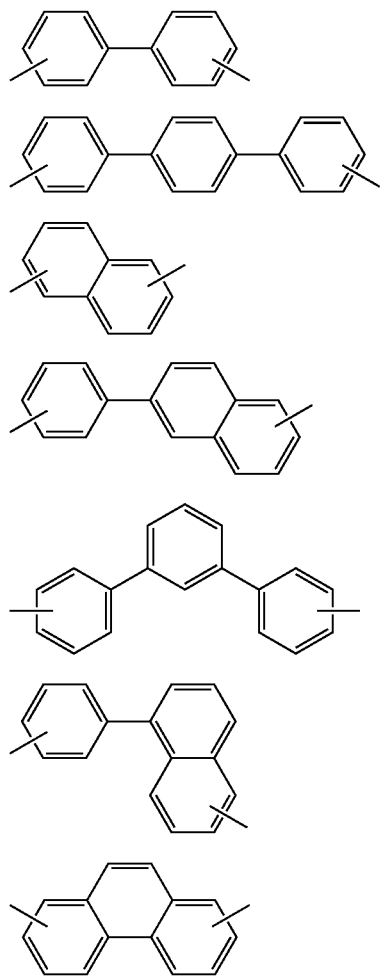

-continued

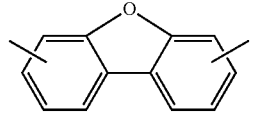
A8

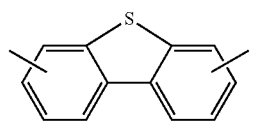
A9 wherein the benzene rings are optionally substituted by one or more groups L, P-Sp-, L$^a$ or L$^a$-Sp-.

In the compounds of formula I and its subformulae as described above and below, -A$^1$-(Z$^1$-A$^2$)$_z$- is preferably selected from formulae A1, A2, A5, A8 and A9, very preferably from formulae A1, A2 and A5.

Preferred compounds of formula I are selected from the following subformulae

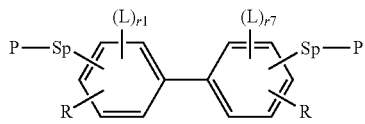
I1

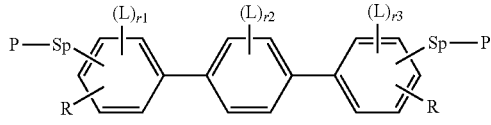
I2

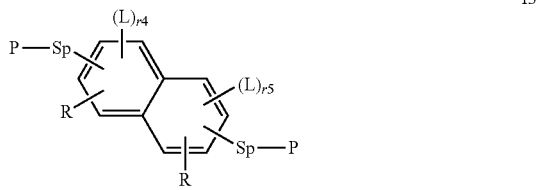
I3

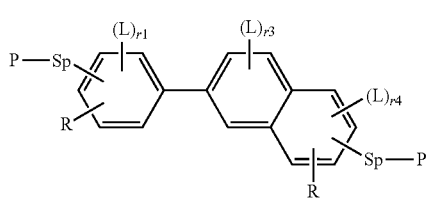
I4

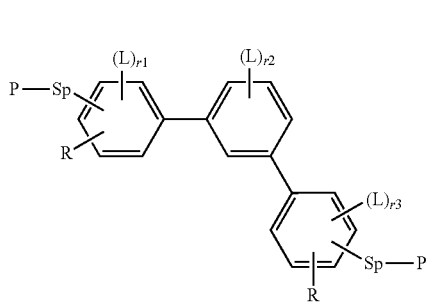
I5

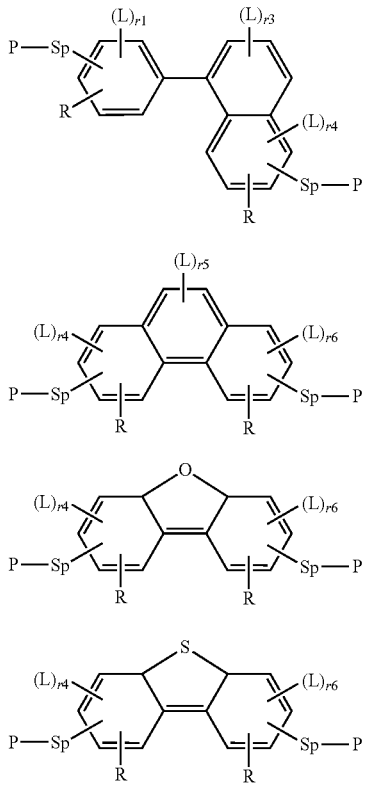

wherein P, Sp, R and L have the meanings given in formula I, r1, r3, r7 are independently of each other 0, 1, 2 or 3, r2 is 0, 1, 2, 3 or 4, r4, r5, r6 are independently of each other 0, 1 or 2, wherein r1+r7≥1, r1+r2+r3≥1, r4+r5≥1, r1+r3+r4≥1, and at least one of L denotes $L^a$ or $L^a$-Sp-, with $L^a$ being as defined in formula I, and/or wherein the compounds contain at least one group Sp that is substituted by $L^a$.

Preferred are compounds of formula I1-I7 wherein one of the two groups R is H and the other is P-Sp.

Further preferred are compounds of formula I1-I7 wherein both groups R denote H.

Further preferred are compounds of formula I1-I7 wherein both groups R denote P-Sp.

Very preferred are compounds of formula I1, I2 and I5.

Further preferred compounds of formula I and I1-I7 are selected from the following subformulae

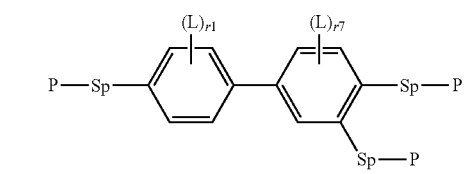

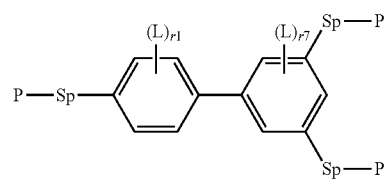

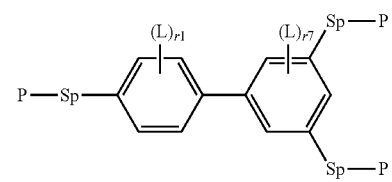

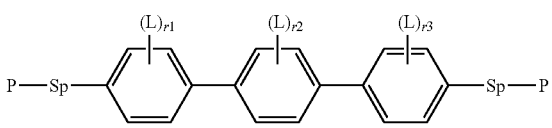

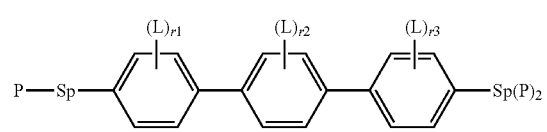

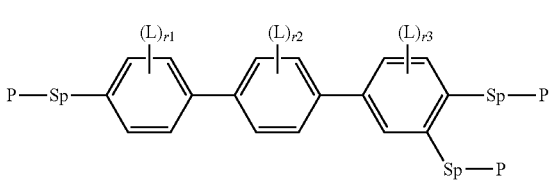

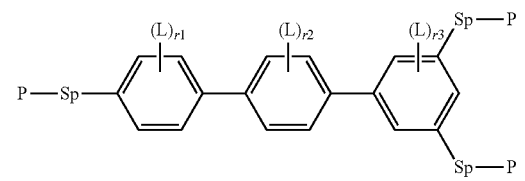

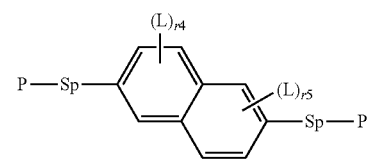

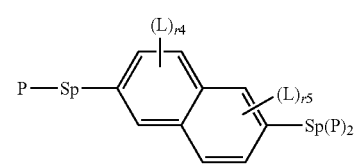

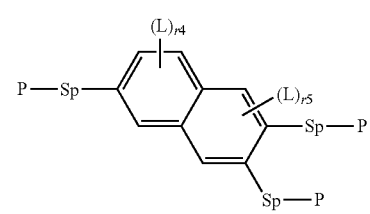

| | |
|---|---|
| I3-4 | I5-1 |
| I4-1 | I5-2 |
| I4-2 | I5-3 |
| I4-3 | I5-4 |
| I4-4 | I5-5 |
| I4-5 | |
| I4-6 | I6-1 |
| I4-7 | |

-continued

I6-2
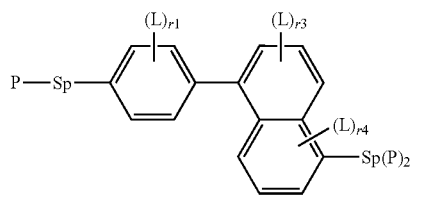

I6-3
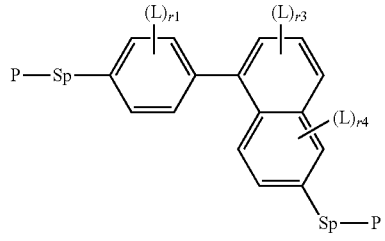

I6-4
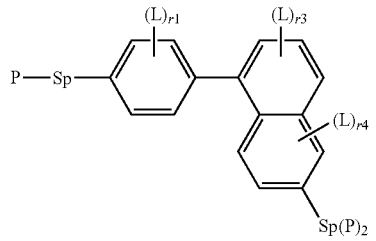

I6-5
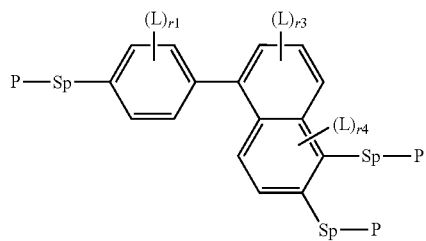

I6-6
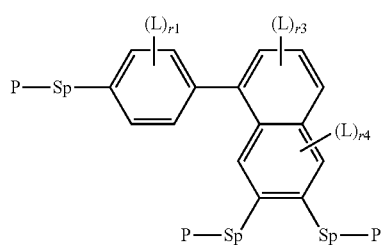

I6-7
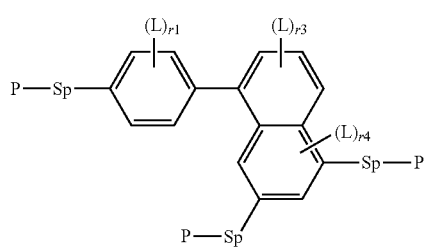

I7-1
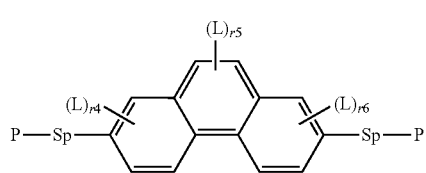

-continued

I7-2
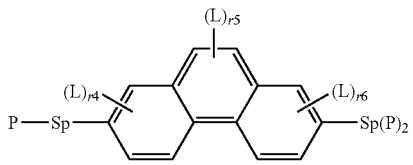

I7-3
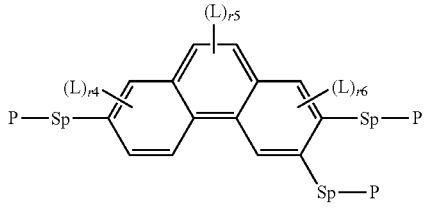

I7-4
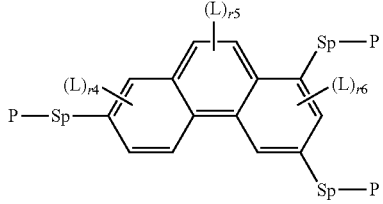

I8-1
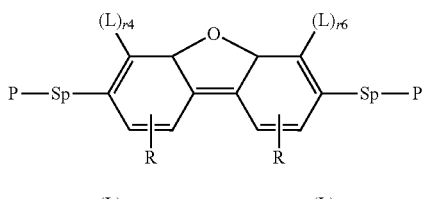

I8-2

I9-1

I9-2
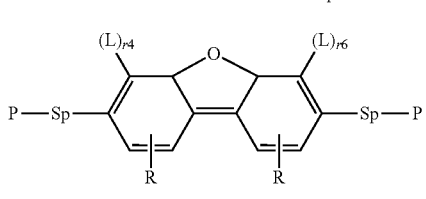

wherein P, Sp, P(Sp)$_2$, L, r1-r7 have the meanings given in formula I or one of the preferred meanings as given above and below, and r1+r7≥1, r1+r2+r3≥1, r4+r5≥1, r1+r3+r4≥1 and at least one of L denotes L$^a$ or L$^a$-Sp-, with L$^a$ being as defined in formula I, and/or the compounds contain at least one group Sp that is substituted by L$^a$.

Preferably in formulae I1-2, I2-2, I3-2, I4-2, I5-2, I6-2, I6-4 and I7-2 the group -Sp(P)$_2$ is selected from formulae S1 to S8 or S1a to S3a as defined above.

Very preferred compounds of formula I are selected from the following subformulae:
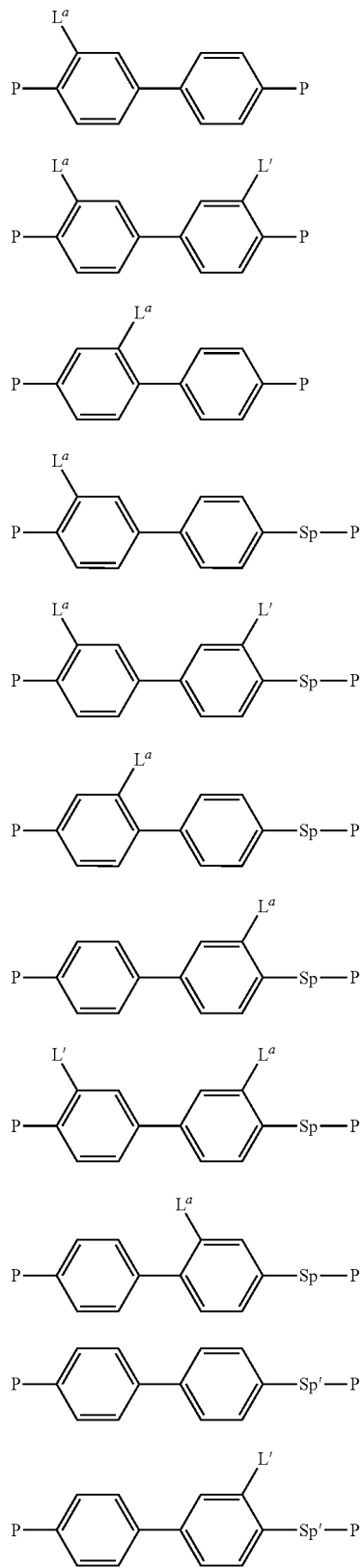
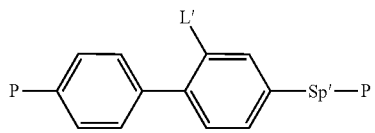
I1-1-12
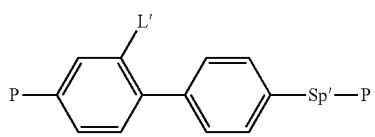
I1-1-13
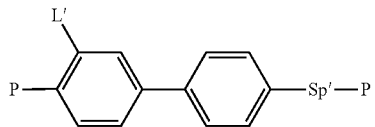
I1-1-14
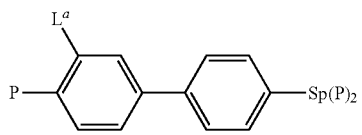
I1-2-1
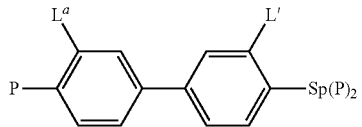
I1-2-2
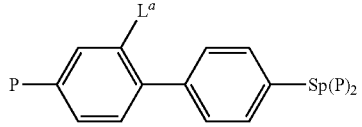
I1-2-3
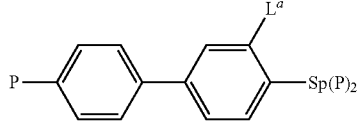
I1-2-4
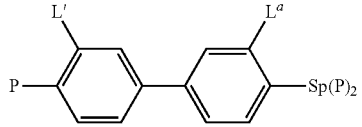
I-1-2-5
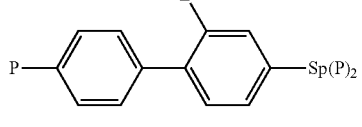
I1-2-6
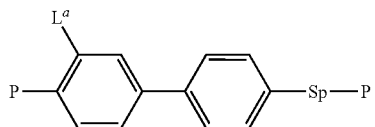
I1-3-1
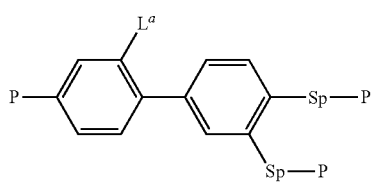
I1-3-2

I1-3-3
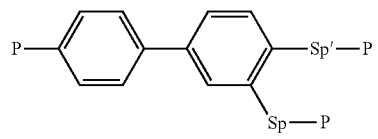
I1-3-4
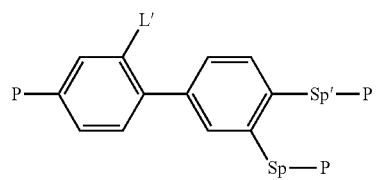
I1-3-5
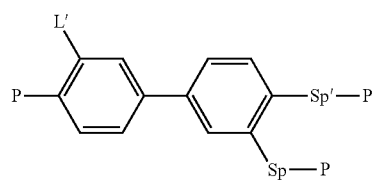
I1-4-1
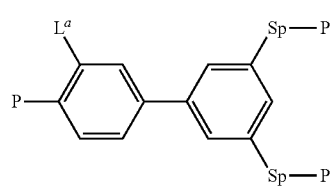
I1-4-2
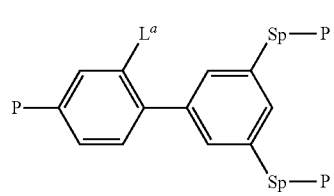
I1-4-3
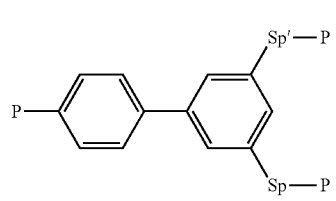
I2-1-1
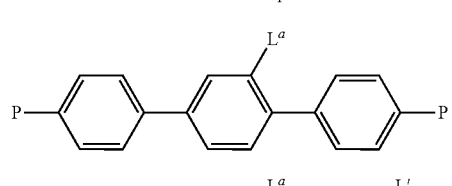
I2-1-2
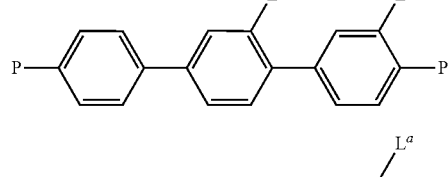
I2-1-3
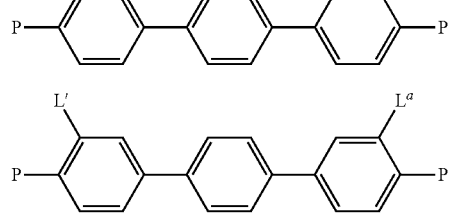
I2-1-4
I2-1-5
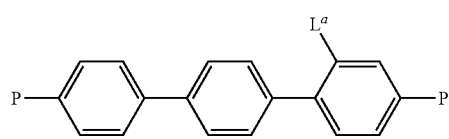
I2-1-6
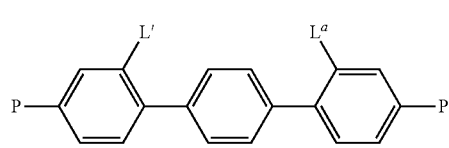
I2-1-7
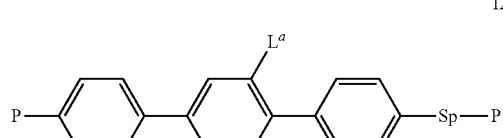
I2-1-8
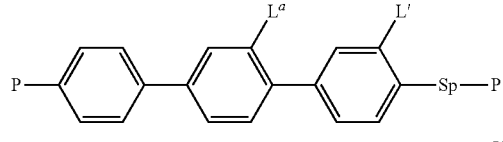
I2-1-9
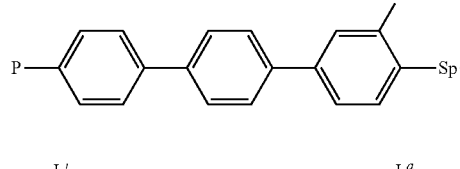
I2-1-10
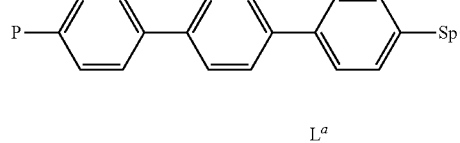
I2-1-11
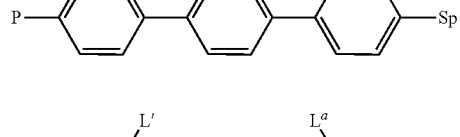
I2-1-12
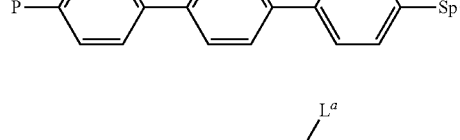
I2-1-13
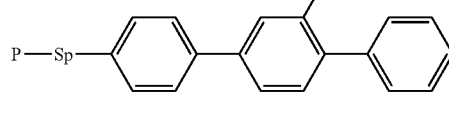
I2-1-14
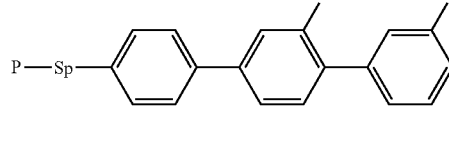

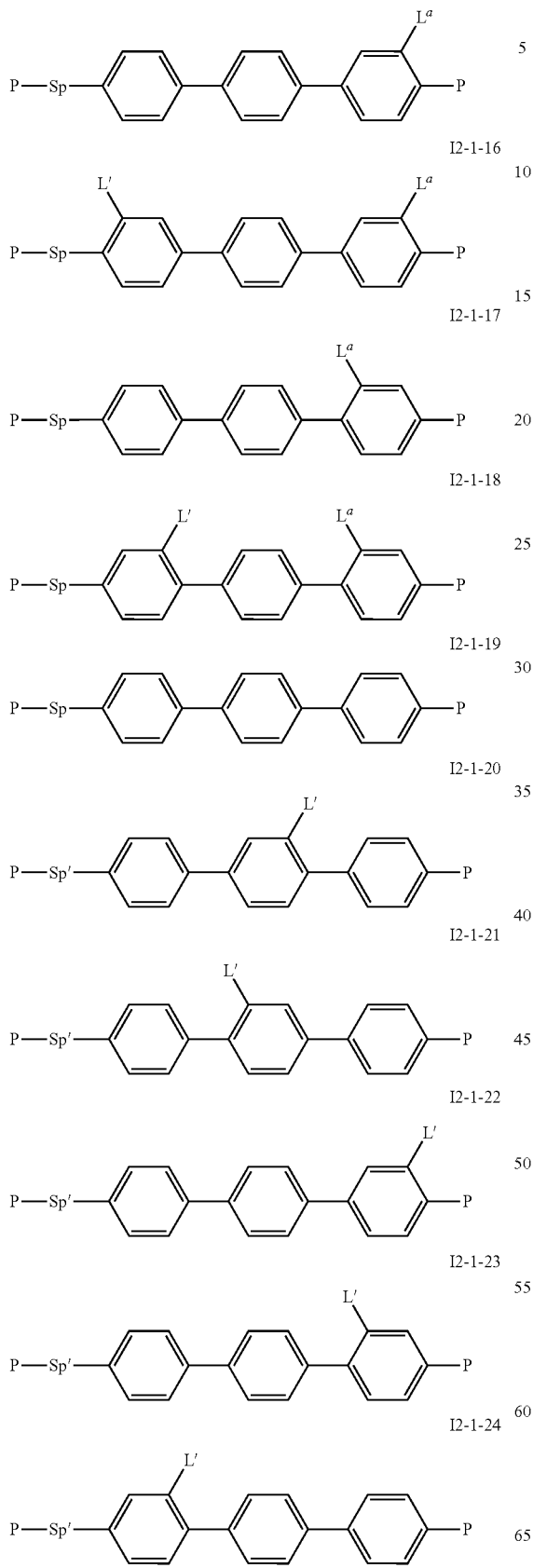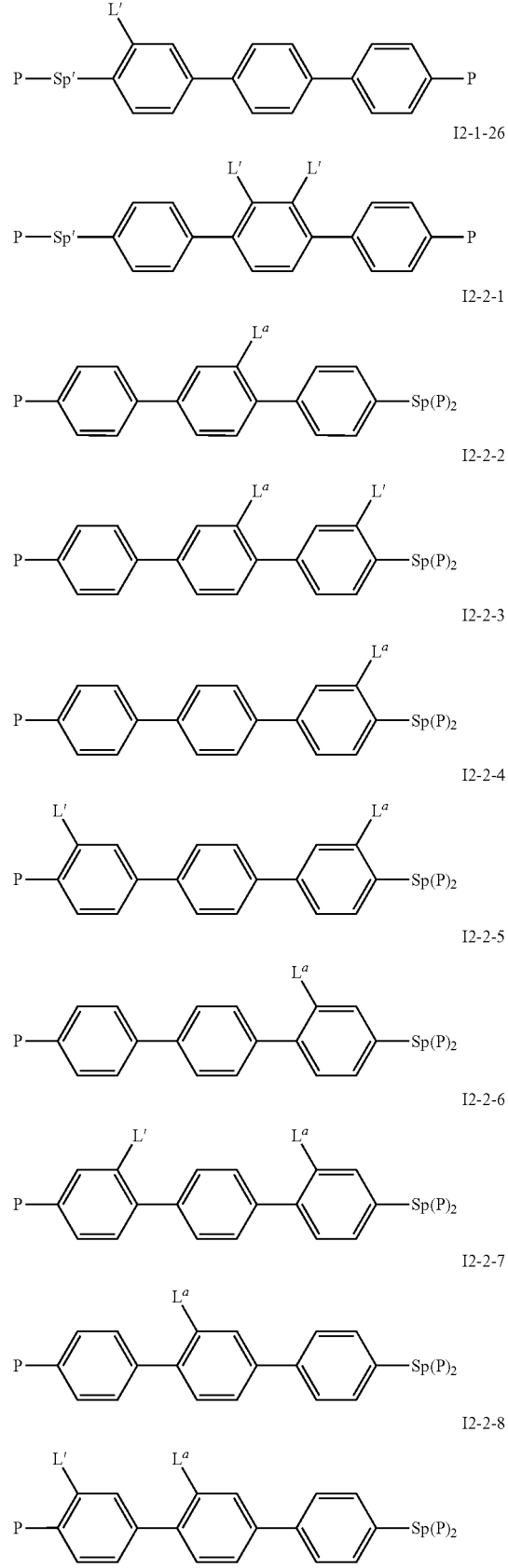

I2-2-9
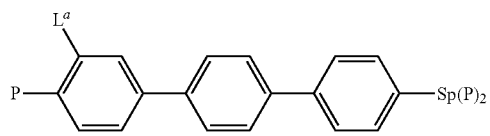
I2-2-10
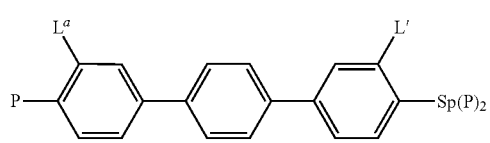
I2-2-11
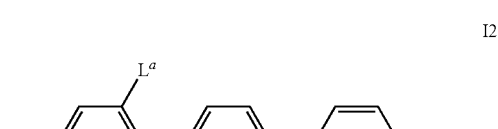
I2-2-12
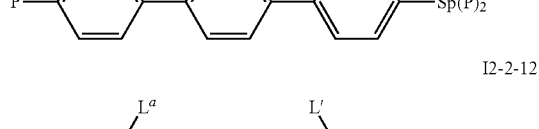
I2-3-1
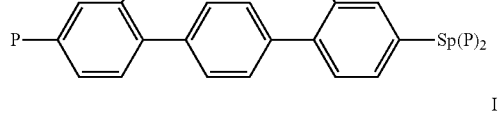
i2-3-2
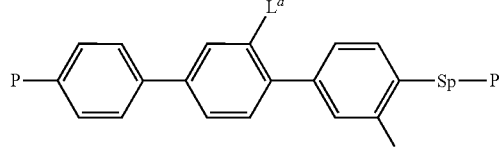
I2-3-3
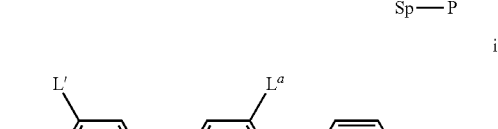
I2-3-4
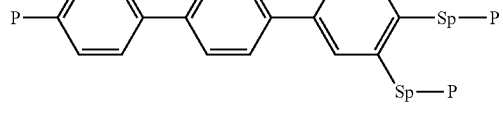
I2-3-5
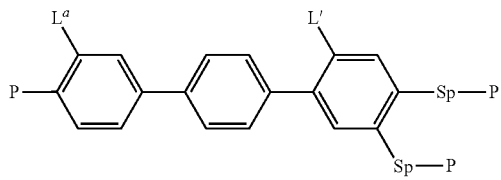
I2-3-6
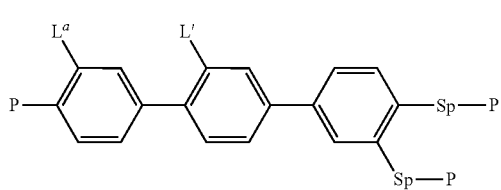
I2-3-7
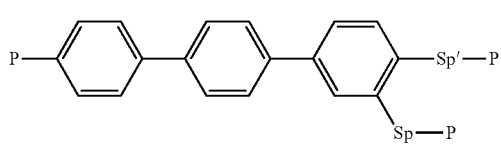
I2-3-8
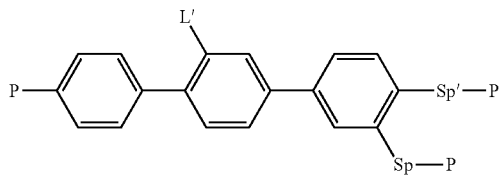
I2-4-1
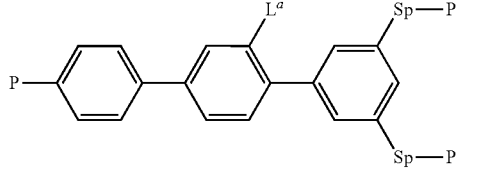
I2-4-2
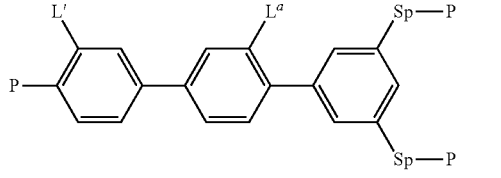
I2-4-3
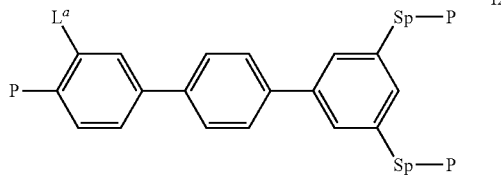
I2-4-4
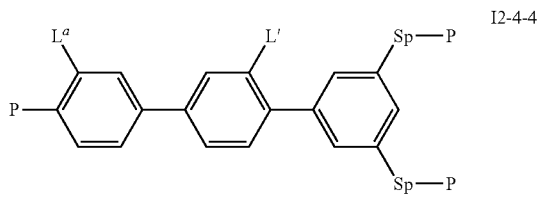

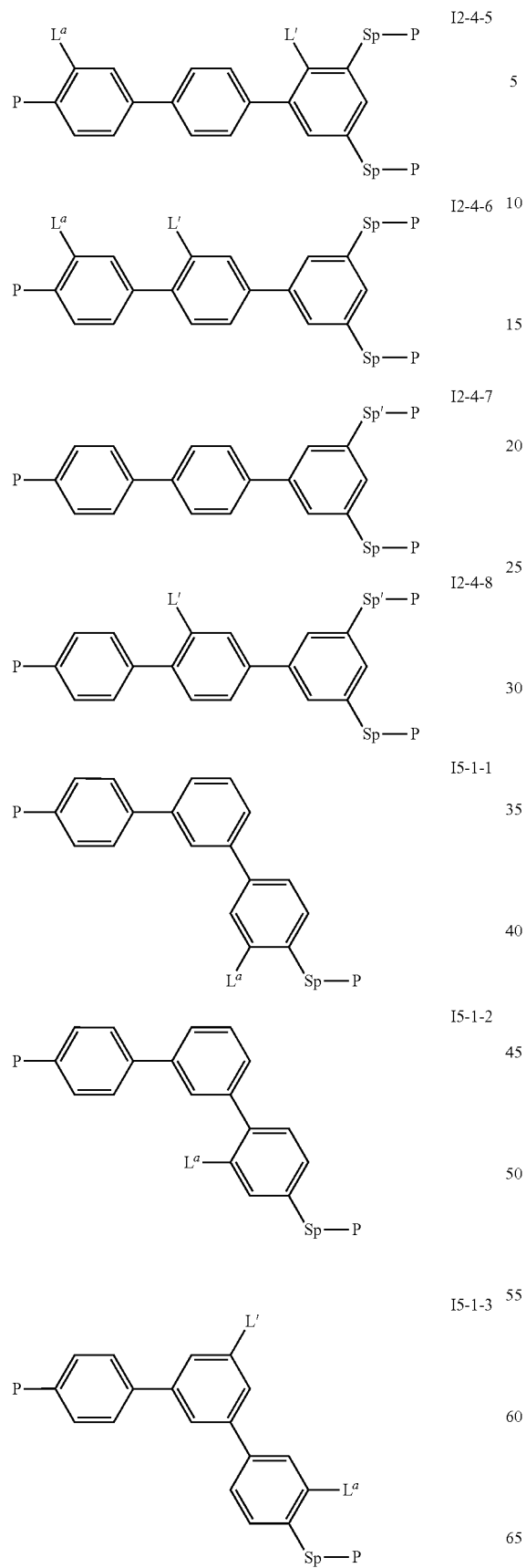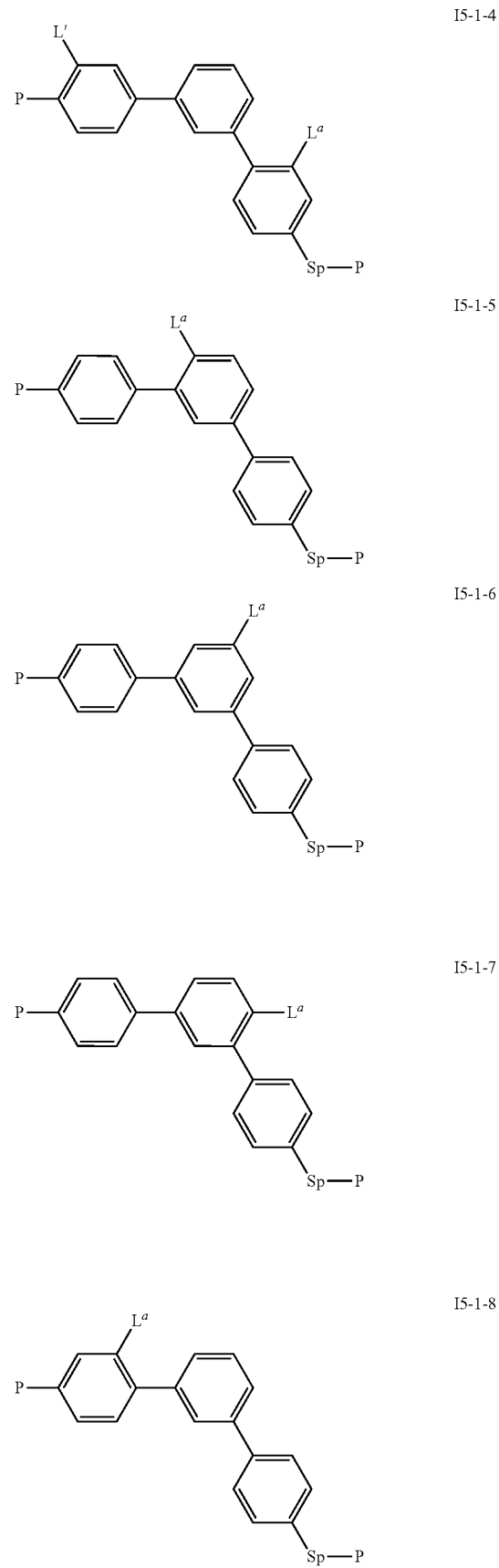

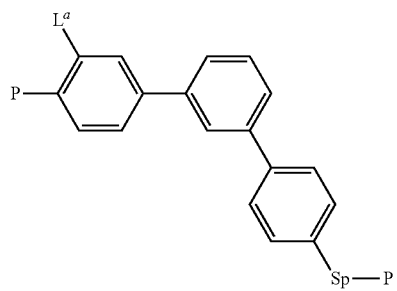 I5-1-9
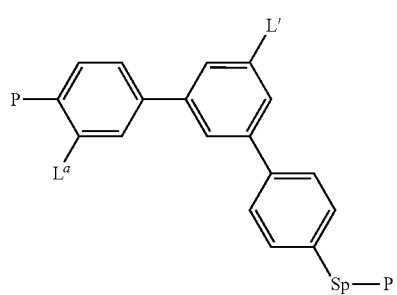 I5-1-10
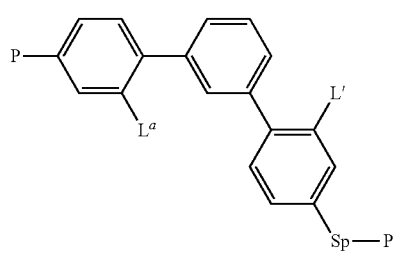 I5-1-11
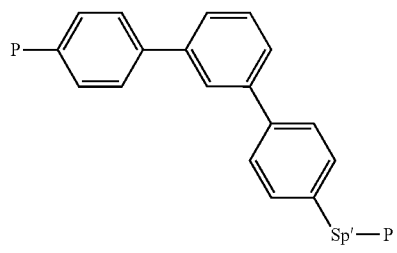 I5-1-12
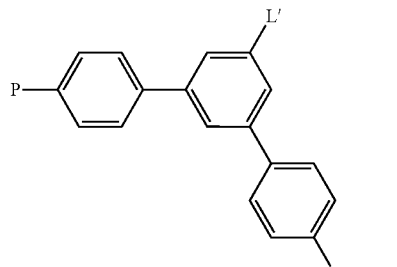 I5-1-13
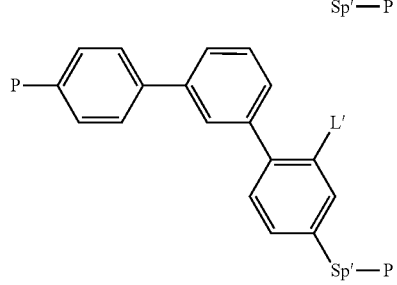 I5-1-14
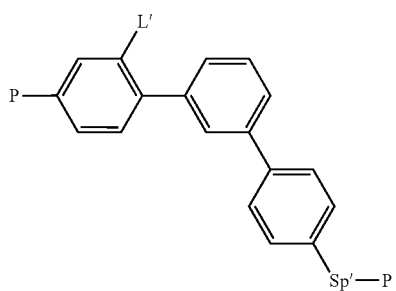 I5-1-15
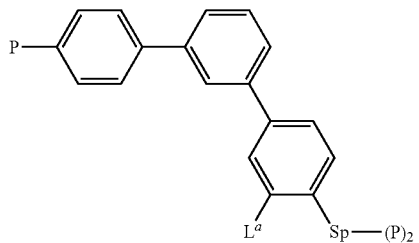 I5-2-1
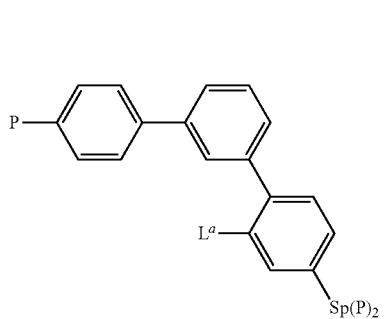 I5-2-2
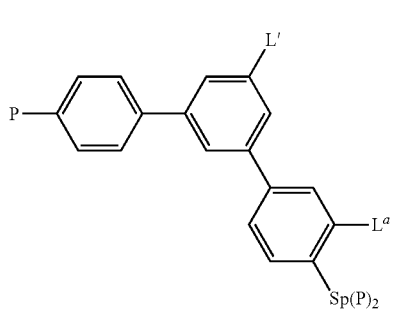 I5-2-3
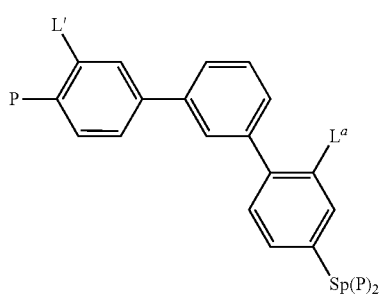 I5-2-4

I5-2-5
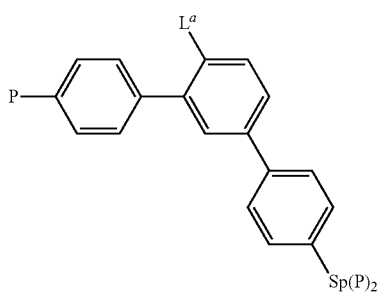
I5-2-6
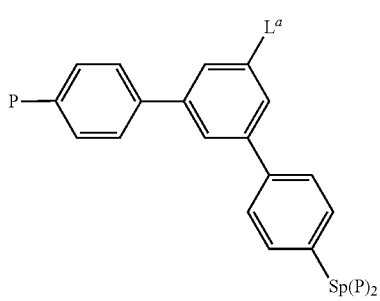
I5-2-7
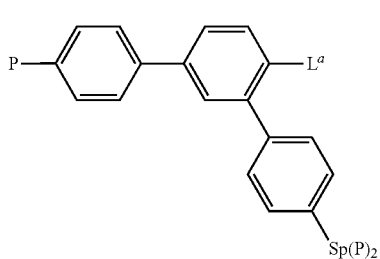
I5-2-8
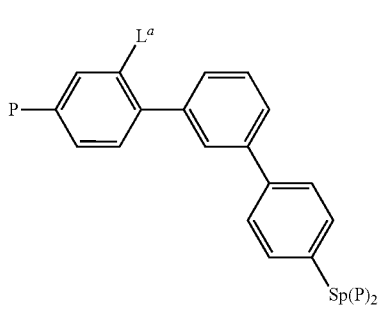
I5-2-9
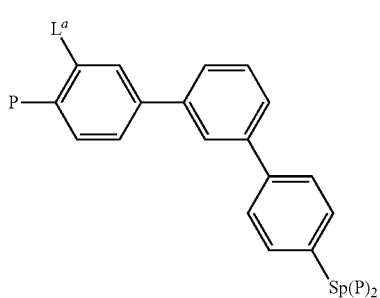
I5-2-10
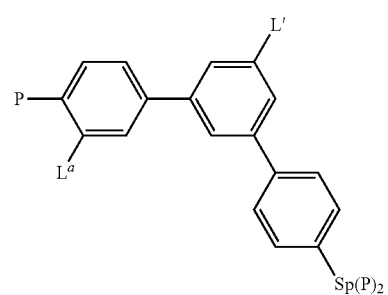
I5-2-11
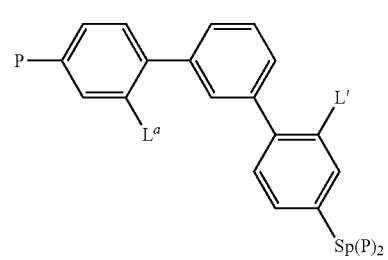
I5-3-1
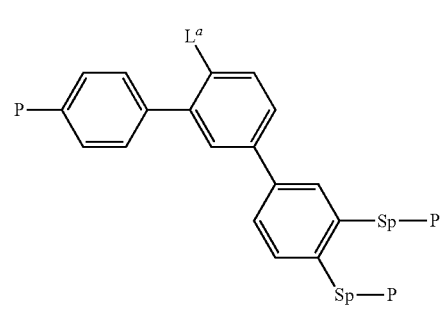
I5-3-2
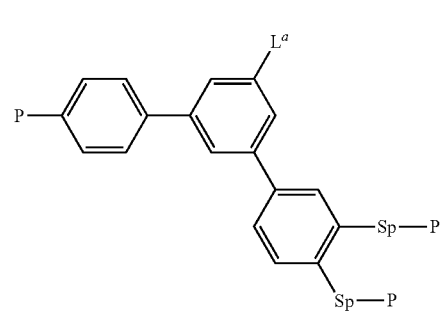
I5-3-3
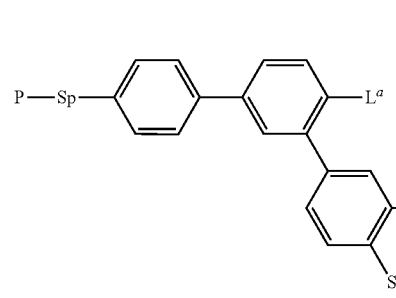

I5-3-4
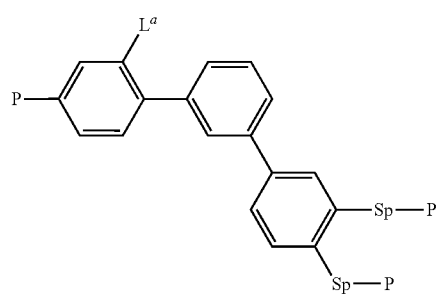
I5-3-5
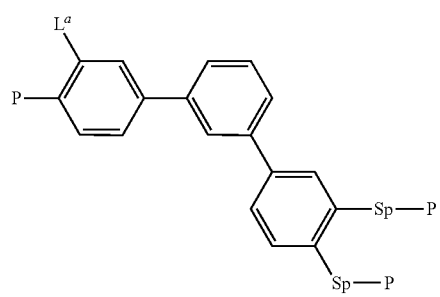
I5-3-6
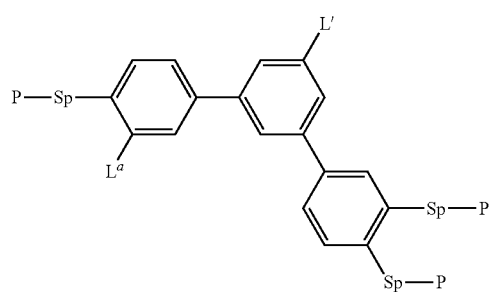
I5-3-7
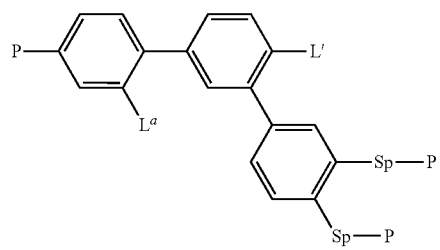
I5-3-8
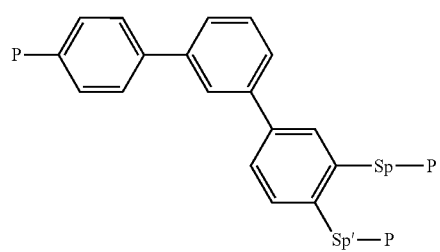
I5-3-9
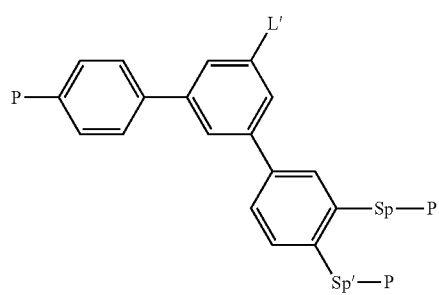
I5-4-1
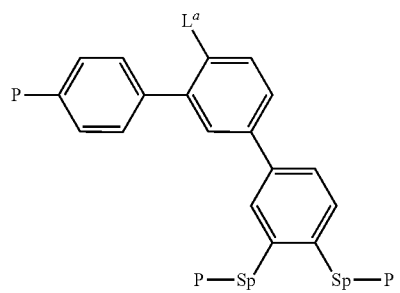
I5-4-2
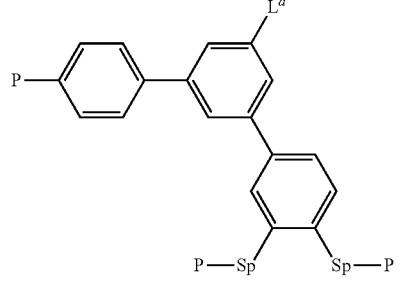
I5-4-3
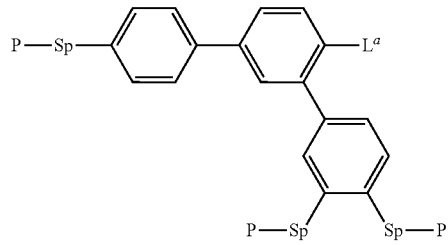
I5-4-4
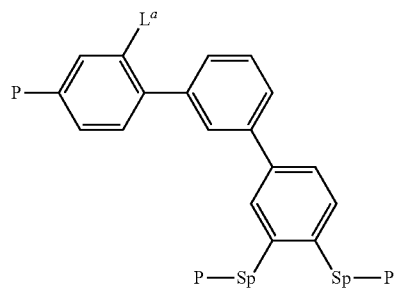

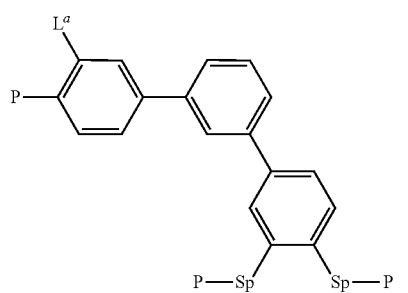
I5-4-5
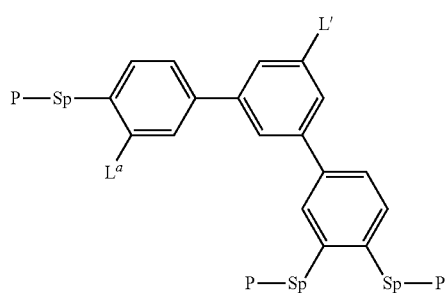
I5-4-6
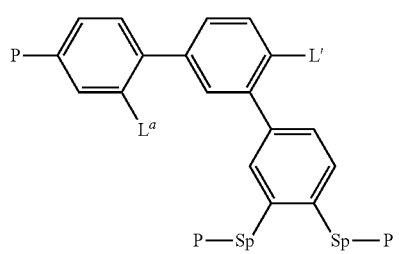
I5-4-7
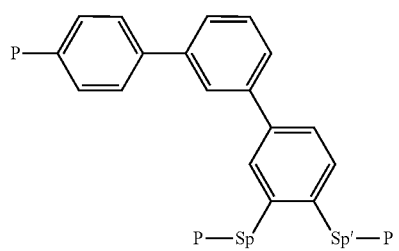
I5-4-8
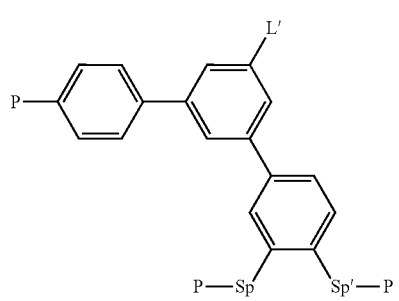
I5-4-9
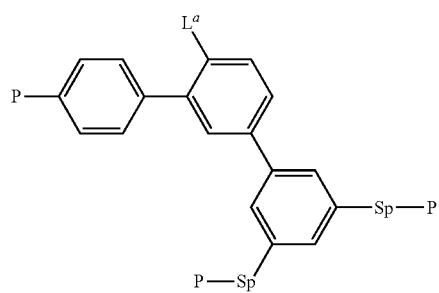
I5-5-1
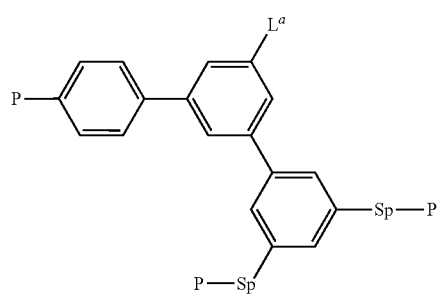
I5-5-2
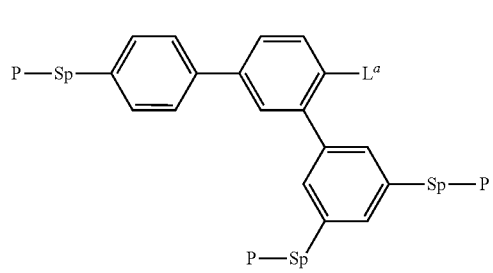
I5-5-3
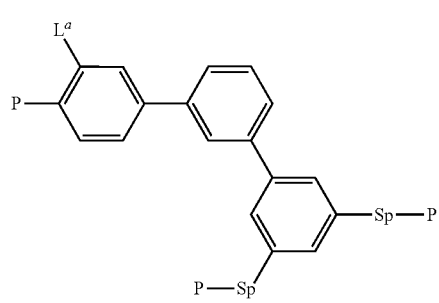
I5-5-4
I5-5-5

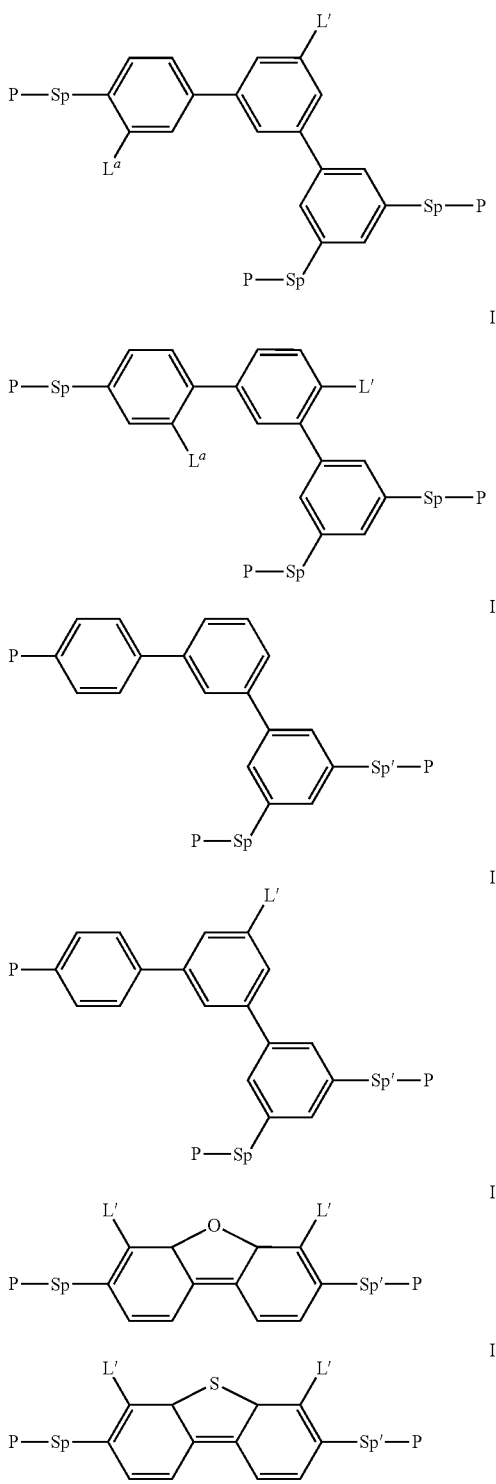

wherein P, Sp, Sp(P)₂ and Lᵃ have the meanings given above or below, with Sp preferably being different from a single bond, Sp' is a spacer group that is substituted by a group Lᵃ, and is preferably selected from formulae SL1-SL4, and L' has one of the meanings given for L above or below that is preferably different from Lᵃ.

Very preferred compounds of subformulae I1-1-1 to I9-1-1 are those wherein all groups P are identical and denote acrylate or methacrylate, preferably methacrylate, furthermore those wherein Sp is, —(CH$_2$)$_{p1}$—, —(CH$_2$)$_{p1}$—O—, —(CH$_2$)$_{p1}$—O—CO— or —(CH$_2$)$_{p1}$—CO—O—, in which p1 is an integer from 1 to 12, preferably 1 to 6, and the O- or CO-group is connected to the benzene ring, furthermore those wherein Sp(P)₂ is selected from formulae S1-S8, very preferably from subformulae S1a-S3a, furthermore those wherein Sp' is selected from formula SL1, furthermore those wherein L' is F or denotes Lᵃ-Sp-, preferably F, furthermore those wherein Lᵃ is selected from formulae 1-5, most preferably of formula 1.

Further preferred compounds of formula I and its subformulae are selected from the following preferred embodiments, including any combination thereof:

All groups P in the compound have the same meaning,
-A¹-(Z¹-A²)$_z$- is selected from formulae A1, A2, A5, A8 and A9, very preferably form formulae A1, A2 and A5,
the compounds contain exactly two polymerizable groups (represented by the groups P),
the compounds contain exactly three polymerizable groups (represented by the groups P),
P is selected from the group consisting of acrylate, methacrylate and oxetane, very preferably acrylate or methacrylate,
the compounds contain at least one, preferably exactly one, group P-Sp- wherein Sp is substituted by Lᵃ, and which is preferably selected from formulae SL1-SL4, very preferably from formulae SL1, SL2 and SL3,
Sp, when being different from a single bond, is —(CH$_2$)$_{p2}$—, —(CH$_2$)$_{p2}$—O—, —(CH$_2$)$_{p2}$—CO—O—, —(CH$_2$)$_{p2}$—O—CO—, wherein p2 is 2, 3, 4, 5 or 6, and the O-atom or the CO-group, respectively, is connected to the benzene ring,
Sp(P)₂ is selected from subformulae S11-S31,
Sp' is selected from formula SL1,
R denotes P-Sp-,
R does not denote or contain a polymerizable group,
R does not denote or contain a polymerizable group and denotes straight chain, branched or cyclic alkyl having 1 to 25 C atoms, wherein one or more non-adjacent CH₂-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl or Lᵃ,
L, when being different from Lᵃ-Sp-, denotes F, Cl or CN,
L' is F,
Lᵃ denotes —C(CH$_3$)$_2$—OH, —C(C$_2$H$_5$)$_2$—OH or —C(CH$_3$)(C$_2$H$_5$)OH, very preferably —C(CH$_3$)$_2$—OH,
Lᵃ is selected from formulae 1-5,
r1, r2 and r3 denote 0 or 1,
r1, r2, r3, r4, r5 and r6 denote 0 or 1,
one of r1 and r7 is 0 and the other is 1,
r1 is 1, and r2 and r3 are 0,
r3 is 1 and r1 and r2 are 0,
one of r4 and r5 is 0 and the other is 1,
r4 and r6 are 0 and r5 is 1,
r1 and r4 are 0 and r3 is 1,
r1 and r3 are 0 and r4 is 1,
r3 and r4 are 0 and r1 is 1, Very preferred compounds of formula I and its subformulae are selected from the following list:
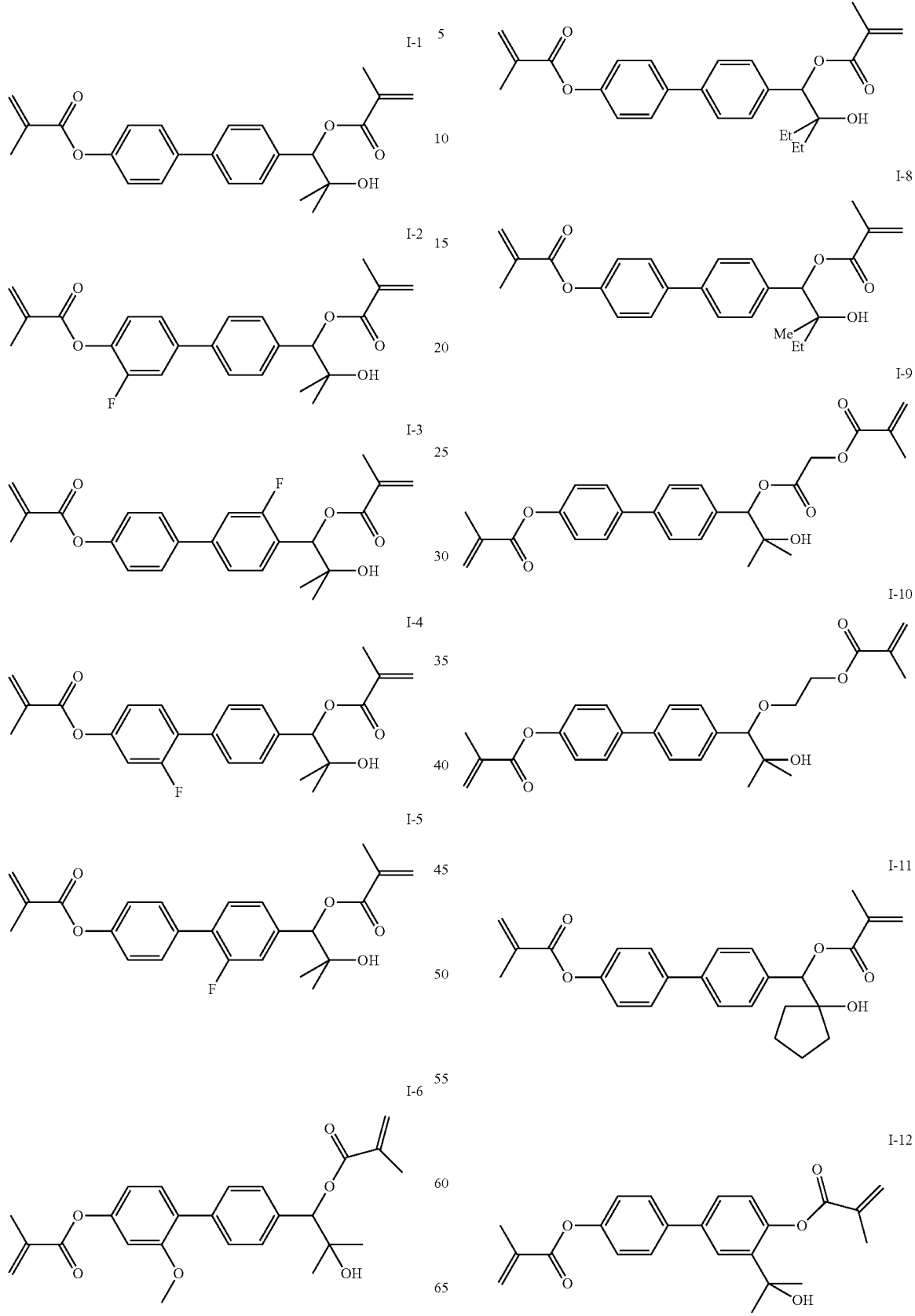

I-13
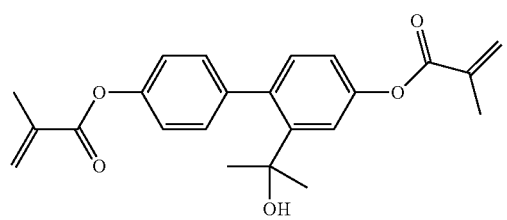
I-14
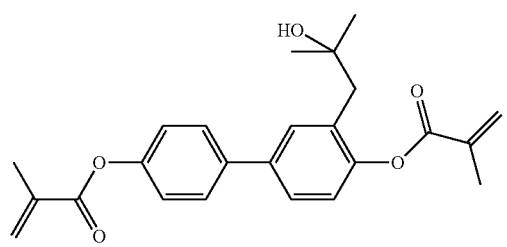
I-15
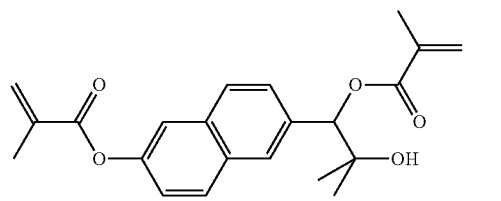
I-16
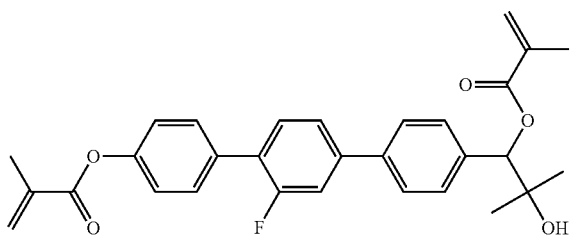
I-17
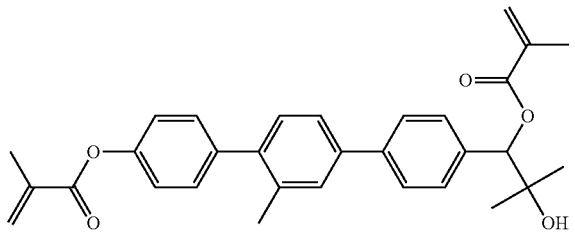
I-18
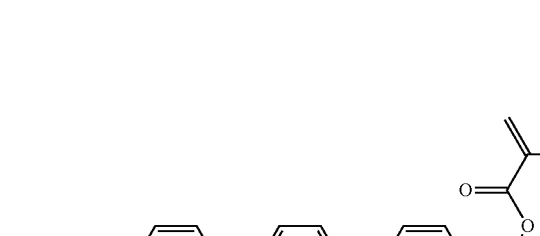
I-19
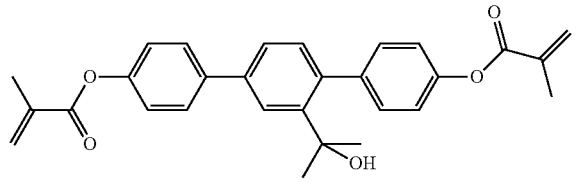
I-20
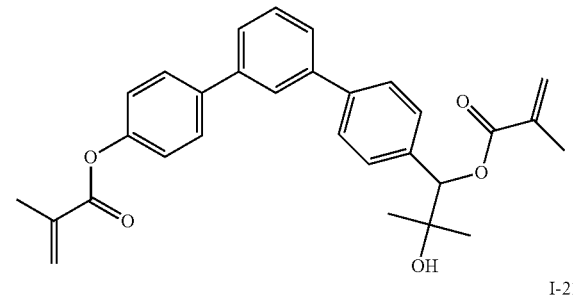
I-21
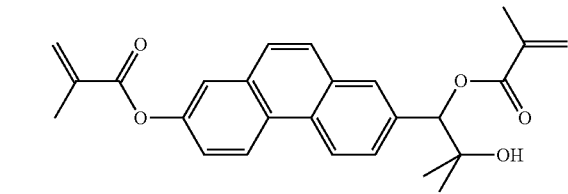
I-22
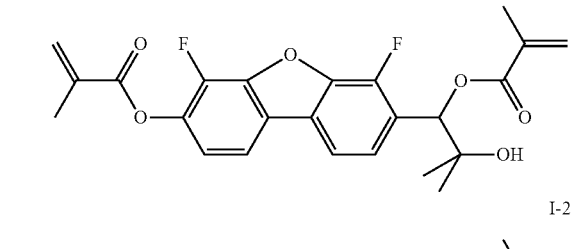
I-23
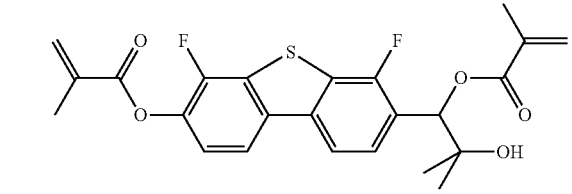
wherein "Met" is methyl and "Et" is ethyl.
The invention furthermore relates to compounds of formula II1-II9
II1
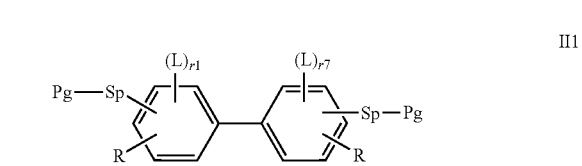
II2
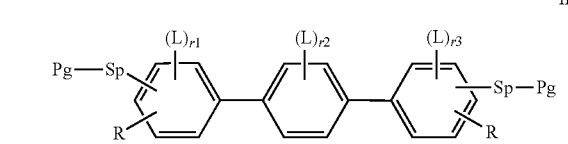

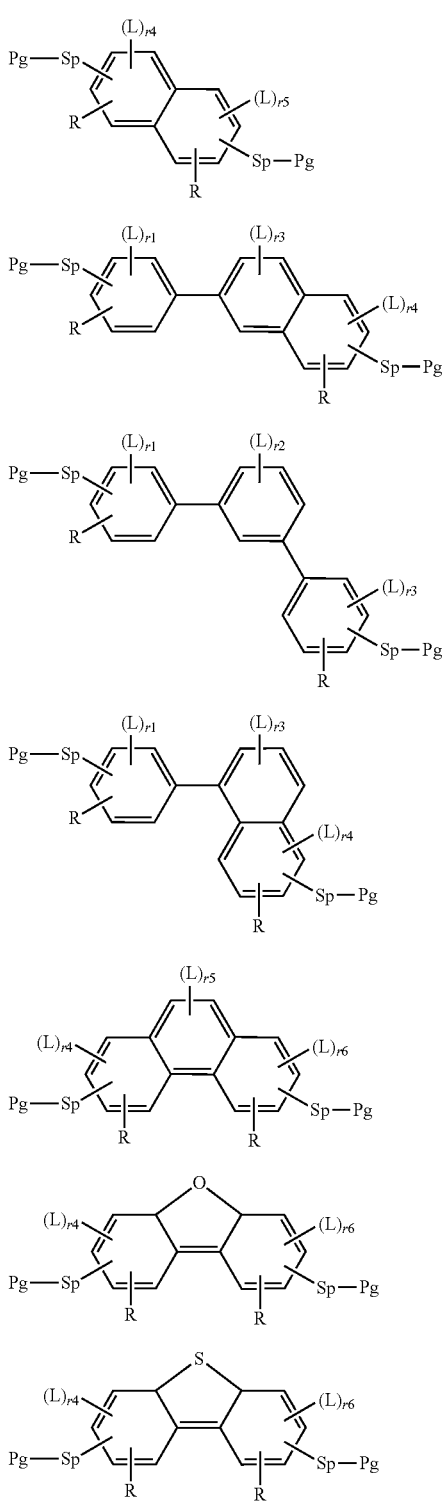

wherein Sp, L, $r^{1-6}$ and q are as defined in formula I1-I9, R denotes H or Pg-Sp, and Pg denotes OH, a protected hydroxyl group or a masked hydroxyl group.

Preferred compounds of formula II1-II9 are selected from subformulae I1-1 to I9-2 and I1-1-1 to I9-1-1 as defined above, wherein P is replaced by Pg.

Suitable protected hydroxyl groups Pg are known to the person skilled in the art. Preferred protecting groups for hydroxyl groups are alkyl, alkoxyalkyl, acyl, alkylsilyl, arylsilyl and arylmethyl groups, especially 2-tetrahydropyranyl, methoxymethyl, methoxyethoxymethyl, acetyl, triisopropylsilyl, tert-butyl-dimethylsilyl or benzyl.

The term "masked hydroxyl group" is understood to mean any functional group that can be chemically converted into a hydroxyl group. Suitable masked hydroxyl groups Pg are known to the person skilled in the art.

The compounds of formula II are suitable as intermediates for the preparation of compounds of the formula I and its subformulae.

The invention further relates to the use of the compounds of formula II as intermediates for the preparation of compounds of the formula I and its subformulae.

The compounds and intermediates of the formulae I and II and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

For example, compounds of formula I can be synthesised by esterification or etherification of the intermediates of formula II, wherein Pg denotes OH, using corresponding acids, acid derivatives, or halogenated compounds containing a polymerizable group P.

For example, acrylic or methacrylic esters can be prepared by esterification of the corresponding alcohols with acid derivatives like, for example, (meth)acryloyl chloride or (meth)acrylic anhydride in the presence of a base like pyridine or triethyl amine, and 4-(N,N-dimethylamino)pyridine (DMAP).

Alternatively the esters can be prepared by esterification of the alcohols with (meth)acrylic acid in the presence of a dehydrating reagent, for example according to Steglich with dicyclohexylcarbodiimide (DCC), N-(3-dimethylaminopropyl)-N'-ethylcarbodiimide (EDC) or N-(3-dimethylaminopropyl)-N'-ethylcarbodiimide hydrochloride and DMAP.

Further suitable methods are shown in the examples.

For the production of PSA displays, the polymerizable compounds contained in the LC medium are polymerized or crosslinked (if one compound contains two or more polymerizable groups) by in-situ polymerization in the LC medium between the substrates of the LC display, optionally while a voltage is applied to the electrodes.

The structure of the PSA displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PS-VA displays are described, for example, in US 2006/0066793 A1.

A preferred PSA type LC display of the present invention comprises:
a first substrate including a pixel electrode defining pixel areas, the pixel electrode being connected to a switching element disposed in each pixel area and optionally including a micro-slit pattern, and optionally a first alignment layer disposed on the pixel electrode,
a second substrate including a common electrode layer, which may be disposed on the entire portion of the second substrate facing the first substrate, and optionally a second alignment layer,
an LC layer disposed between the first and second substrates and including an LC medium comprising a polymerizable component A and a liquid crystal component B as described above and below, wherein the polymerizable component A may also be polymerized.

The first and/or second alignment layer controls the alignment direction of the LC molecules of the LC layer. For example, in PS-VA displays the alignment layer is selected such that it imparts to the LC molecules homeotropic (or vertical) alignment (i.e. perpendicular to the surface) or tilted alignment. Such an alignment layer may for example comprise a polyimide, which may also be rubbed, or may be prepared by a photoalignment method.

The LC layer with the LC medium can be deposited between the substrates of the display by methods that are conventionally used by display manufacturers, for example the so-called one-drop-filling (ODF) method. The polymerizable component of the LC medium is then polymerized for example by UV photopolymerization. The polymerization can be carried out in one step or in two or more steps.

The PSA display may comprise further elements, like a colour filter, a black matrix, a passivation layer, optical retardation layers, transistor elements for addressing the individual pixels, etc., all of which are well known to the person skilled in the art and can be employed without inventive skill.

The electrode structure can be designed by the skilled person depending on the individual display type. For example for PS-VA displays a multi-domain orientation of the LC molecules can be induced by providing electrodes having slits and/or bumps or protrusions in order to create two, four or more different tilt alignment directions.

Upon polymerization the polymerizable compounds form a crosslinked polymer, which causes a certain pretilt of the LC molecules in the LC medium. Without wishing to be bound to a specific theory, it is believed that at least a part of the crosslinked polymer, which is formed by the polymerizable compounds, will phase-separate or precipitate from the LC medium and form a polymer layer on the substrates or electrodes, or the alignment layer provided thereon. Microscopic measurement data (like SEM and AFM) have confirmed that at least a part of the formed polymer accumulates at the LC/substrate interface.

The polymerization can be carried out in one step. It is also possible firstly to carry out the polymerization, optionally while applying a voltage, in a first step in order to produce a pretilt angle, and subsequently, in a second polymerization step without an applied voltage, to polymerize or crosslink the compounds which have not reacted in the first step ("end curing").

Suitable and preferred polymerization methods are, for example, thermal or photopolymerization, preferably photopolymerization, in particular UV induced photopolymerization, which can be achieved by exposure of the polymerizable compounds to UV radiation.

Optionally one or more polymerization initiators are added to the LC medium. Suitable conditions for the polymerization and suitable types and amounts of initiators are known to the person skilled in the art and are described in the literature. Suitable for free-radical polymerization are, for example, the commercially available photoinitiators Irgacure651®, Irgacure184®, Irgacure907®, Irgacure369® or Darocure1173® (Ciba AG). If a polymerization initiator is employed, its proportion is preferably 0.001 to 5% by weight, particularly preferably 0.001 to 1% by weight.

The polymerizable compounds according to the invention are also suitable for polymerization without an initiator, which is accompanied by considerable advantages, such, for example, lower material costs and in particular less contamination of the LC medium by possible residual amounts of the initiator or degradation products thereof. The polymerization can thus also be carried out without the addition of an initiator. In a preferred embodiment, the LC medium thus does not contain a polymerization initiator.

The LC medium may also comprise one or more stabilizers in order to prevent undesired spontaneous polymerization of the RMs, for example during storage or transport. Suitable types and amounts of stabilizers are known to the person skilled in the art and are described in the literature. Particularly suitable are, for example, the commercially available stabilizers from the Irganox® series (Ciba AG), such as, for example, Irganox® 1076. If stabilizers are employed, their proportion, based on the total amount of RMs or the polymerizable component (component A), is preferably 10-500,000 ppm, particularly preferably 50-50,000 ppm.

The compounds of formula I do in particular show good UV absorption in, and are therefore especially suitable for, a process of preparing a PSA display including one or more of the following features:

the polymerizable medium is exposed to UV light in the display in a 2-step process, including a first UV exposure step ("UV-1 step") to generate the tilt angle, and a second UV exposure step ("UV-2 step") to finish polymerization, the polymerizable medium is exposed to UV light in the display generated by an energy-saving UV lamp (also known as "green UV lamps"). These lamps are characterized by a relative low intensity (1/100-1/10 of a conventional UV1 lamp) in their absorption spectra from 300-380 nm, and are preferably used in the UV2 step, but are optionally also used in the UV1 step when avoiding high intensity is necessary for the process.

the polymerizable medium is exposed to UV light in the display generated by a UV lamp with a radiation spectrum that is shifted to longer wavelengths, preferably 340 nm or more, to avoid short UV light exposure in the PS-VA process.

Both using lower intensity and a UV shift to longer wavelengths protect the organic layer against damage that may be caused by the UV light.

A preferred embodiment of the present invention relates to a process for preparing a PSA display as described above and below, comprising one or more of the following features:

the polymerizable LC medium is exposed to UV light in a 2-step process, including a first UV exposure step ("UV-1 step") to generate the tilt angle, and a second UV exposure step ("UV-2 step") to finish polymerization, the polymerizable LC medium is exposed to UV light generated by a UV lamp having an intensity of from 0.5 mW/cm$^2$ to 10 mW/cm$^2$ in the wavelength range from 300-380 nm, preferably used in the UV2 step, and optionally also in the UV1 step, the polymerizable LC medium is exposed to UV light having a wavelength of 340 nm or more, and preferably 400 nm or less.

This preferred process can be carried out for example by using the desired UV lamps or by using a band pass filter and/or a cut-off filter, which are substantially transmissive for UV light with the respective desired wavelength(s) and are substantially blocking light with the respective undesired wavelengths. For example, when irradiation with UV light of wavelengths λ of 300-400 nm is desired, UV exposure can be carried out using a wide band pass filter being substantially transmissive for wavelengths 300 nm<λ<400 nm. When irradiation with UV light of wavelength λ of more than 340 nm is desired, UV exposure can be carried out using a cut-off filter being substantially transmissive for wavelengths λ>340 nm.

"Substantially transmissive" means that the filter transmits a substantial part, preferably at least 50% of the intensity, of incident light of the desired wavelength(s). "Substantially blocking" means that the filter does not transmit a substantial part, preferably at least 50% of the intensity, of incident light of the undesired wavelengths. "Desired (undesired) wavelength" e.g. in case of a band pass filter means the wavelengths inside (outside) the given range of λ, and in case of a cut-off filter means the wavelengths above (below) the given value of λ.

This preferred process enables the manufacture of displays by using longer UV wavelengths, thereby reducing or even avoiding the hazardous and damaging effects of short UV light components.

UV radiation energy is in general from 6 to 100 J, depending on the production process conditions.

Preferably an LC medium according to the present invention for use in PSA displays does essentially consist of a polymerizable component A), or one or more compounds of formula I, and an LC component B), or LC host mixture, as described above and below. However, the LC medium may additionally comprise one or more further components or additives, preferably selected from the list including but not limited to co-monomers, chiral dopants, polymerization initiators, inhibitors, stabilizers, surfactants, wetting agents, lubricating agents, dispersing agents, hydrophobing agents, adhesive agents, flow improvers, defoaming agents, deaerators, diluents, reactive diluents, auxiliaries, colourants, dyes, pigments and nanoparticles.

Particular preference is given to LC media comprising one, two or three compounds of formula I.

Preference is furthermore given to LC media in which the polymerizable component A) comprises exclusively compounds of formula I.

Preference is furthermore given to LC media in which the liquid-crystalline component B) or the LC host mixture has a nematic LC phase, and preferably has no chiral liquid crystal phase.

The LC component B), or LC host mixture, is preferably a nematic LC mixture.

Preference is furthermore given to achiral compounds of formula I, and to LC media in which the compounds of component A and/or B are selected exclusively from the group consisting of achiral compounds.

Preferably the proportion of the polymerizable component A) in the LC medium is from >0 to <5%, very preferably from >0 to <1%, most preferably from 0.01 to 0.5%.

Preferably the proportion of compounds of formula I in the LC medium is from >0 to <5%, very preferably from >0 to <1%, most preferably from 0.01 to 0.5%.

Preferably the proportion of the LC component B) in the LC medium is from 95 to <100%, very preferably from 99 to <100%.

In a preferred embodiment the polymerizable compounds of the polymerizable component B) are exclusively selected from formula I.

In another preferred embodiment the polymerizable component B) comprises, in addition to the compounds of formula I, one or more further polymerizable compounds ("co-monomers"), preferably selected from RMs.

Suitable and preferred mesogenic comonomers are selected from the following formulae:

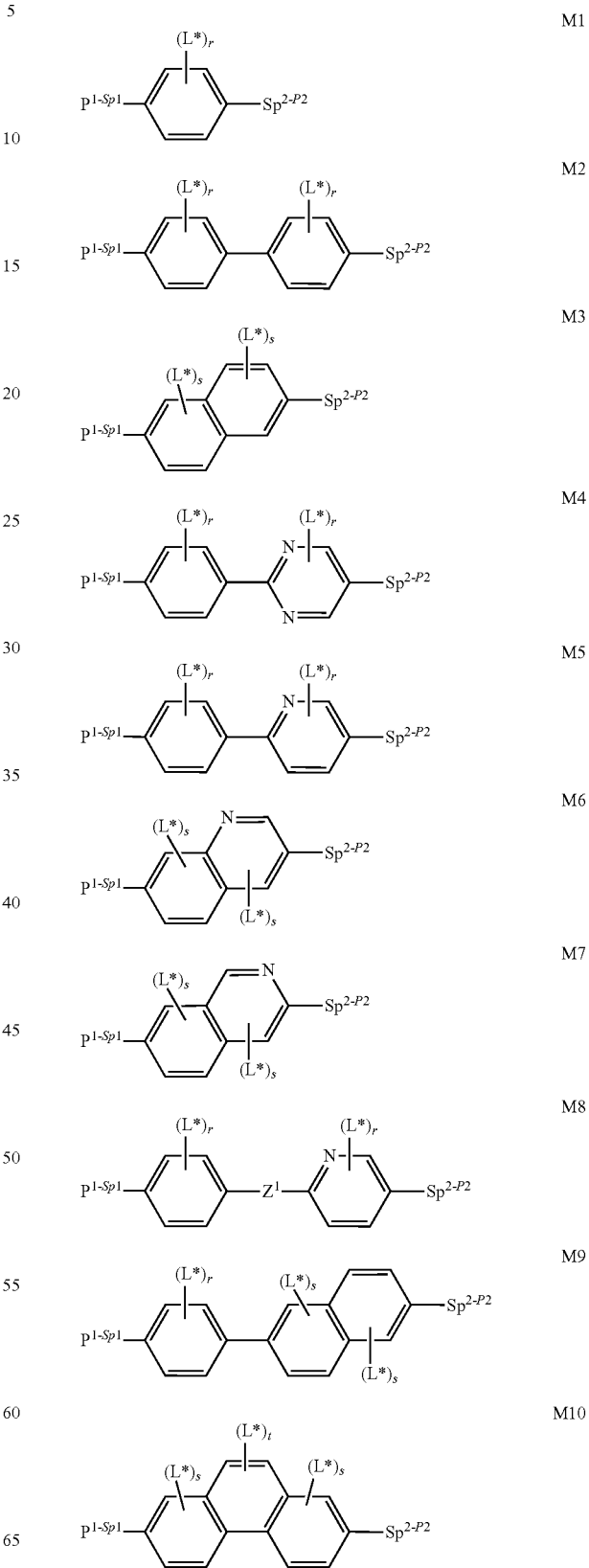

M11
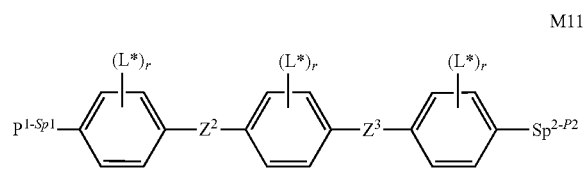
M12
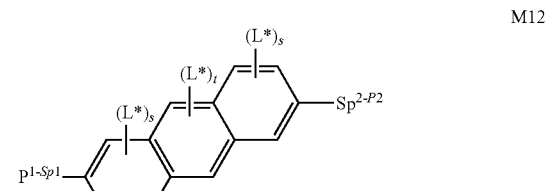
M13
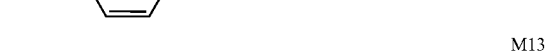
M14
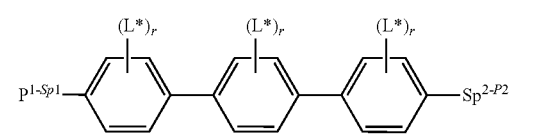
M15
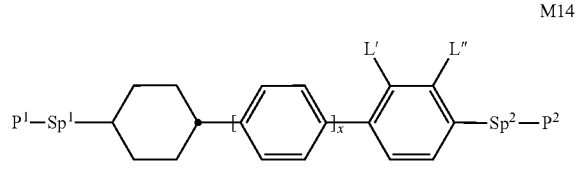
M16
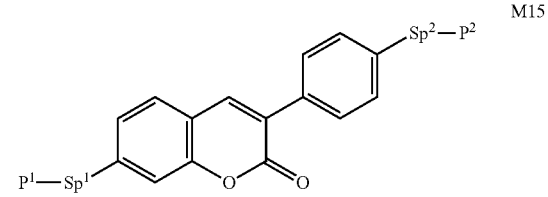
M17

M18
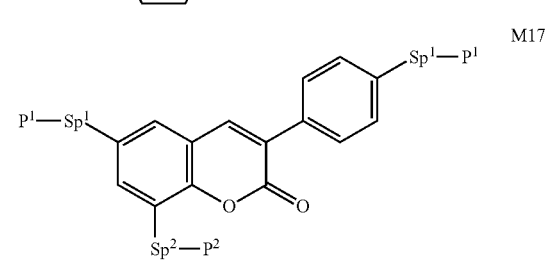
M19
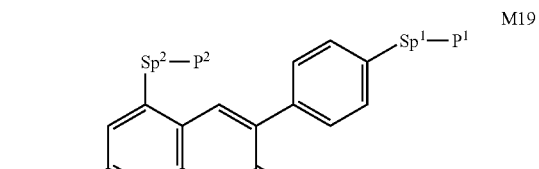
M20
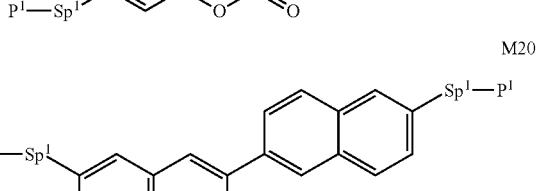
M21
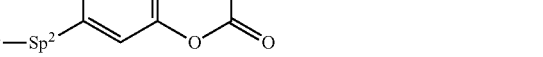
M22
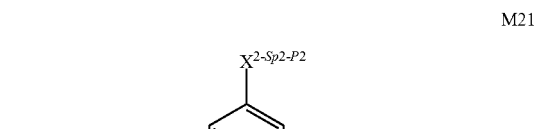
M23
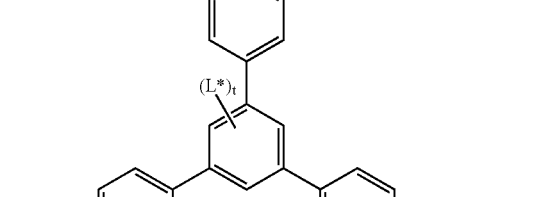
M24
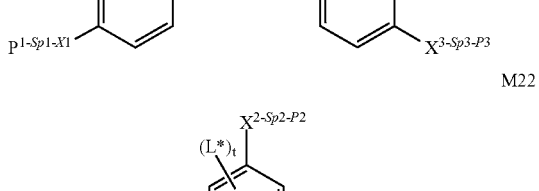
M25
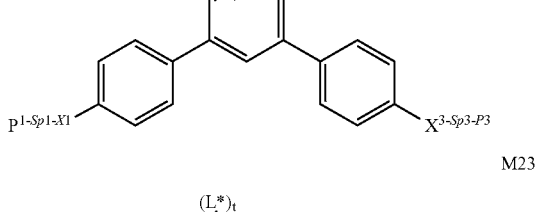

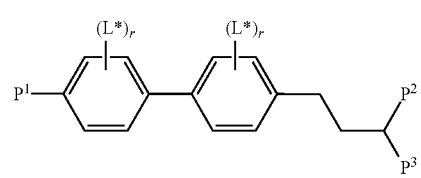
M26

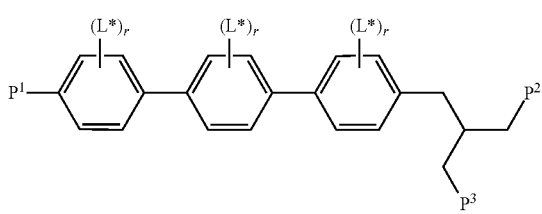
M27

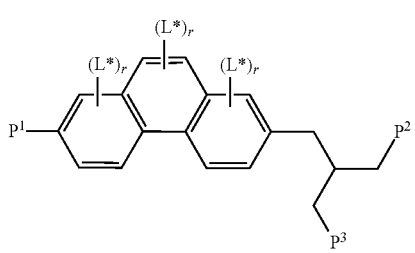
M28

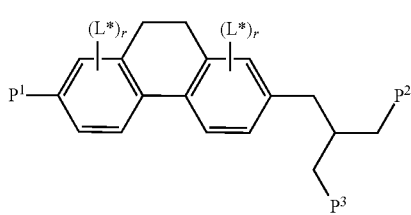
M29

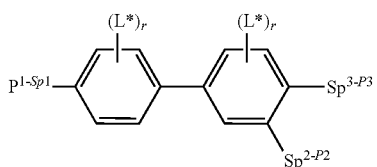
M30

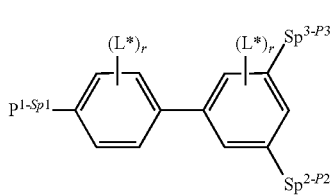
M31 in which the individual radicals have the following meanings:

$P^1$, $P^2$ and $P^3$ each, independently of one another, denote an acrylate or methacrylate group, $Sp^1$, $Sp^2$ and $Sp^a$ each, independently of one another, denote a single bond or a spacer group having one of the meanings indicated above and below for Sp, and particularly preferably denote —$(CH_2)_{p1}$—, —$(CH_2)_{p1}$—O—, —$(CH_2)_{p1}$—CO—O—, —$(CH_2)_{p1}$—O—CO— or —$(CH_2)_{p1}$—O—CO—O—, in which p1 is an integer from 1 to 12, where, in addition, one or more of the radicals $P^1$-Sp'-, $P^1$—$Sp^2$- and $P^3$—$Sp^3$- may denote $R^{aa}$, with the proviso that at least one of the radicals $P^1$-$Sp^1$-, $P^2$-$Sp^2$ and $P^3$-$Sp^3$- present is different from $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)$=$C(R^{00})$—, —C≡C—, —$N(R^0)$—, —$N(R^0)$—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), $R^0$, $R^{00}$ each, independently of one another and identically or differently on each occurrence, denote H or alkyl having 1 to 12 C atoms, $R^y$ and $R^z$ each, independently of one another, denote H, F, $CH_3$ or $CF_3$, $X^1$, $X^2$ and $X^3$ each, independently of one another, denote —CO—O—, —O—CO— or a single bond, $Z^1$ denotes —O—, —CO—, —$C(R^yR^z)$— or —$CF_2CF_2$—, $Z^2$ and $Z^3$ each, independently of one another, denote —CO—O—, —O—CO—, —$CH_2O$—, —$OCH_2$—, —$CF_2O$—, —$OCF_2$— or —$(CH_2)_n$—, where n is 2, 3 or 4, L* on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, x denotes 0 or 1.

Especially preferred are compounds of formulae M2, M13, M17, M22, M23, M24 and M30.

Further preferred are trireactive compounds M15 to M30, in particular M17, M18, M19, M22, M23, M24, M25, M26, M30 and M31.

In the compounds of formulae M1 to M31 the group

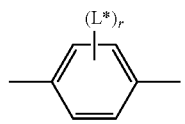

is preferably

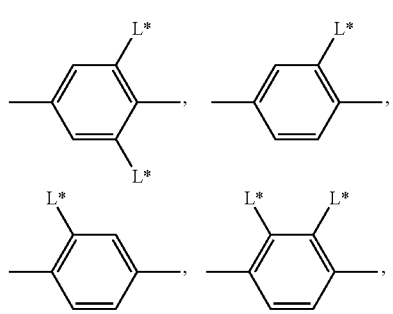

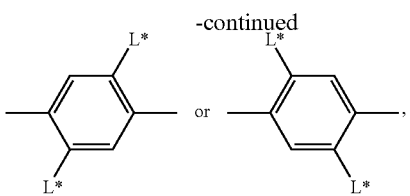

wherein L on each occurrence, identically or differently, has one of the meanings given above or below, and is preferably F, Cl, CN, CH$_3$, C$_2$H$_5$, C(CH$_3$)$_3$, CH(CH$_3$)$_2$, CH$_2$CH(CH$_3$) C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$ or P-Sp-, very preferably F, Cl, CN, CH$_3$, C$_2$H$_5$, OCH$_3$, COCH$_3$, OCF$_3$ or P-Sp-, more preferably F, Cl, CH$_3$, OCH$_3$, COCH$_3$ or OCF$_3$, especially F or CH$_3$.

In another preferred embodiment of the invention the LC medium does not contain any polymerizable compounds other than the compounds of formula I.

If the compounds of formula I are used as stabilizers, their proportion in the LC medium according to the invention is preferably from >0 to 1000 ppm, particularly preferably from 100 to 750 ppm, very particularly preferably from 300 to 600 ppm.

Further to the compounds of formula I the LC medium may also comprise one or more additional stabilizers. Suitable additional stabilizers are, for example, the commercially available stabilizers from the Irganox® series (Ciba AG), like, for example, Irganox® 1076, or the stabilizers selected from Table C below. If additional stabilizers are employed, their proportion in the LC medium is preferably 10-1000 ppm, particularly preferably 50-500 ppm.

Besides the compounds of formula I and the optional further polymerizable compounds described above, the LC media for use in the LC displays according to the invention comprise an LC mixture ("host mixture") comprising one or more, preferably two or more LC compounds which are selected from low-molecular-weight compounds that are unpolymerizable. These LC compounds are selected such that they stable and/or unreactive to a polymerization reaction under the conditions applied to the polymerization of the polymerizable compounds.

In principle, any LC mixture which is suitable for use in conventional displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

The compounds of formula I are especially suitable for use in an LC host mixture that comprises one or more mesogenic or LC compounds comprising an alkenyl group (hereinafter also referred to as "alkenyl compounds"), wherein said alkenyl group is stable to a polymerization reaction under the conditions used for polymerization of the compounds of formula I and of the other polymerizable compounds contained in the LC medium. Compared to RMs known from prior art the compounds of formula I do in such an LC host mixture exhibit improved properties, like solubility, reactivity or capability of generating a tilt angle.

Thus, in addition to the compounds of formula I, the LC medium according to the present invention comprises one or more mesogenic or liquid crystalline compounds comprising an alkenyl group, ("alkenyl compound"), where this alkenyl group is preferably stable to a polymerization reaction under the conditions used for the polymerization of the compounds of formula I or of the other polymerizable compounds contained in the LC medium.

The alkenyl groups in the alkenyl compounds are preferably selected from straight-chain, branched or cyclic alkenyl, in particular having 2 to 25 C atoms, particularly preferably having 2 to 12 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F and/or Cl.

Preferred alkenyl groups are straight-chain alkenyl having 2 to 7 C atoms and cyclohexenyl, in particular ethenyl, propenyl, butenyl, pentenyl, hexenyl, heptenyl, 1,4-cyclohexen-1-yl and 1,4-cyclohexen-3-yl.

The concentration of compounds containing an alkenyl group in the LC host mixture (i.e. without any polymerizable compounds) is preferably from 5% to 100%, very preferably from 20% to 60%.

Especially preferred are LC mixtures containing 1 to 5, preferably 1, 2 or 3 compounds having an alkenyl group.

The mesogenic and LC compounds containing an alkenyl group are preferably selected from formulae AN and AY as defined below.

Besides the compounds of formula I or the polymerizable component A) as described above, the LC media according to the present invention comprise an LC component B), or LC host mixture, comprising one or more, preferably two or more LC compounds which are selected from low-molecular-weight compounds that are unpolymerizable. These LC compounds are selected such that they stable and/or unreactive to a polymerization reaction under the conditions applied to the polymerization of the polymerizable compounds.

In a first preferred embodiment the LC medium contains an LC component B), or LC host mixture, based on compounds with negative dielectric anisotropy. Such LC media are especially suitable for use in VA, IPS, UB-FFS, PS-VA, PS-IPS and PS-UB-FFS displays. Particularly preferred embodiments of such an LC medium are those of sections a)-z3) below:

a) LC medium wherein the component B) or LC host mixture comprises one or more compounds selected from formulae CY and PY:

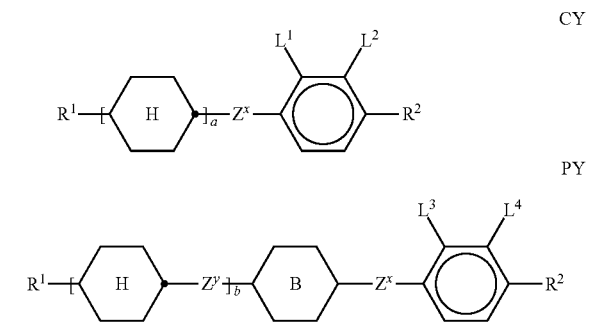

wherein
a denotes 1 or 2,
b denotes 0 or 1,

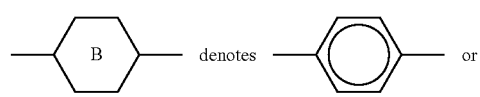

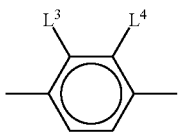

R[1] and R[2] each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond, $L^{1-4}$ each, independently of one another, denote F, Cl, $OCF_3$, $CF_3$, $CH_3$, $CH_2F$, $CHF_2$.

Preferably, both $L^1$ and $L^2$ denote F or one of $L^1$ and $L^2$ denotes F and the other denotes Cl, or both $L^3$ and $L^4$ denote F or one of $L^3$ and $L^4$ denotes F and the other denotes Cl.

The compounds of the formula CY are preferably selected from the group consisting of the following sub-formulae:

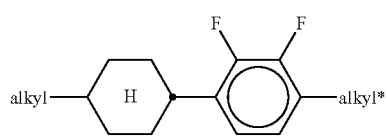

CY1

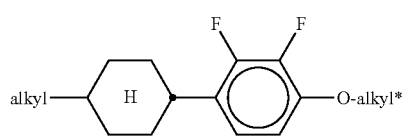

CY2

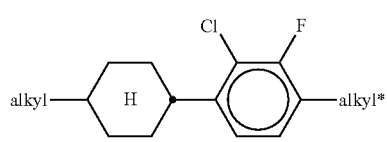

CY3

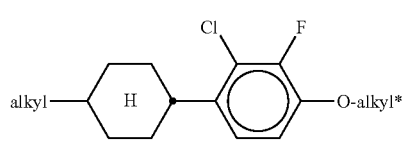

CY4

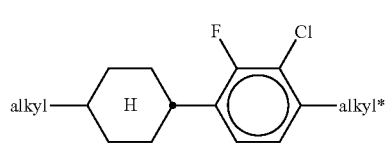

CY5

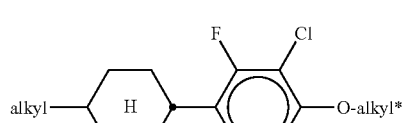

CY6

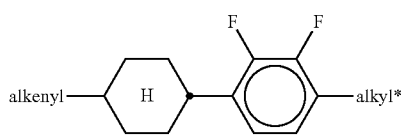

CY7

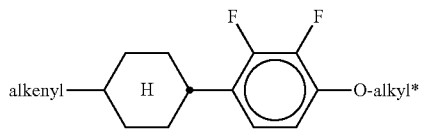

CY8

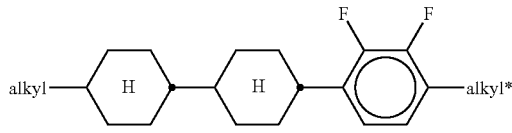

CY9

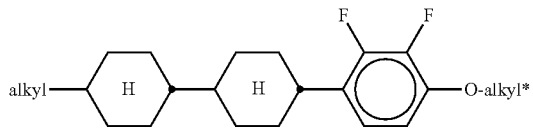

CY10

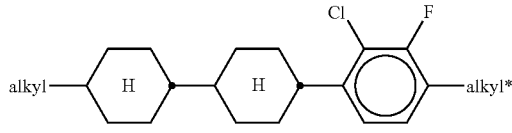

CY11

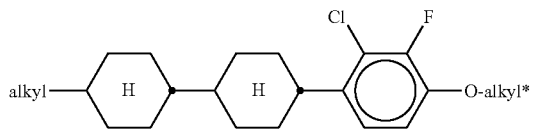

CY12

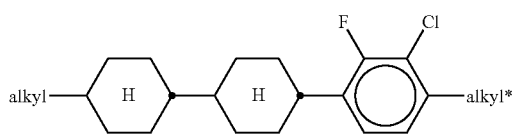

CY13

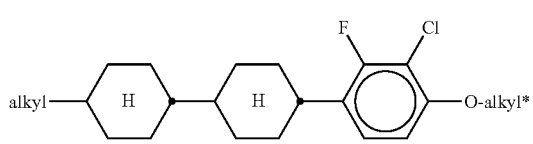

CY14

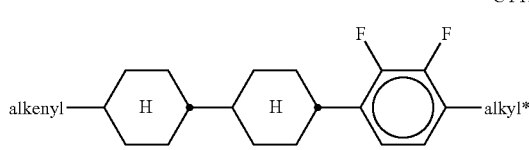

CY15

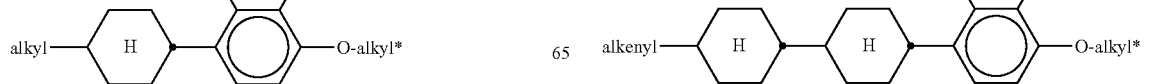

CY16

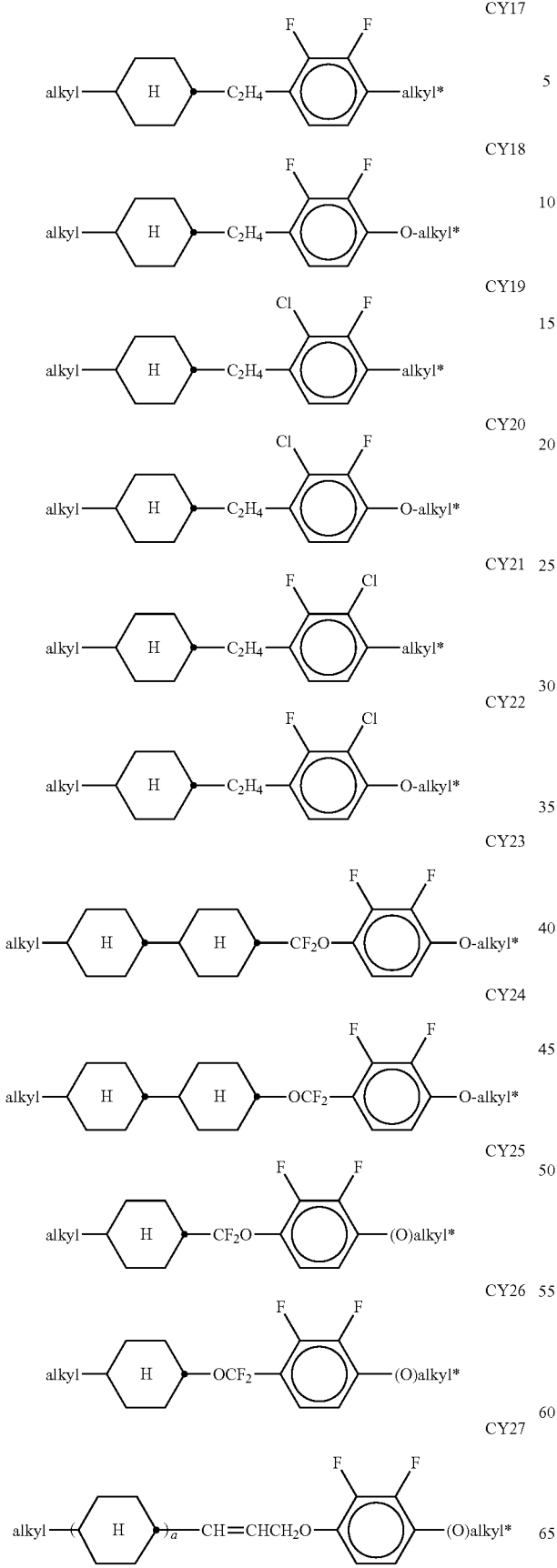
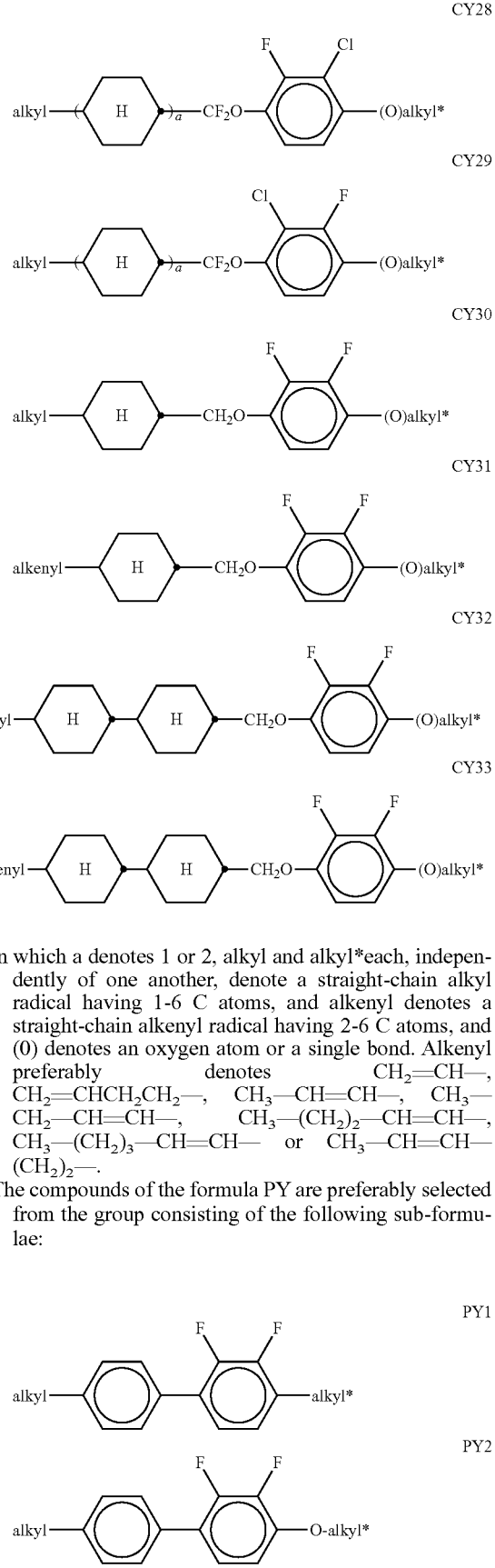

in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

PY3
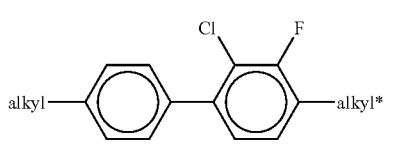

PY-4
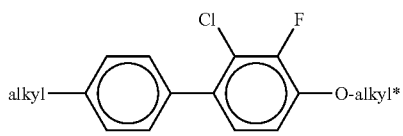

PY5
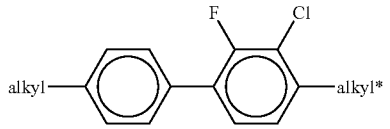

PY6
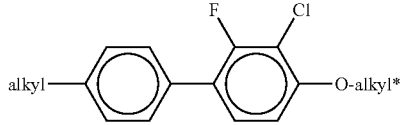

PY-7
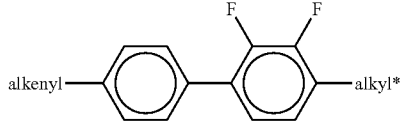

PY8
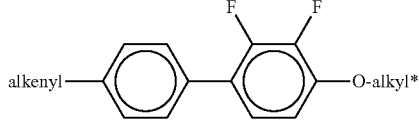

PY9
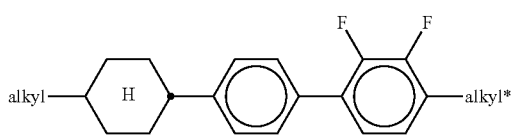

PY10
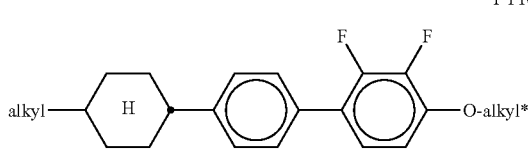

PY11
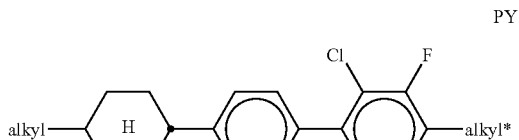

PY12
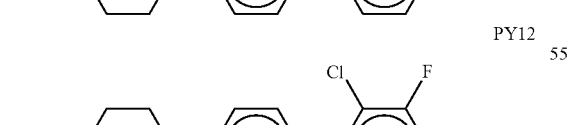

PY13

PY14
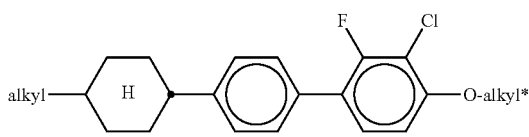

PY15
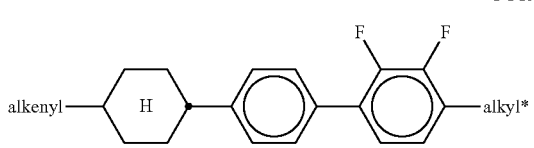

PY16
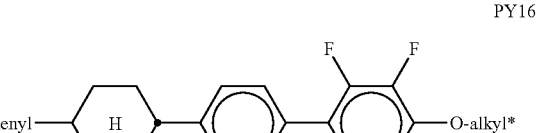

PY17
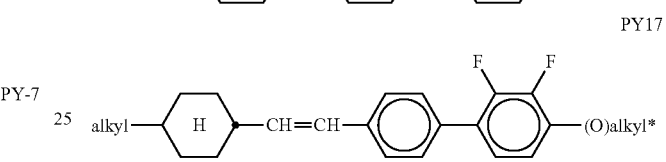

PY18
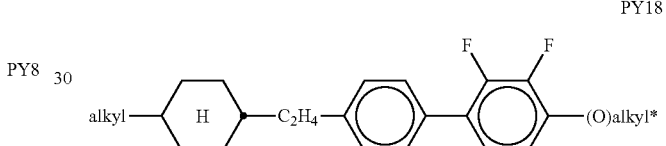

PY19

PY20
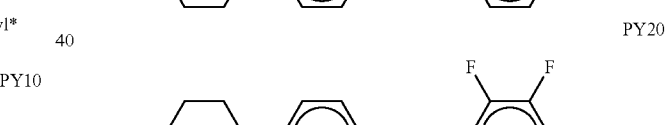

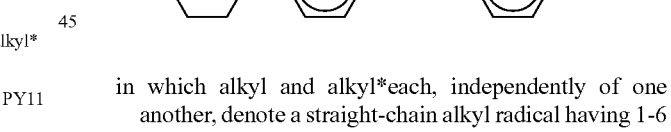

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium wherein the component B) or LC host mixture comprises one or more mesogenic or LC compounds comprising an alkenyl group (hereinafter also referred to as "alkenyl compounds"), wherein said alkenyl group is stable to a polymerization reaction under the conditions used for polymerization of the polymerizable compounds contained in the LC medium.

Preferably the component B) or LC host mixture comprises one or more alkenyl compounds selected from formulae AN and AY

AN

![AN formula: R^A1—X_x—Y—R^A2]

AY

![AY formula: R^A1—X—Z_z—Z^x—phenyl(L1,L2)—R^A2]

in which the individual radicals, on each occurrence identically or differently, and each, independently of one another, have the following meaning:

X ![ring], H ![ring with dot],

![phenyl], ![pyran],

![pyran], ![cyclohexenyl] or

Y ![ring],

H ![ring with dot], ![phenyl],

![pyran with O top], ![pyran with O top],

![cyclohexenyl] or ![cyclohexenyl],

Z ![ring], H ![ring with dot],

![phenyl], ![pyran],

![pyran], ![cyclohexenyl] or

![phenyl with L3, L4]

$R^{A1}$ alkenyl having 2 to 9 C atoms or, if at least one of the rings X, Y and Z denotes cyclohexenyl, also one of the meanings of $R^{A2}$, $R^{A2}$ alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, $Z^x$ —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$—, or a single bond, preferably a single bond, $L^{1,2}$ H, F, Cl, $OCF_3$, $CF_3$, $CH_3$, $CH_2F$ or $CHF_2H$, preferably H, F or Cl, x 1 or 2, z 0 or 1.

Preferred compounds of formula AN and AY are those wherein $R^{A2}$ is selected from ethenyl, propenyl, butenyl, pentenyl, hexenyl and heptenyl.

In a preferred embodiment the component B) or LC host mixture comprises one or more compounds of formula AN selected from the following sub-formulae:

AN1 alkyl—[H cyclohexyl]—[H cyclohexyl]—alkenyl

AN2 alkenyl—[H cyclohexyl]—[H cyclohexyl]—alkenyl*

AN3 alkyl—[phenyl]—[phenyl]—alkenyl

AN4 alkenyl—[phenyl]—[phenyl]—O-alkyl

AN5 alkenyl—[phenyl]—[phenyl]—alkenyl*

AN6 alkenyl—[H cyclohexyl]—[H cyclohexyl]—[phenyl]—alkyl

AN7 alkenyl—[H cyclohexyl]—[H cyclohexyl]—[phenyl]—O-alkyl

AN8 alkenyl—[H cyclohexyl]—[phenyl]—[phenyl]—alkyl

AN9 alkenyl—[H cyclohexyl]—[phenyl]—[phenyl]—O-alkyl

AN10 alkyl—[H cyclohexyl]—[H cyclohexyl]—[cyclohexenyl]—alkyl*

AN11 alkyl—[H cyclohexyl]—[H cyclohexyl]—[cyclohexenyl]—alkyl*

AN12

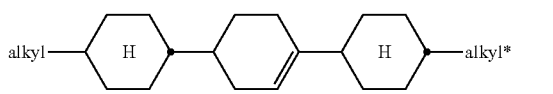

in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Preferably the component B) or LC host mixture comprises one or more compounds selected from formulae AN1, AN2, AN3 and AN6, very preferably one or more compounds of formula AN1.

In another preferred embodiment the component B) or LC host mixture comprises one or more compounds of formula AN selected from the following sub-formulae:

AN1a

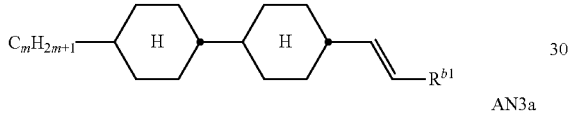

AN3a

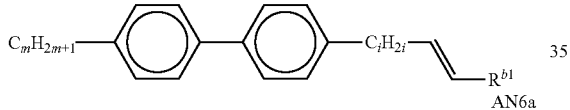

AN6a

in which m denotes 1, 2, 3, 4, 5 or 6, i denotes 0, 1, 2 or 3, and R$^{b1}$ denotes H, CH$_3$ or C$_2$H$_5$.

In another preferred embodiment the component B) or LC host mixture comprises one or more compounds selected from the following sub-formulae:

AN1a1

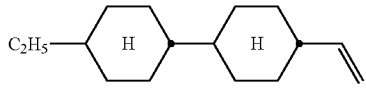

AN1a2

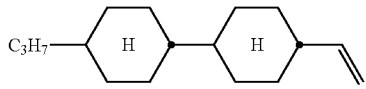

AN1a3

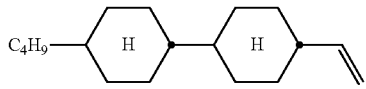

AN1a4

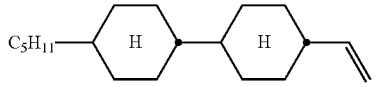

AN1a5

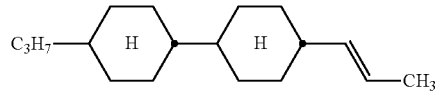

Most preferred are compounds of formula AN1a2 and AN1a5.

In another preferred embodiment the component B) or LC host mixture comprises one or more compounds of formula AY selected from the following sub-formulae:

AY1

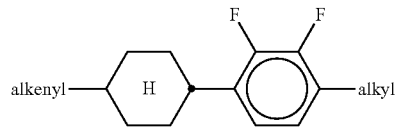

AY2

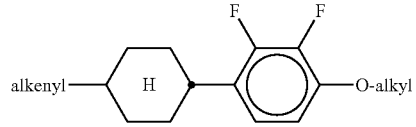

AY3

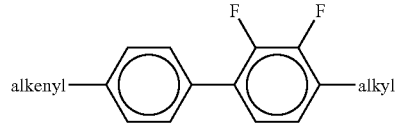

AY4

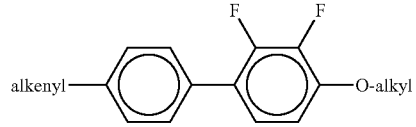

AY5

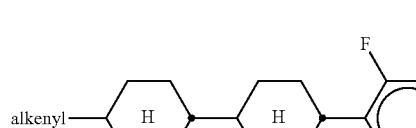

AY6

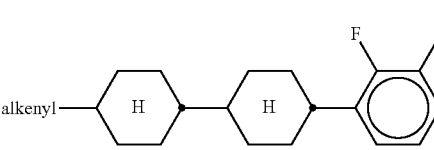

AY7

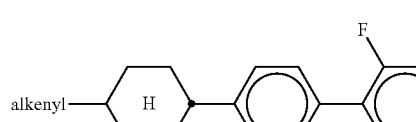

AY8

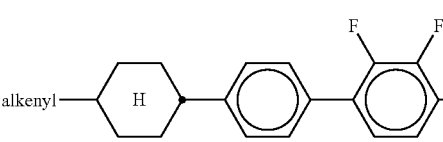

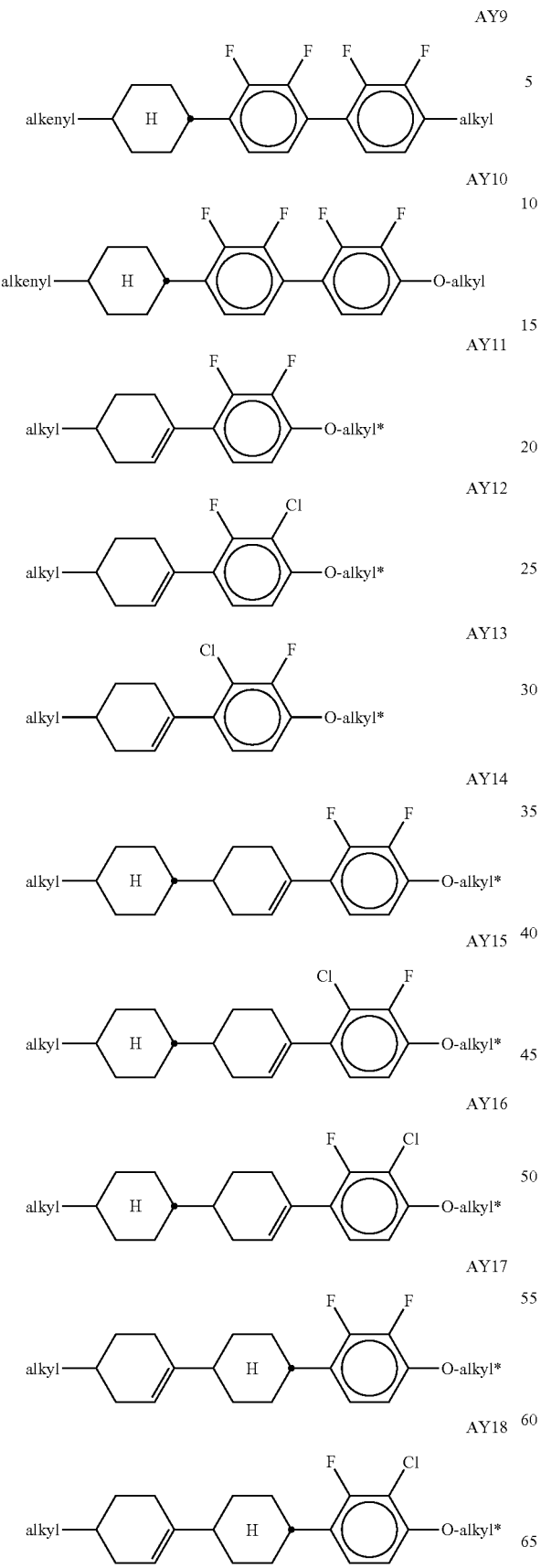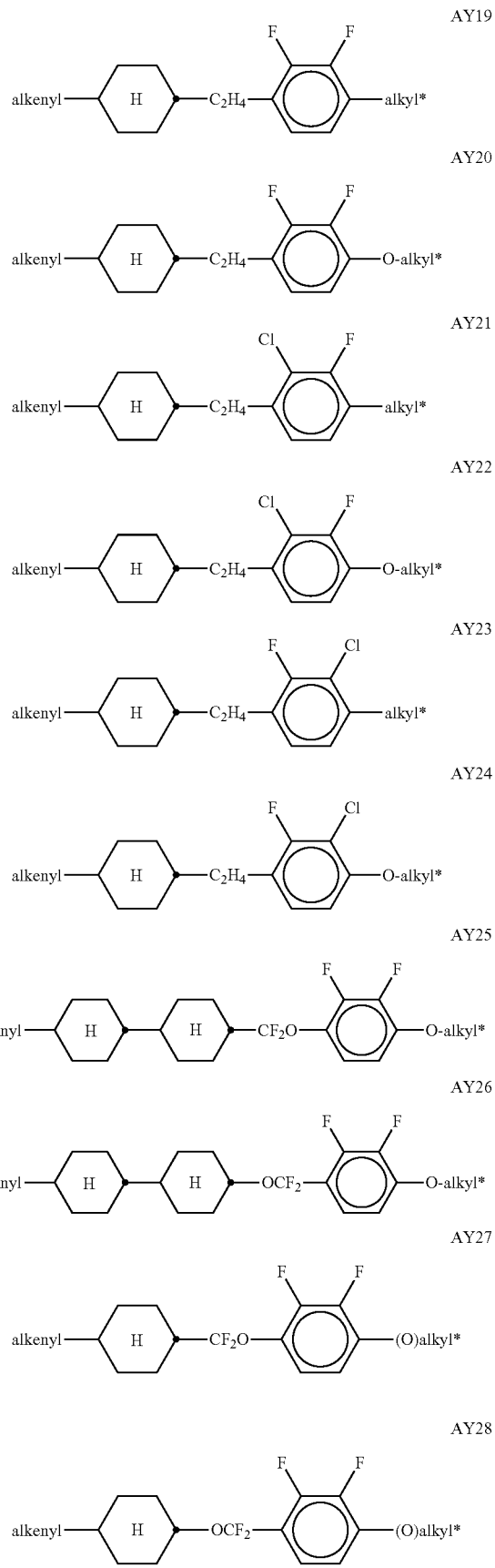

-continued

AY29

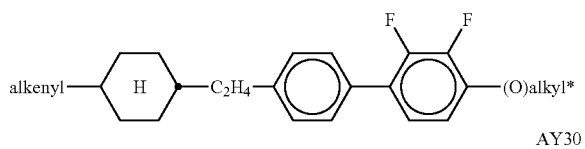

AY30

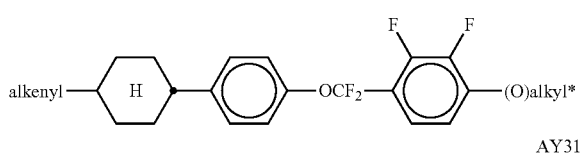

AY31

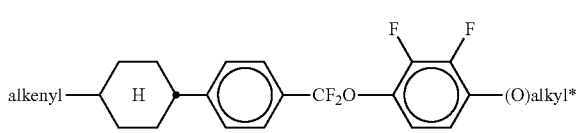

in which alkyl and alkyl* each, independently of one another, denote a straight-chain alkyl radical having 1-6 C atoms, "(0)" denotes an 0-atom or a single bond, and alkenyl and alkenyl* each, independently of one another, denote a straight-chain alkenyl radical having 2-7 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

In another preferred embodiment the component B) or LC host mixture comprises one or more compounds of formula AY selected from the following sub-formulae:

AY5a

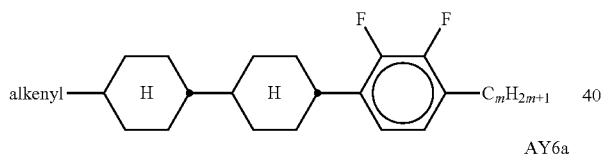

AY6a

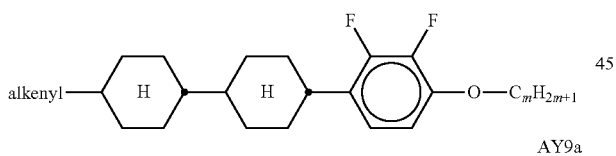

AY9a

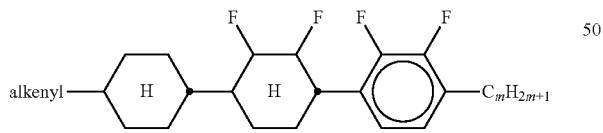

AY10a

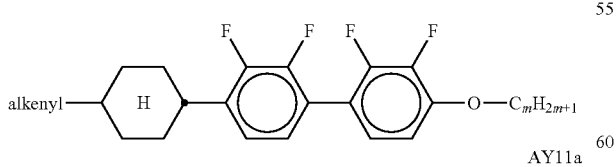

AY11a

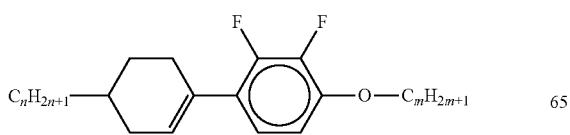

-continued

AY14a

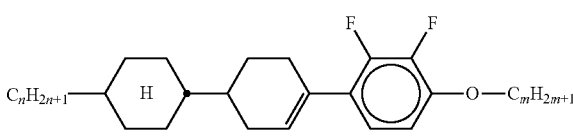

in which m and n each, independently of one another, denote 1, 2, 3, 4, 5 or 6, and alkenyl denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Preferably the proportion of compounds of formula AN and AY in the LC medium is from 2 to 70% by weight, very preferably from 5 to 60% by weight, most preferably from 10 to 50% by weight.

Preferably the LC medium or LC host mixture contains 1 to 5, preferably 1, 2 or 3 compounds selected from formulae AN and AY.

In another preferred embodiment of the present invention the LC medium comprises one or more compounds of formula AY14, very preferably of AY14a. The proportion of compounds of formula AY14 or AY14a in the LC medium is preferably 3 to 20% by weight.

The addition of alkenyl compounds of formula AN and/or AY enables a reduction of the viscosity and response time of the LC medium.

c) LC medium wherein the component B) or LC host mixture comprises one or more compounds of the following formula:

ZK $$R^3 \text{—} \boxed{C} \text{—} Z^y \text{—} \boxed{D} \text{—} R^4$$

in which the individual radicals have the following meanings:

C denotes (cyclohexyl), (tetrahydropyran O-containing ring), (tetrahydropyran O-containing ring), (cyclohexenyl) or (cyclohexenyl), D denotes (cyclohexyl) or (phenyl), $R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another, $Z^y$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond.

The compounds of the formula ZK are preferably selected from the group consisting of the following sub-formulae:

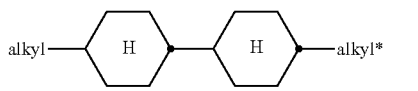
ZK1

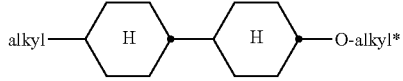
ZK2

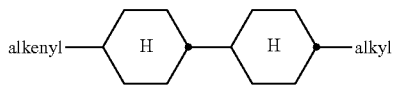
ZK3

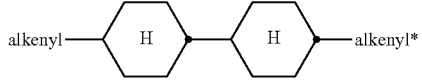
ZK4

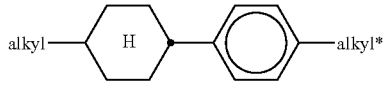
ZK5

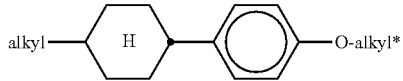
ZK6

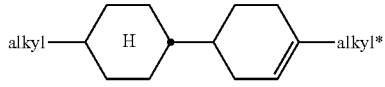
ZK7

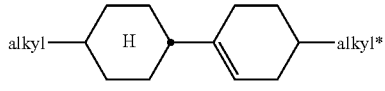
ZK8

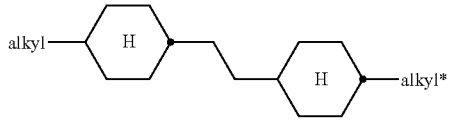
ZK9

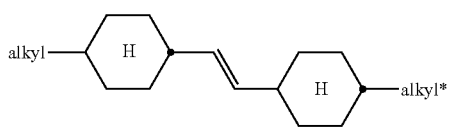
ZK10 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Especially preferred are compounds of formula ZK1.

Particularly preferred compounds of formula ZK are selected from the following sub-formulae:

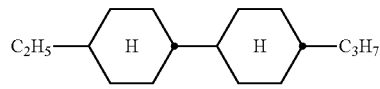
ZK1a

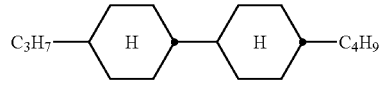
ZK1b

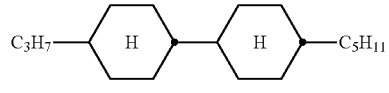
ZK1c wherein the propyl, butyl and pentyl groups are straight-chain groups.

Most preferred are compounds of formula ZK1a.

d) LC medium wherein component B) or the LC host mixture additionally comprises one or more compounds of the following formula:

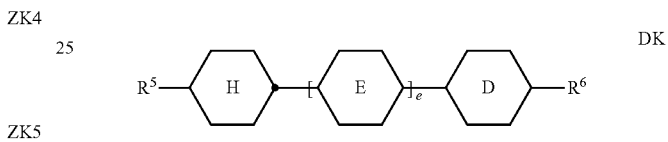
DK in which the individual radicals on each occurrence, identically or differently, have the following meanings:

$R^5$ and $R^6$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms,

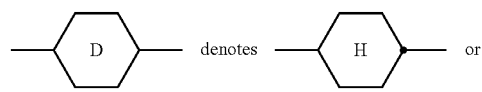

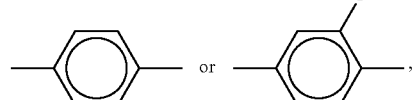

and
e denotes 1 or 2.

The compounds of the formula DK are preferably selected from the group consisting of the following sub-formulae:

DK1

-continued

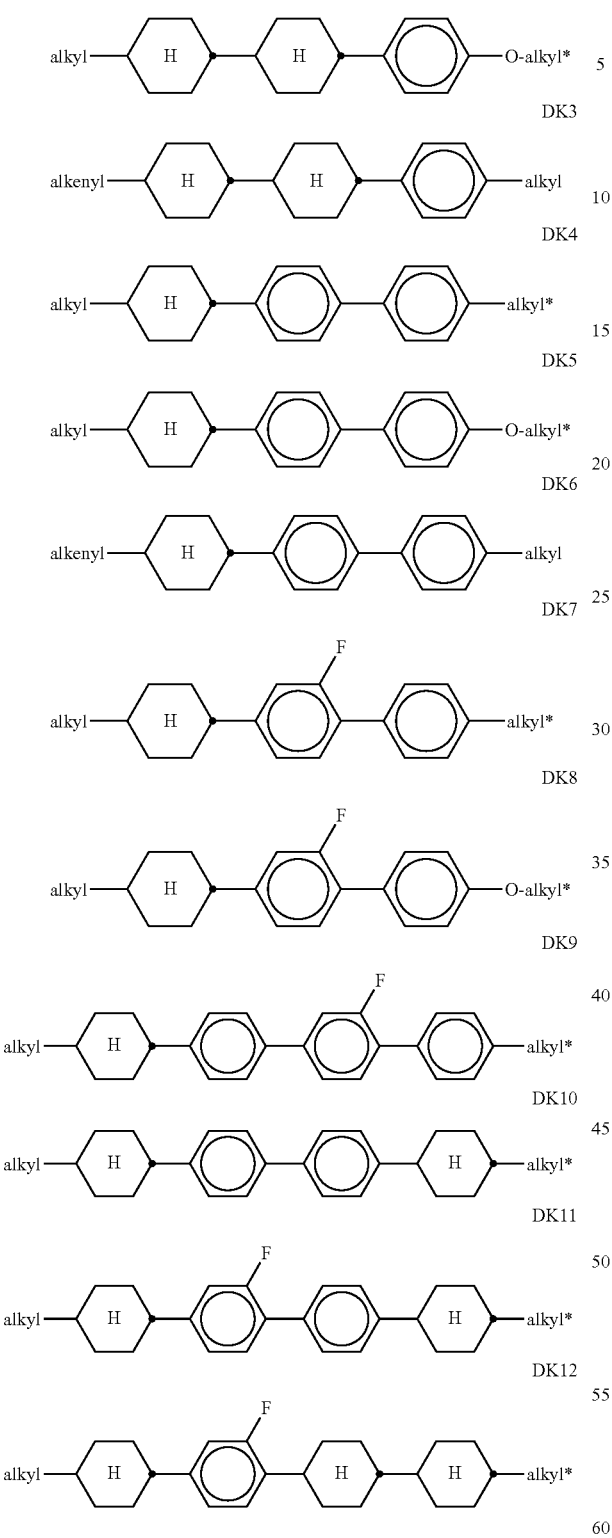

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2$=CH—, $CH_2$=CHCH$_2$CH$_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

e) LC medium wherein component B) or the LC host mixture additionally comprises one or more compounds of the following formula:

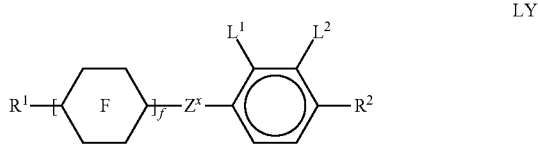

LY in which the individual radicals have the following meanings:

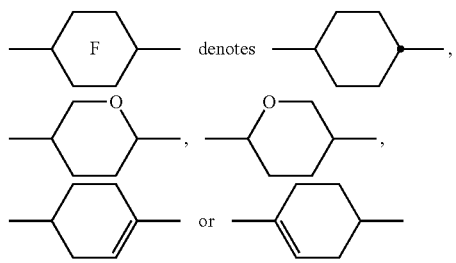

with at least one ring F being different from cyclohexylene, f denotes 1 or 2, $R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, $Z^x$ denotes —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond, $L^1$ and $L^2$ each, independently of one another, denote F, Cl, $OCF_3$, $CF_3$, $CH_3$, $CH_2F$, $CHF_2$.

Preferably, both radicals $L^1$ and $L^2$ denote F or one of the radicals $L^1$ and $L^2$ denotes F and the other denotes Cl.

The compounds of the formula LY are preferably selected from the group consisting of the following sub-formulae:

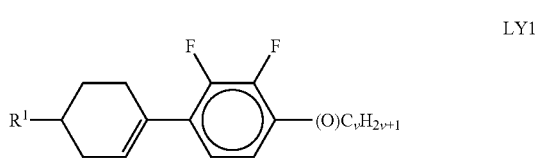

LY1

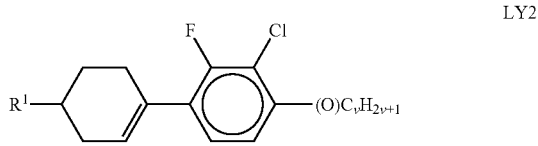

LY2

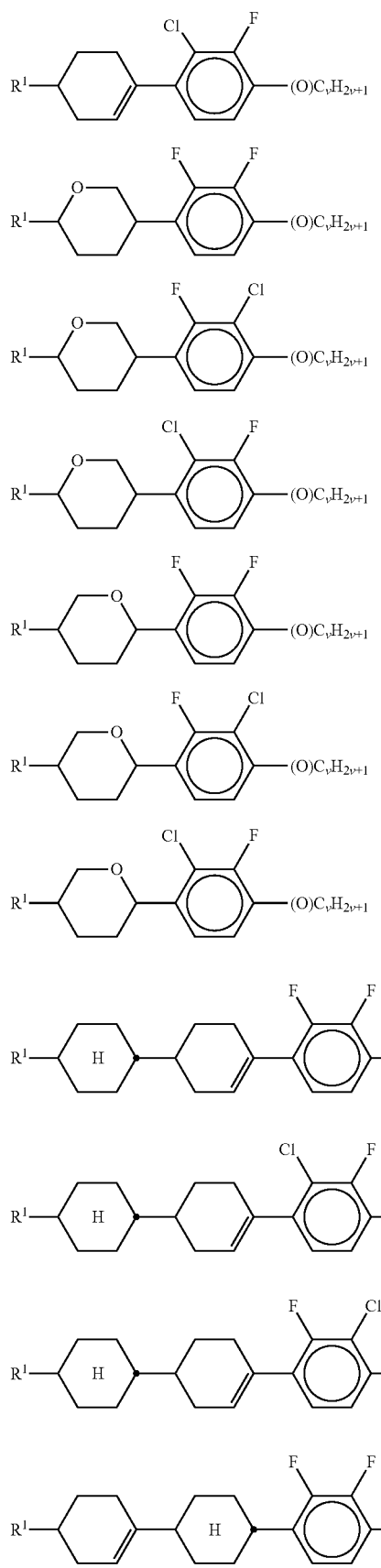
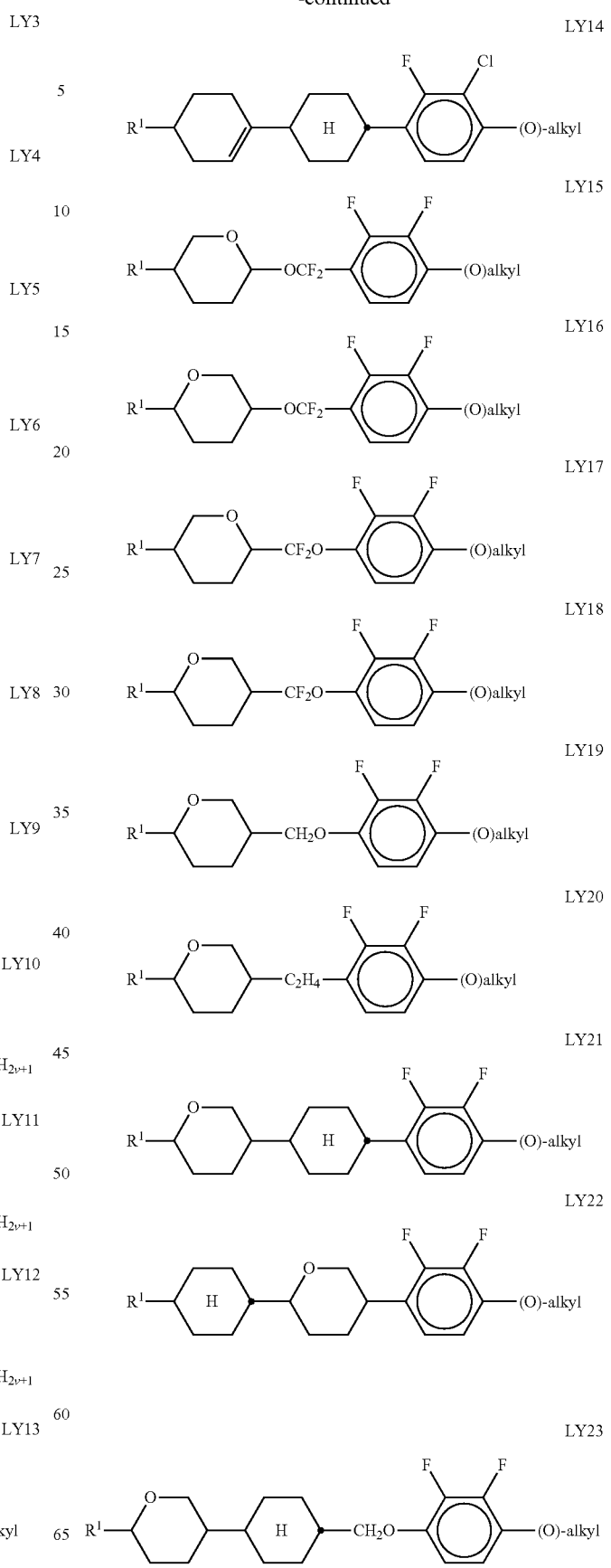

LY24

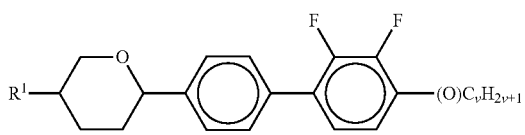

in which R¹ has the meaning indicated above, alkyl denotes a straight-chain alkyl radical having 1-6 C atoms, (0) denotes an oxygen atom or a single bond, and v denotes an integer from 1 to 6. R¹ preferably denotes straight-chain alkyl having 1 to 6 C atoms or straight-chain alkenyl having 2 to 6 C atoms, in particular $CH_3$, $C_2H_5$, $n\text{-}C_3H_7$, $n\text{-}C_4H_9$, $n\text{-}C_5H_{11}$, $CH_2\!=\!CH\text{—}$, $CH_2\!=\!CHCH_2CH_2\text{—}$, $CH_3\text{—}CH\!=\!CH\text{—}$, $CH_3\text{—}CH_2\text{—}CH\!=\!CH\text{—}$, $CH_3\text{—}(CH_2)_2\text{—}CH\!=\!CH\text{—}$, $CH_3\text{—}(CH_2)_3\text{—}CH\!=\!CH\text{—}$ or $CH_3\text{—}CH\!=\!CH\text{—}(CH_2)_2\text{—}$.

f) LC medium wherein component B) or the LC host mixture additionally comprises one or more compounds selected from the group consisting of the following formulae:

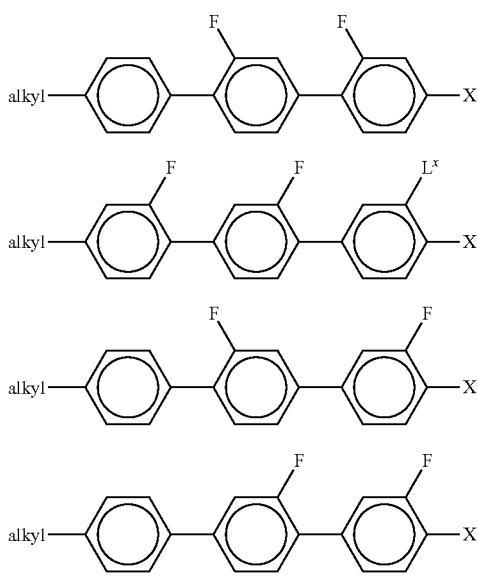

in which alkyl denotes $C_{1-6}$-alkyl, Lx denotes H or F, and X denotes F, Cl, $OCF_3$, $OCHF_2$ or $OCH\!=\!CF_2$. Particular preference is given to compounds of the formula G1 in which X denotes F.

g) LC medium wherein component B) or the LC host mixture additionally comprises one or more compounds selected from the group consisting of the following formulae:

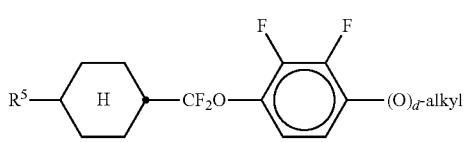

YC1

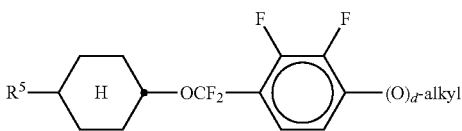

YC2

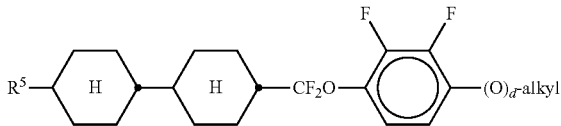

YC3

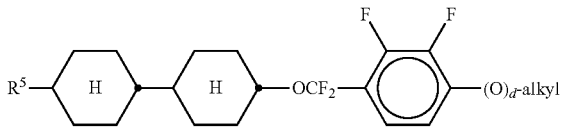

YC4

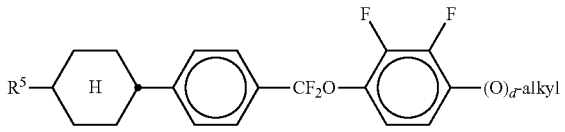

YC5

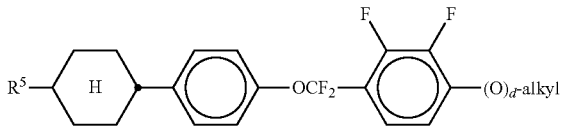

YC6

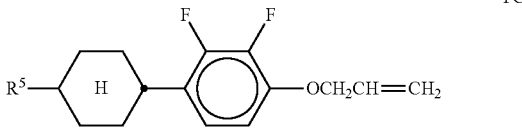

YC7

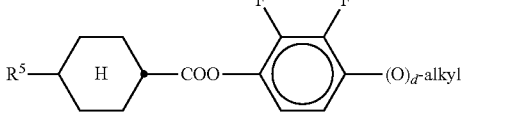

YC8

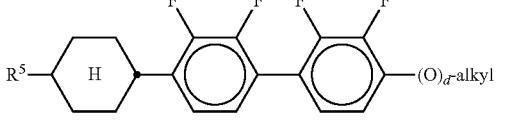

YC9

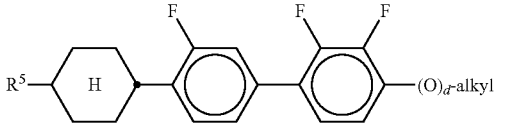

YC10

YC11

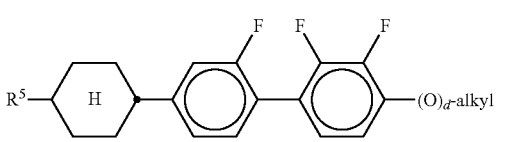

-continued

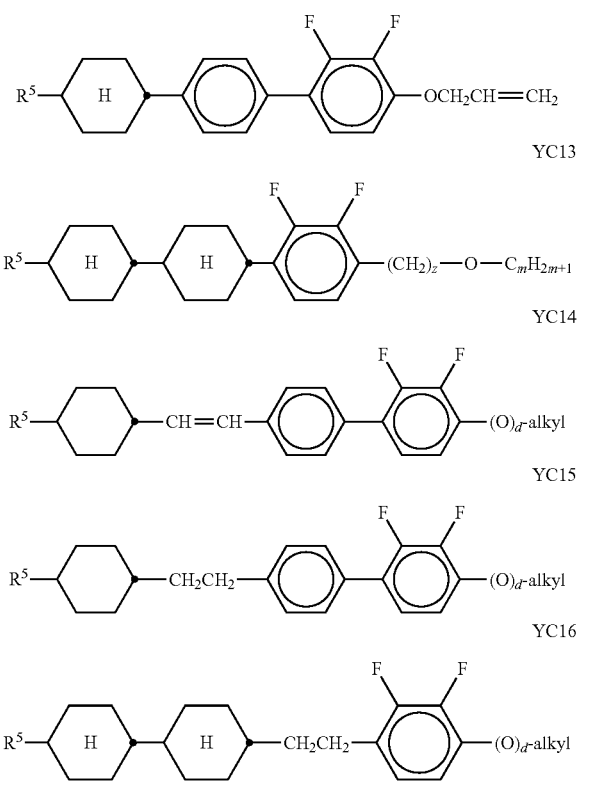

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 5% by weight.

h) LC medium wherein component B) or the LC host mixture additionally comprises one or more biphenyl compounds selected from the group consisting of the following formulae:

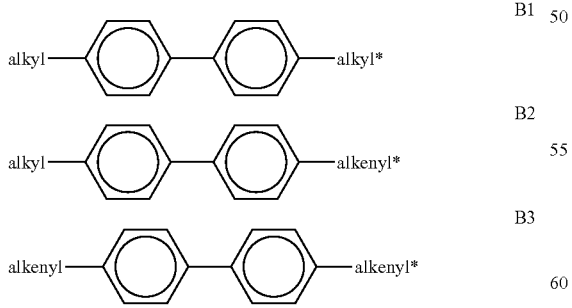

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

The proportion of the biphenyls of the formulae B1 to B3 in the LC host mixture is preferably at least 3% by weight, in particular ≥5% by weight.

The compounds of the formula B2 are particularly preferred.

The compounds of the formulae B1 to B3 are preferably selected from the group consisting of the following sub-formulae:

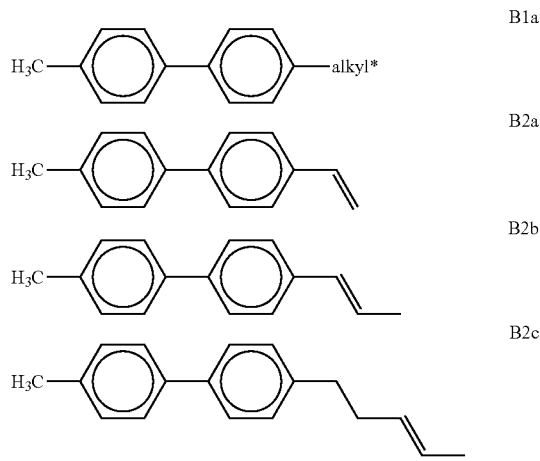

in which alkyl* denotes an alkyl radical having 1-6 C atoms. The medium according to the invention particularly preferably comprises one or more compounds of the formulae B1a and/or B2c.

i) LC medium wherein component B) or the LC host mixture additionally comprises one or more terphenyl compounds of the following formula:

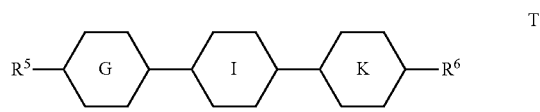

in which $R^5$ and $R^6$ each, independently of one another, have one of the meanings indicated above, and

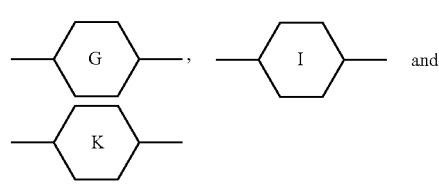

each, independently of one another, denote

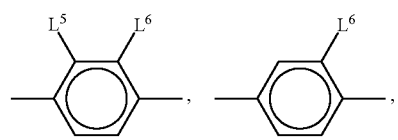

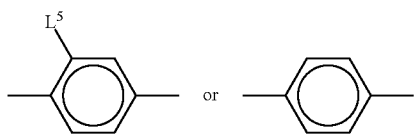 or
in which $L^5$ denotes F or Cl, preferably F, and $L^6$ denotes F, Cl, $OCF_3$, $CF_3$, $CH_3$, $CH_2F$ or $CHF_2$, preferably F.
The compounds of the formula T are preferably selected from the group consisting of the following sub-formulae:
T1
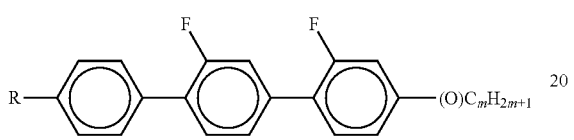
T2
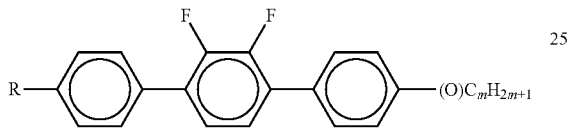
T3
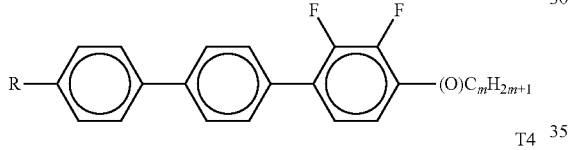
T4

T5
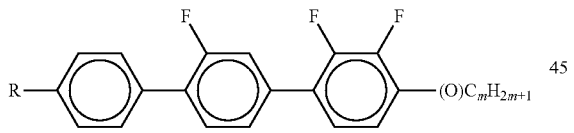
T6
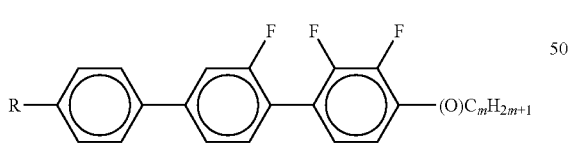
T7
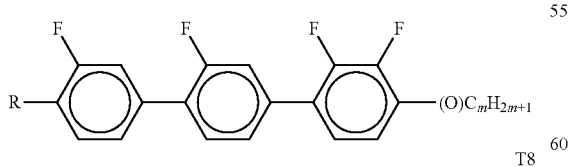
T8
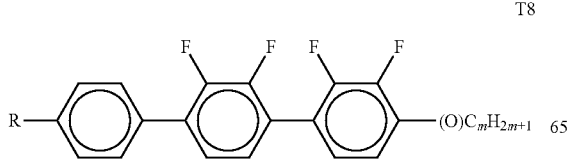
T9
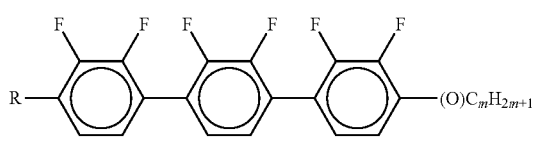
T10
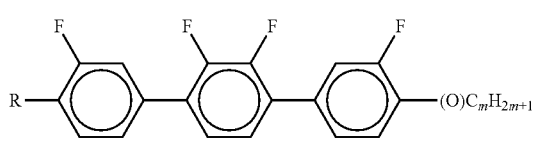
T11
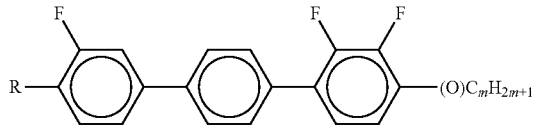
T12
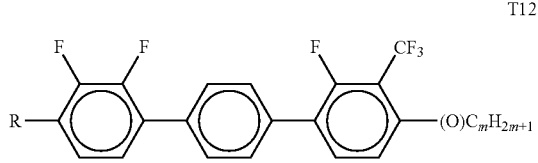
T13
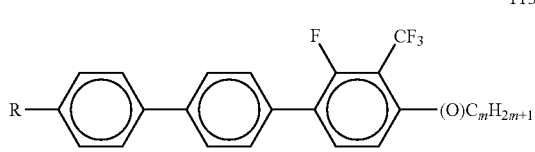
T14
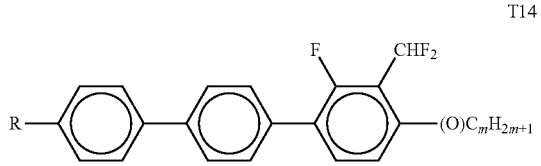
T15
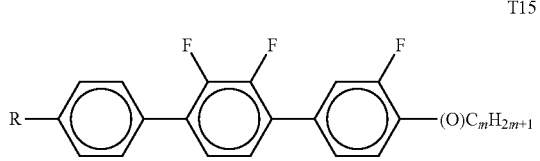
T16
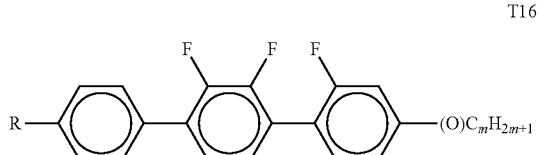
T17
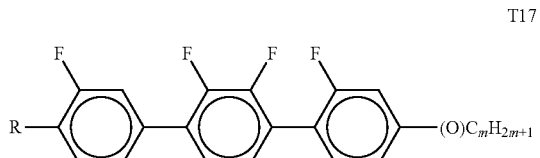
T18
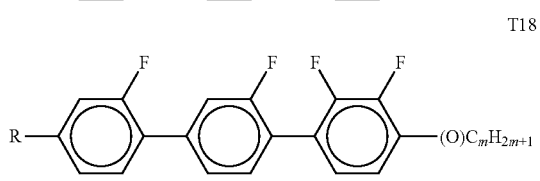

-continued

T19
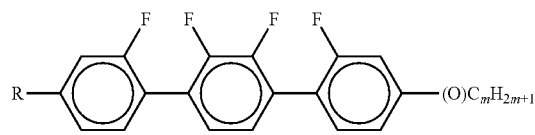

T20

T21
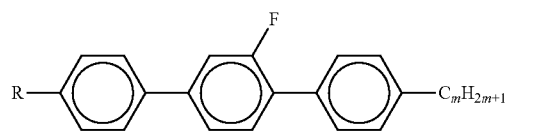

T22
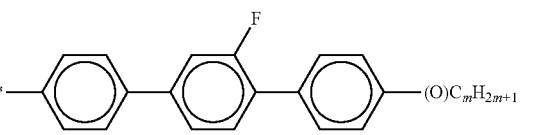

T23
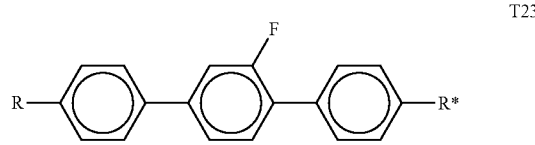

T24
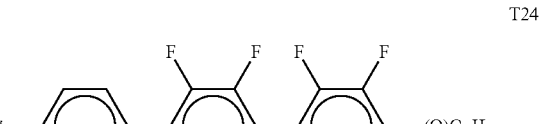

in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC host mixture according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in LC media according to the invention if the Δn value of the mixture is to be ≥0.1. Preferred LC media comprise 2-20% by weight of one or more terphenyl compounds of the formula T, preferably selected from the group of compounds T1 to T22.

k) LC medium wherein component B) or the LC host mixture additionally comprises one or more quaterphenyl compounds selected from the group consisting of the following formulae:

Q
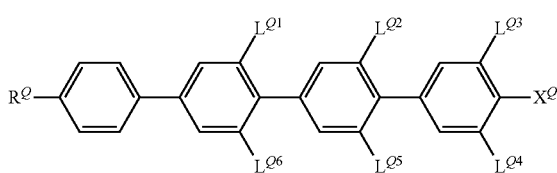

wherein
$R^Q$ is alkyl, alkoxy, oxaalkyl or alkoxyalkyl having 1 to 9 C atoms or alkenyl or alkenyloxy having 2 to 9 C atoms, all of which are optionally fluorinated,
$X^Q$ is F, Cl, halogenated alkyl or alkoxy having 1 to 6 C atoms or halogenated alkenyl or alkenyloxy having 2 to 6 C atoms,
$L^{Q1}$ to $L^{Q6}$ independently of each other are H or F, with at least one of $L^{Q1}$ to $L^{Q6}$ being F.

Preferred compounds of formula Q are those wherein $R^Q$ denotes straight-chain alkyl with 2 to 6 C-atoms, very preferably ethyl, n-propyl or n-butyl.

Preferred compounds of formula Q are those wherein $L^{Q3}$ and $L^{Q4}$ are F. Further preferred compounds of formula Q are those wherein $L^{Q3}$, $L^{Q4}$ and one or two of $L^{Q1}$ and $L^{Q2}$ are F.

Preferred compounds of formula Q are those wherein $X^Q$ denotes F or $OCF_3$, very preferably F.

The compounds of formula Q are preferably selected from the following subformulae Q1
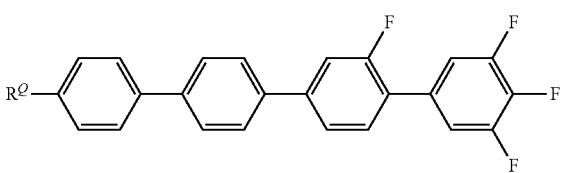

Q2
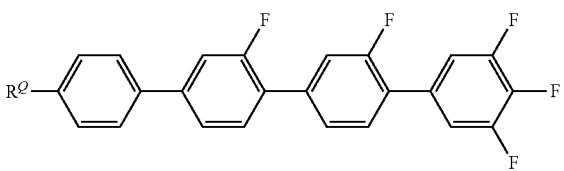

wherein $R^Q$ has one of the meanings of formula Q or one of its preferred meanings given above and below, and is preferably ethyl, n-propyl or n-butyl.

Especially preferred are compounds of formula Q1, in particular those wherein $R^Q$ is n-propyl.

Preferably the proportion of compounds of formula Q in the LC host mixture is from >0 to 5% by weight, very preferably from 0.1 to 2% by weight, most preferably from 0.2 to 1.5% by weight.

Preferably the LC host mixture contains 1 to 5, preferably 1 or 2 compounds of formula Q.

The addition of quaterphenyl compounds of formula Q to the LC host mixture enables to reduce ODF mura, whilst maintaining high UV absorption, enabling quick and complete polymerization, enabling strong and quick tilt angle generation, and increasing the UV stability of the LC medium.

Besides, the addition of compounds of formula Q, which have positive dielectric anisotropy, to the LC medium with negative dielectric anisotropy allows a better control of the values of the dielectric constants $\in_\|$ and $\in_\perp$, and in particular enables to achieve a high value of the dielectric constant $\in_\|$ while keeping the dielectric anisotropy $\Delta\in$ constant, thereby reducing the kick-back voltage and reducing image sticking.

l) LC medium wherein component B) or the LC host mixture additionally comprises one or more compounds of formula C:

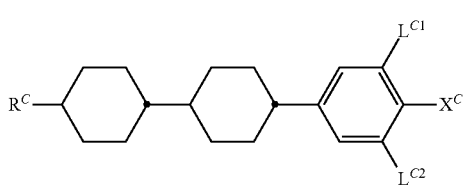

wherein
R$^C$ denotes alkyl, alkoxy, oxaalkyl or alkoxyalkyl having 1 to 9 C atoms or alkenyl or alkenyloxy having 2 to 9 C atoms, all of which are optionally fluorinated,
X$^C$ denotes F, Cl, halogenated alkyl or alkoxy having 1 to 6 C atoms or halogenated alkenyl or alkenyloxy having 2 to 6 C atoms,
L$^{C1}$, L$^{C2}$ independently of each other denote H or F, with at least one of L$^{C1}$ and L$^{C2}$ being F.
Preferred compounds of formula C are those wherein R$^C$ denotes straight-chain alkyl with 2 to 6 C-atoms, very preferably ethyl, n-propyl or n-butyl.
Preferred compounds of formula C are those wherein L$^{C1}$ and L$^{C2}$ are F.
Preferred compounds of formula C are those wherein X$^C$ denotes F or OCF$_3$, very preferably F.
Preferred compounds of formula C are selected from the following formula

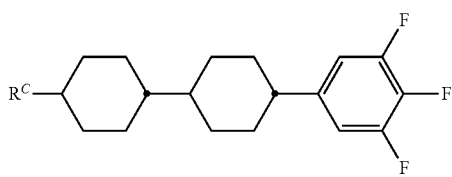

wherein R$^C$ has one of the meanings of formula C or one of its preferred meanings given above and below, and is preferably ethyl, n-propyl or n-butyl, very preferably n-propyl.
Preferably the proportion of compounds of formula C in the LC host mixture is from >0 to ≤10% by weight, very preferably from 0.1 to 8% by weight, most preferably from 0.2 to 5% by weight.
Preferably the LC host mixture contains 1 to 5, preferably 1, 2 or 3 compounds of formula C.
The addition of compounds of formula C, which have positive dielectric anisotropy, to the LC medium with negative dielectric anisotropy allows a better control of the values of the dielectric constants $\in_\|$ and $\in_\perp$, and in particular enables to achieve a high value of the dielectric constant $\in_\|$ while keeping the dielectric anisotropy $\Delta\in$ constant, thereby reducing the kick-back voltage and reducing image sticking. Besides, the addition of compounds of formula C enables to reduce the viscosity and the response time of the LC medium.

m) LC medium wherein component B) or the LC host mixture additionally comprises one or more compounds selected from the group consisting of the following formulae:

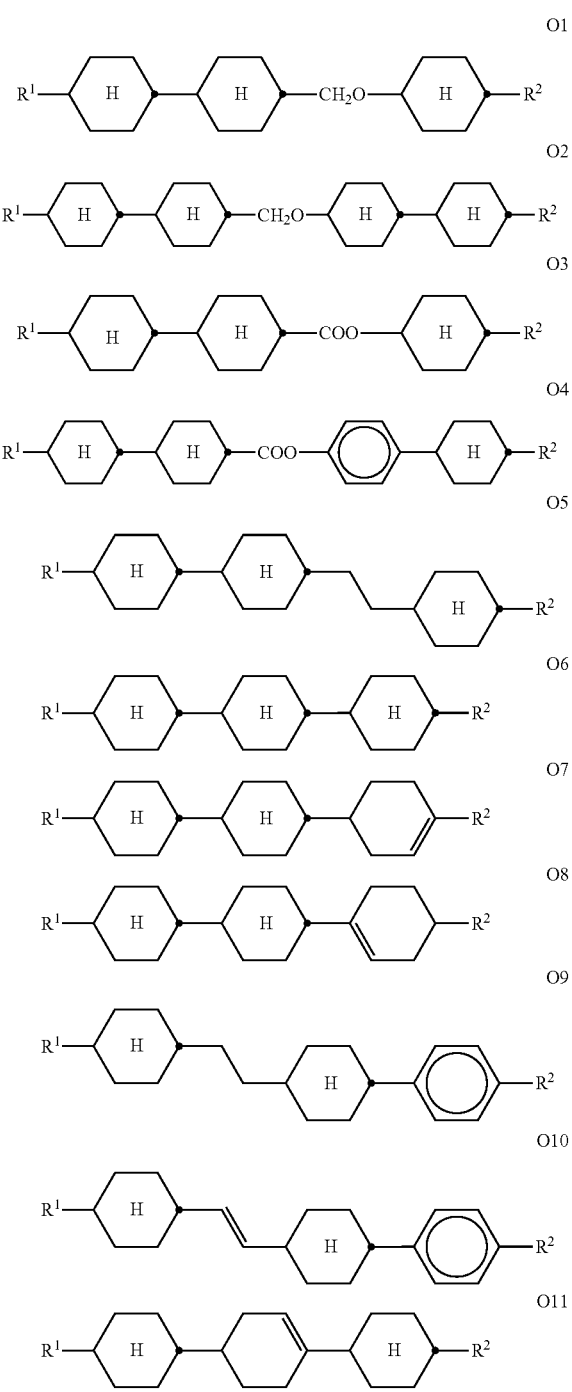

in which R$^1$ and R$^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae 01, 03 and 04.

n) LC medium wherein component B) or the LC host mixture additionally comprises one or more compounds of the following formula:

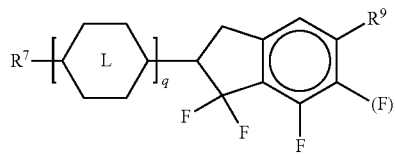
FI in which

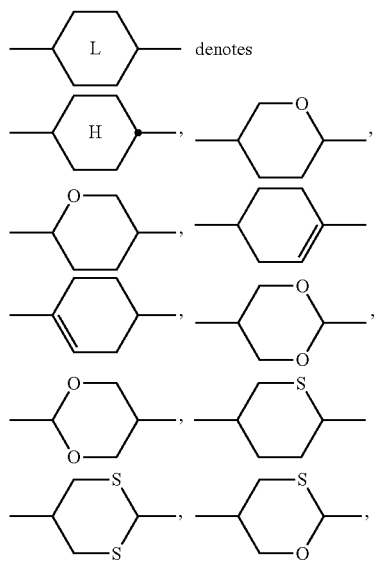

R⁹ denotes H, CH₃, C₂H₅ or n-C₃H₇, (F) denotes an optional fluorine substituent, and q denotes 1, 2 or 3, and R⁷ has one of the meanings indicated for R¹, preferably in amounts of >3% by weight, in particular 5% by weight and very particularly preferably 5-30% by weight.

Particularly preferred compounds of the formula FI are selected from the group consisting of the following sub-formulae:

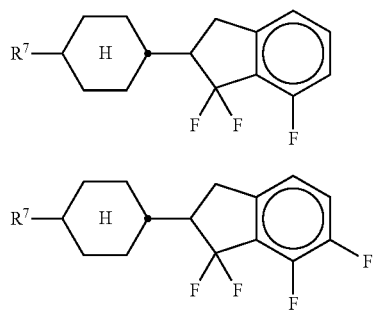
FI1

FI2

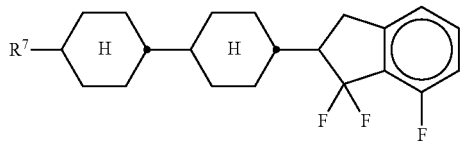
FI3

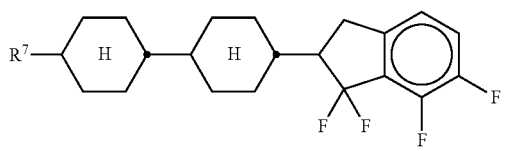
FI4

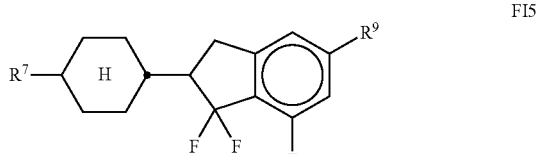
FI5

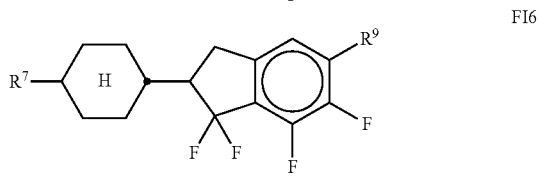
FI6

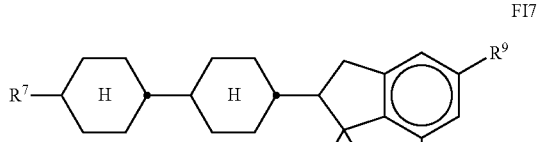
FI7

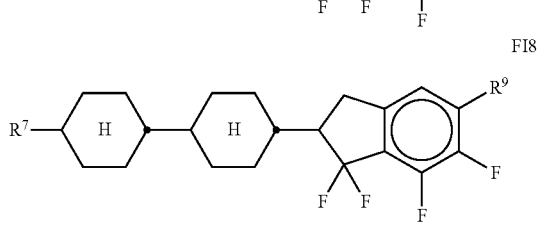
FI8 in which R⁷ preferably denotes straight-chain alkyl, and R⁹ denotes CH₃, C₂H₅ or n-C₃H₇. Particular preference is given to the compounds of the formulae FI1, FI2 and FI3.

o) LC medium wherein component B) or the LC host mixture additionally comprises one or more compounds selected from the group consisting of the following formulae:

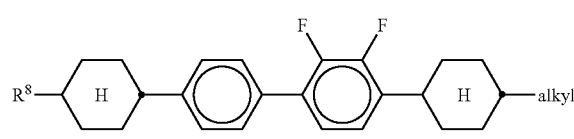
VK1

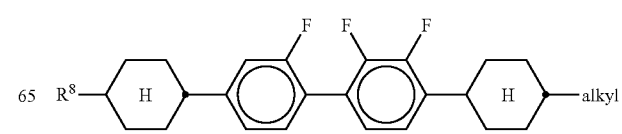
VK2

VK3

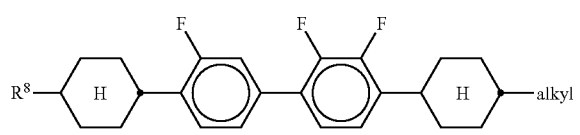

VK4

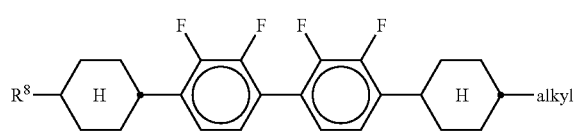

in which R⁸ has the meaning indicated for R¹, and alkyl denotes a straight-chain alkyl radical having 1-6 C atoms.

p) LC medium wherein component B) or the LC host mixture additionally comprises one or more compounds which contain a tetrahydronaphthyl or naphthyl unit, such as, for example, the compounds selected from the group consisting of the following formulae:

N1

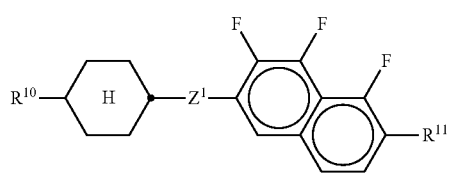

N2

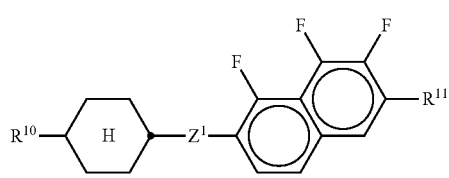

N3

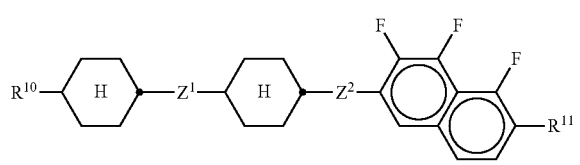

N4

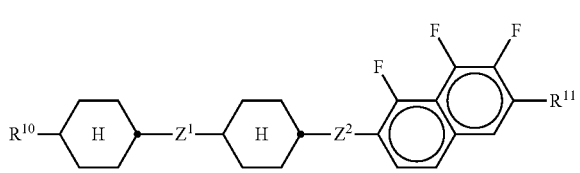

N5

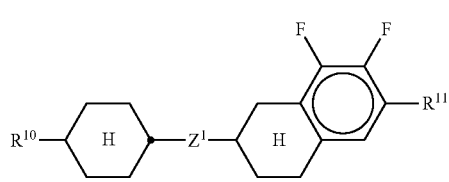

N6

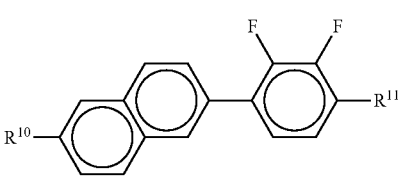

N7

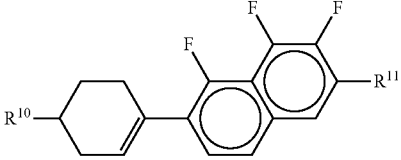

N8

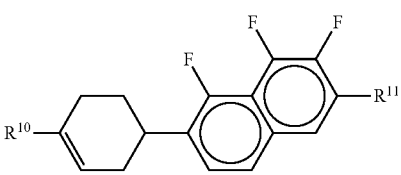

N9

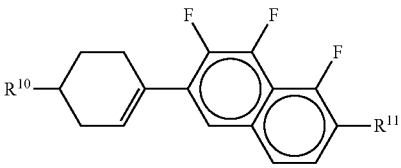

N10

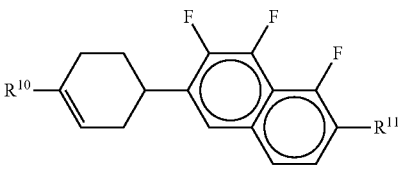

in which
R¹⁰ and R¹¹ each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms,
and R¹⁰ and R¹¹ preferably denote straight-chain alkyl or alkoxy having 1 to 6 C atoms or straight-chain alkenyl having 2 to 6 C atoms, and
Z¹ and Z² each, independently of one another, denote —C₂H₄—, —CH=CH—, —(CH₂)₄—, —(CH₂)₃O—, —O(CH₂)₃—, —CH=CH—CH₂CH₂—, —CH₂CH₂CH=CH—, —CH₂O—, —OCH₂—, —CO—O—, —O—CO—, —C₂F₄—, —CF=CF—, —CF=CH—, —CH=CF—, —CH₂— or a single bond.

q) LC medium wherein component B) or the LC host mixture additionally comprises one or more difluorodibenzochromans and/or chromans of the following formulae:

BC

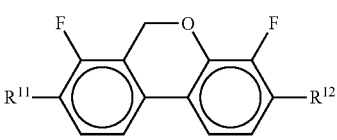

-continued

CR
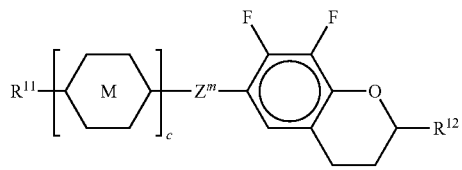

RC
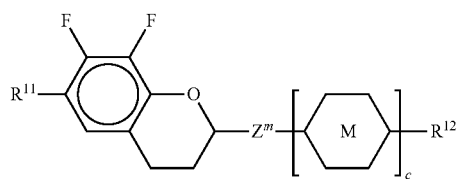

in which

R$^{11}$ and R$^{12}$ each, independently of one another, have one of the meanings indicated above for R$^{11}$, ring M is trans-1,4-cyclohexylene or 1,4-phenylene, Z$^m$ —C$_2$H$_4$—, —CH$_2$O—, —OCH$_2$—, —CO—O— or —O—CO—, c is 0, 1 or 2, preferably in amounts of 3 to 20% by weight, in particular in amounts of 3 to 15% by weight.

Particularly preferred compounds of the formulae BC, CR and RC are selected from the group consisting of the following sub-formulae:

BC1
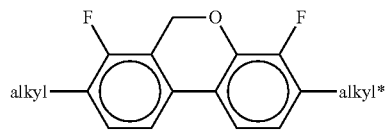

BC2
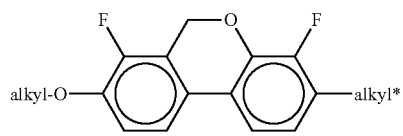

BC3
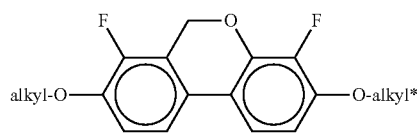

BC4
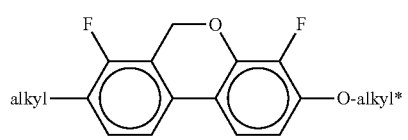

BC5
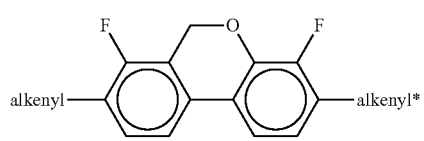

BC6
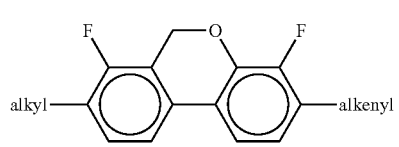

BC7
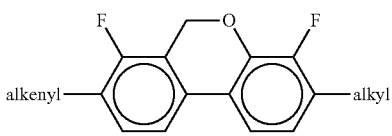

CR1
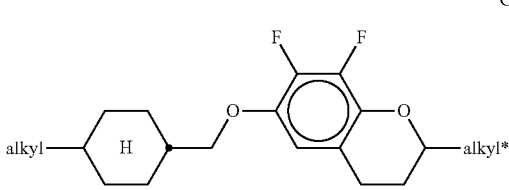

CR2
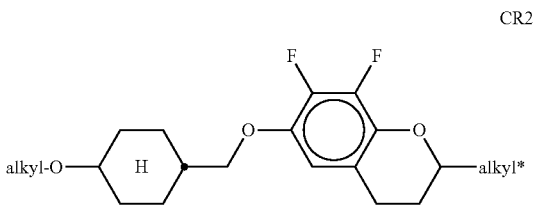

CR3
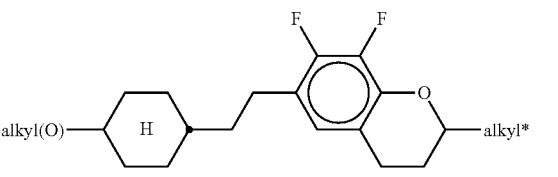

CR4
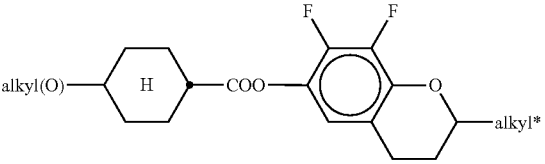

CR5
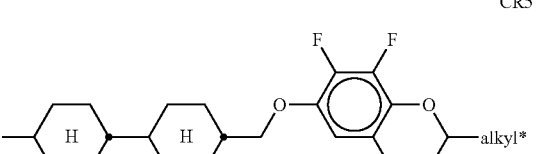

CR6
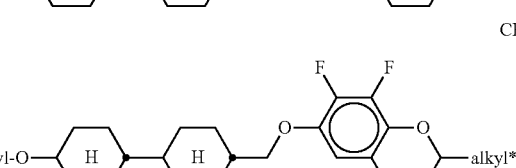

CR7
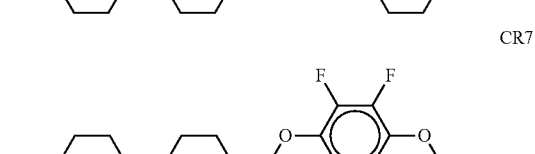

CR8
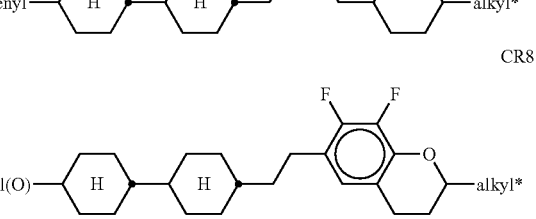

-continued

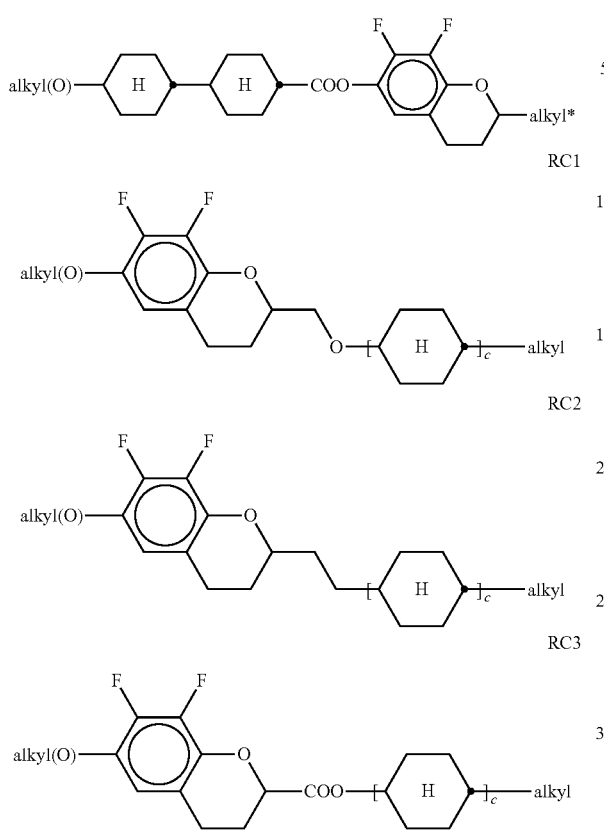

in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particular preference is given to LC host mixtures comprising one, two or three compounds of the formula BC-2.

r) LC medium wherein component B) or the LC host mixture additionally comprises one or more fluorinated phenanthrenes and/or dibenzofurans of the following formulae:

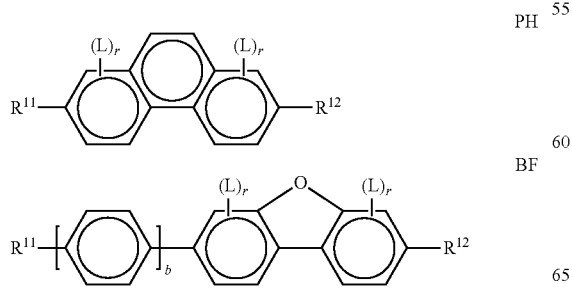

in which $R^{11}$ and $R^{12}$ each, independently of one another, have one of the meanings indicated above for $R^{11}$, b denotes 0 or 1, L denotes F, and r denotes 1, 2 or 3.

Particularly preferred compounds of the formulae PH and BF are selected from the group consisting of the following sub-formulae:

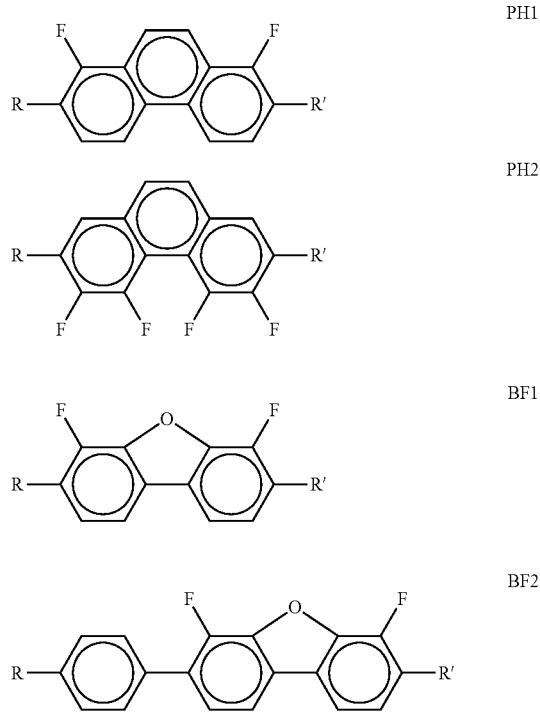

in which R and R' each, independently of one another, denote a straight-chain alkyl or alkoxy radical having 1-7 C atoms.

s) LC medium wherein component B) or the LC host mixture additionally comprises one or more monocyclic compounds of the following formula

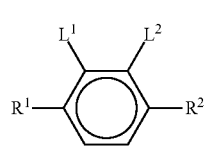

wherein $R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $L^1$ and $L^2$ each, independently of one another, denote F, Cl, $OCF_3$, $CF_3$, $CH_3$, $CH_2F$, $CHF_2$.

Preferably, both $L^1$ and $L^2$ denote F or one of $L^1$ and $L^2$ denotes F and the other denotes Cl, The compounds of the formula Y are preferably selected from the group consisting of the following sub-formulae:

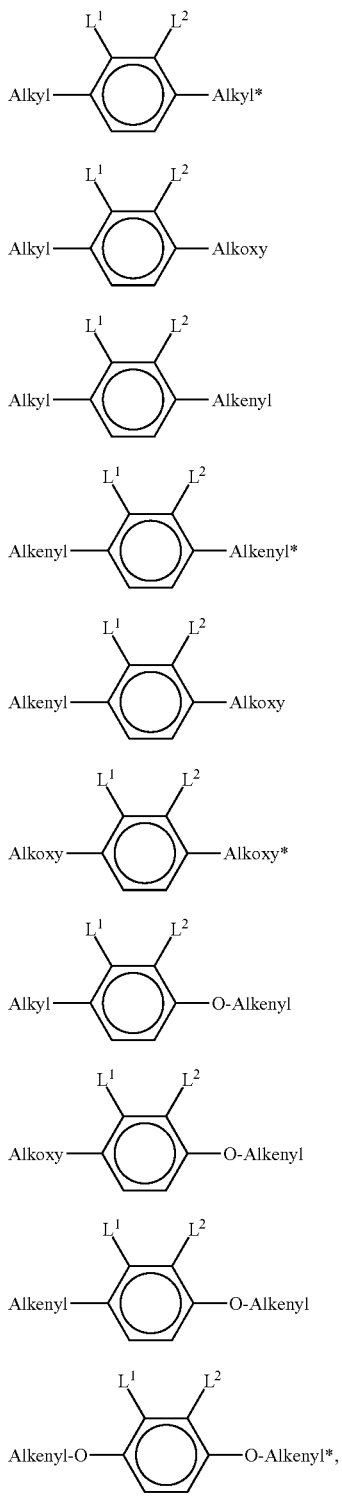

in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms. Alkenyl and Alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Particularly preferred compounds of the formula Y are selected from the group consisting of the following sub-formulae:

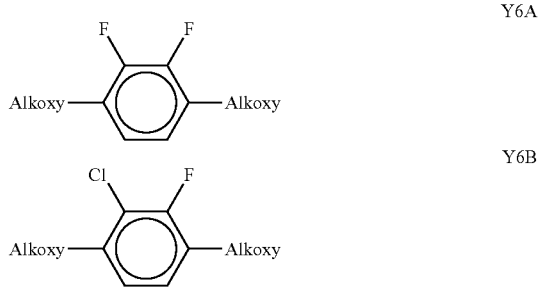

wherein Alkoxy preferably denotes straight-chain alkoxy with 3, 4, or 5 C atoms.

t) LC medium which, apart from the polymerizable compounds as described above and below, does not contain a compound which contains a terminal vinyloxy group ($-O-CH=CH_2$).

u) LC medium wherein component B) or the LC host mixture comprises 1 to 8, preferably 1 to 5, compounds of the formulae CY1, CY2, PY1 and/or PY2. The proportion of these compounds in the LC host mixture as a whole is preferably 5 to 60%, particularly preferably 10 to 35%. The content of these individual compounds is preferably in each case 2 to 20%.

v) LC medium wherein component B) or the LC host mixture comprises 1 to 8, preferably 1 to 5, compounds of the formulae CY9, CY10, PY9 and/or PY10. The proportion of these compounds in the LC host mixture as a whole is preferably 5 to 60%, particularly preferably 10 to 35%. The content of these individual compounds is preferably in each case 2 to 20%.

w) LC medium wherein component B) or the LC host mixture comprises 1 to 10, preferably 1 to 8, compounds of the formula ZK, in particular compounds of the formulae ZK1, ZK2 and/or ZK6. The proportion of these compounds in the LC host mixture as a whole is preferably 3 to 25%, particularly preferably 5 to 45%. The content of these individual compounds is preferably in each case 2 to 20%.

x) LC medium in which the proportion of compounds of the formulae CY, PY and ZK in the LC host mixture as a whole is greater than 70%, preferably greater than 80%.

y) LC medium in which the LC host mixture contains one or more compounds containing an alkenyl group, preferably selected from formulae AN and AY, very preferably selected from formulae AN1, AN3, AN6 and AY14, most preferably from formulae AN1a, AN3a, AN6a and AY14. The concentration of these compounds in the LC host mixture is preferably from 2 to 70%, very preferably from 3 to 55%.

z) LC medium wherein component B) or the LC host mixture contains one or more, preferably 1 to 5, compounds selected of formula PY1-PY8, very preferably of formula PY2. The proportion of these compounds in the LC host mixture as a whole is preferably 1 to 30%, particularly preferably 2 to 20%. The content of these individual compounds is preferably in each case 1 to 20%.

z1) LC medium wherein component B) or the LC host mixture contains one or more, preferably 1, 2 or 3, compounds selected from formulae T1, T2 and T5, very preferably from formula T2. The content of these compounds in the LC host mixture as a whole is preferably 1 to 20%.

z2) LC medium in which the LC host mixture contains one or more compounds selected from formulae CY and PY, one or more compounds selected from formulae AN and AY, and one or more compounds selected from formulae T and Q.

z3) LC medium in which the LC host mixture contains one or more, preferably 1, 2 or 3, compounds of formula BF1, and one or more, preferably 1, 2 or 3, compounds selected from formulae AY14, AY15 and AY16, very preferably of formula AY14. The proportion of the compounds of formula AY14-AY16 in the LC host mixture is preferably from 2 to 35%, very preferably from 3 to 30%. The proportion of the compounds of formula BF1 in the LC host mixture is preferably from 0.5 to 20%, very preferably from 1 to 15%. Further preferably the LC host mixture according to this preferred embodiment contains one or more, preferably 1, 2 or 3 compounds of formula T, preferably selected from formula T1, T2 and T5, very preferably from formula T2 or T5. The proportion of the compounds of formula T in the LC host mixture medium is preferably from 0.5 to 15%, very preferably from 1 to 10%.

In a second preferred embodiment the LC medium contains an LC host mixture based on compounds with positive dielectric anisotropy. Such LC media are especially suitable for use in TN, OCB, Posi-VA, IPS, FFS, PS-OCB-, PS-TN-, PS-Posi-VA-, PS-IPS- or PS-FFS-displays.

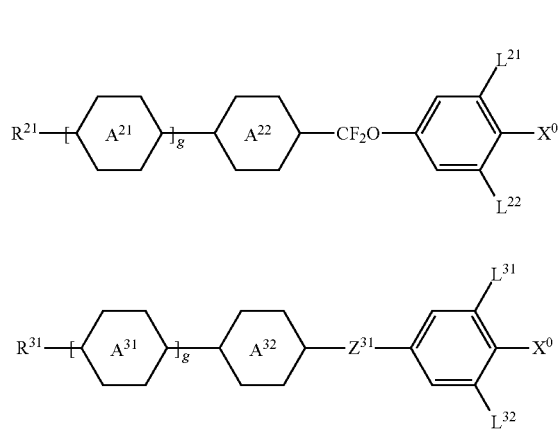

in which the individual radicals have, independently of each other and on each occurrence identically or differently, the following meanings:

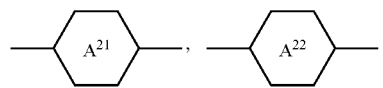

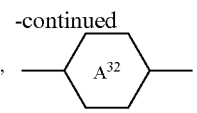

each, independently of one another, and on each occurrence, identically or differently

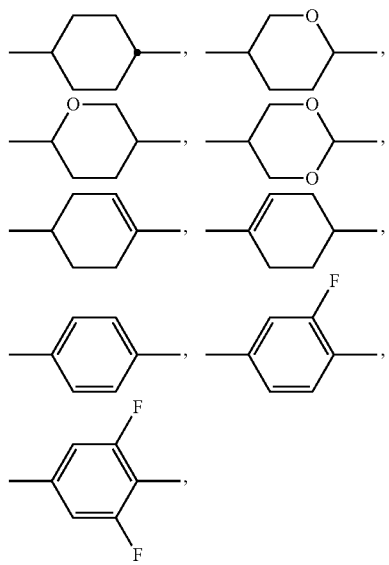

$R^{21}$, $R^{31}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $X^0$ F, Cl, halogenated alkyl or alkoxy having 1 to 6 C atoms or halogenated alkenyl or alkenyloxy having 2 to 6 C atoms, $Z^{31}$ —CH$_2$CH$_2$—, —CF$_2$CF$_2$—, —COO—, trans-CH=CH—, trans-CF=CF—, —CH$_2$O— or a single bond, preferably —CH$_2$CH$_2$—, —COO—, trans-CH=CH— or a single bond, particularly preferably —COO—, trans-CH=CH— or a single bond, $L^{21}$, $L^{22}$, $L^{31}$, $L^{32}$ each, independently of one another, H or F, g 0, 1, 2 or 3.

In the compounds of formula A and B, $X^0$ is preferably F, Cl, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CF$_2$, very preferably F or OCF$_3$, most preferably F.

In the compounds of formula A and B, $R^{21}$ and $R^{31}$ are preferably selected from straight-chain alkyl or alkoxy with 1, 2, 3, 4, 5 or 6 C atoms, and straight-chain alkenyl with 2, 3, 4, 5, 6 or 7 C atoms.

In the compounds of formula A and B, g is preferably 1 or 2.

In the compounds of formula B, $Z^{31}$ is preferably COO, trans-CH=CH or a single bond, very preferably COO or a single bond.

Preferably component B) of the LC medium comprises one or more compounds of formula A selected from the group consisting of the following formulae:

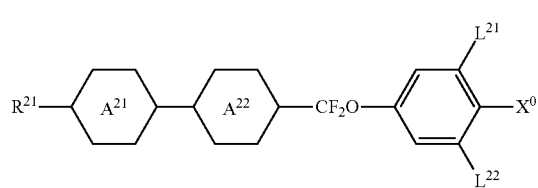

A1

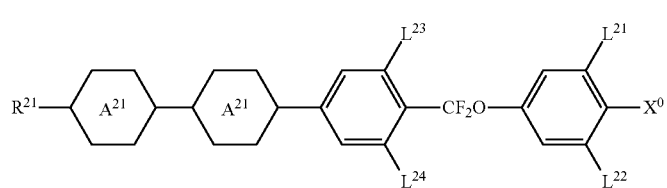

A2

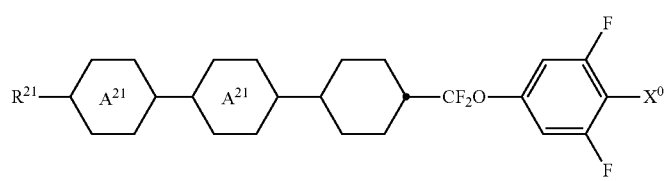

A3

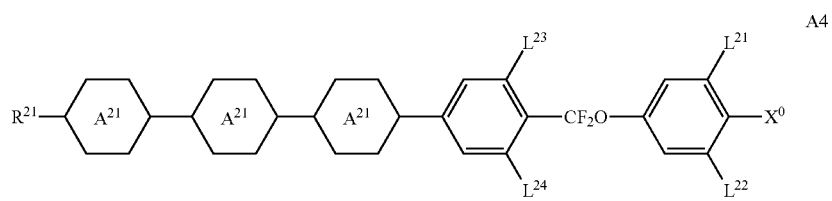

A4 in which $A^{21}$, $R^{21}$, $X^0$, $L^{21}$ and $L^{22}$ have the meanings given in formula A, $L^{23}$ and $L^{24}$ each, independently of one another, are H or F, and $X^0$ is preferably F. Particularly preferred are compounds of formulae A1 and A2.

Particularly preferred compounds of formula A1 are selected from the group consisting of the following subformulae:

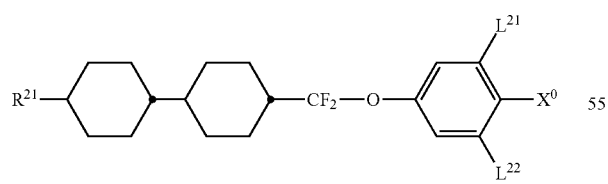

A1a

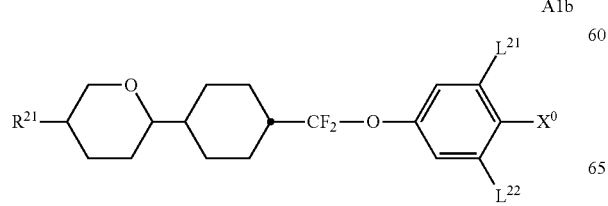

A1b

-continued

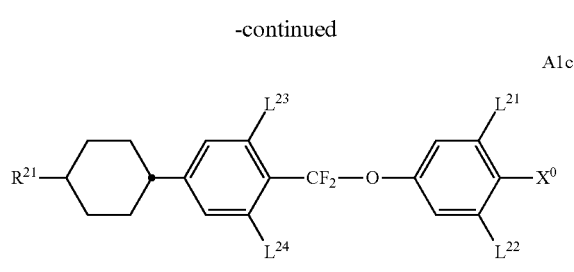

A1c

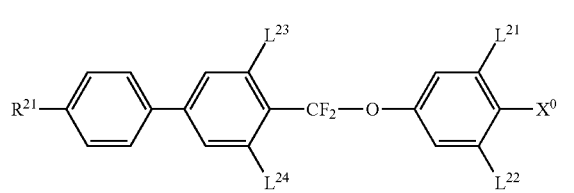

A1d

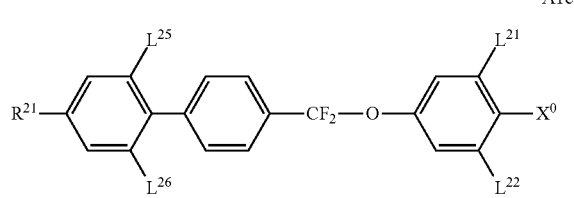

A1e

-continued

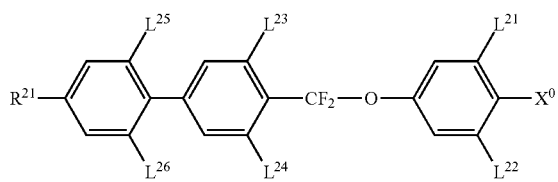

A1f in which $R^{21}$, $X^0$, $L^{21}$ and $L^{22}$ have the meaning given in formula $A^1$, $L^{23}$, $L^{24}$, $L^{25}$ and $L^{26}$ are each, independently of one another, H or F, and $X^0$ is preferably F.

Very particularly preferred compounds of formula A1 are selected from the group consisting of the following subformulae:

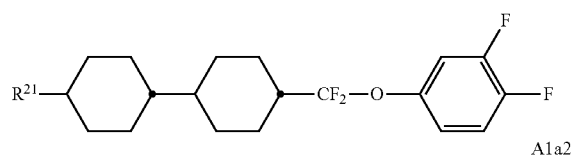

A1a1

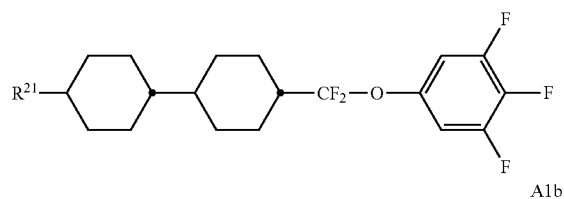

A1a2

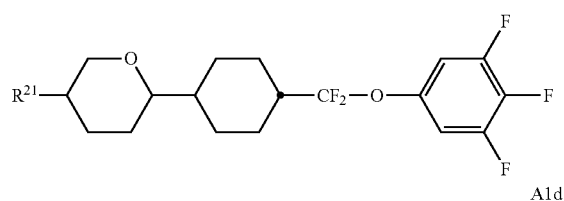

A1b1

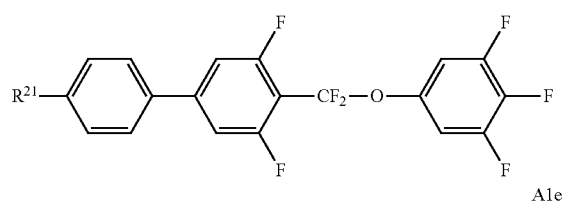

A1d1

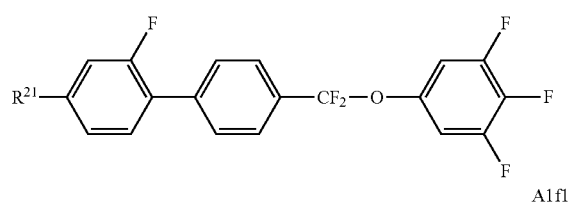

A1e1

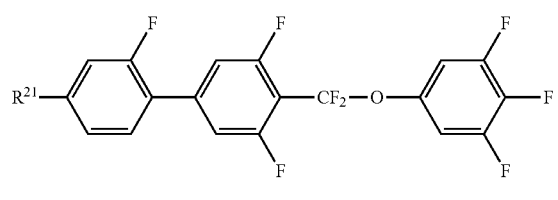

A1f1

In which $R^{21}$ is as defined in formula A1.

Particularly preferred compounds of formula A2 are selected from the group consisting of the following subformulae:

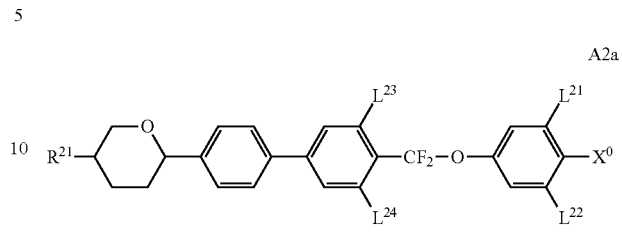

A2a

A2b

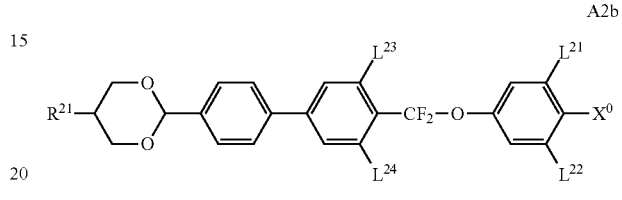

A2c

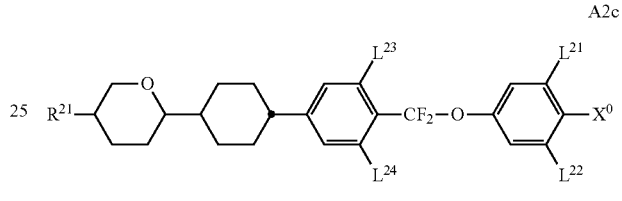

A2d

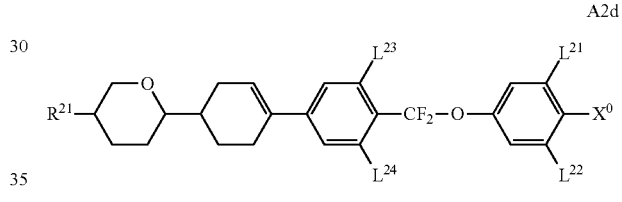

A2e

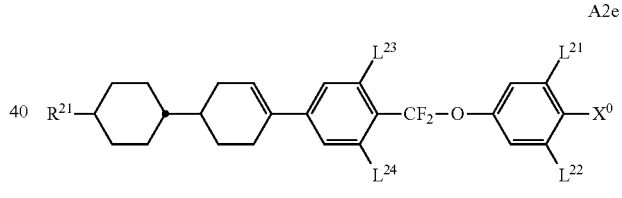

A2f

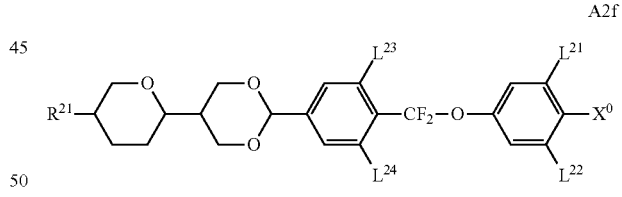

A2g

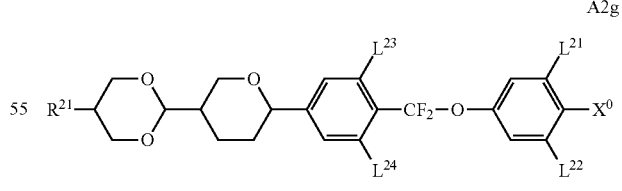

A2h

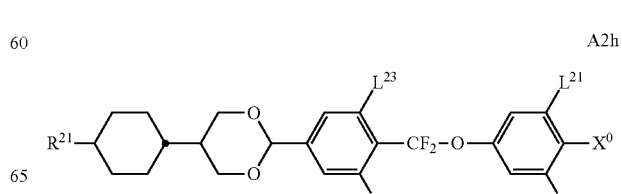

in which $R^{21}$, $X^0$, $L^{21}$ and $L^{22}$ have the meaning given in formula A2, $L^{23}$, $L^{24}$, $L^{25}$ and $L^{26}$ each, independently of one another, are H or F, and $X^0$ is preferably F.

Very particularly preferred compounds of formula A2 are selected from the group consisting of the following subformulae:

in which $R^{21}$ and $X^0$ are as defined in formula A2.

Particularly preferred compounds of formula A3 are selected from the group consisting of the following subformulae:

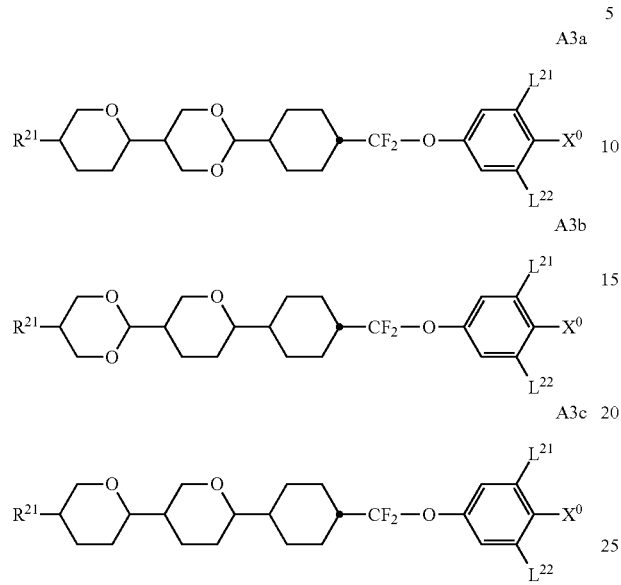

in which $R^{21}$, $X^0$, $L^{21}$ and $L^{22}$ have the meaning given in formula A3, and $X^0$ is preferably F.

Particularly preferred compounds of formula A4 are selected from the group consisting of the following subformulae:

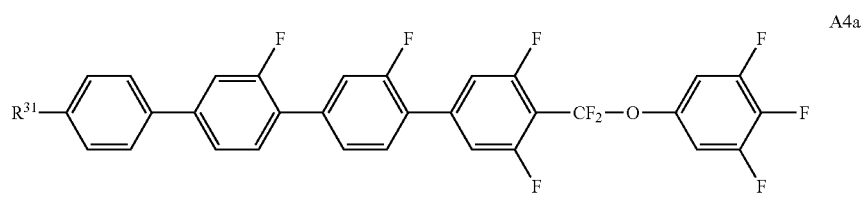

in which $R^{21}$ is as defined in formula A4.

Preferably component B) of the LC medium comprises one or more compounds of formula B selected from the group consisting of the following formulae:

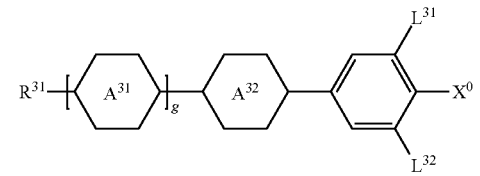

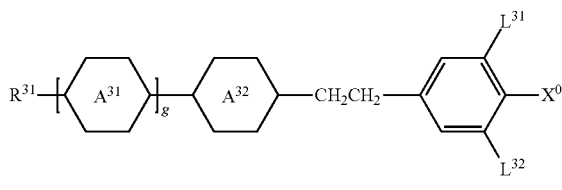

in which g, $A^{31}$, $A^{32}$, $R^{31}$, $X^0$, $L^{31}$ and $L^{32}$ have the meanings given in formula B, and $X^0$ is preferably F. Particularly preferred are compounds of formulae B1 and B2.

Particularly preferred compounds of formula B1 are selected from the group consisting of the following subformulae:

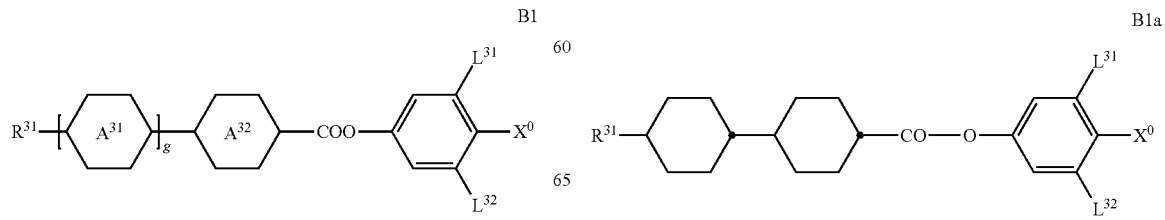

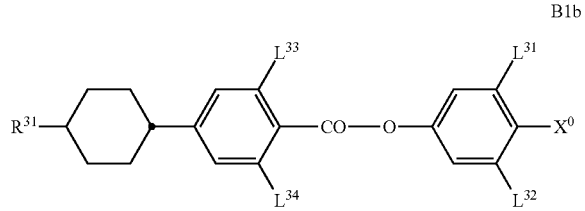
B1b in which $R^{31}$, $X^0$, $L^{31}$ and $L^{32}$ have the meaning given in formula B1, and $X^0$ is preferably F.

Very particularly preferred compounds of formula B1a are selected from the group consisting of the following subformulae:

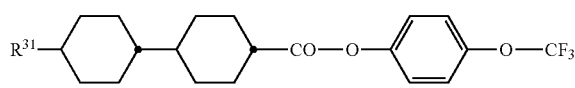
B1a1

B1a2

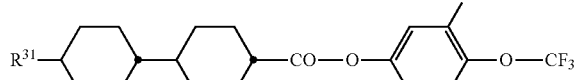
B1a3

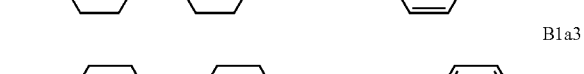
B1a4

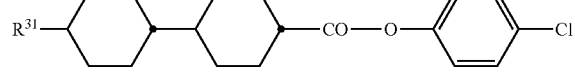
B1a5

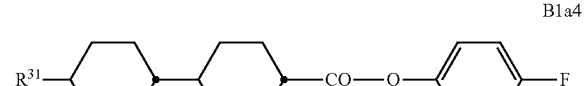
B1a6 in which $R^{31}$ is as defined in formula B1.

Very particularly preferred compounds of formula B1 b are selected from the group consisting of the following subformulae:

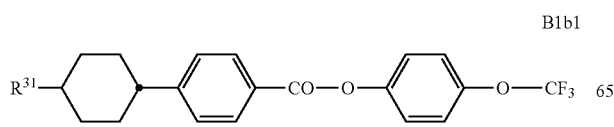
B1b1

B1b2

B1b3

B1b4 in which $R^{31}$ is as defined in formula B1.

Particularly preferred compounds of formula B2 are selected from the group consisting of the following subformulae:

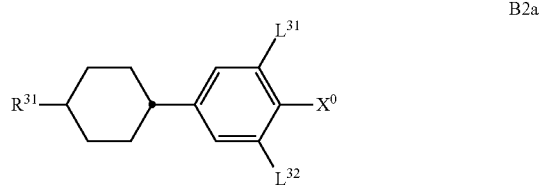
B2a

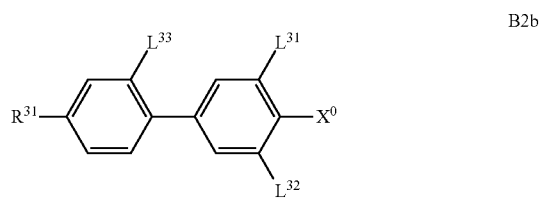
B2b

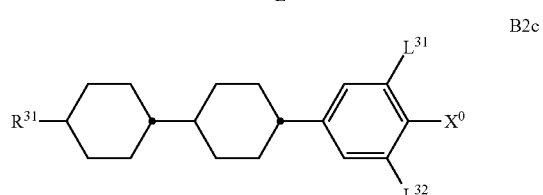
B2c

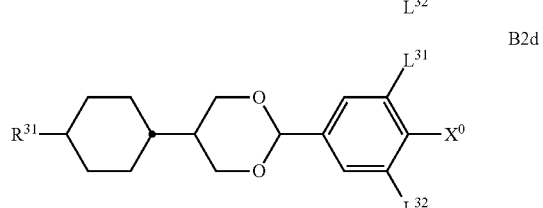
B2d

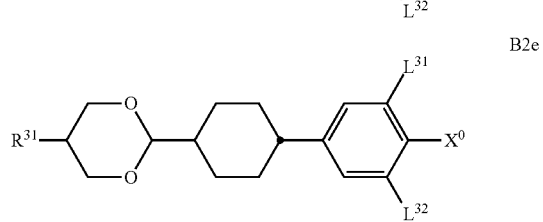
B2e

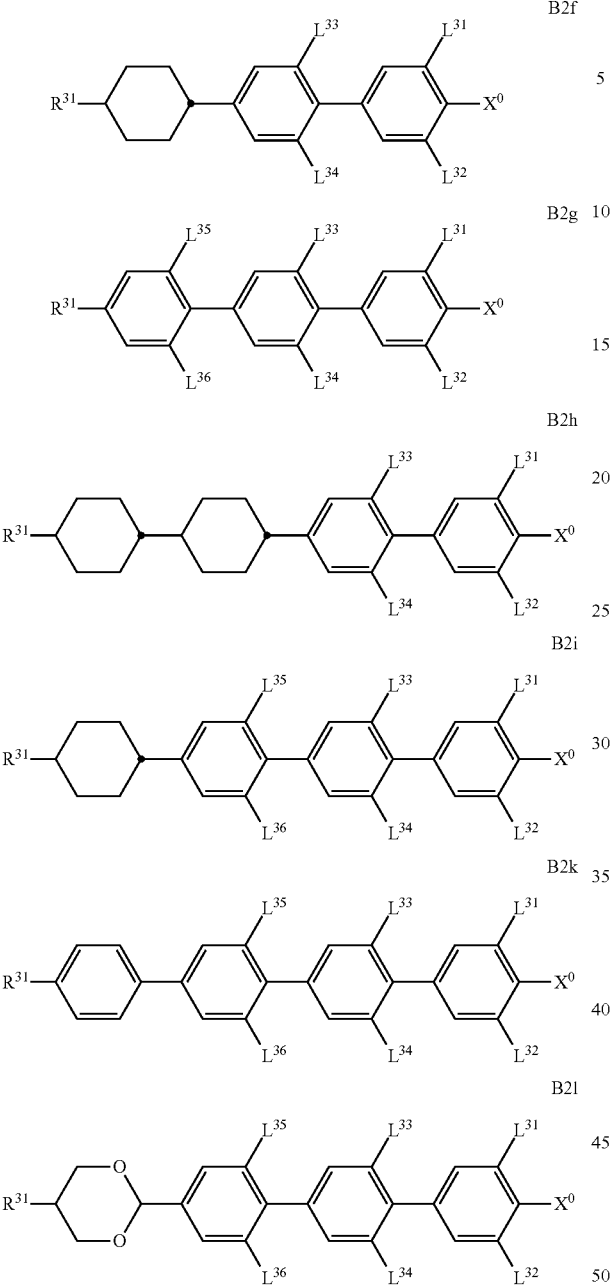

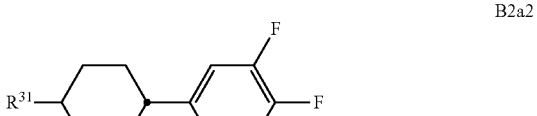

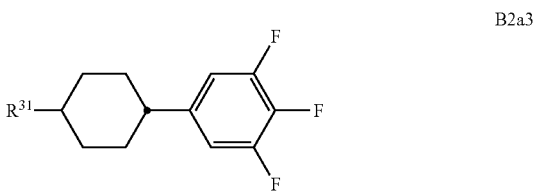

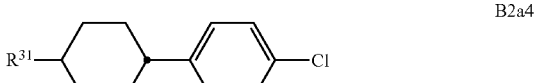

in which R³¹ is as defined in formula B2.

Very particularly preferred compounds of formula B2b are selected from the group consisting of the following subformulae

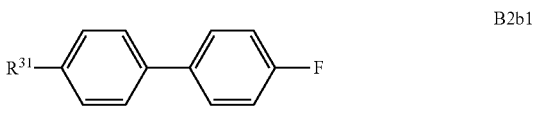

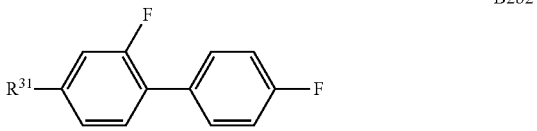

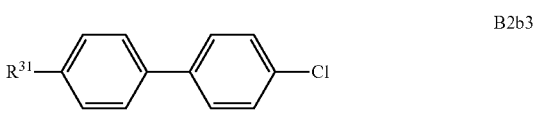

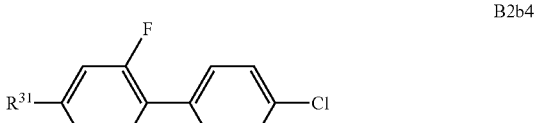

in which $R^{31}$ is as defined in formula B2.

in which $R^{31}$, $X^0$, $L^{31}$ and $L^{32}$ have the meaning given in formula B2, $L^{33}$, $L^{34}$, $L^{35}$ and $L^{36}$ are each, independently of one another, H or F, and $X^0$ is preferably F.

Very particularly preferred compounds of formula B2 are selected from the group consisting of the following subformulae:

Very particularly preferred compounds of formula B2c are selected from the group consisting of the following subformulae:

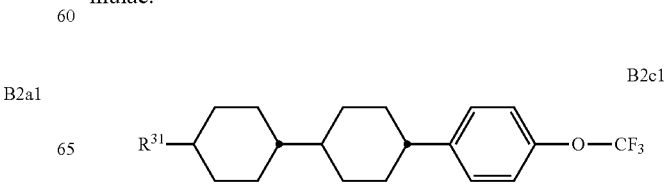

-continued

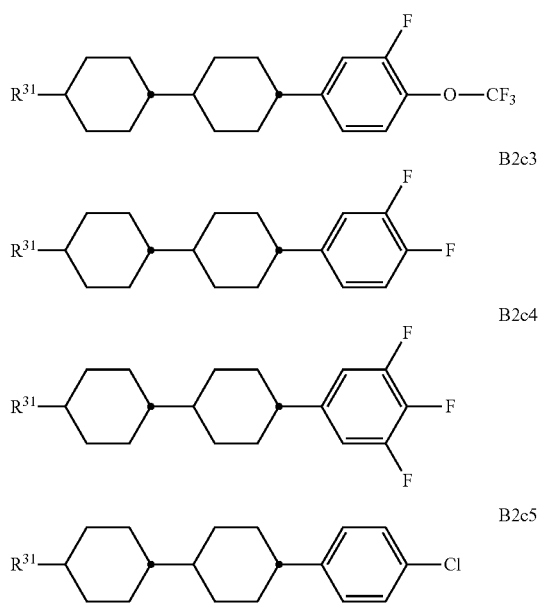

B2c2
B2c3
B2c4
B2c5 in which R$^{31}$ is as defined in formula B2.

Very particularly preferred compounds of formula B2d and B2e are selected from the group consisting of the following subformulae:

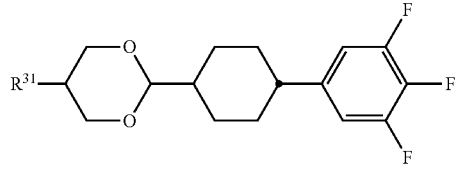

B2d1

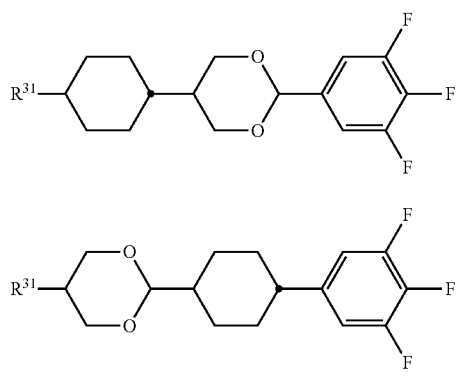

B2e1 in which R$^{31}$ is as defined in formula B2.

Very particularly preferred compounds of formula B2f are selected from the group consisting of the following subformulae:

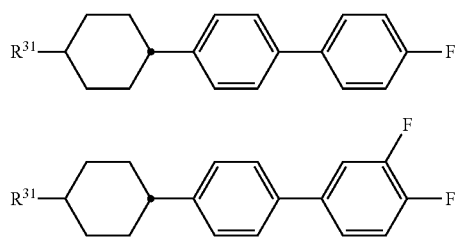

B2f1
B2f2

-continued

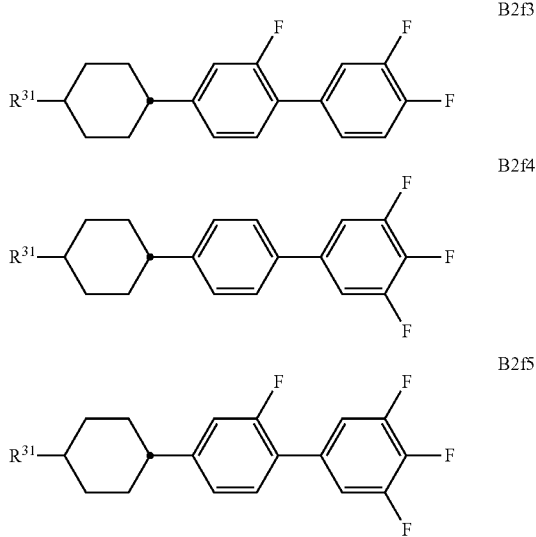

B2f3
B2f4
B2f5 in which R$^{31}$ is as defined in formula B2.

Very particularly preferred compounds of formula B2g are selected from the group consisting of the following subformulae:

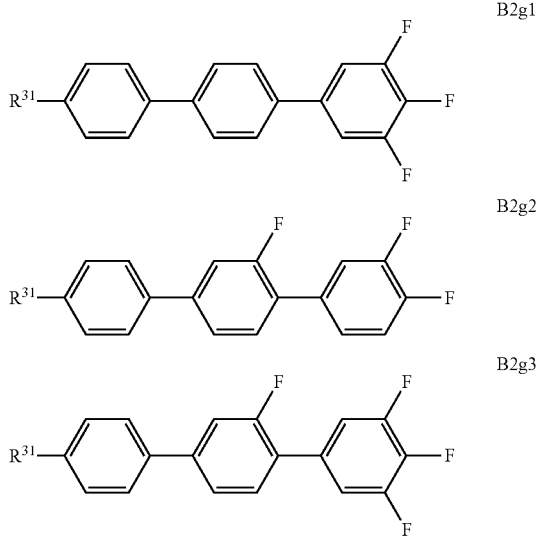

B2g1
B2g2
B2g3
B2g4
B2g5 in which R$^{31}$ is as defined in formula B2.

Very particularly preferred compounds of formula B2h are selected from the group consisting of the following subformulae:

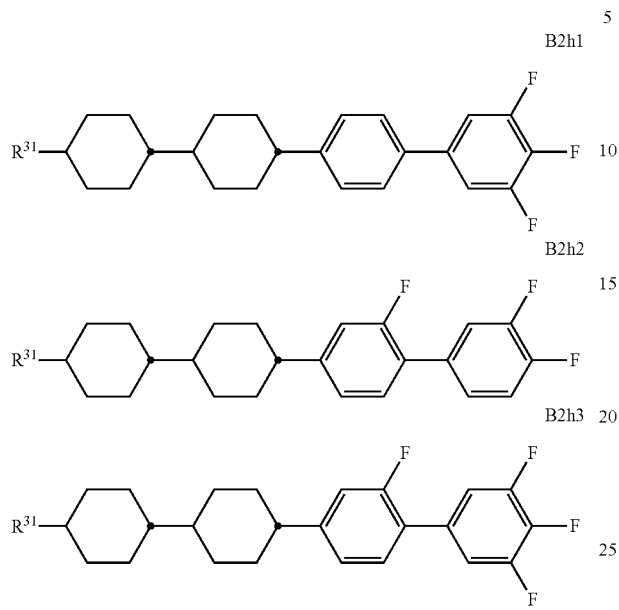

in which $R^{31}$ is as defined in formula B2.

Very particularly preferred compounds of formula B2i are selected from the group consisting of the following subformulae:

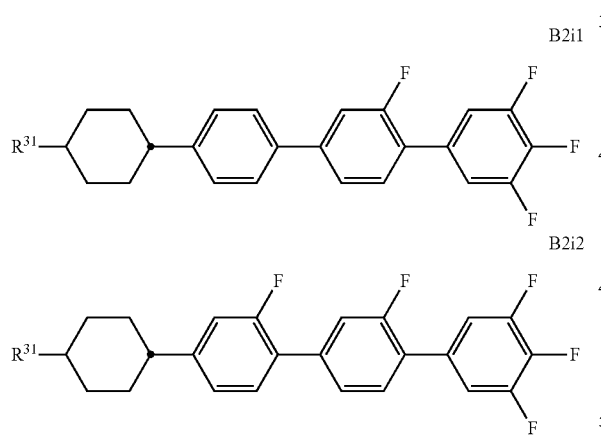

in which $R^{31}$ is as defined in formula B2.

Very particularly preferred compounds of formula B2k are selected from the group consisting of the following subformulae:

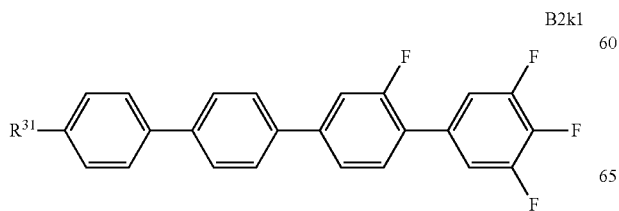

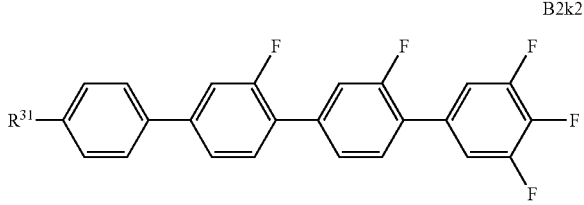

in which $R^{31}$ is as defined in formula B2.

Very particularly preferred compounds of formula B2l are selected from the group consisting of the following subformulae:

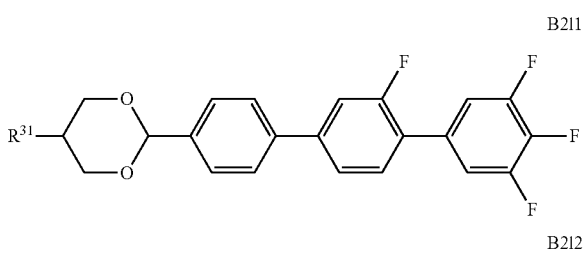

in which $R^{31}$ is as defined in formula B2.

Alternatively to, or in addition to, the compounds of formula B1 and/or B2 component B) of the LC medium may also comprise one or more compounds of formula B3 as defined above.

Particularly preferred compounds of formula B3 are selected from the group consisting of the following subformulae:

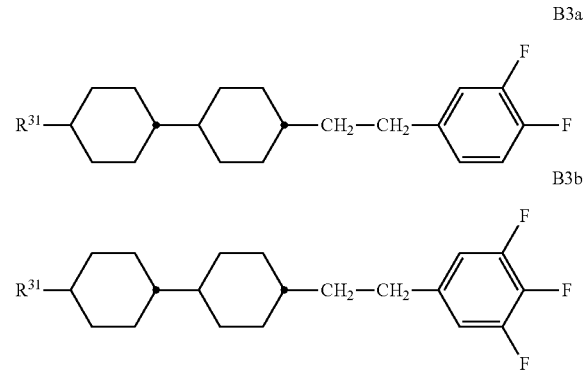

in which $R^{31}$ is as defined in formula B3.

Preferably component B) of the LC medium comprises, in addition to the compounds of formula A and/or B, one or more compounds of formula C

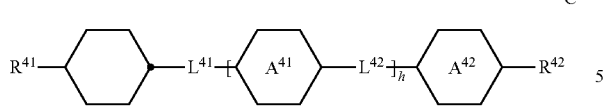

in which the individual radicals have the following meanings:

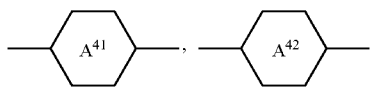

each, independently of one another, and on each occurrence, identically or differently

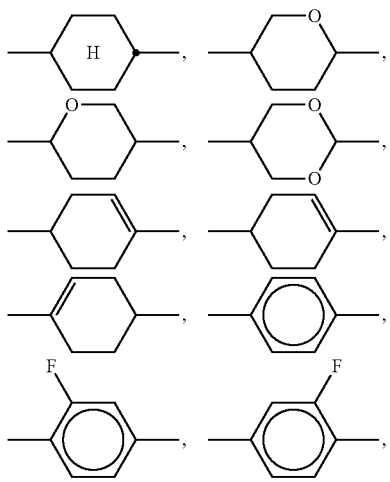

R⁴¹, R⁴² each, independently of one another, alkyl, alkoxy, oxaalkyl or alkoxyalkyl having 1 to 9 C atoms or alkenyl or alkenyloxy having 2 to 9 C atoms, all of which are optionally fluorinated, Z⁴¹, Z⁴² each, independently of one another, —CH₂CH₂—, —COO—, trans-CH=CH—, trans-CF=CF—, —CH₂O—, —CF₂O—, —C≡C— or a single bond, preferably a single bond, h 0, 1, 2 or 3.

In the compounds of formula C, R⁴¹ and R⁴² are preferably selected from straight-chain alkyl or alkoxy with 1, 2, 3, 4, 5 or 6 C atoms, and straight-chain alkenyl with 2, 3, 4, 5, 6 or 7 C atoms.

In the compounds of formula C, h is preferably 0, 1 or 2.

In the compounds of formula C, Z⁴¹ and Z⁴² are preferably selected from COO, trans-CH=CH and a single bond, very preferably from COO and a single bond.

Preferred compounds of formula C are selected from the group consisting of the following subformulae:

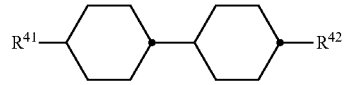

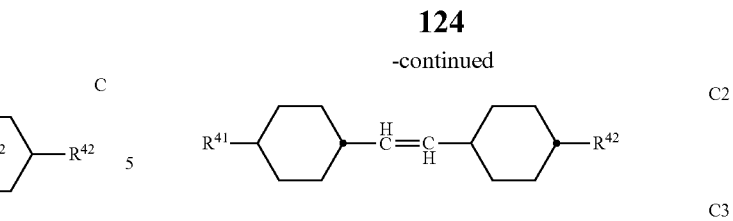

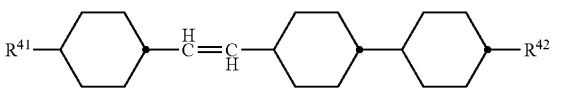

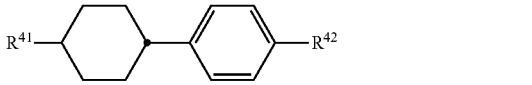

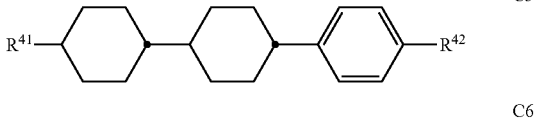

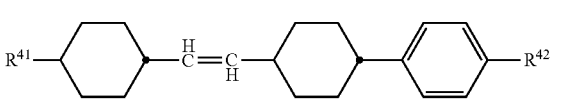

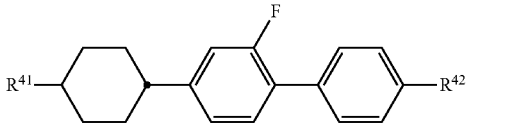

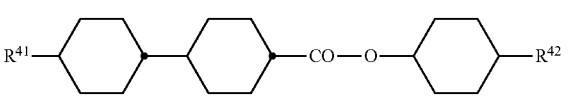

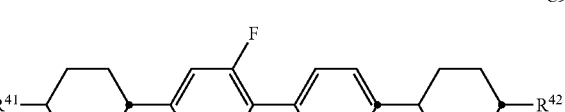

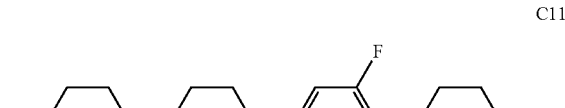

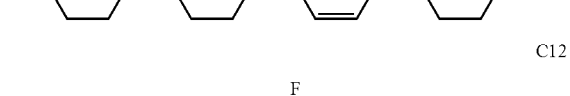

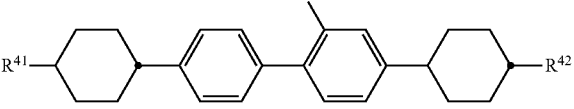

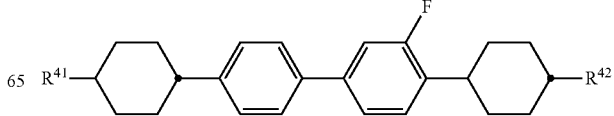

-continued

C14
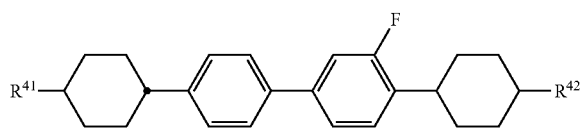

wherein $R^{41}$ and $R^{42}$ have the meanings given in formula C, and preferably denote each, independently of one another, alkyl, alkoxy, fluorinated alkyl or fluorinated alkoxy with 1 to 7 C atoms, or alkenyl, alkenyloxy, alkoxyalkyl or fluorinated alkenyl with 2 to 7 C atoms.

Further preferably component B) of the LC medium comprises, in addition to the compounds of formula A and/or B, one or more compounds of formula D D
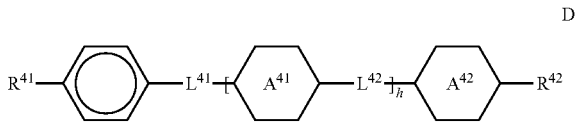

in which $A^{41}$, $A^{42}$, $Z^{41}$, $Z^{42}$, $R^{41}$, $R^{42}$ and h have the meanings given in formula C or one of the preferred meanings given above.

Preferred compounds of formula D are selected from the group consisting of the following subformulae:

D1
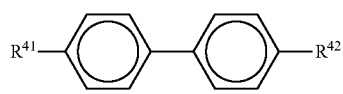

D2
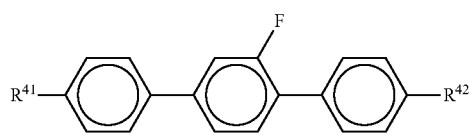

in which $R^{41}$ and $R^{42}$ have the meanings given in formula D and $R^{41}$ preferably denotes alkyl bedeutet, and in formula D1 $R^{42}$ preferably denotes alkenyl, particularly preferably —(CH$_2$)$_2$—CH=CH—CH$_3$, and in formula D2 $R^{42}$ preferably denotes alkyl, —(CH$_2$)$_2$—CH=CH$_2$ or —(CH$_2$)$_2$—CH=CH—CH$_3$.

Further preferably component B) of the LC medium comprises, in addition to the compounds of formula A and/or B, one or more compounds of formula E containing an alkenyl group E
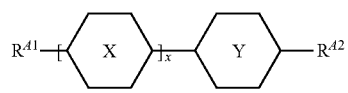

in which the individual radicals, on each occurrence identically or differently, each, independently of one another, have the following meaning:

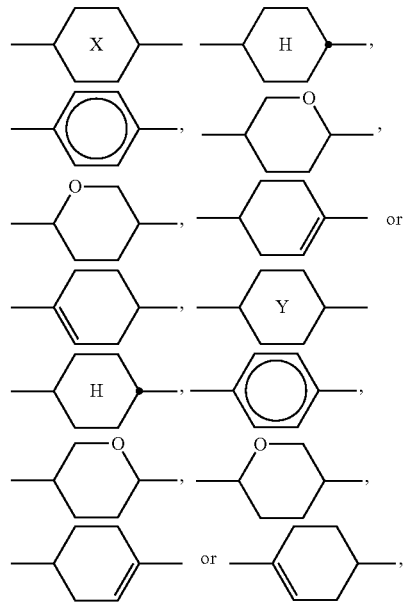

$R^{A1}$ alkenyl having 2 to 9 C atoms or, if at least one of the rings X, Y and Z denotes cyclohexenyl, also one of the meanings of $R^{A2}$, $R^{A2}$ alkyl having 1 to 12 C atoms, in which, in addition, one or two non-adjacent CH$_2$ groups may be replaced by —O—, —CH=CH—, —CO—, —OCO— or —COO— in such a way that O atoms are not linked directly to one another, x 1 or 2.

$R^{A2}$ is preferably straight-chain alkyl or alkoxy having 1 to 8 C atoms or straight-chain alkenyl having 2 to 7 C atoms.

Preferred compounds of formula E are selected from the following sub-formulae:

E1
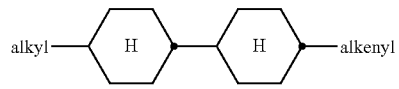

E2
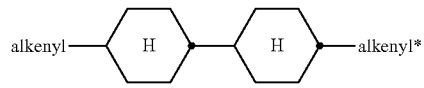

E3
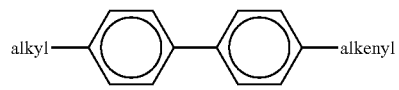

E4
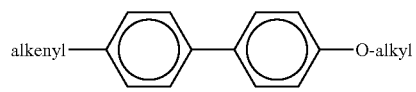

E5
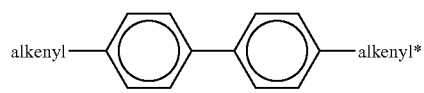

-continued

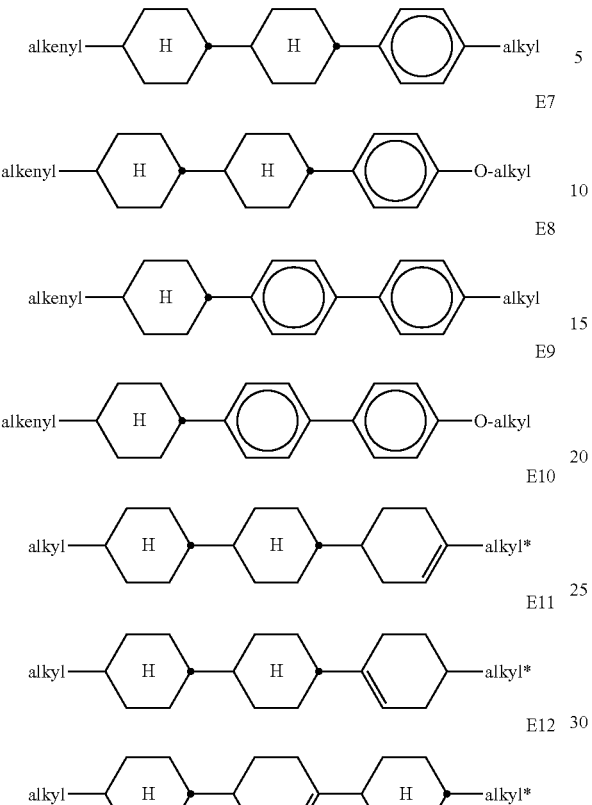

in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very preferred compounds of the formula E are selected from the following sub-formulae:

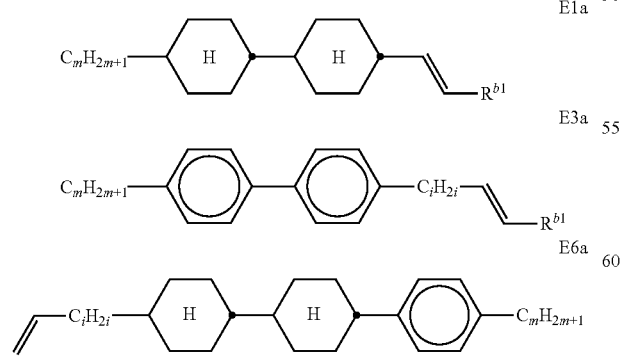

in which m denotes 1, 2, 3, 4, 5 or 6, i denotes 0, 1, 2 or 3, and $R^{b1}$ denotes H, $CH_3$ or $C_2H_5$.

Very particularly preferred compounds of the formula E are selected from the following sub-formulae:

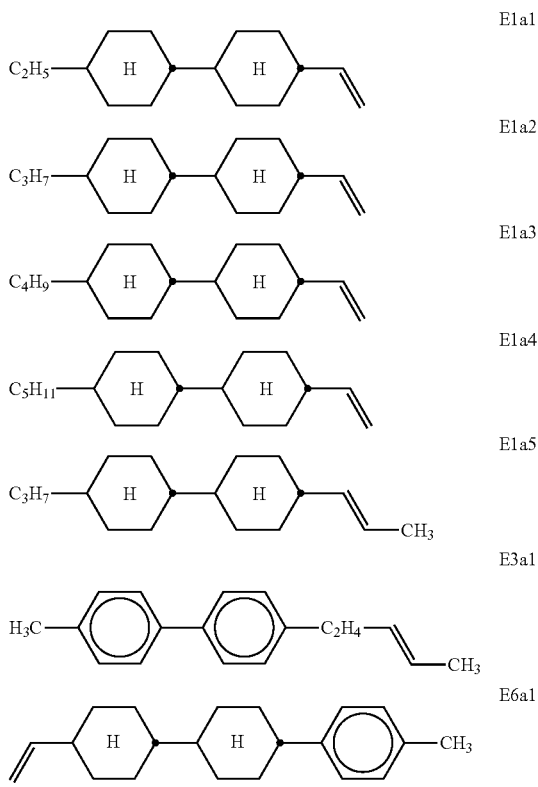

Most preferred are compounds of formula E1a2, E1a5, E3a1 and E6a1.

Further preferably component B) of the LC medium comprises, in addition to the compounds of formula A and/or B, one or more compounds of formula F

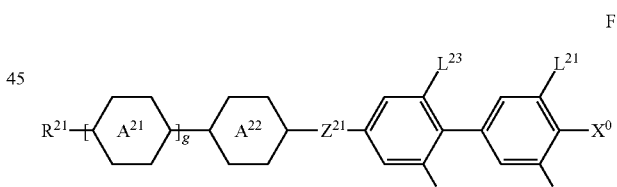

in which the individual radicals have, independently of each other and on each occurrence identically or differently, the following meanings:

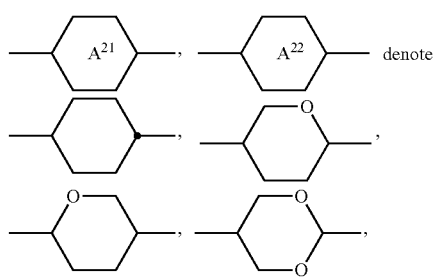

-continued

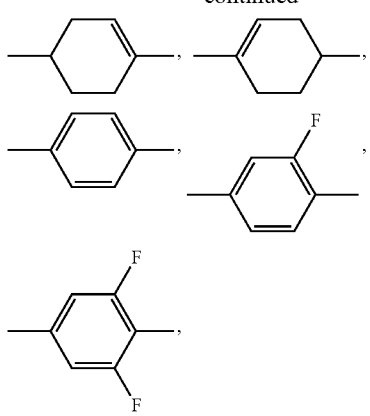

$R^{21}$, $R^{31}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $X^0$ F, Cl, halogenated alkyl or alkoxy having 1 to 6 C atoms or halogenated alkenyl or alkenyloxy having 2 to 6 C atoms, $Z^{21}$ —$CH_2CH_2$—, —$CF_2CF_2$—, —COO—, trans-CH=CH—, trans-CF=CF—, —$CH_2O$—, —$CF_2O$—, —C≡C— or a single bond, preferably —$CF_2O$—, $L^{21}$, $L^{22}$, $L^{23}$, $L^{24}$ each, independently of one another, H or F, g 0, 1, 2 or 3.

Particularly preferred compounds of formula F are selected from the group consisting of the following formulae:

F1

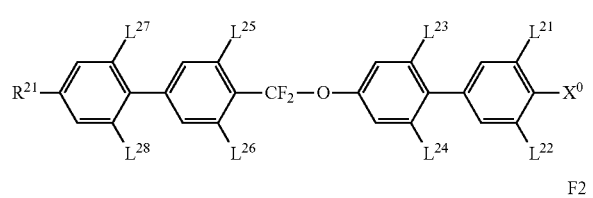

F2

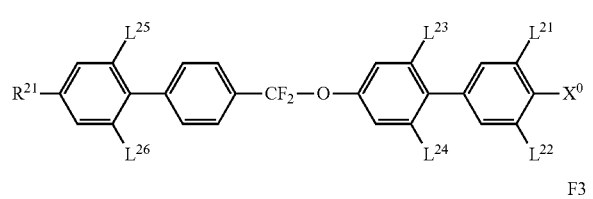

F3

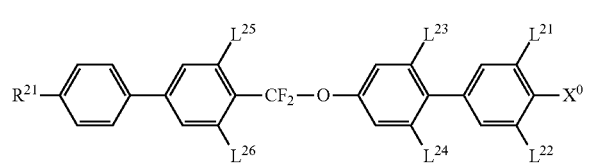

in which $R^{21}$, $X^0$, $L^{21}$ and $L^{22}$ have the meaning given in formula F, $L^{25}$ and $L^{26}$ are each, independently of one another, H or F, and $X^0$ is preferably F.

Very particularly preferred compounds of formula F1-F3 are selected from the group consisting of the following subformulae:

F1a

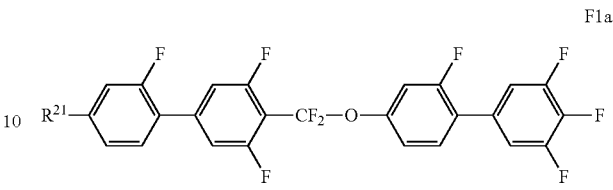

F1b

F2a

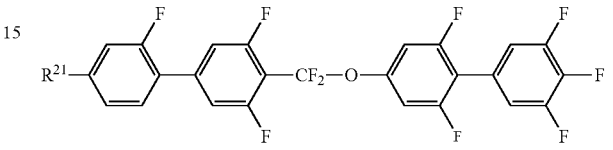

F2b

F3a

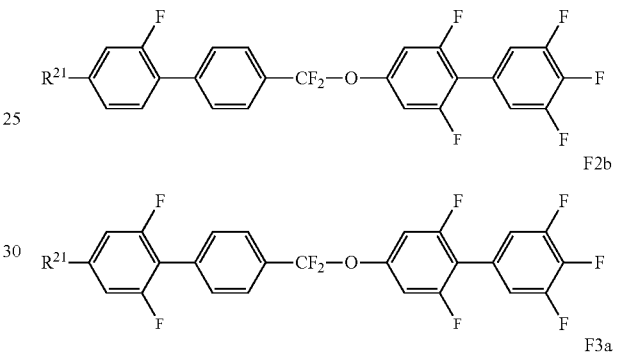

F3b

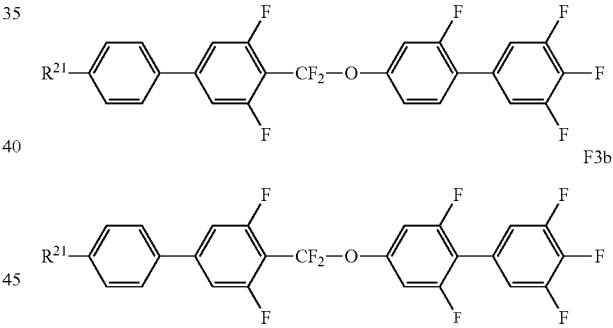

In which $R^{21}$ is as defined in formula F1.

The concentration of the compounds of formula A and B in the LC host mixture is preferably from 2 to 60%, very preferably from 3 to 45%, most preferably from 4 to 35%.

The concentration of the compounds of formula C and D in the LC host mixture is preferably from 2 to 70%, very preferably from 5 to 65%, most preferably from 10 to 60%.

The concentration of the compounds of formula E in the LC host mixture is preferably from 5 to 50%, very preferably from 5 to 35%.

The concentration of the compounds of formula F in the LC host mixture is preferably from 2 to 30%, very preferably from 5 to 20%.

Further preferred embodiments of this second preferred embodiment of the present invention are listed below, including any combination thereof.

2a) The LC host mixture comprises one or more compounds of formula A and/or B with high positive dielectric anisotropy, preferably with Δϵ>15.

2b) The LC host mixture comprises one or more compounds selected from the group consisting of formulae A1a2, A1b1, A1 d1, A1 f1, A2a1, A2h1, A2l2, A2k1, B2h3, B2l1, F1a. The proportion of these compounds in the LC host mixture is preferably from 4 to 40%, very preferably from 5 to 35%.

2c) The LC host mixture comprises one or more compounds selected from the group consisting of formulae B2c1, B2c4, B2f4, C14. The proportion of these compounds in the LC host mixture is preferably from 4 to 40%, very preferably from 5 to 35%.

2d) The LC host mixture comprises one or more compounds selected from the group consisting of formulae C3, C4, C5, C9 and D2. The proportion of these compounds in the LC host mixture is preferably from 8 to 70%, very preferably from 10 to 60%.

2e) The LC host mixture comprises one or more compounds selected from the group consisting of formulae G1, G2 and G5, preferably G1a, G2a and G5a. The proportion of these compounds in the LC host mixture is preferably from 4 to 40%, very preferably from 5 to 35%.

2f) The LC host mixture comprises one or more compounds selected from the group consisting of formulae E1, E3 and E6, preferably E1a, E3a and E6a, very preferably E1a2, E1a5, E3a1 and E6a1. The proportion of these compounds in the LC host mixture is preferably from 5 to 60%, very preferably from 10 to 50%.

The combination of compounds of the preferred embodiments mentioned above with the polymerized compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The LC media and LC host mixtures of the present invention preferably have a nematic phase range of at least 80 K, particularly preferably at least 100 K, and a rotational viscosity ≤250 mPa·s, preferably ≤200 mPa·s, at 20° C.

In the VA-type displays according to the invention, the molecules in the layer of the LC medium in the switched-off state are aligned perpendicular to the electrode surfaces (homeotropically) or have a a tilted homeotropic alignment. On application of an electrical voltage to the electrodes, a realignment of the LC molecules takes place with the longitudinal molecular axes parallel to the electrode surfaces.

LC media according to the invention based on compounds with negative dielectric anisotropy according to the first preferred embodiment, in particular for use in displays of the VA, UB-FFS, PS-VA and PS-UB-FFS type, have a negative dielectric anisotropy $\Delta\epsilon$, preferably from −0.5 to −10, in particular from −2.5 to −7.5, at 20° C. and 1 kHz.

The birefringence $\Delta n$ in LC media according to the invention for use in displays of the VA, UB-FFS, PS-VA and PS-UB-FFS type is preferably below 0.16, particularly preferably from 0.06 to 0.14, very particularly preferably from 0.07 to 0.12.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention for use in displays of the OCB, TN, IPS, posi-VA, FFS, PS-OCB, PS-TN, PS-IPS, PS-posi-VA and PS-FFS type are preferably those based on compounds with positive dielectric anisotropy according to the second preferred embodiment, and preferably have a positive dielectric anisotropy $\Delta\epsilon$ from +4 to +17 at 20° C. and 1 kHz.

The birefringence $\Delta n$ in LC media according to the invention for use in displays of the OCB and PS-OCB type is preferably from 0.14 to 0.22, particularly preferably from 0.16 to 0.22.

The birefringence $\Delta n$ in LC media according to the invention for use in displays of the TN, posi-VA, IPS, FFS, PS-TN, PS-posi-VA, PS-IPS and PS-FFS-type is preferably from 0.07 to 0.15, particularly preferably from 0.08 to 0.13.

LC media according to the invention, based on compounds with positive dielectric anisotropy according to the second preferred embodiment, for use in displays of the TN, posi-VA, IPS, FFS, PS-TN, PS-posi-VA, PS-IPS and PS-FFS-type, preferably have a positive dielectric anisotropy $\Delta\epsilon$ from +2 to +30, particularly preferably from +3 to +20, at 20° C. and 1 kHz.

The LC media according to the invention may also comprise further additives which are known to the person skilled in the art and are described in the literature, such as, for example, polymerization initiators, inhibitors, stabilizers, surface-active substances or chiral dopants. These may be polymerizable or non-polymerizable. Polymerizable additives are accordingly ascribed to the polymerizable component or component A). Non-polymerizable additives are accordingly ascribed to the non-polymerizable component or component B).

In a preferred embodiment the LC media contain one or more chiral dopants, preferably in a concentration from 0.01 to 1%, very preferably from 0.05 to 0.5%. The chiral dopants are preferably selected from the group consisting of compounds from Table B below, very preferably from the group consisting of R- or S-1011, R- or S-2011, R- or S-3011, R- or S-4011, and R- or S-5011.

In another preferred embodiment the LC media contain a racemate of one or more chiral dopants, which are preferably selected from the chiral dopants mentioned in the previous paragraph.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutyl-ammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerizable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

In a preferred embodiment the process of stabilization of the LC media according to the present invention comprises mixing one or more of the above-mentioned compounds with one or more stabilizers of formula I, and optionally with further liquid crystalline compounds and/or additives. In a particularly preferred embodiment, the desired amount of the components used in lesser amount is dissolved in the components making up the principal constituent.

When using a compound of formula I as stabilizers, it is further preferred to add it to the LC mixture under inert atmosphere, preferably under nitrogen or argon.

Advantageously, the mixing process is performed at elevated temperature, preferably above 20° C. and below 120° C., more preferably above 30° C. and below 100° C., most preferably above 40° C. and below 80° C.

It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

The stabilization process according to the present invention is particularly useful for LC media exposed to an LCD backlight, typically during the operation of an LC display. Such backlights are preferably cold cathode fluorescent lamps (CCFL) or LED (light-emitting diode) light sources. Advantage of these types of light source is the fact that they do not emit UV light or if so, to a negligible extent. Hence, the light stress the LC mixture is exposed to is comparatively small, because of the absence of UV light which could trigger photochemical reactions.

The stabilizers of formula I are particularly effective when exposed to light with a very small or preferably no portion in the UV region of the spectrum and when used in concentrations of 1000 ppm in the LC mixtures.

The present invention further relates to LC displays comprising LC mixtures described above and below. The liquid crystal display panel includes first and second substrates, an active region on the first substrate, the active region including a plurality of thin film transistors and pixel electrodes, a sealing region along a periphery of the active region and along a corresponding region of the second substrate, sealant in the sealing region, the sealant attaching the first substrate and the second substrate to one another and maintaining a gap therebetween, and a liquid crystal layer within the gap and on the active region side of the sealant.

In another aspect of the present invention, a method of manufacturing an LCD panel includes forming a plurality of pixel electrodes in an active region on a first substrate, applying UV-type hardening sealant on a sealing region positioned along a periphery of the active region, attaching the first and second substrates to each other, and irradiating UV-rays to the sealant to harden the sealant.

In yet another aspect of the present invention, a method of manufacturing an LCD panel includes forming an UV-type hardening sealant in a first sealing region of a first substrate, and dropping liquid crystal on a surface of the first substrate. The first and second substrates are attached to each other at the first and second sealing regions and UV-rays are used to harden the sealant.

In a preferred embodiment according to the present invention, the active area of the display, i.e. the region of the display that contains switchable LC molecules, is during the LC display manufacturing process not exposed to UV light, at least not exposed to UV light except for the UV portion of ambient light, and preferably shielded from UV light. For example, when hardening a UV-type hardening sealant of the panel, the active region, i.e. the part of the display panel inside the frame used for displaying information, is preferably covered by a shadow mask.

In another preferred embodiment of the present invention, the LC display manufacturing process does not include a step of polymerizing the polymerizable compounds contained in the LC medium, for example by exposing the LC medium to heat or actinic radiation as applied in the process of manufacturing an PSA display.

It goes without saying to the person skilled in the art that the LC media according to the invention may also comprise compounds in which, for example, H, N, O, Cl, F have been replaced by the corresponding isotopes like deuterium etc.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 15003124.3, filed Oct. 30, 2015, are incorporated by reference herein.

Throughout the patent application and in the working examples, the structures of the liquid-crystal compounds are indicated by means of acronyms. Unless indicated otherwise, the transformation into chemical formulae takes place in accordance with Tables I-III. All radicals $C_nH_{2n+1}$, $C_mH_{2m+1}$, $C_nH_{2n}$, $C_mH_{2m}$ and $C_kH_{2k}$ are straight-chain alkyl radicals or alkenyl radicals respectively, in each case having n, m or k C atoms; n and m each, independently of one another, denote 1, 2, 3, 4, 5, 6, 7, 8, 9, 10, 11 or 12, preferably 1, 2, 3, 4, 5 or 6, and k is 0, 1, 2, 3, 4, 5 or 6. In Table I the ring elements of the respective compound are coded, in Table II the bridging members are listed and in Table III the meanings of the symbols for the left-hand and right-hand side chains of the compounds are indicated.

TABLE I

Ring elements

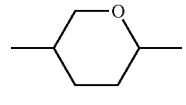

A

TABLE I-continued
Ring elements
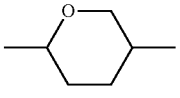
AI
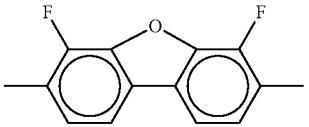
B
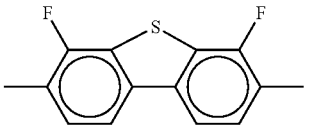
B(S)
C
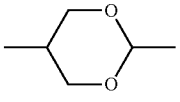
D
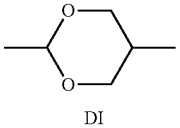
DI
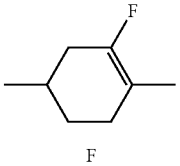
F
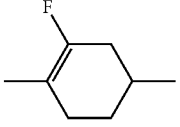
FI
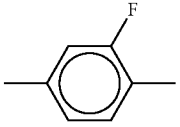
G
TABLE I-continued
Ring elements
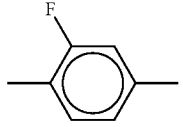
GI
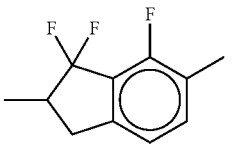
K
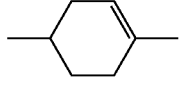
L
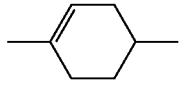
LI
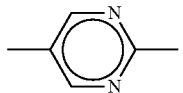
M
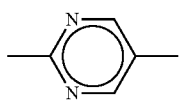
MI
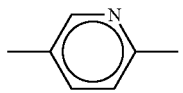
N TABLE I-continued Ring elements

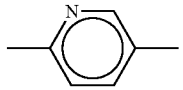

N1

P

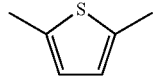

S

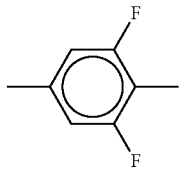

U

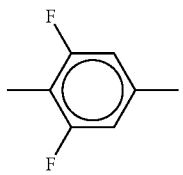

UI

TABLE I-continued

Ring elements

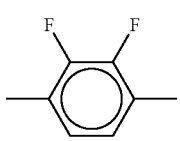

Y

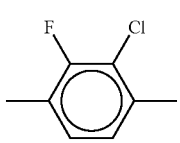

Y(F,Cl)

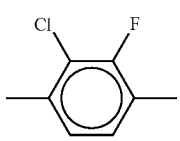

Y(Cl,F)

TABLE II

| | Bridging members | | |
|---|---|---|---|
| E | —CH$_2$CH$_2$— | | |
| V | —CH=CH— | | |
| T | —C≡C— | | |
| W | —CF$_2$CF$_2$— | | |
| Z | —COO— | ZI | —OCO— |
| O | —CH$_2$O— | OI | —OCH$_2$— |
| Q | —CF$_2$O— | QI | —OCF$_2$— |

TABLE III

Side chains

| | Left-hand side chain | | Right-hand side chain |
|---|---|---|---|
| n- | C$_n$H$_{2n+1}$— | -n | —C$_n$H$_{2n+1}$ |
| nO- | C$_n$H$_{2n+1}$—O— | -On | —O—C$_n$H$_{2n+1}$ |
| V- | CH$_2$=CH— | -V | —CH=CH$_2$ |
| nV- | C$_n$H$_{2n+1}$—CH=CH— | -nV | —C$_n$H$_{2n}$—CH=CH$_2$ |
| Vn- | CH$_2$=CH—C$_n$H$_{2n}$— | -Vn | —CH=CH—C$_n$H$_{2n+1}$ |
| nVm- | C$_n$H$_{2n+1}$—CH=CH—C$_m$H$_{2m}$— | -nVm | —C$_n$H$_{2n}$—CH=CH—C$_m$H$_{2m+1}$ |
| N- | N≡C— | -N | —C≡N |
| F- | F— | -F | —F |
| Cl- | Cl— | -Cl | —Cl |
| M- | CFH$_2$— | -M | —CFH$_2$ |
| D- | CF$_2$H— | -D | —CF$_2$H |
| T- | CF$_3$— | -T | —CF$_3$ |
| MO- | CFH$_2$O— | -OM | —OCFH$_2$ |
| DO- | CF$_2$HO— | -OD | —OCF$_2$H |
| TO- | CF$_3$O— | -OT | —OCF$_3$ |
| T- | CF$_3$— | -T | —CF$_3$ |
| A- | H—C≡C— | -A | —C≡C—H |
| FXO- | CF$_2$=CHO— | -OXF | —OCH=CF$_2$ |

Preferred mixture components are shown in Tables A1 and A2 below. The compounds shown in Table A1 are especially suitable for use in LC mixtures with positive dielectric anisotropy. The compounds shown in Table A2 are especially suitable for use in LC mixtures with negative dielectric anisotropy.
TABLE A1
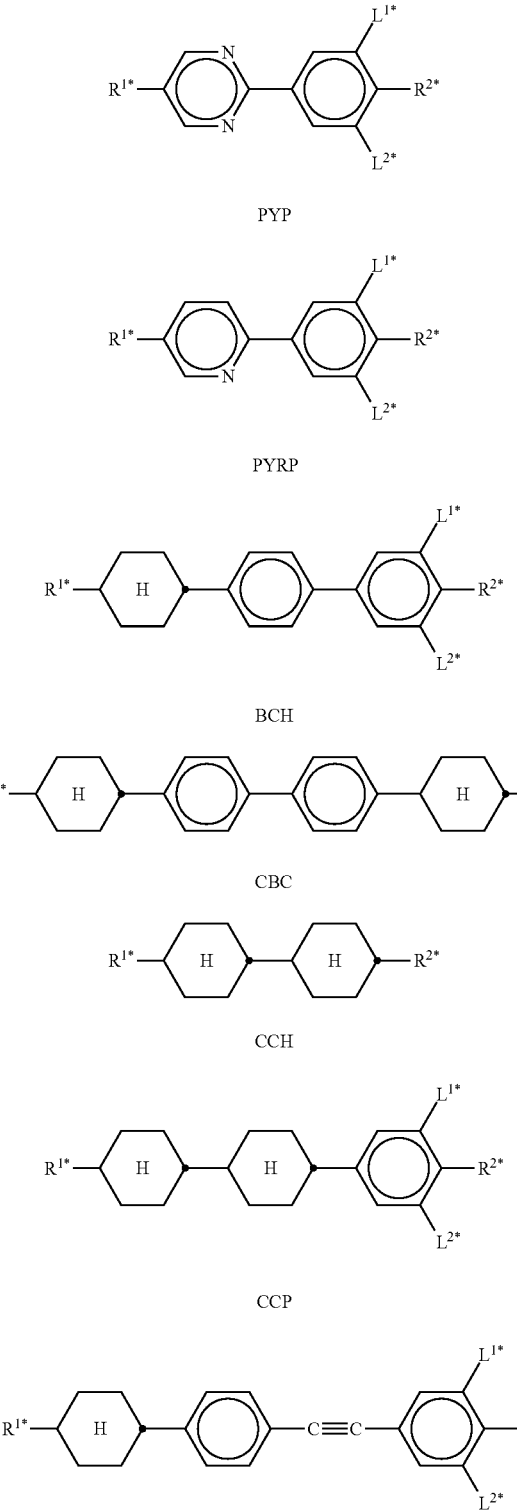
PYP
PYRP
BCH
CBC
CCH
CCP
CPTP TABLE A1-continued
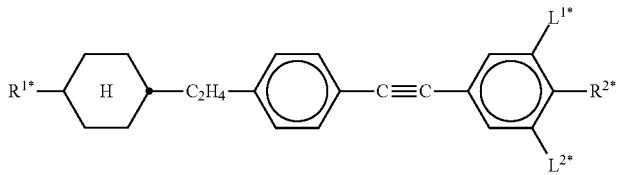
CEPTP
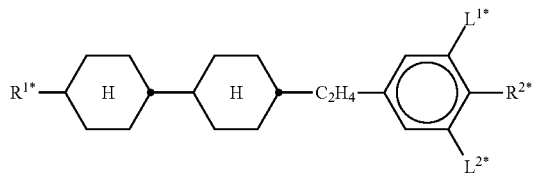
ECCP
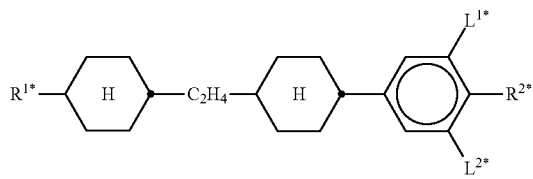
CECP
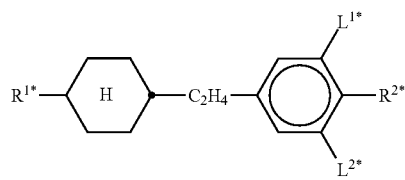
EPCH
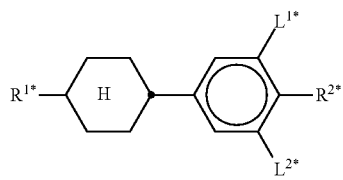
PCH
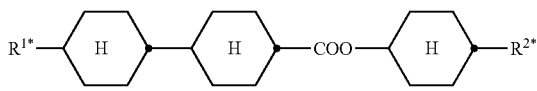
CH
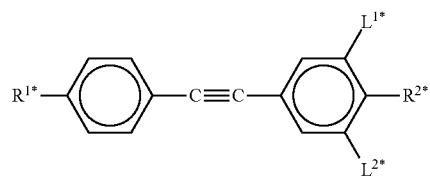
PTP TABLE A1-continued
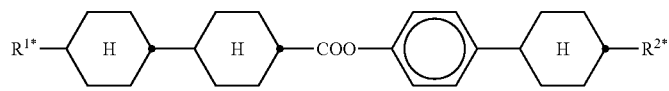
CCPC
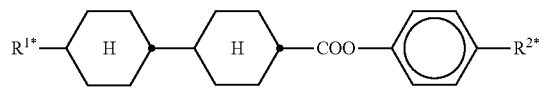
CP
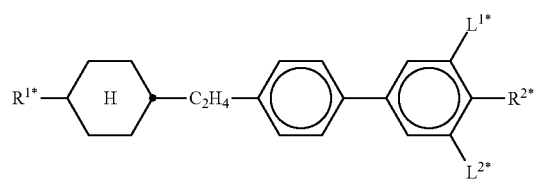
BECH
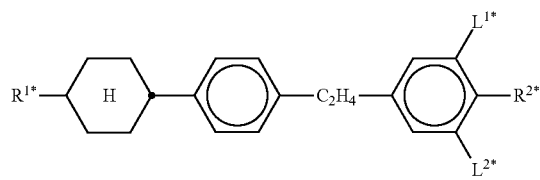
EBCH
CPC
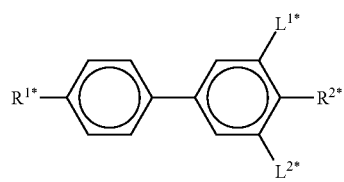
B
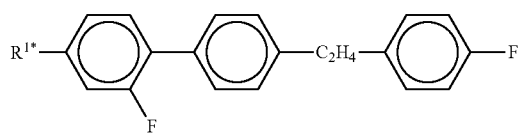
FET-nF
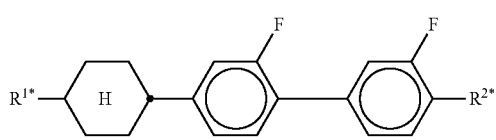
CGG TABLE A1-continued
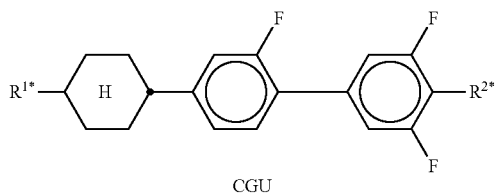
CGU
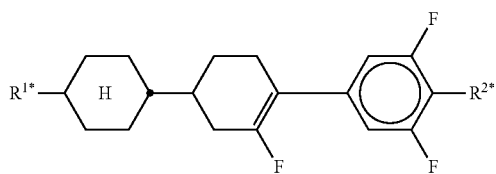
CFU
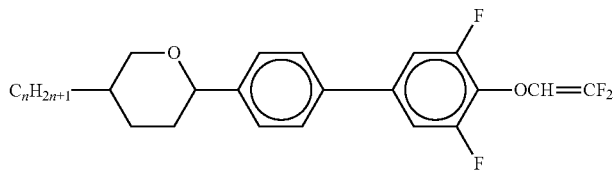
APU-n-OXF
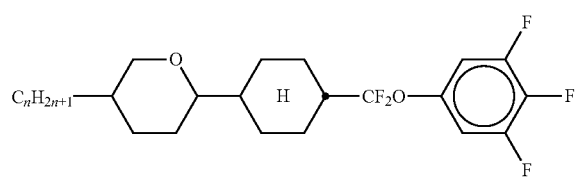
ACQU-n-F
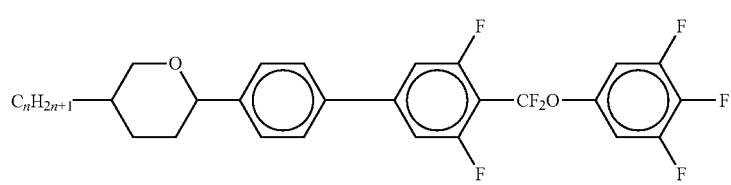
APUQU-n-F
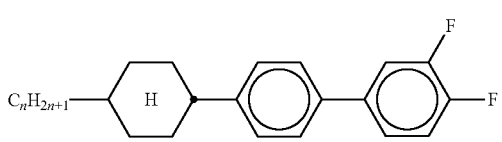
BCH-nF.F
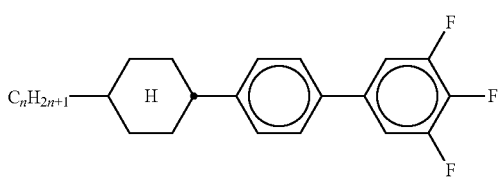
BCH-nF.F.F TABLE A1-continued
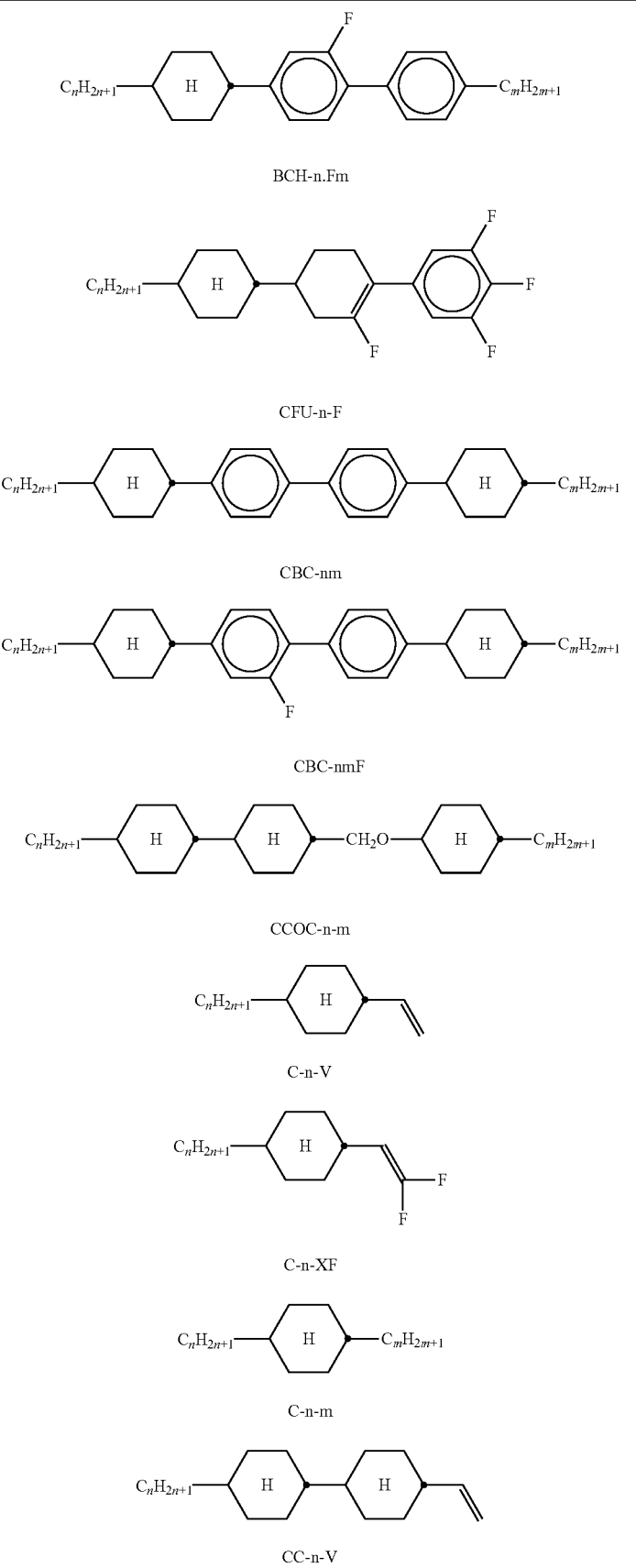

TABLE A1-continued
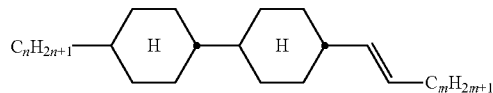
CC-n-Vm
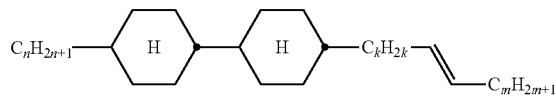
CC-n-kVm
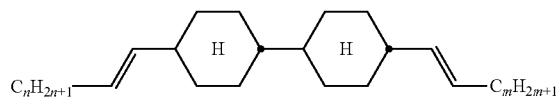
CC-nV-Vm
CCP-nV-m
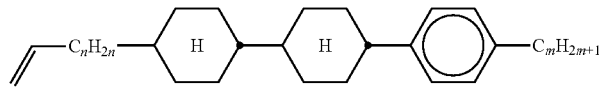
CCP-Vn-m
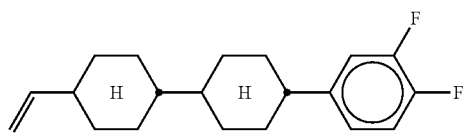
CCG-V-F
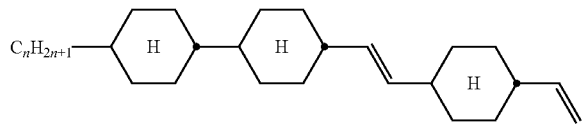
CCVC-n-V
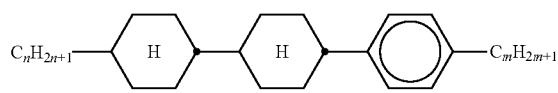
CCP-n-m
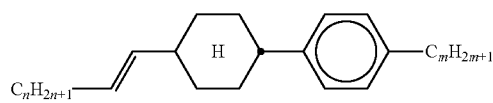
CP-nV-m
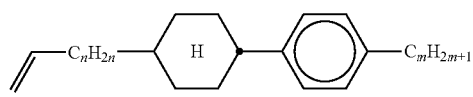
CP-Vn-m TABLE A1-continued
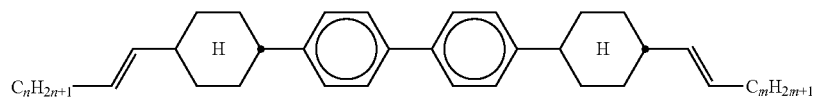
CPPC-nV-Vm
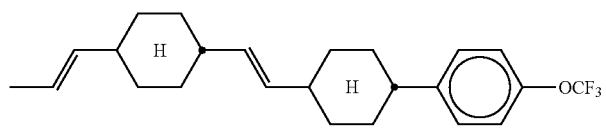
CVCP-1V-OT
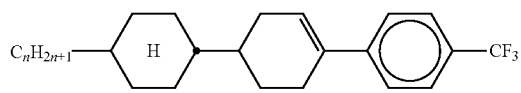
CLP-n-T
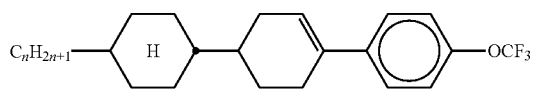
CLP-n-OT
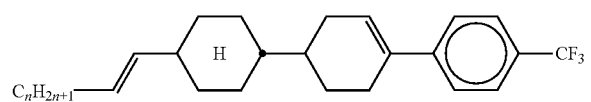
CLP-nV-T
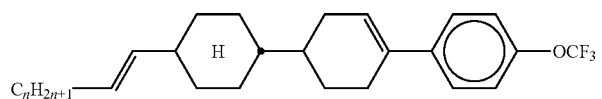
CLP-nV-OT
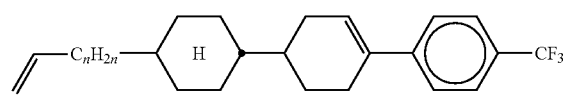
CLP-Vn-T
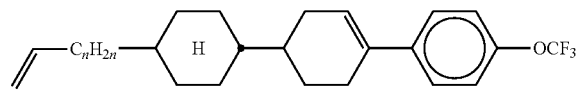
CLP-Vn-OT
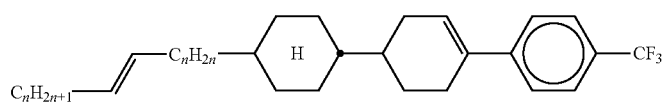
CLP-nVm-T TABLE A1-continued
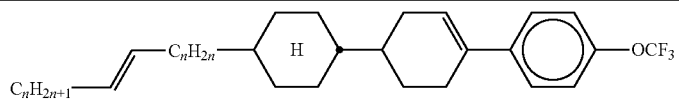
CLP-nVm-OT
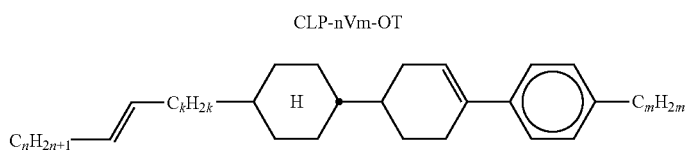
CLP-nVk-m
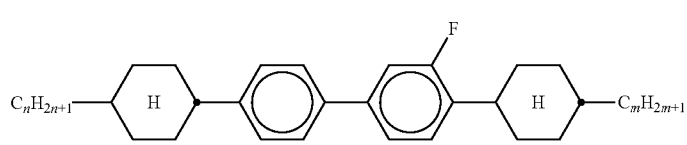
CPGP-n-m
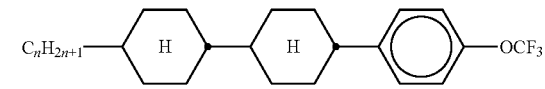
CCP-nOCF₃
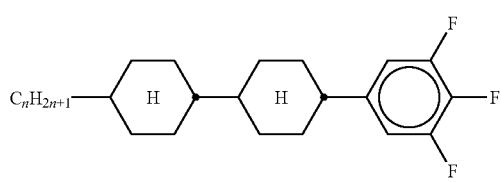
CCP-nF.F.F
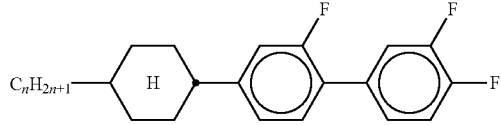
CGG-n-F
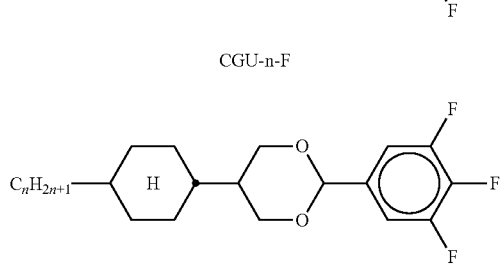
CGU-n-F
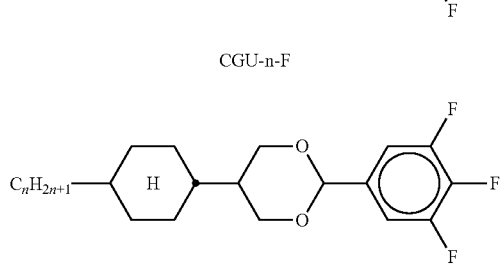
CDU-n-F TABLE A1-continued
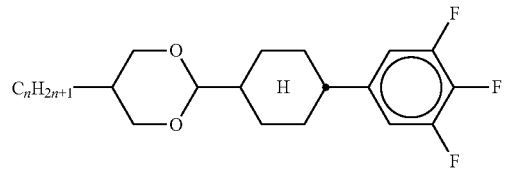
DCU-n-F
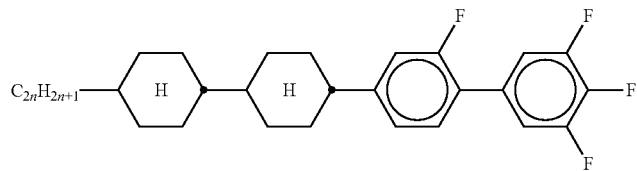
CCGU-n-F
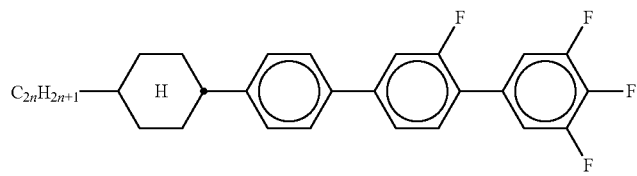
CPGU-n-F
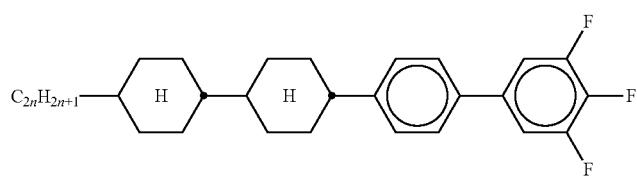
CCPU-n-F
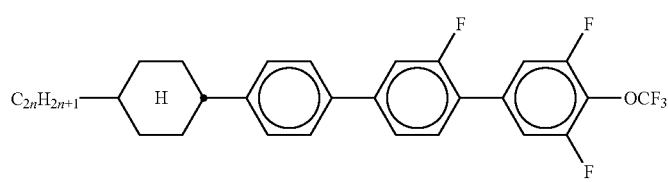
CPGU-n-OT
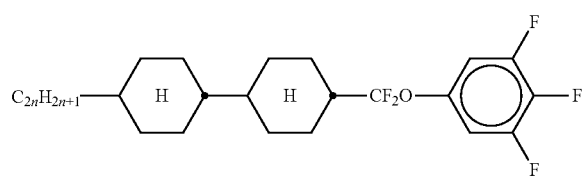
CCQU-n-F TABLE A1-continued
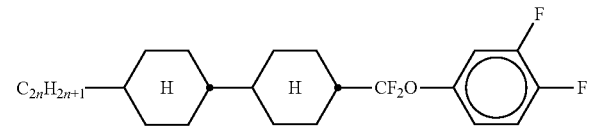
CCQG-n-F
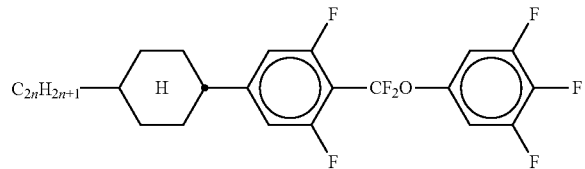
CUQU-n-F
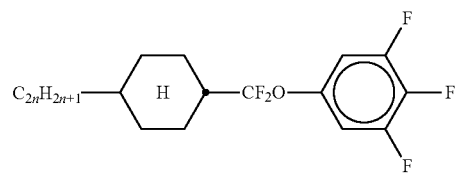
CQU-n-F
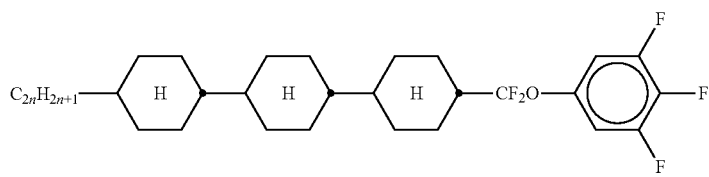
CCCQU-n-F
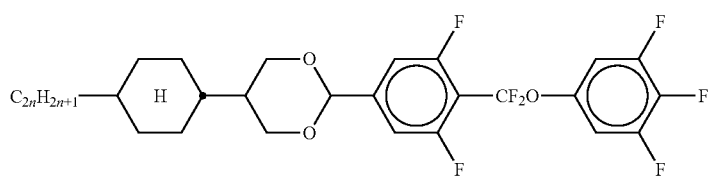
CDUQU-n-F
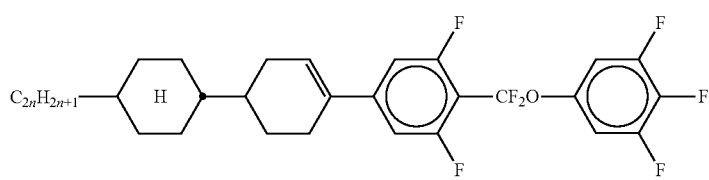
CLUQU-n-F TABLE A1-continued
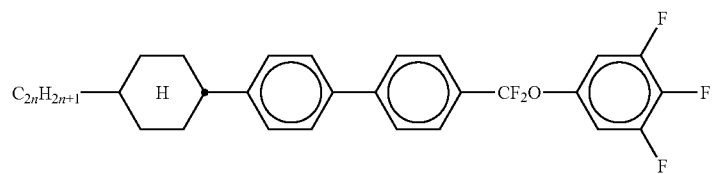
CPPQU-n-F
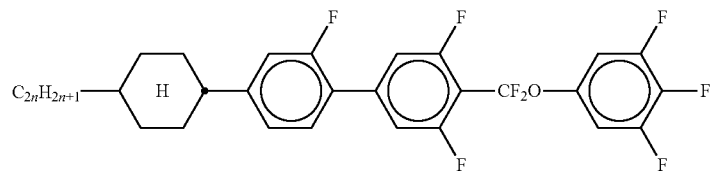
CGUQU-n-F
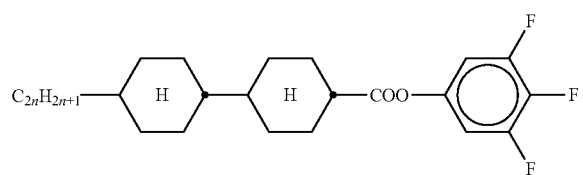
CCZU-n-F
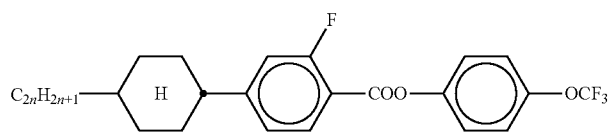
CGZP-n-OT
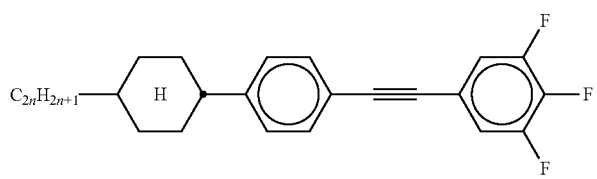
CPTU-n-F
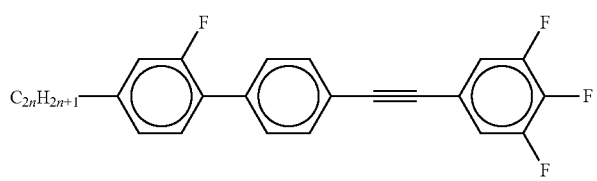
GPTU-n-F TABLE A1-continued
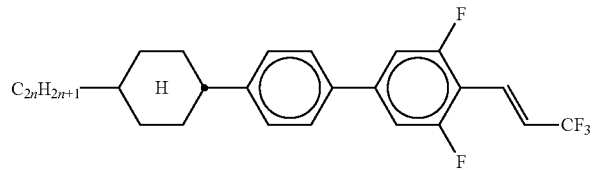
CPU-n-VT
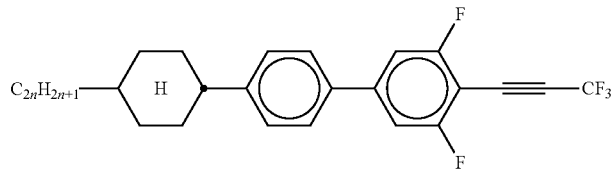
CPU-n-AT
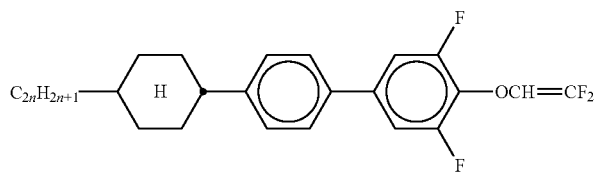
CPU-n-OXF
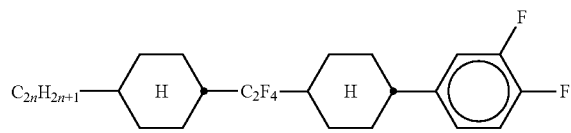
CWCG-n-F
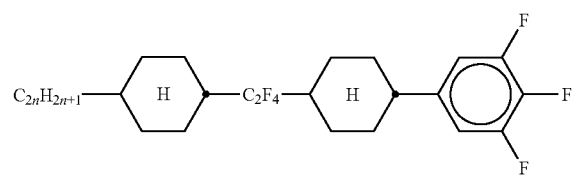
CWCU-n-F
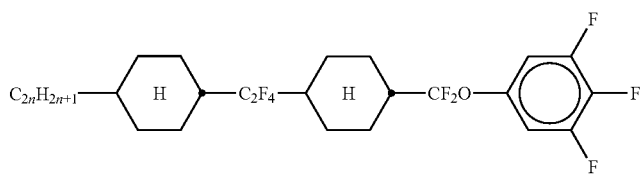
CWCQU-n-F TABLE A1-continued
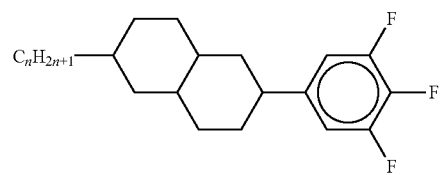
Dec-U-n-F
LPP-n-m
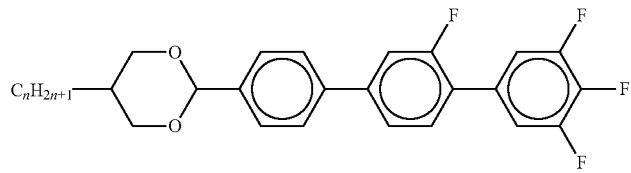
DPGU-n-F
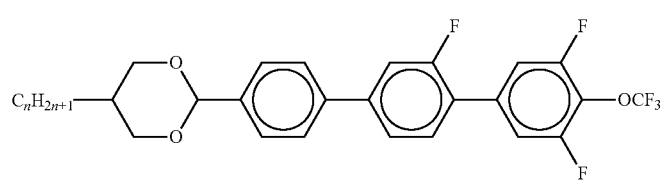
DPGU-n-OT
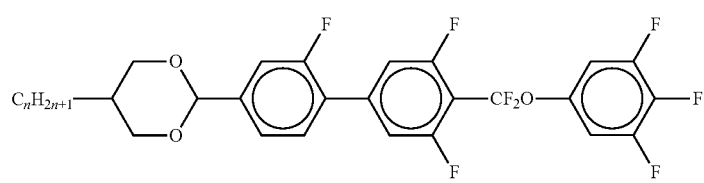
DGUQU-n-F
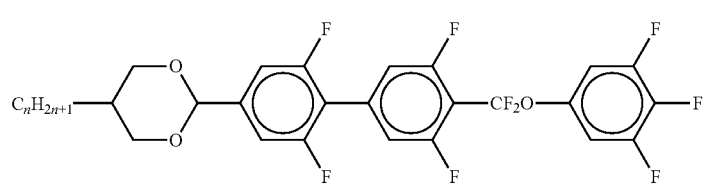
DUUQU-n-F
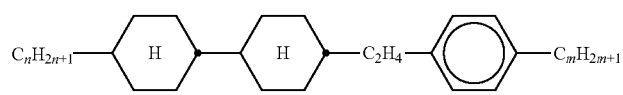
ECCP-nm TABLE A1-continued
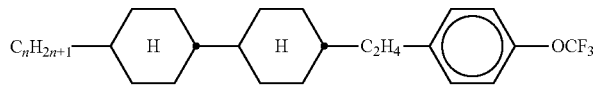
ECCP-nOCF₃
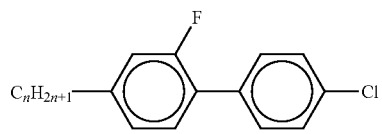
GP-n-Cl
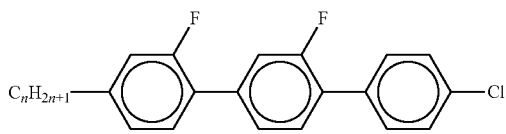
GGP-n-Cl
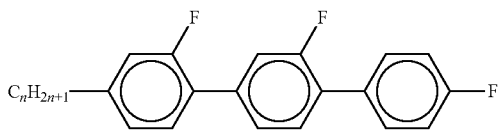
GGP-n-F
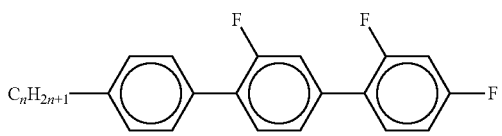
PGIGI-n-F
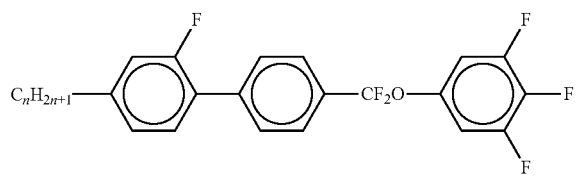
GPQU-n-F
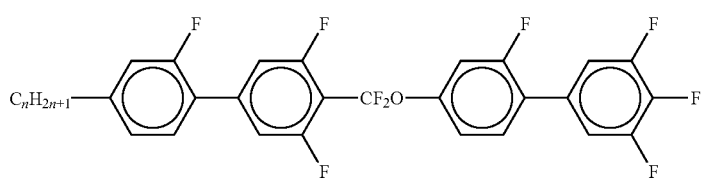
GUQGU-n-F
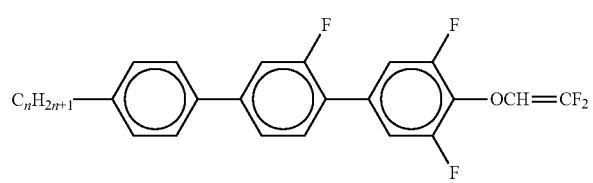
PGU-n-OXF TABLE A1-continued
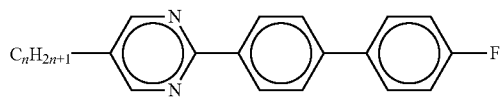
MPP-n-F
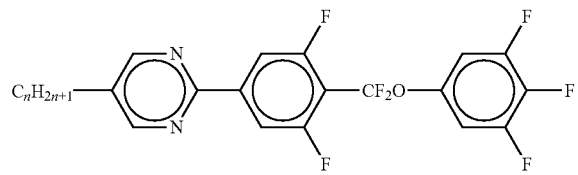
MUQU-n-F
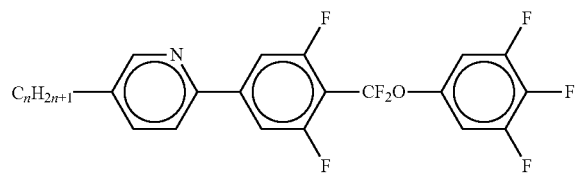
NUQU-n-F
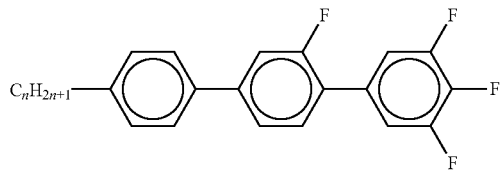
PGU-n-F
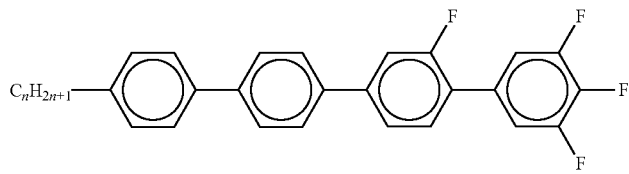
PPGU-n-F
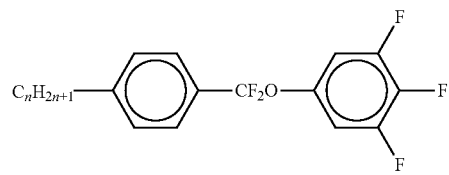
PQU-n-F
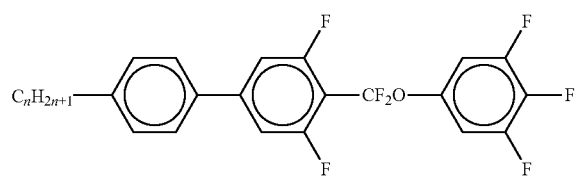
PUQU-n-F TABLE A1-continued
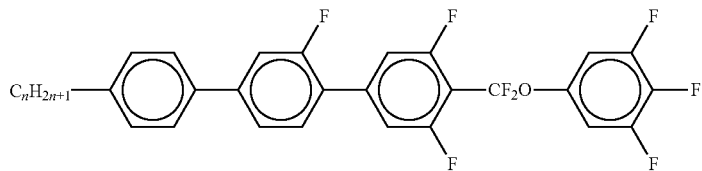
PGUQU-n-F
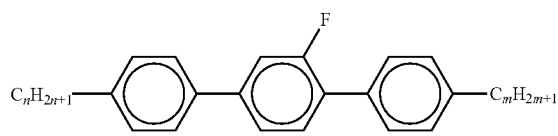
PGP-n-m
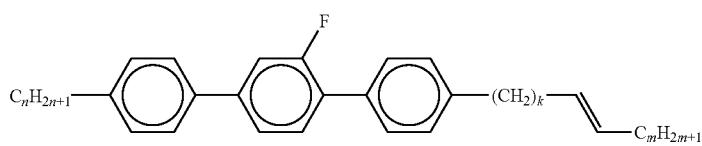
PGP-n-kVm
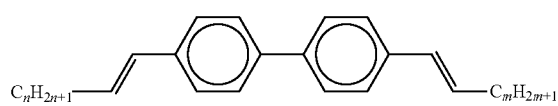
PP-nV-Vm
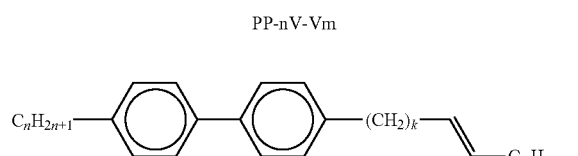
PP-n-kVm
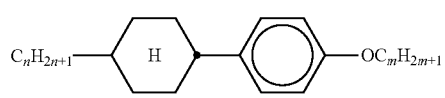
PCH-nOm
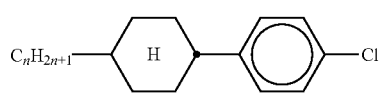
PCH-nCl
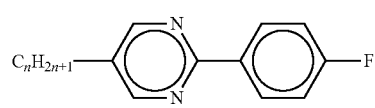
PYP-nF In Table A1, R¹* denotes a group selected from the left-hand side chains and R²* denotes a group selected from the right-hand side chains listed in Table III, L¹* and L²* are independently of each other H or F, m and n are independently of each other an integer from 1 to 12, preferably 1, 2, 3, 4, 5 or 6, k is 0, 1, 2, 3, 4, 5 or 6, and (O)$C_mH_{2m+1}$ means $C_mH_{2m+1}$ or $OC_mH_{2m+1}$.
TABLE A2
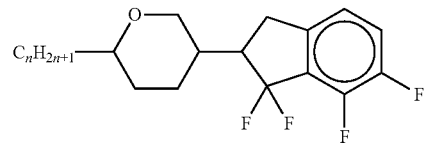
AIK-n-F
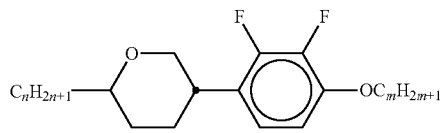
AIY-n-Om
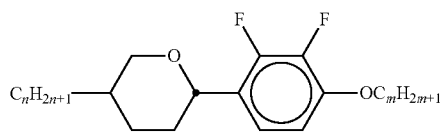
AY-n-Om
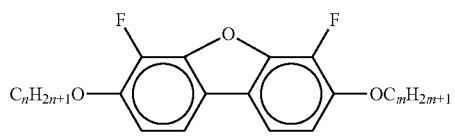
B-nO-Om
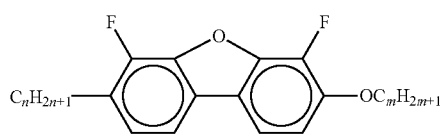
B-n-Om
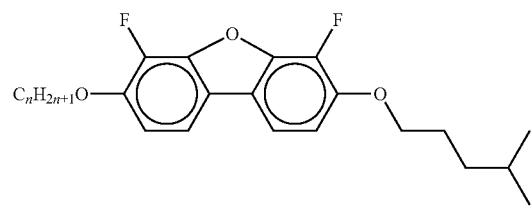
B-nO-O5i
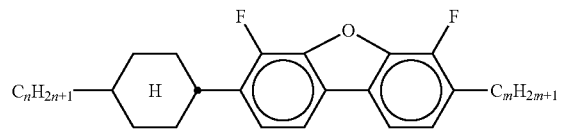
CB-n-m TABLE A2-continued
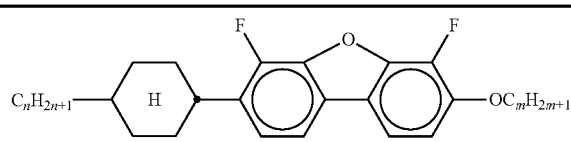
CB-n-Om
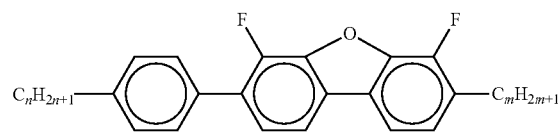
PB-n-m
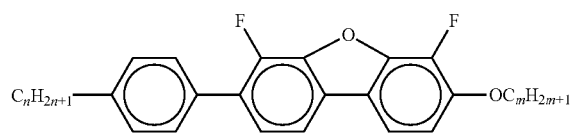
PB-n-Om
BCH-nm
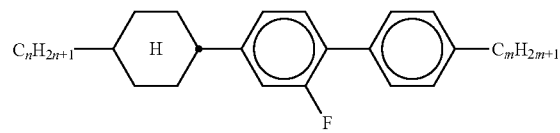
BCH-nmF
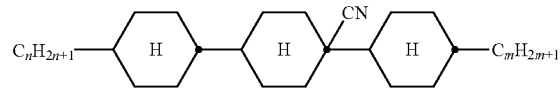
BCN-nm
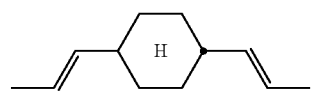
C-1V-V1
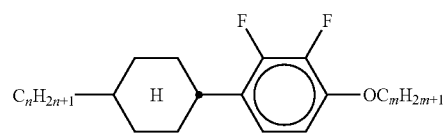
CY-n-Om
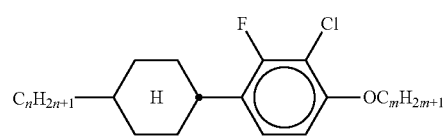
CY(F,Cl)-n-Om TABLE A2-continued
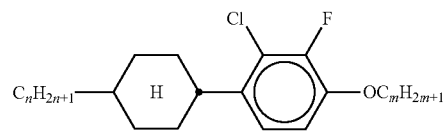
CY(Cl,F)-n-Om
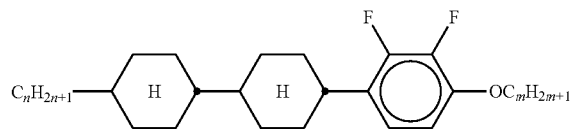
CCY-n-Om
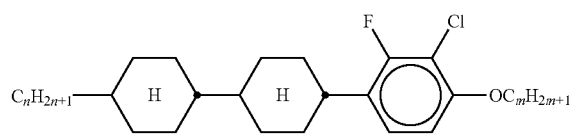
CCY(F,Cl)-n-Om
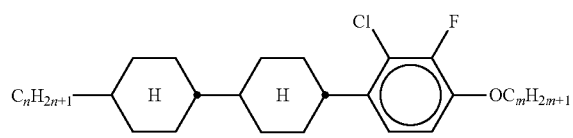
CCY(Cl,F)-n-Om
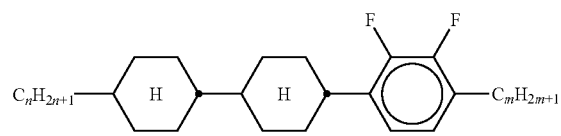
CCY-n-m
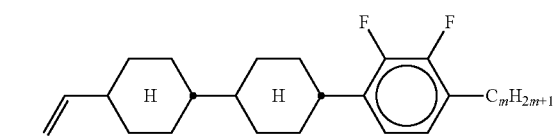
CCY-V-m
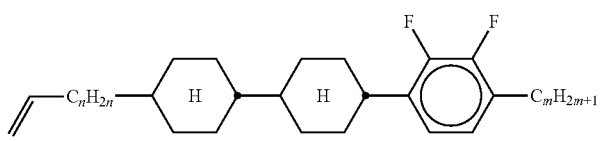
CCY-Vn-m
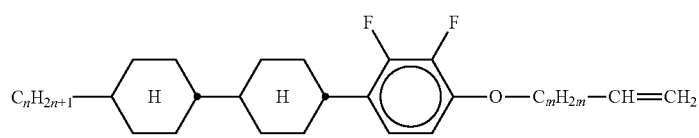
CCY-n-OmV TABLE A2-continued
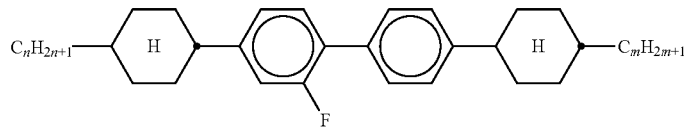
CBC-nmF
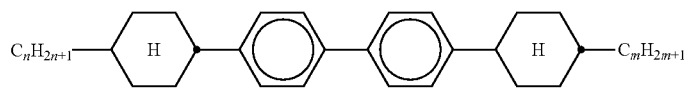
CBC-nm
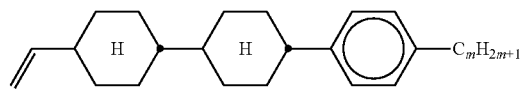
CCP-V-m
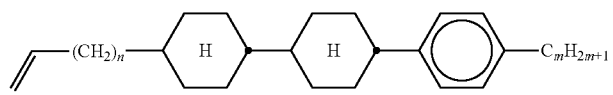
CCP-Vn-m
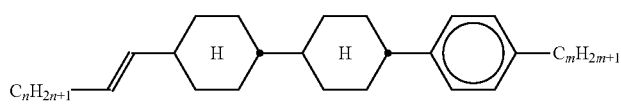
CCP-nV-m
CCP-n-m
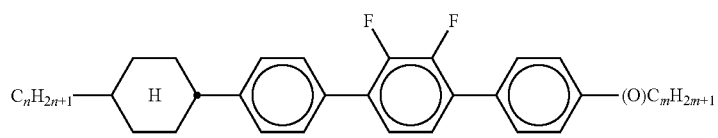
CPYP-n-(O)m
CYYC-n-m TABLE A2-continued
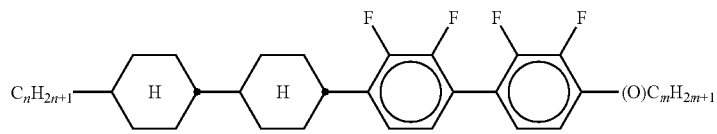
CCYY-n-(O)m
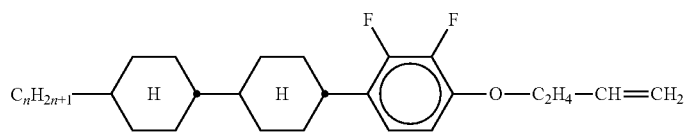
CCY-n-O2V
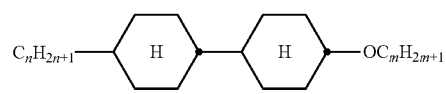
CCH-nOm
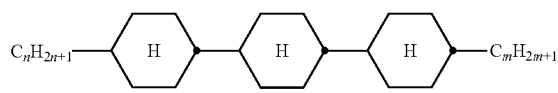
CCC-n-m
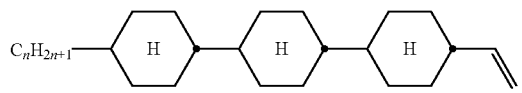
CCC-n-V
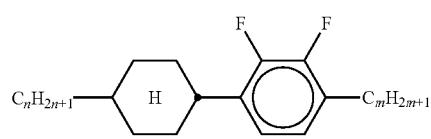
CY-n-m
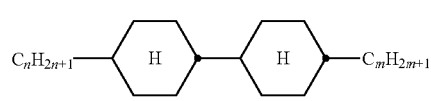
CCH-nm
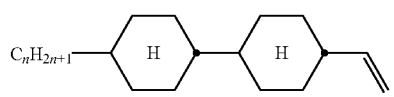
CC-n-V
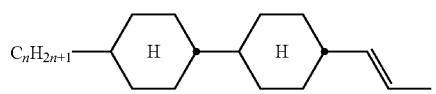
CC-n-V1

TABLE A2-continued
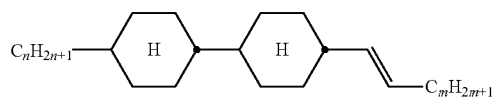
CC-n-Vm
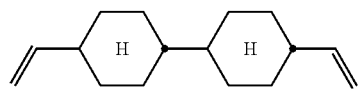
CC-V-V
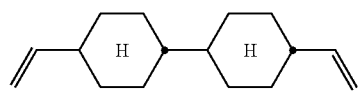
CC-V-V1
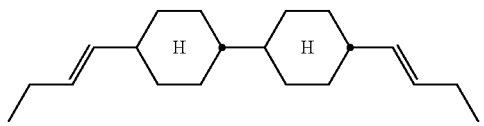
CC-2V-V2
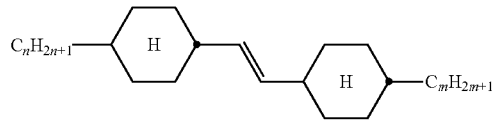
CVC-n-m
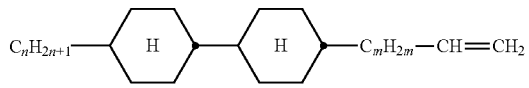
CC-n-mV
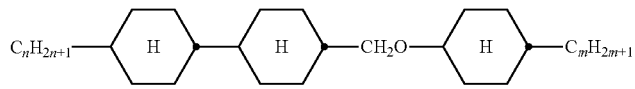
CCOC-n-m
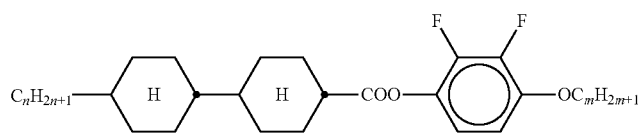
CP-nOmFF
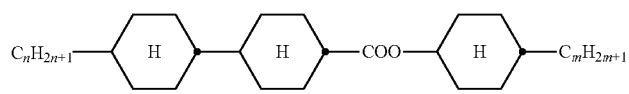
CH-nm TABLE A2-continued
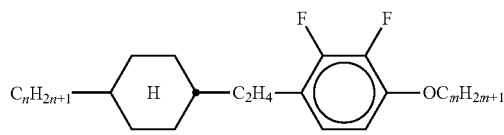
CEY-n-Om
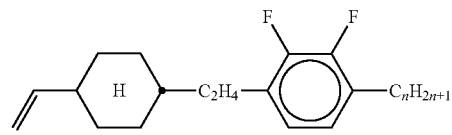
CEY-V-n
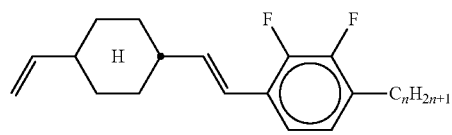
CVY-V-n
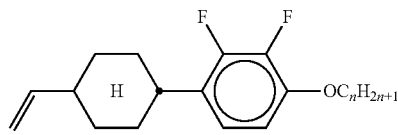
CY-V-On
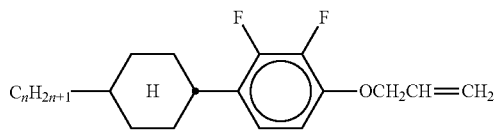
CY-n-O1V
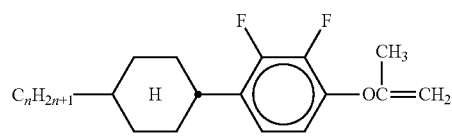
CY-n-OC(CH₃)═CH₂
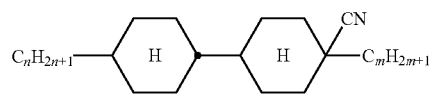
CCN-nm
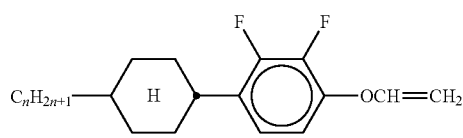
CY-n-OV TABLE A2-continued
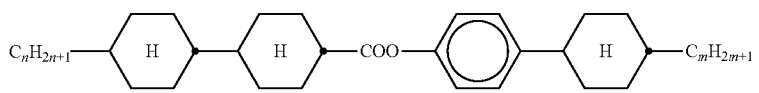
CCPC-nm
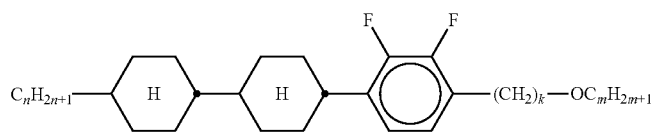
CCY-n-kOm
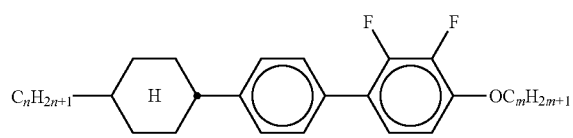
CPY-n-Om
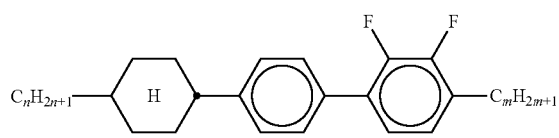
CPY-n-m
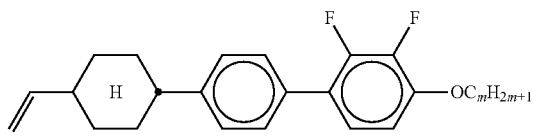
CPY-V-Om
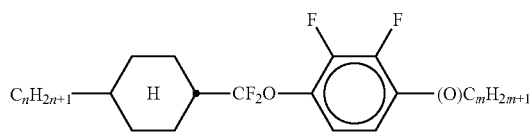
CQY-n-(O)m
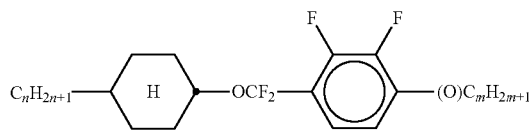
CQIY-n-(O)m
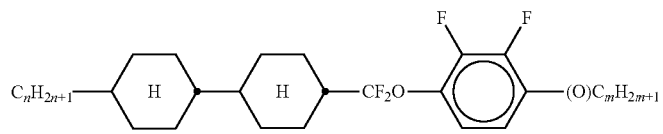
CCQY-n-(O)m TABLE A2-continued
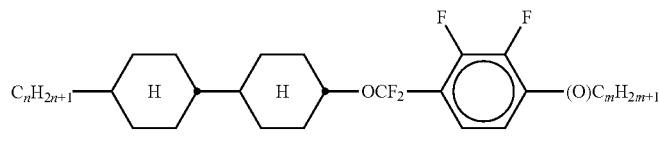
CCQIY-n-(O)m
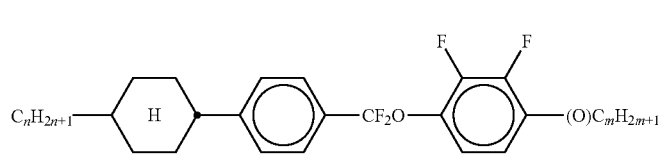
CPQY-n-(O)m
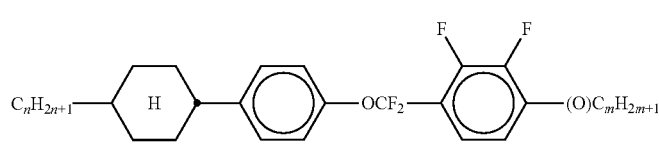
CPQIY-n-(O)m
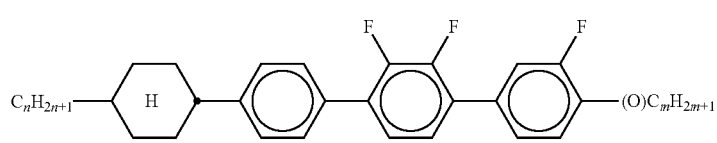
CPYG-n-(O)m
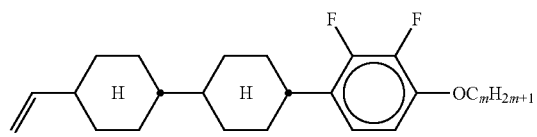
CCY-V-Om
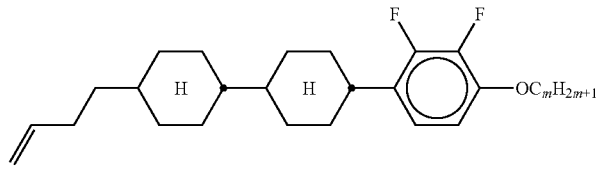
CCY-V2-(O)m
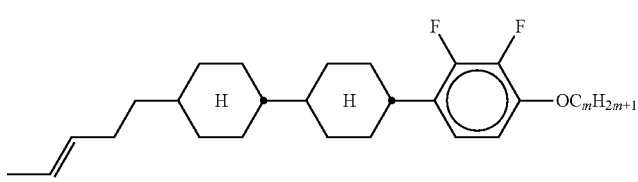
CCY-1V2-(O)m TABLE A2-continued
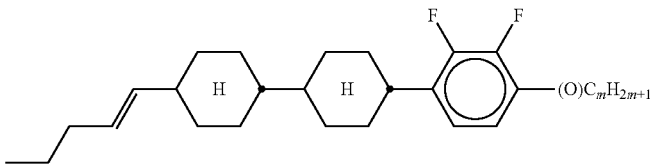
CCY-3V-(O)m
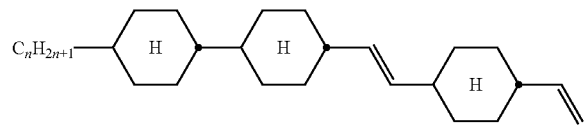
CCVC-n-V
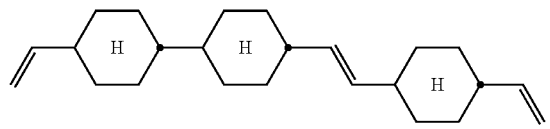
CCVC-V-V
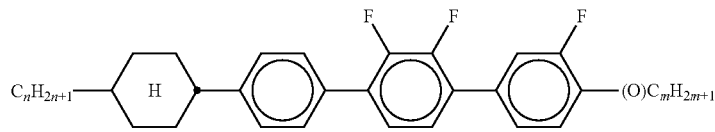
CPYG-n-(O)m
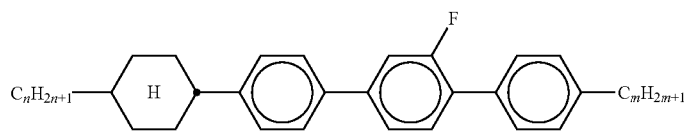
CPGP-n-m
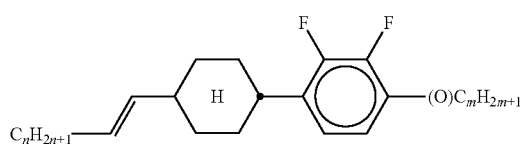
CY-nV-(O)m
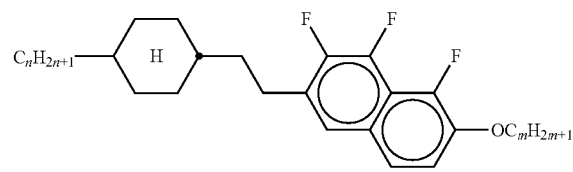
CENaph-n-Om TABLE A2-continued
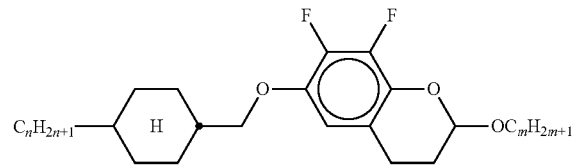
COChrom-n-Om
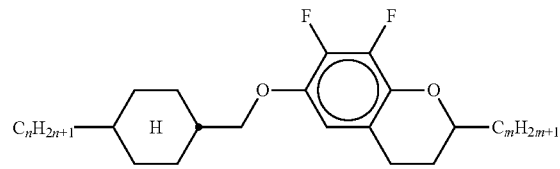
COChrom-n-m
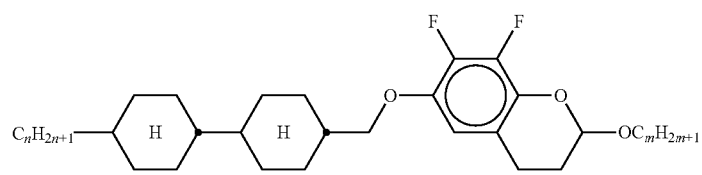
CCOChrom-n-Om
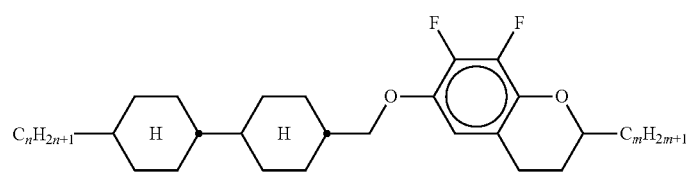
CCOChrom-n-m
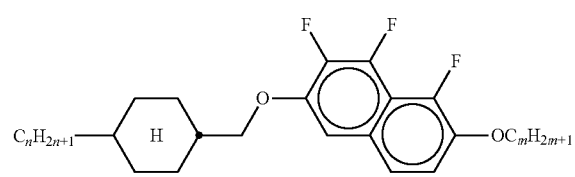
CONaph-n-Om
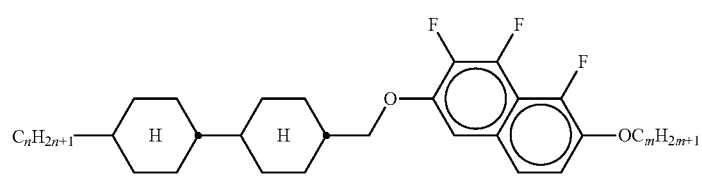
CCONaph-n-Om TABLE A2-continued
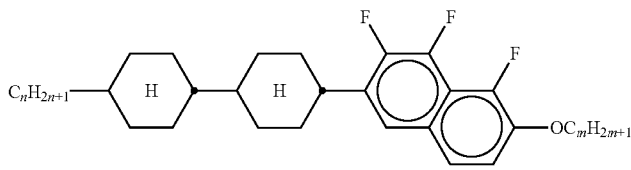
CCNaph-n-Om
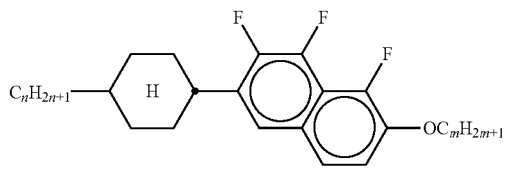
CNaph-n-Om
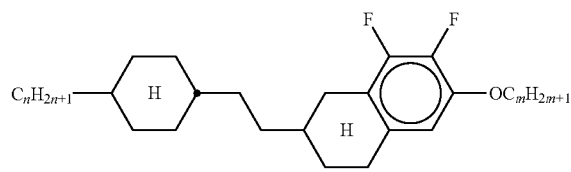
CETNaph-n-Om
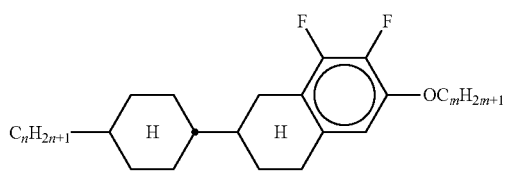
CTNaph-n-Om
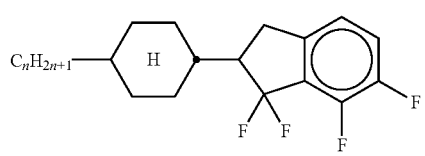
CK-n-F
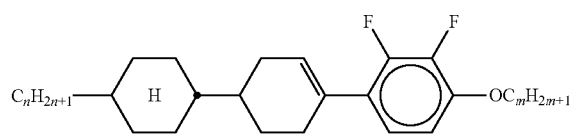
CLY-n-Om
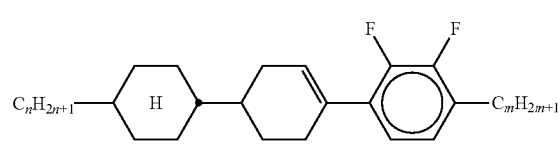
CLY-n-m TABLE A2-continued
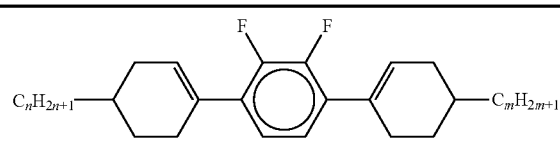
LYLI-n-m
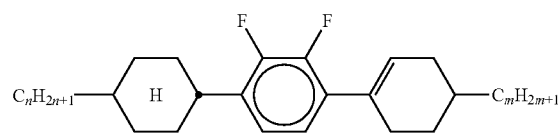
CYLI-n-m
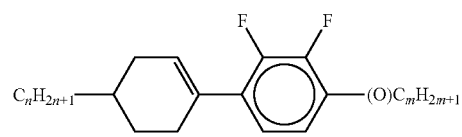
LY-n-(O)m
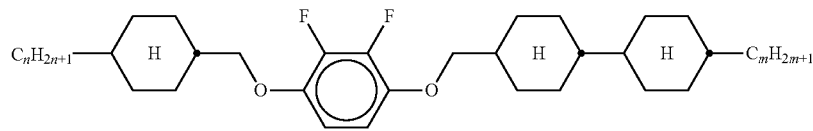
COYOICC-n-m
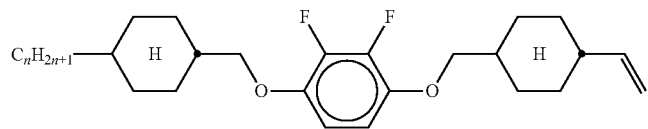
COYOIC-n-V
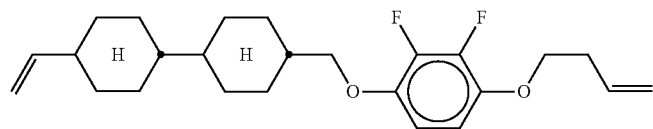
CCOY-V-O2V
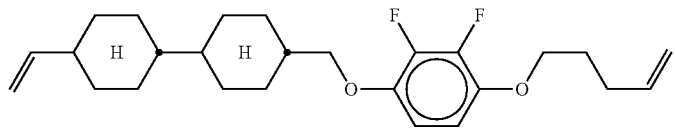
CCOY-V-O3V
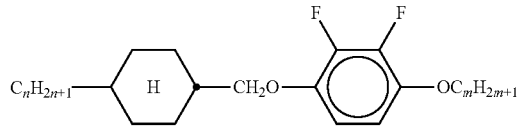
COY-n-Om TABLE A2-continued
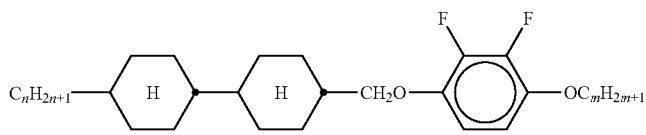
CCOY-n-Om
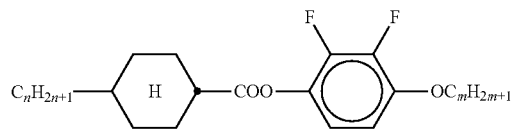
D-nOmFF
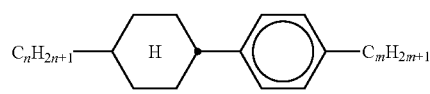
PCH-nm
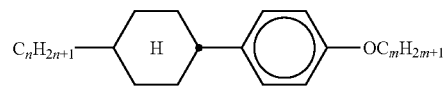
PCH-nOm
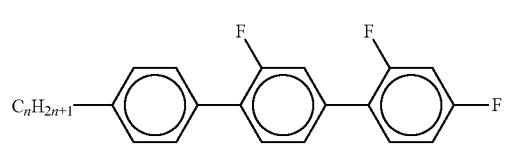
PGIGI-n-F
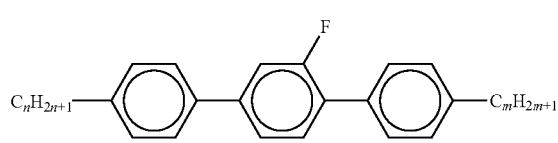
PGP-n-m
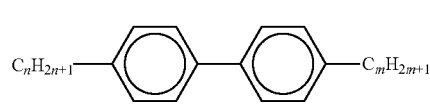
PP-n-m
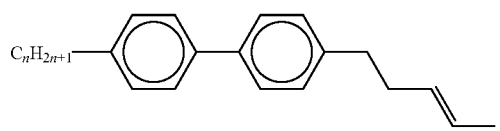
PP-n-2V1

TABLE A2-continued
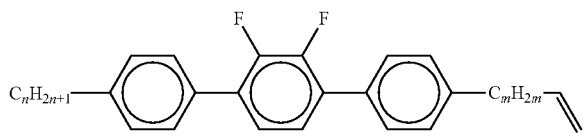
PYP-n-mV
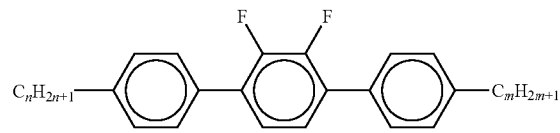
PYP-n-m
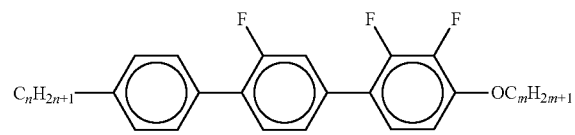
PGIY-n-Om
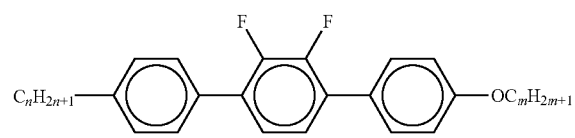
PYP-n-Om
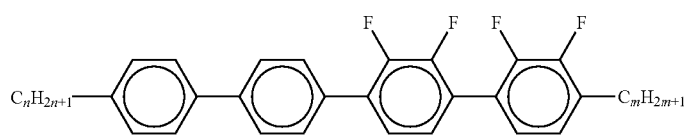
PPYY-n-m
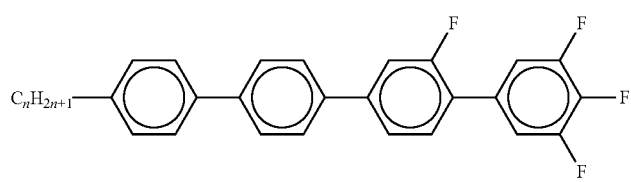
PPGU-n-F
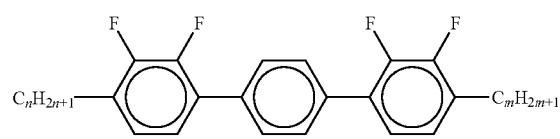
YPY-n-m TABLE A2-continued
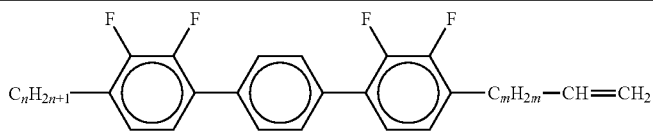
YPY-n-mV
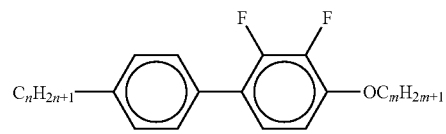
PY-n-Om
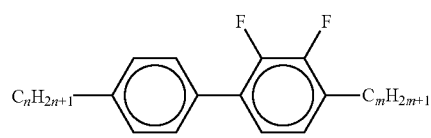
PY-n-m
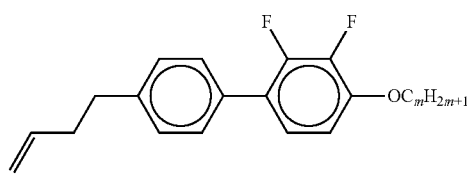
PY-V2-Om
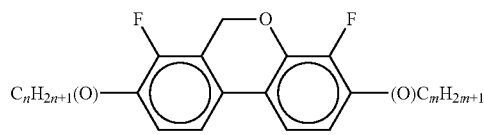
DFDBC-n(O)-(O)m
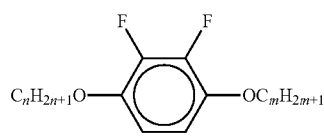
Y-nO-Om
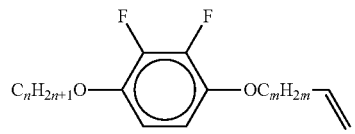
Y-nO-OmV
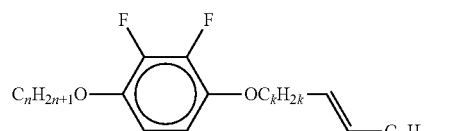
Y-nO-OkVm TABLE A2-continued
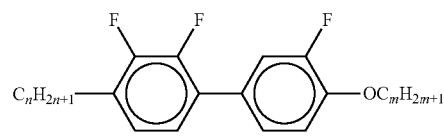
YG-n-Om
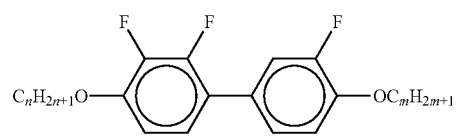
YG-nO-Om
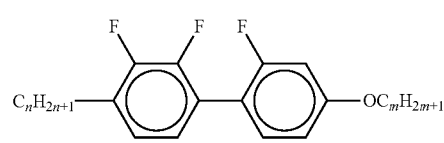
YGI-n-Om
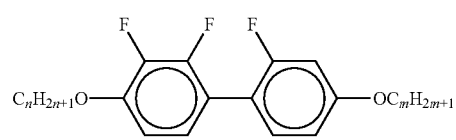
YGI-n-Om
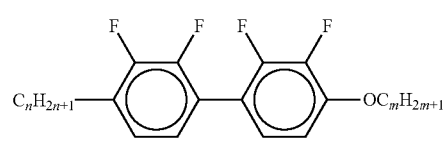
YY-n-Om
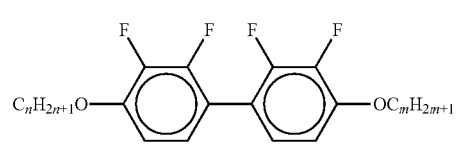
YY-nO-Om In the formulae below m and n are independently of each other an integer from 1 to 12, preferably 1, 2, 3, 4, 5 or 6, k is 0, 1, 2, 3, 4, 5 or 6 and $(O)C_mH_{2m+1}$ means $C_mH_{2m+1}$ or $OC_mH_{2m+1}$.

In a first preferred embodiment of the present invention, the LC media according to the invention, especially those with positive dielectric anisotropy, comprise one or more compounds selected from the group consisting of compounds from Table A1.

In a second preferred embodiment of the present invention, the LC media according to the invention, especially those with negaitve dielectric anisotropy, comprise one or more compounds selected from the group consisting of compounds from Table A2.

TABLE B

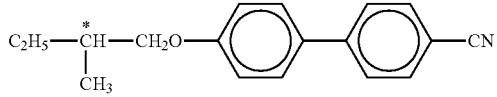

C 15

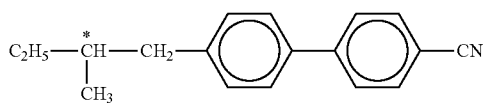

CB 15

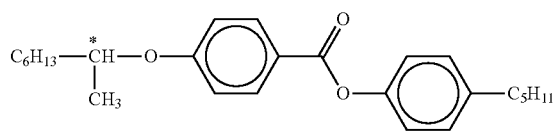

CM 21

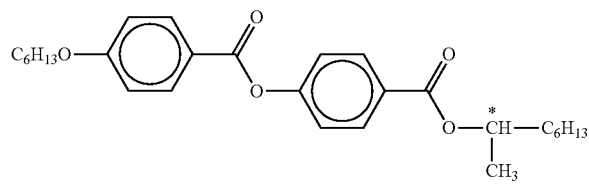

R/S-811

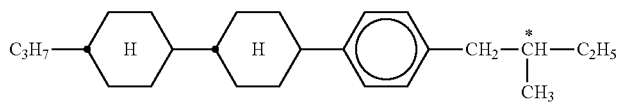

CM 44

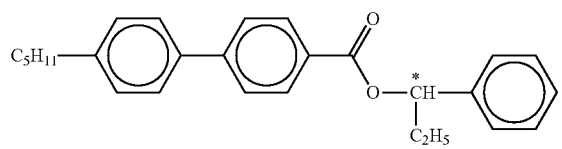

CM 45

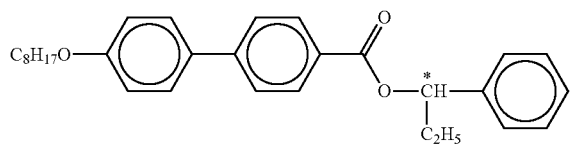

CM 47

TABLE B-continued
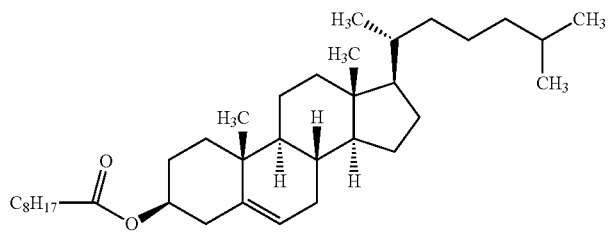
CN
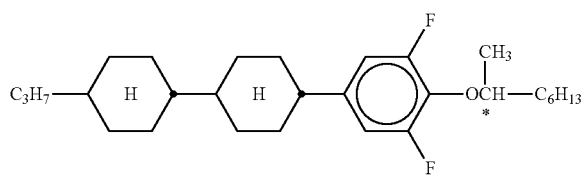
R/S-2011
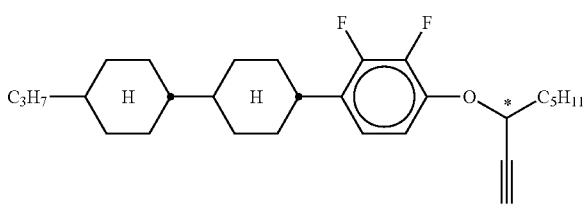
R/S-3011
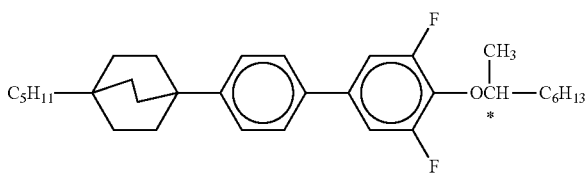
R/S-4011
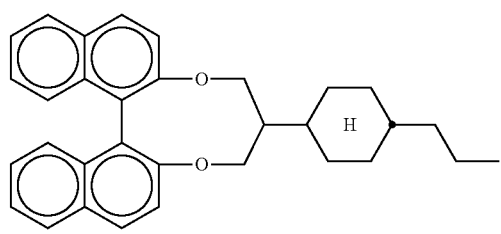
R/S-5011
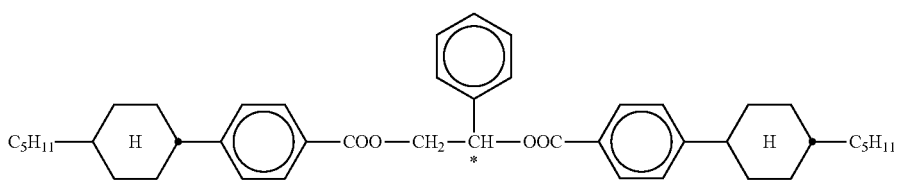
R/S-1011

Table B shows possible chiral dopants which can be added to the LC media according to the invention.
The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.
TABLE C
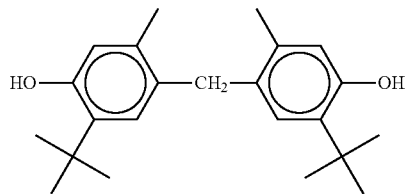
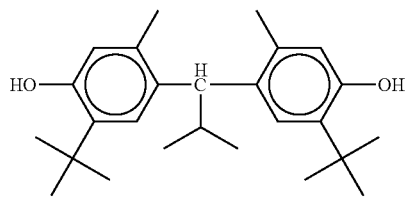
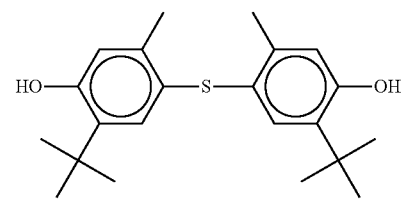
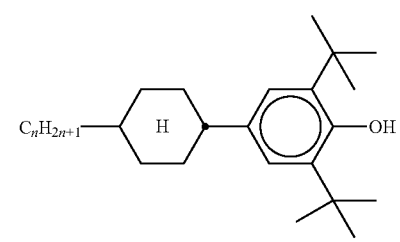
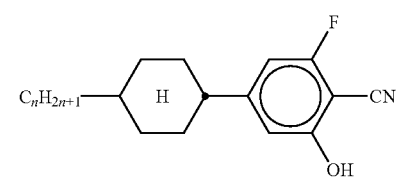
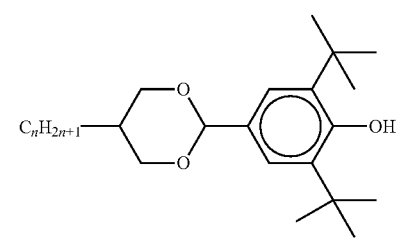
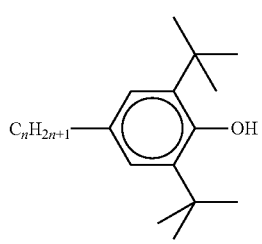

TABLE C-continued
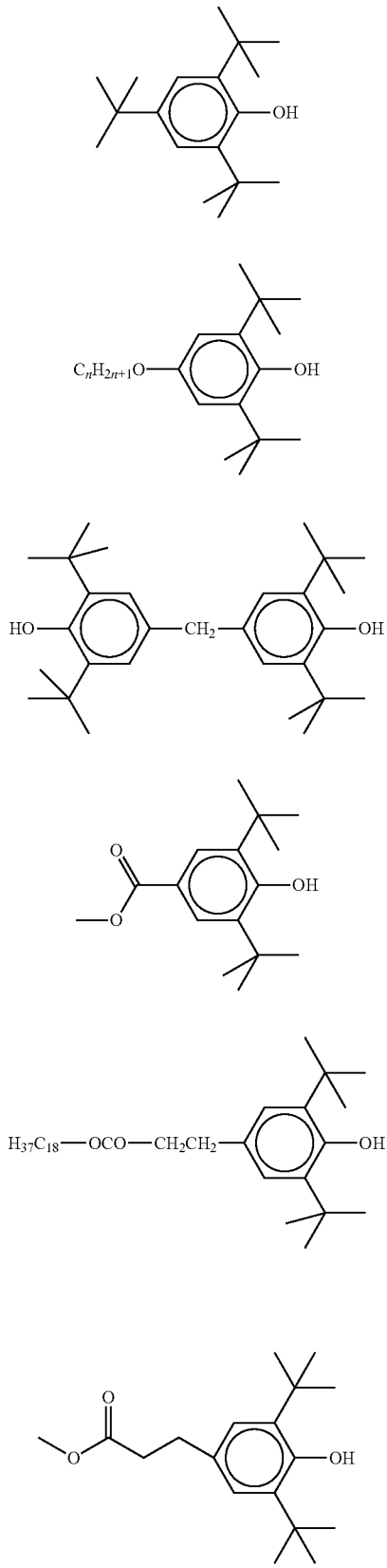

TABLE C-continued
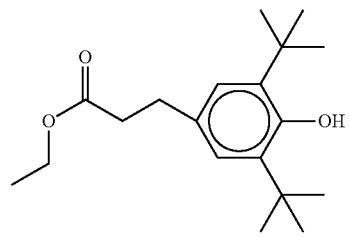
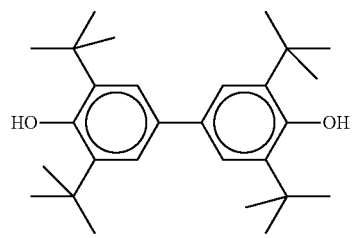
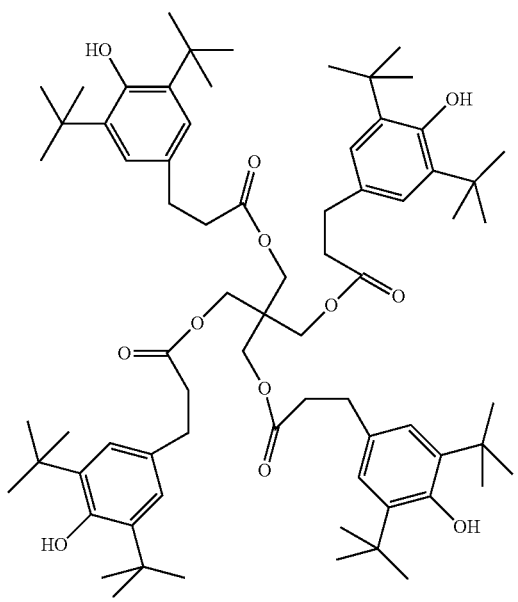 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
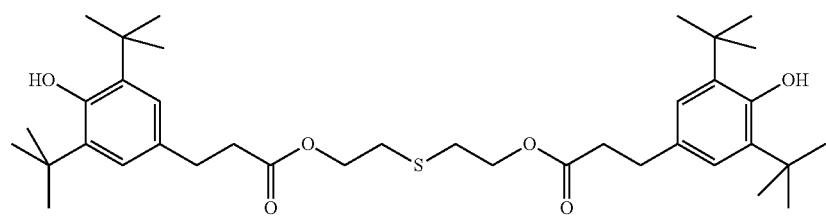 [SMILES: CC(C)(C)c1cc(CCC(=O)OCCSCCOC(=O)CCc2cc(C(C)(C)C)c(O)c(C(C)(C)C)c2)cc(C(C)(C)C)c1O]

TABLE C-continued
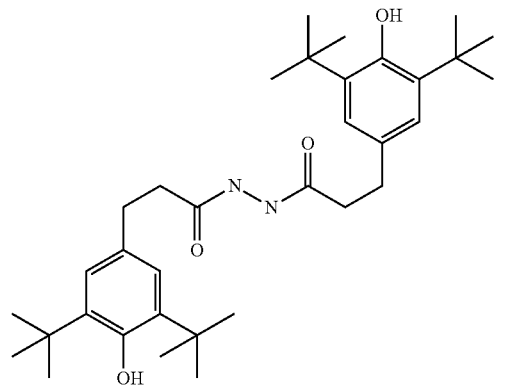 [SMILES: CC(C)(C)c1cc(CCC(=O)NNC(=O)CCc2cc(C(C)(C)C)c(O)c(C(C)(C)C)c2)cc(C(C)(C)C)c1O]
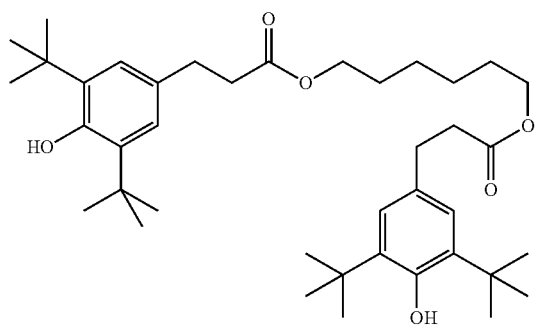 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
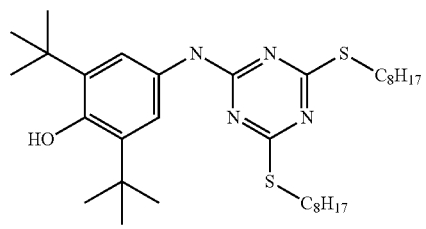
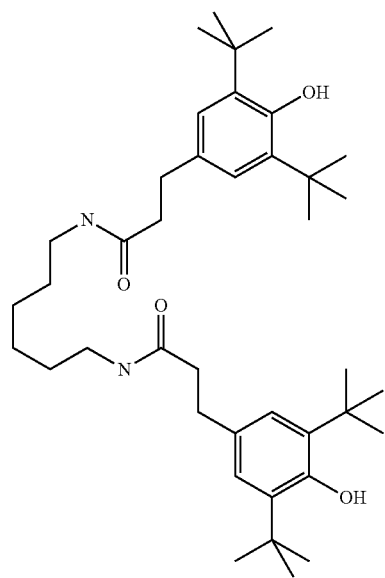 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

TABLE C-continued
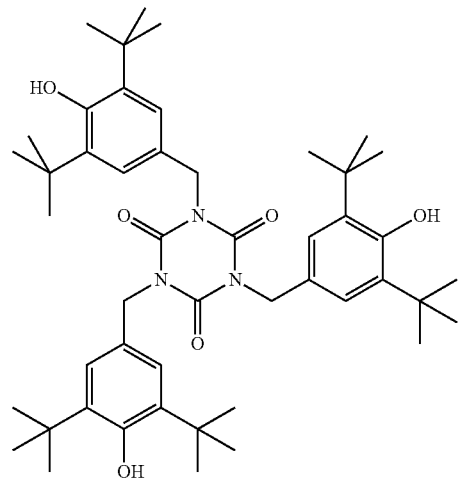 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
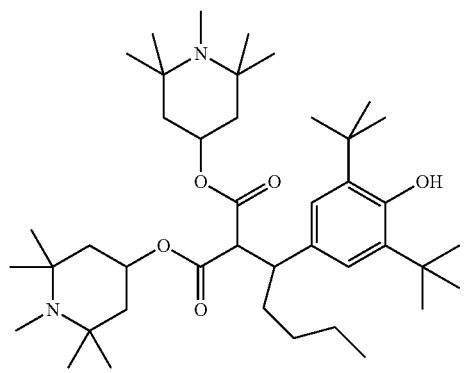 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
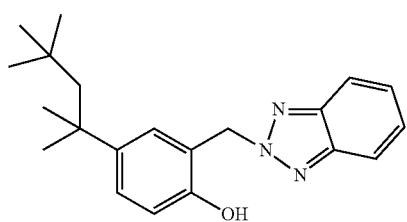 [SMILES: CC(C)(C)CC(C)(C)c1ccc(O)c(Cn2nc3ccccc3n2)c1]
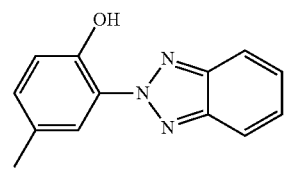 [SMILES: Cc1ccc(O)c(-n2nc3ccccc3n2)c1]
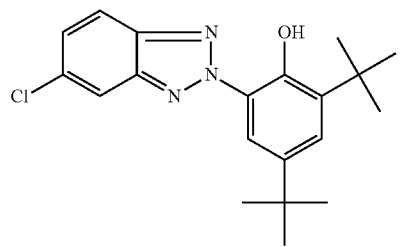 [SMILES: CC(C)(C)c1cc(-n2nc3ccc(Cl)cc3n2)c(O)c(C(C)(C)C)c1]

TABLE C-continued
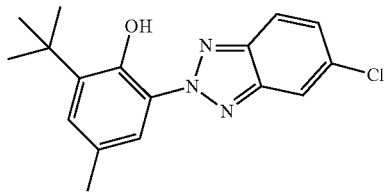 [SMILES: Cc1cc(-n2nc3ccc(Cl)cc3n2)c(O)c(C(C)(C)C)c1]
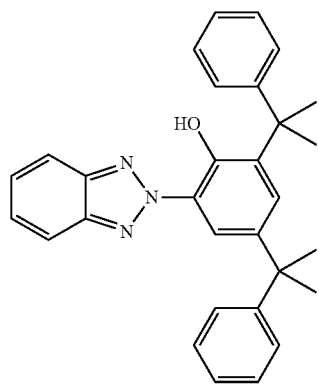 [SMILES: CC(C)(c1ccccc1)c1cc(-n2nc3ccccc3n2)c(O)c(C(C)(C)c2ccccc2)c1]
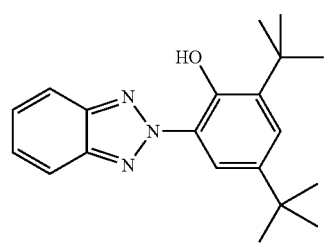 [SMILES: CC(C)(C)c1cc(-n2nc3ccccc3n2)c(O)c(C(C)(C)C)c1]
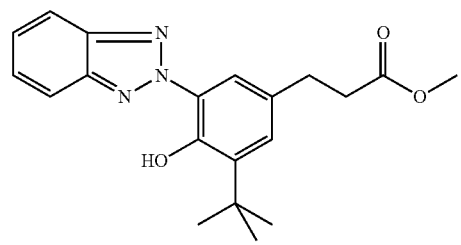 [SMILES: COC(=O)CCc1cc(-n2nc3ccccc3n2)c(O)c(C(C)(C)C)c1]
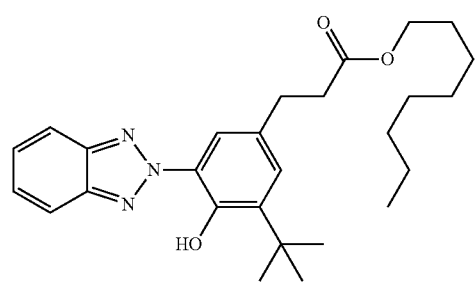 [SMILES: CCCCCCCCOC(=O)CCc1cc(-n2nc3ccccc3n2)c(O)c(C(C)(C)C)c1]

TABLE C-continued
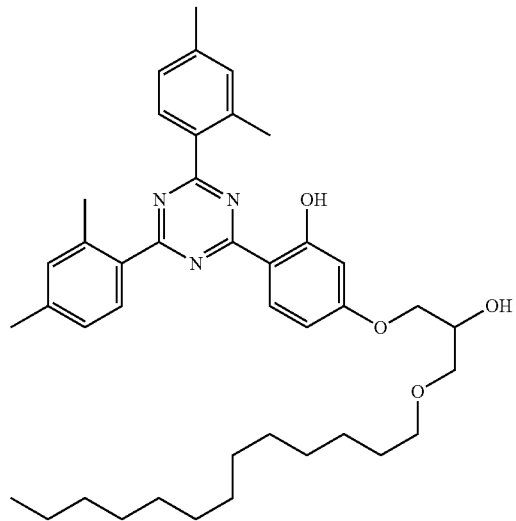 [SMILES: CCCCCCCCCCCCCOCC(O)COc1ccc(-c2nc(-c3ccc(C)cc3C)nc(-c3ccc(C)cc3C)n2)c(O)c1]
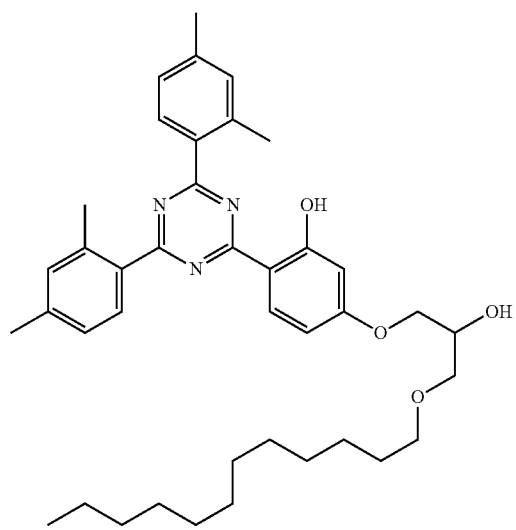 [SMILES: CCCCCCCCCCCCOCC(O)COc1ccc(-c2nc(-c3ccc(C)cc3C)nc(-c3ccc(C)cc3C)n2)c(O)c1]
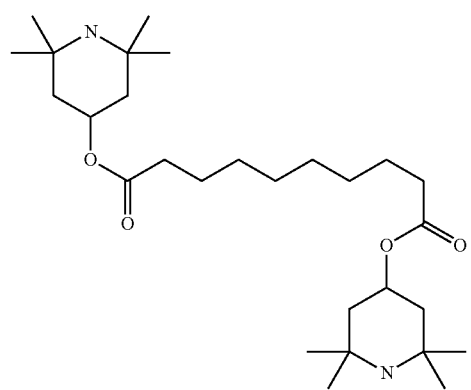

TABLE C-continued
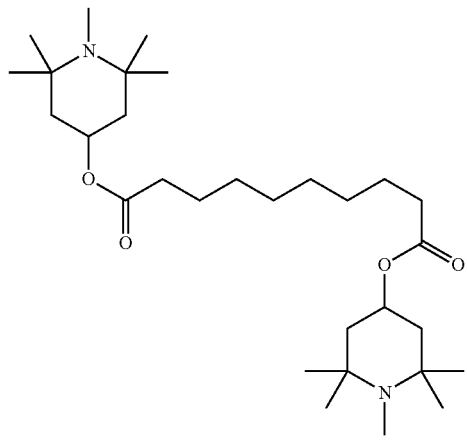
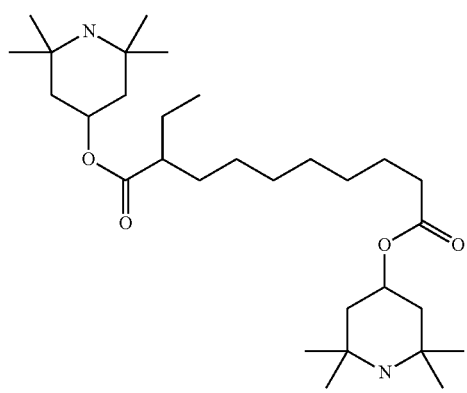
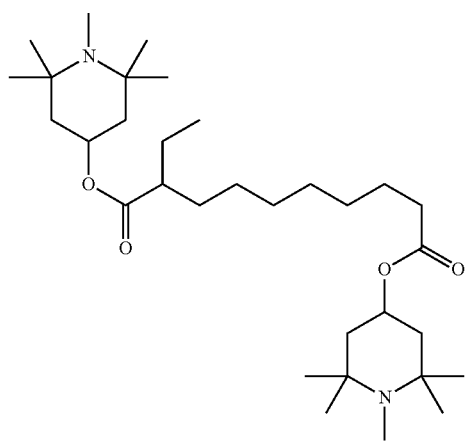

TABLE C-continued
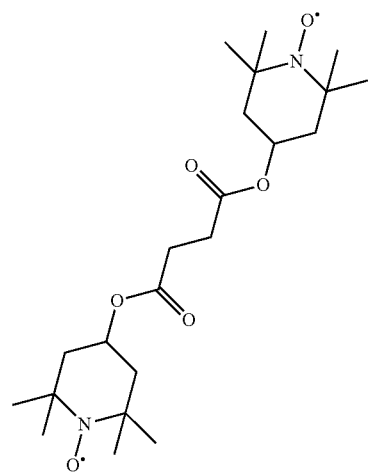
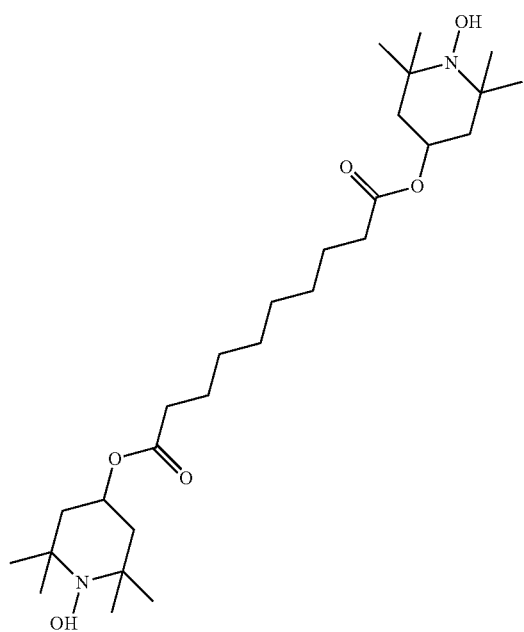
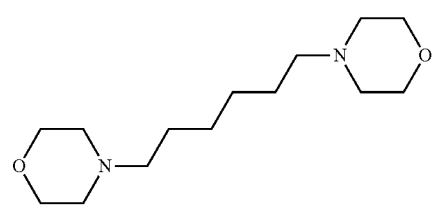 [SMILES: C(CCCN1CCOCC1)CCN1CCOCC1]

TABLE C-continued
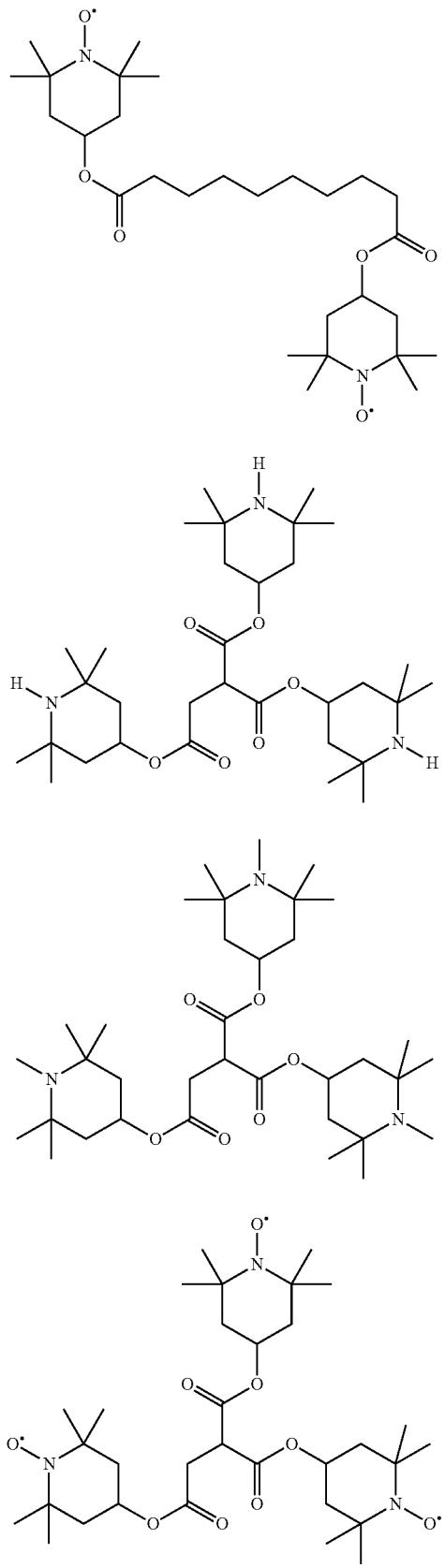

TABLE C-continued
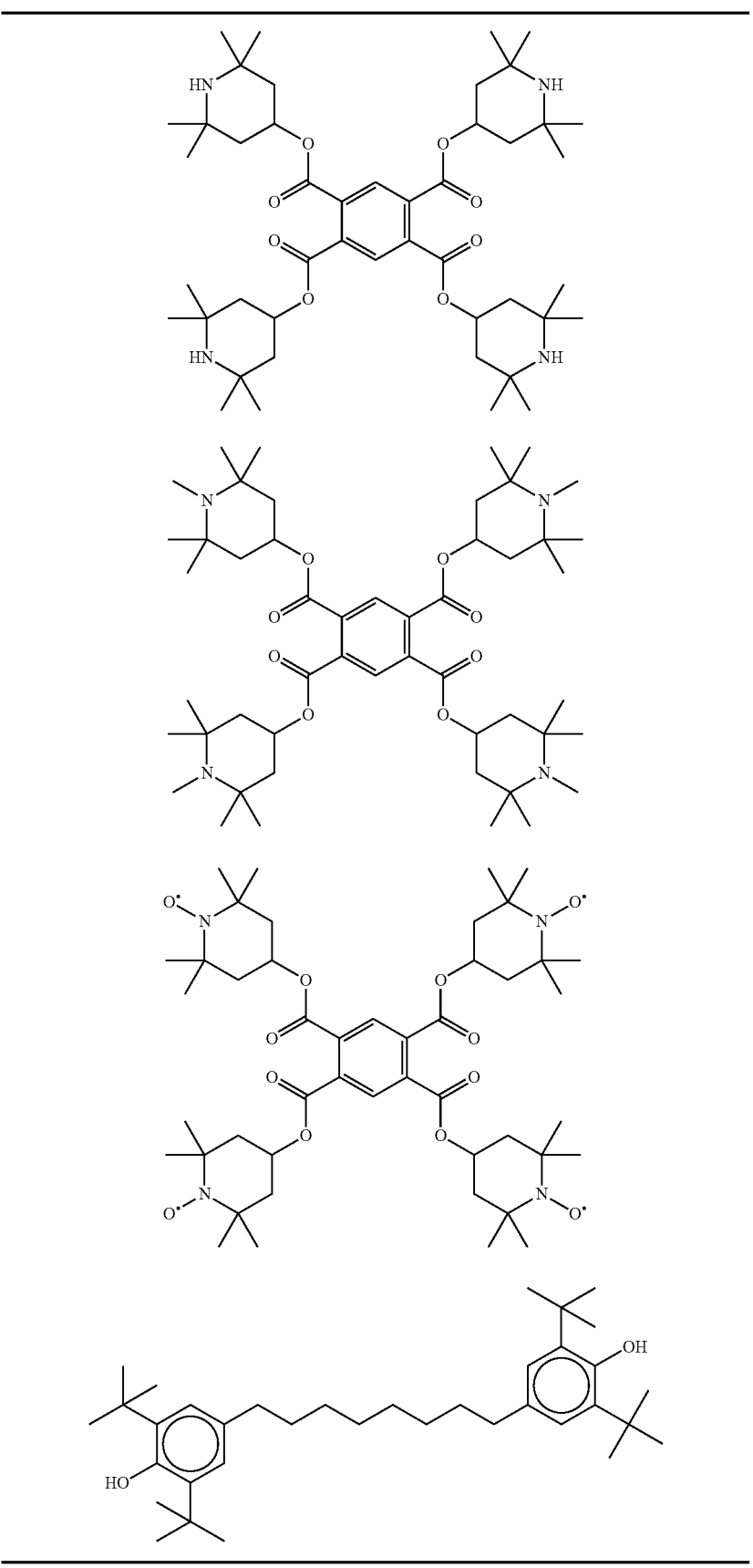

Table C shows possible stabilizers which can be added to the LC media according to the invention. Therein n denotes an integer from 1 to 12, preferably 1, 2, 3, 4, 5, 6, 7 or 8, and terminal methyl groups are not shown.

The LC media preferably comprise 0 to 10% by weight, in particular 1 ppm to 5% by weight, particularly preferably 1 ppm to 1% by weight, of stabilizers. The LC media preferably comprise one or more stabilizers selected from the group consisting of compounds from Table C.

TABLE D

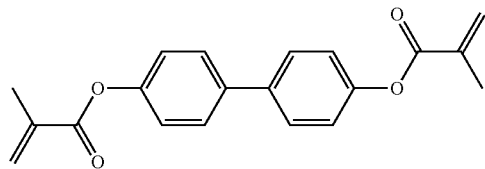

RM-1

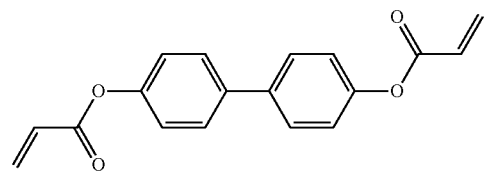

RM-2

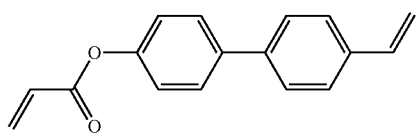 [SMILES: C=CC(=O)Oc1ccc(-c2ccc(C=C)cc2)cc1]

RM-3

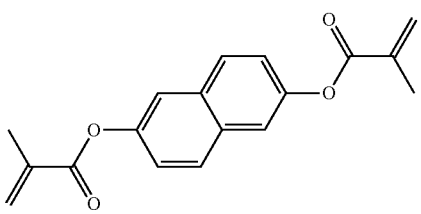 [SMILES: C=C(C)C(=O)Oc1ccc2cc(OC(=O)C(=C)C)ccc2c1]

RM-4

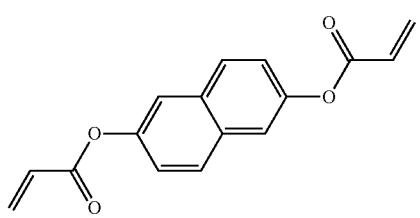 [SMILES: C=CC(=O)Oc1ccc2cc(OC(=O)C=C)ccc2c1]

RM-5

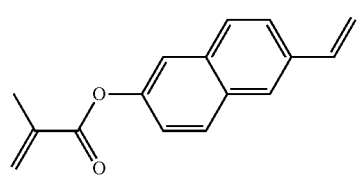 [SMILES: C=Cc1ccc2cc(OC(=O)C(=C)C)ccc2c1]

RM-6

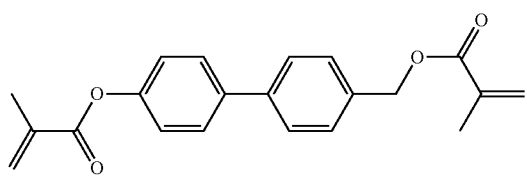 [SMILES: C=C(C)C(=O)OCc1ccc(-c2ccc(OC(=O)C(=C)C)cc2)cc1]

RM-7

TABLE D-continued
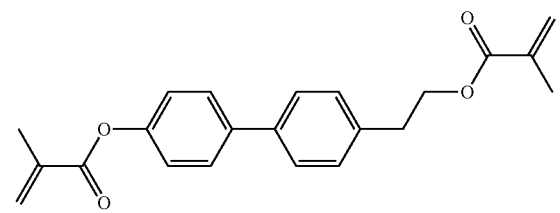 [SMILES: C=C(C)C(=O)OCCc1ccc(-c2ccc(OC(=O)C(=C)C)cc2)cc1] RM-8
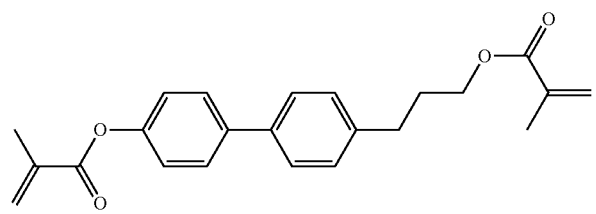 [SMILES: C=C(C)C(=O)OCCCc1ccc(-c2ccc(OC(=O)C(=C)C)cc2)cc1] RM-9
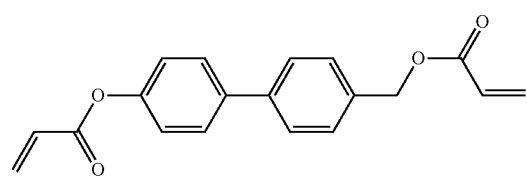 [SMILES: C=CC(=O)OCc1ccc(-c2ccc(OC(=O)C=C)cc2)cc1] RM-10
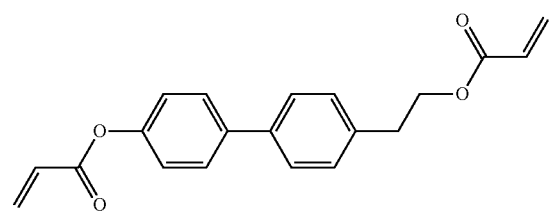 [SMILES: C=CC(=O)OCCc1ccc(-c2ccc(OC(=O)C=C)cc2)cc1] RM-11
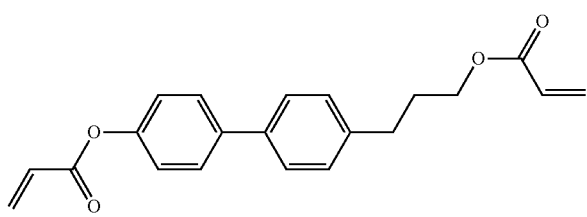 [SMILES: C=CC(=O)OCCCc1ccc(-c2ccc(OC(=O)C=C)cc2)cc1] RM-12
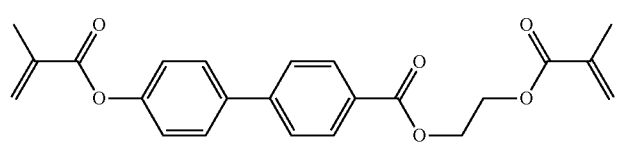 RM-13
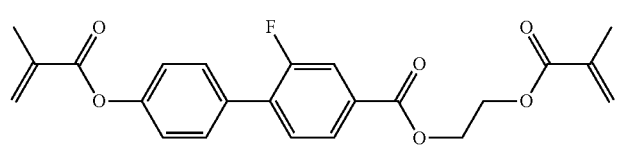 [SMILES: C=C(C)C(=O)OCCOC(=O)c1ccc(-c2ccc(OC(=O)C(=C)C)cc2)c(F)c1] RM-14
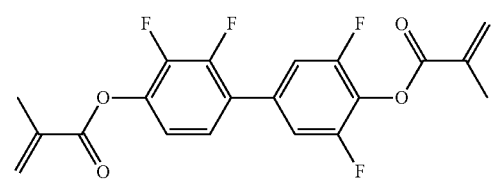 RM-15

TABLE D-continued
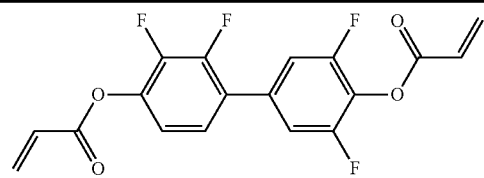 RM-16
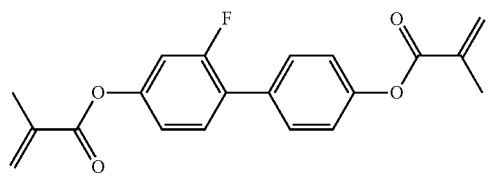 RM-17
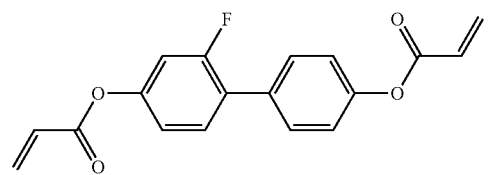 RM-18
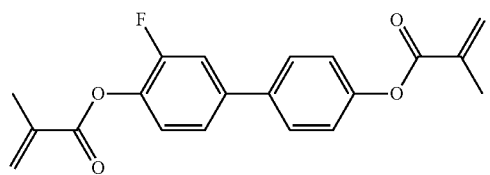 RM-19
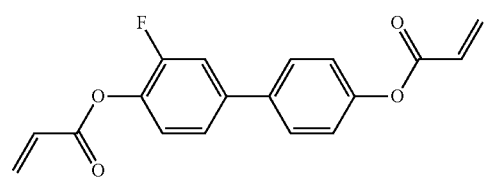 RM-20
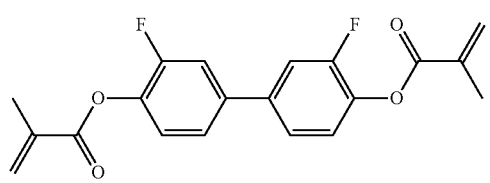 RM-21
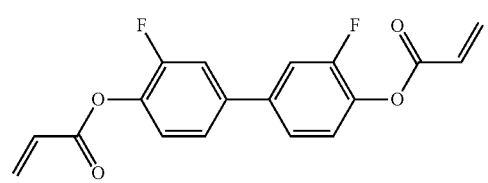 RM-22
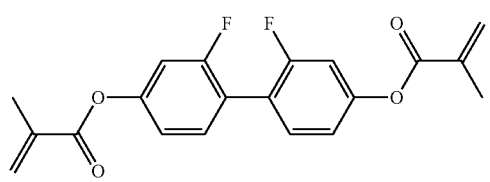 RM-23
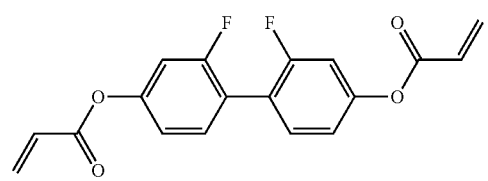 [SMILES: C=CC(=O)Oc1ccc(-c2ccc(OC(=O)C=C)cc2F)cc1] RM-24

TABLE D-continued
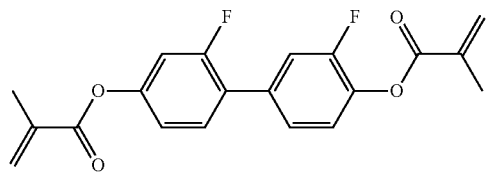 RM-25
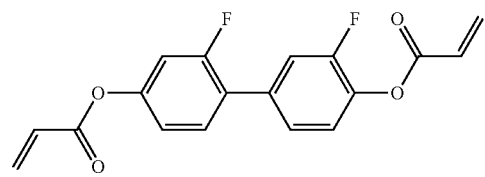 [SMILES: C=CC(=O)Oc1ccc(-c2ccc(OC(=O)C=C)c(F)c2)c(F)c1] RM-26
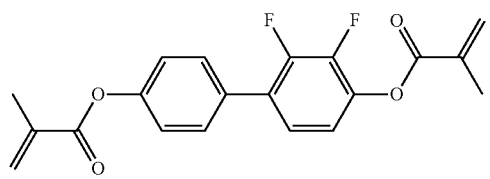 [SMILES: C=C(C)C(=O)Oc1ccc(-c2ccc(OC(=O)C(=C)C)c(F)c2F)cc1] RM-27
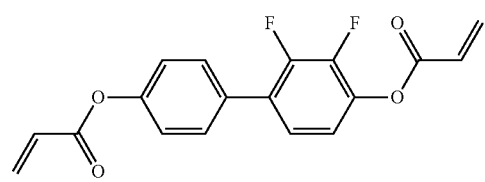 RM-28
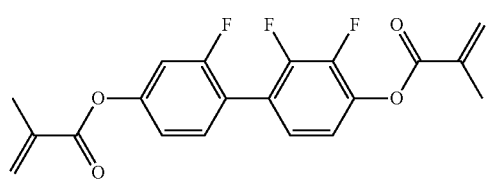 RM-29
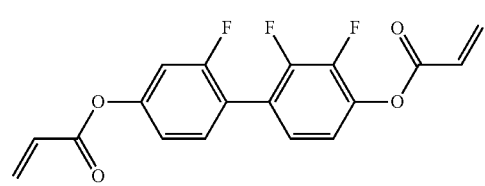 [SMILES: C=CC(=O)Oc1ccc(-c2ccc(OC(=O)C=C)c(F)c2F)c(F)c1] RM-30
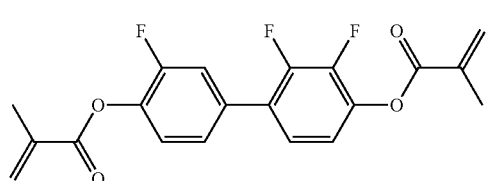 RM-31
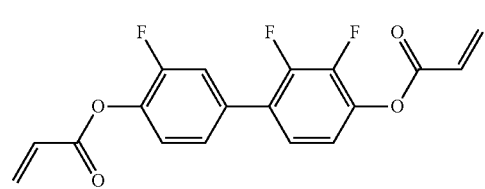 RM-32

TABLE D-continued
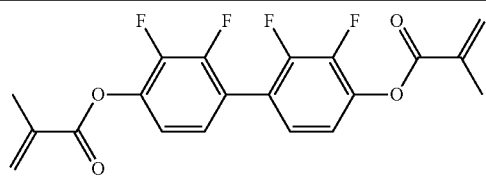
RM-33
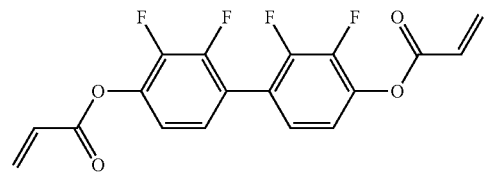 [SMILES: C=CC(=O)Oc1ccc(-c2ccc(OC(=O)C=C)c(F)c2F)cc1F]
RM-34
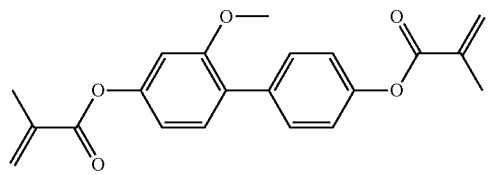 [SMILES: C=C(C)C(=O)Oc1ccc(-c2ccc(OC(=O)C(=C)C)cc2OC)cc1]
RM-35
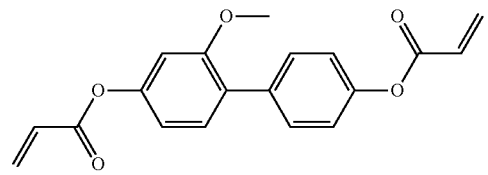 [SMILES: C=CC(=O)Oc1ccc(-c2ccc(OC(=O)C=C)cc2OC)cc1]
RM-36
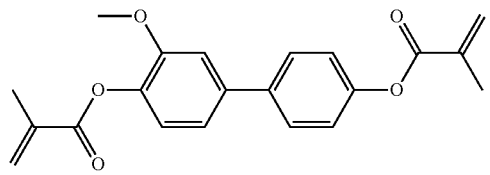 [SMILES: C=C(C)C(=O)Oc1ccc(-c2ccc(OC(=O)C(=C)C)c(OC)c2)cc1]
RM-37
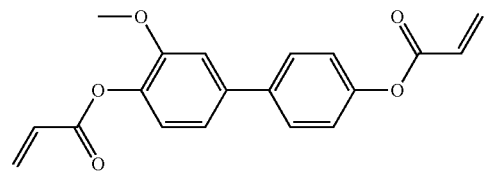 [SMILES: C=CC(=O)Oc1ccc(-c2ccc(OC(=O)C=C)c(OC)c2)cc1]
RM-38
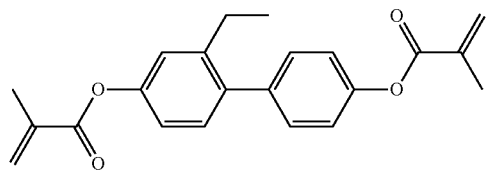 [SMILES: C=C(C)C(=O)Oc1ccc(-c2ccc(OC(=O)C(=C)C)cc2C)cc1]
RM-39
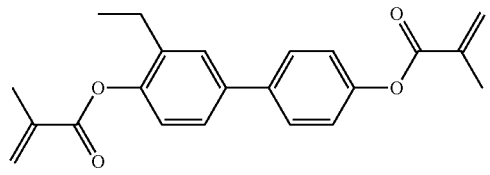
RM-40
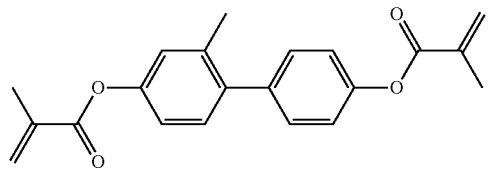
RM-41

TABLE D-continued
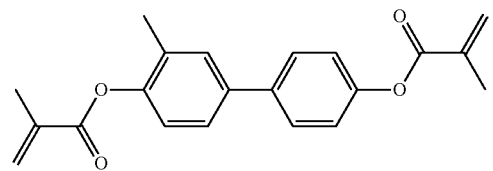 [SMILES: C=C(C)C(=O)Oc1ccc(-c2ccc(OC(=O)C(=C)C)c(C)c2)cc1] RM-42
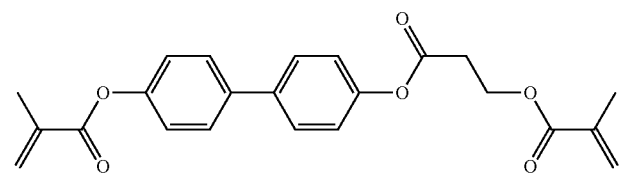 [SMILES: C=C(C)C(=O)OCCC(=O)Oc1ccc(-c2ccc(OC(=O)C(=C)C)cc2)cc1] RM-43
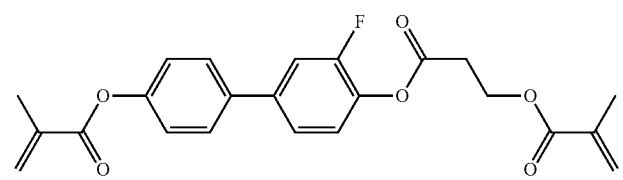 [SMILES: C=C(C)C(=O)OCCC(=O)Oc1ccc(-c2ccc(OC(=O)C(=C)C)cc2)cc1F] RM-44
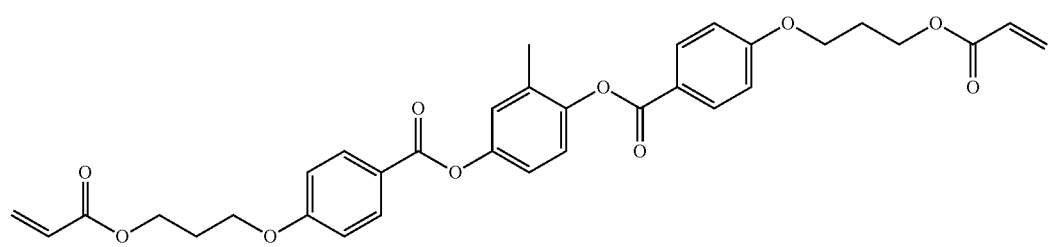 [SMILES: C=CC(=O)OCCCOc1ccc(C(=O)Oc2ccc(OC(=O)c3ccc(OCCCOC(=O)C=C)cc3)c(C)c2)cc1] RM-45
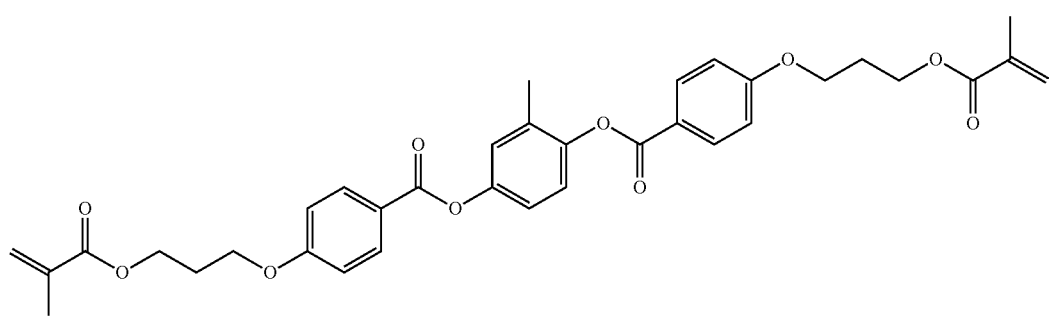 [SMILES: C=C(C)C(=O)OCCCOc1ccc(C(=O)Oc2ccc(OC(=O)c3ccc(OCCCOC(=O)C(=C)C)cc3)c(C)c2)cc1] RM-46
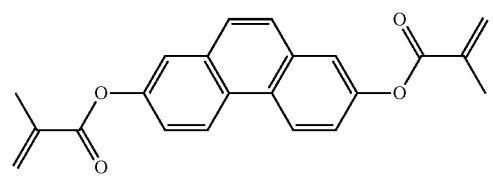 [SMILES: C=C(C)C(=O)Oc1ccc2c(ccc3cc(OC(=O)C(=C)C)ccc32)c1] RM-47
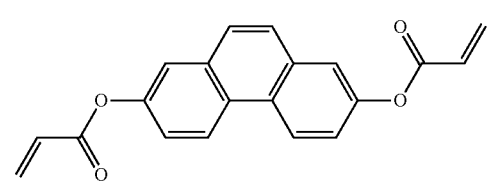 [SMILES: C=CC(=O)Oc1ccc2c(ccc3cc(OC(=O)C=C)ccc32)c1] RM-48

TABLE D-continued
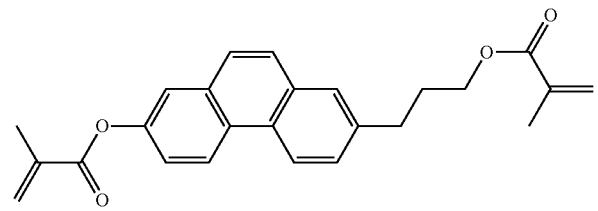 [SMILES: C=C(C)C(=O)OCCCc1ccc2c(ccc3cc(OC(=O)C(=C)C)ccc32)c1]
RM-49
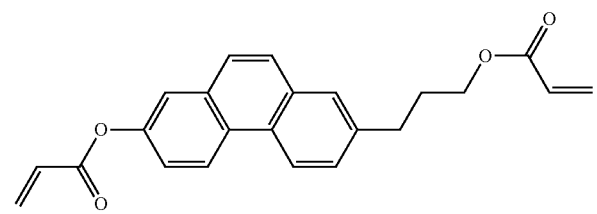 [SMILES: C=CC(=O)OCCCc1ccc2c(ccc3cc(OC(=O)C=C)ccc32)c1]
RM-50
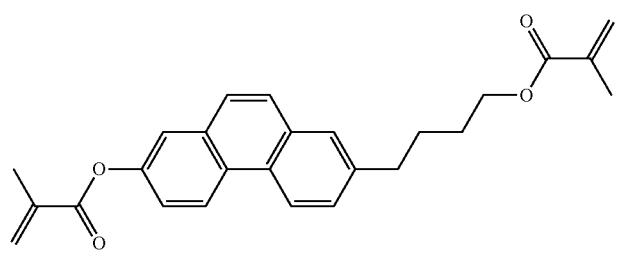 [SMILES: C=C(C)C(=O)OCCCCc1ccc2c(ccc3cc(OC(=O)C(=C)C)ccc32)c1]
RM-51
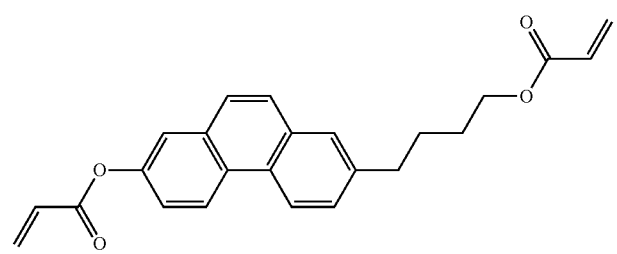 [SMILES: C=CC(=O)OCCCCc1ccc2c(ccc3cc(OC(=O)C=C)ccc32)c1]
RM-52
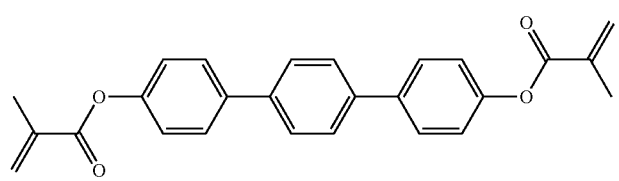
RM-53
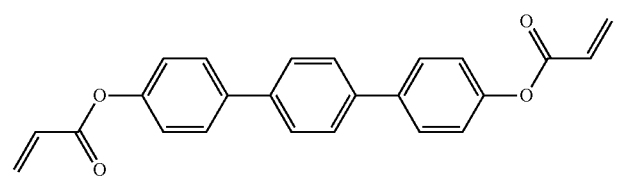
RM-54
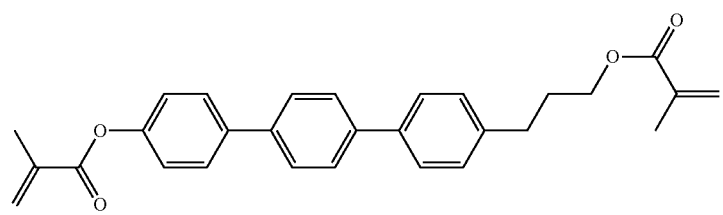
RM-55

TABLE D-continued
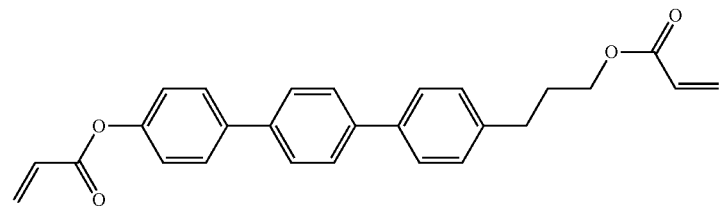
RM-56
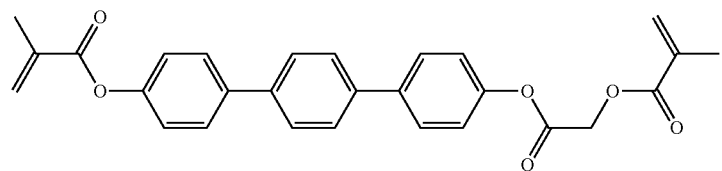
RM-57
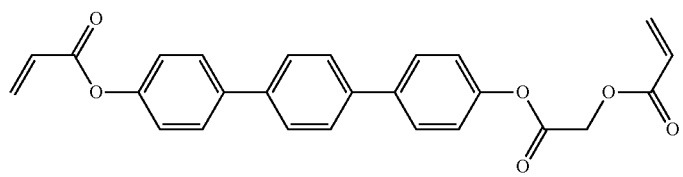
RM-58
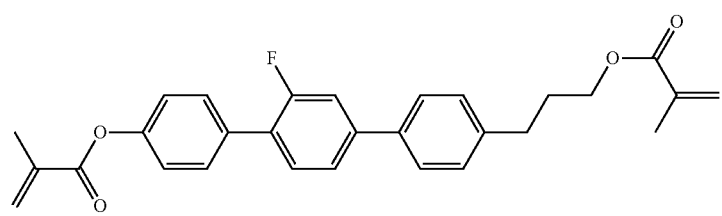 [SMILES: C=C(C)C(=O)OCCCc1ccc(-c2ccc(-c3ccc(OC(=O)C(=C)C)cc3)cc2)cc1]
RM-59
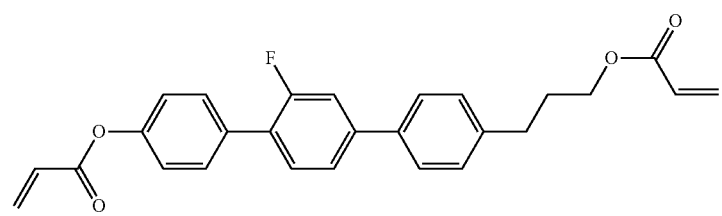 [SMILES: C=CC(=O)OCCCc1ccc(-c2ccc(-c3ccc(OC(=O)C=C)cc3)c(F)c2)cc1]
RM-60
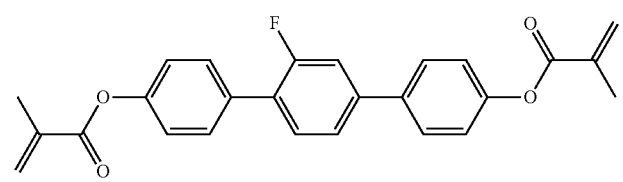
RM-61
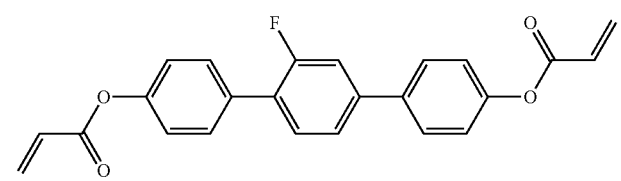 [SMILES: C=C(C)C(=O)Oc1ccc(-c2ccc(-c3ccc(OC(=O)C(=C)C)cc3)c(F)c2)cc1]
RM-62
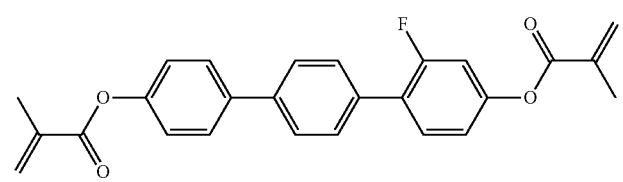 [SMILES: C=C(C)C(=O)Oc1ccc(-c2ccc(-c3ccc(OC(=O)C(=C)C)cc3F)cc2)cc1]
RM-63

TABLE D-continued
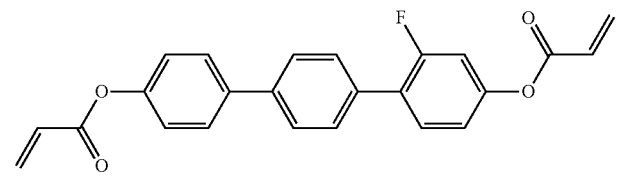 RM-64
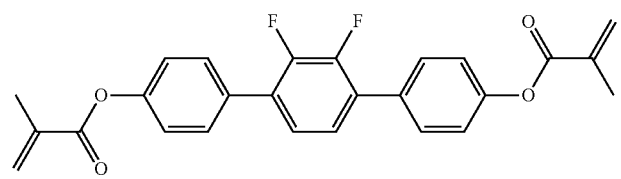 RM-65
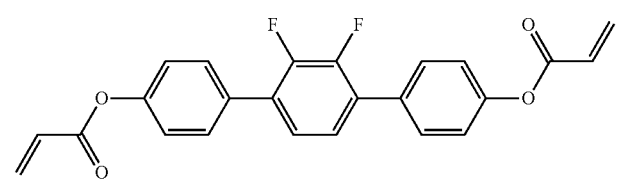 [SMILES: C=CC(=O)Oc1ccc(-c2ccc(-c3ccc(OC(=O)C=C)cc3)c(F)c2F)cc1] RM-66
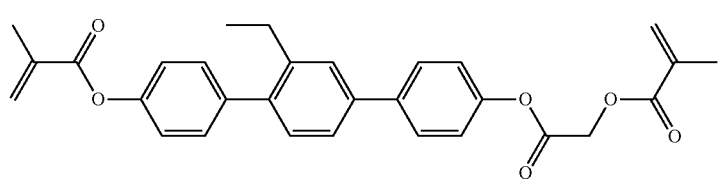 [SMILES: C=C(C)C(=O)OCC(=O)Oc1ccc(-c2ccc(-c3ccc(OC(=O)C(=C)C)cc3)c(CC)c2)cc1] RM-67
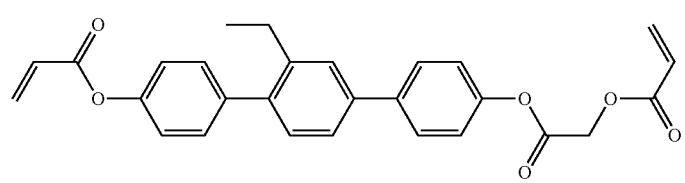 RM-68
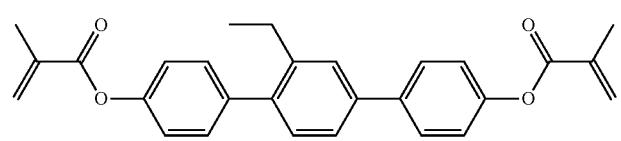 RM-69
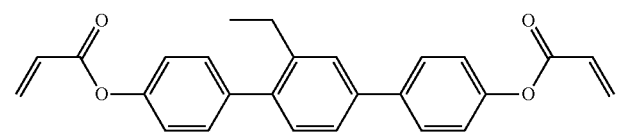 [SMILES: C=C(C)C(=O)Oc1ccc(-c2ccc(-c3ccc(OC(=O)C(=C)C)cc3)c(CC)c2)cc1] RM-70
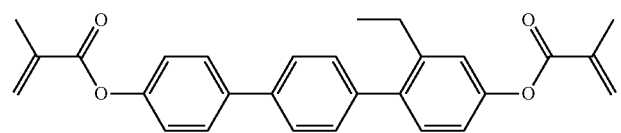 [SMILES: C=C(C)C(=O)Oc1ccc(-c2ccc(-c3ccc(OC(=O)C(=C)C)cc3CC)cc2)cc1] RM-71
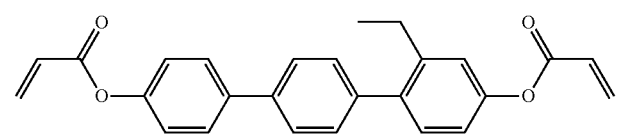 RM-72

TABLE D-continued
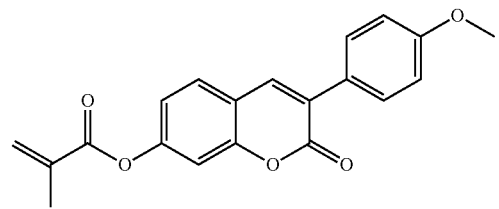 [SMILES: C=C(C)C(=O)Oc1ccc2cc(-c3ccc(OC)cc3)c(=O)oc2c1]
RM-73
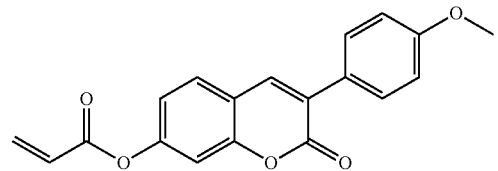 [SMILES: C=CC(=O)Oc1ccc2cc(-c3ccc(OC)cc3)c(=O)oc2c1]
RM-74
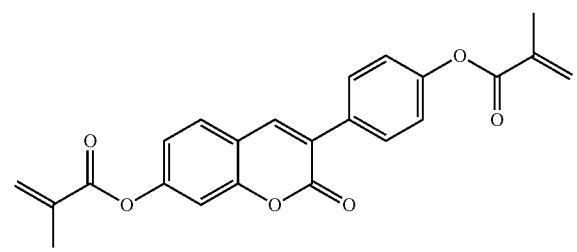 [SMILES: C=C(C)C(=O)Oc1ccc(-c2cc3ccc(OC(=O)C(=C)C)cc3oc2=O)cc1]
RM-75
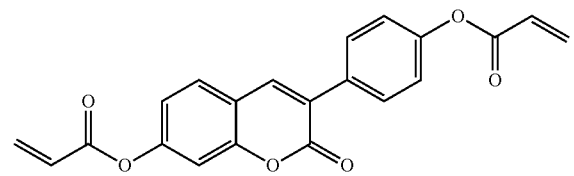 [SMILES: C=CC(=O)Oc1ccc(-c2cc3ccc(OC(=O)C=C)cc3oc2=O)cc1]
RM-76
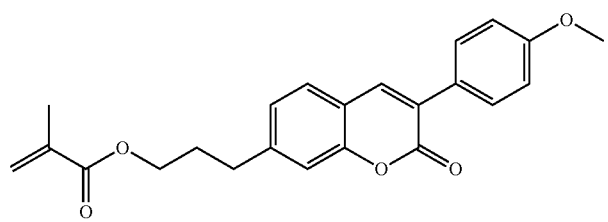 [SMILES: C=C(C)C(=O)OCCCc1ccc2cc(-c3ccc(OC)cc3)c(=O)oc2c1]
RM-77
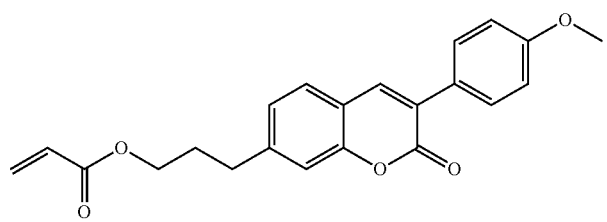 [SMILES: C=CC(=O)OCCCc1ccc2cc(-c3ccc(OC)cc3)c(=O)oc2c1]
RM-78
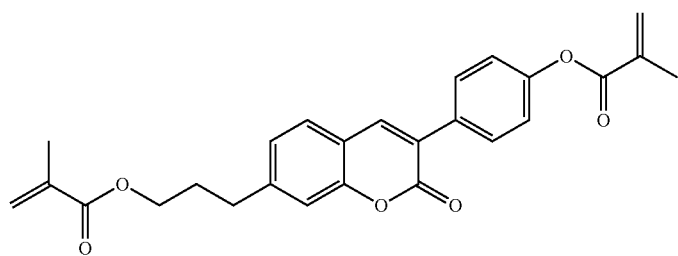 [SMILES: C=C(C)C(=O)OCCCc1ccc2cc(-c3ccc(OC(=O)C(=C)C)cc3)c(=O)oc2c1]
RM-79

TABLE D-continued
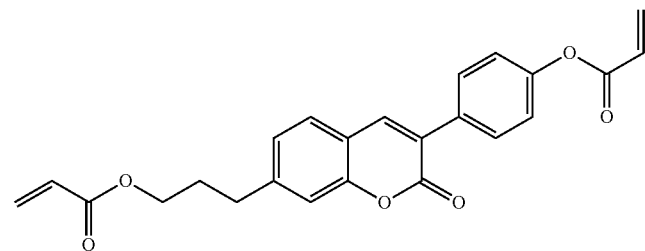 [SMILES: C=CC(=O)OCCCc1ccc2cc(-c3ccc(OC(=O)C=C)cc3)c(=O)oc2c1]
RM-80
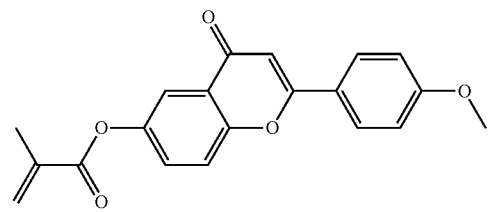 [SMILES: C=C(C)C(=O)Oc1ccc2oc(-c3ccc(OC)cc3)cc(=O)c2c1]
RM-81
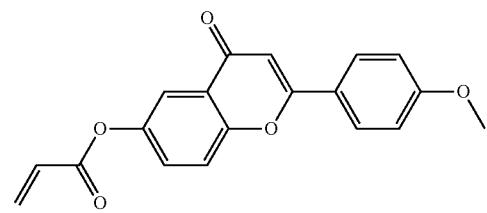 [SMILES: C=CC(=O)Oc1ccc2oc(-c3ccc(OC)cc3)cc(=O)c2c1]
RM-82
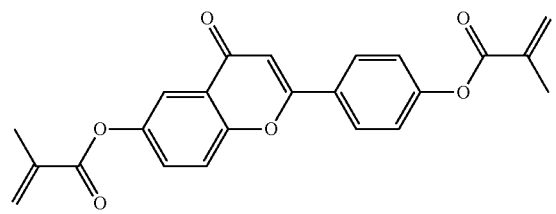 [SMILES: C=C(C)C(=O)Oc1ccc(-c2cc(=O)c3cc(OC(=O)C(=C)C)ccc3o2)cc1]
RM-83
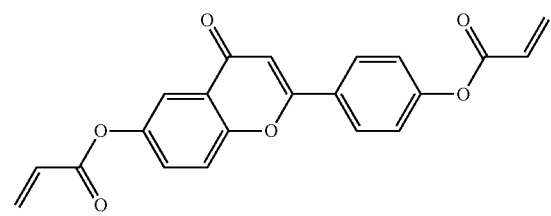 [SMILES: C=CC(=O)Oc1ccc(-c2cc(=O)c3cc(OC(=O)C=C)ccc3o2)cc1]
RM-84
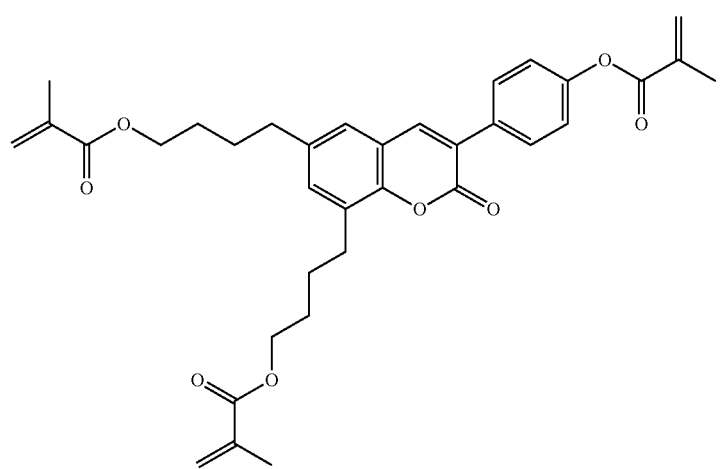 [SMILES: C=C(C)C(=O)OCCCCc1cc(CCCCOC(=O)C(=C)C)c2oc(=O)c(-c3ccc(OC(=O)C(=C)C)cc3)cc2c1]
RM-85

TABLE D-continued
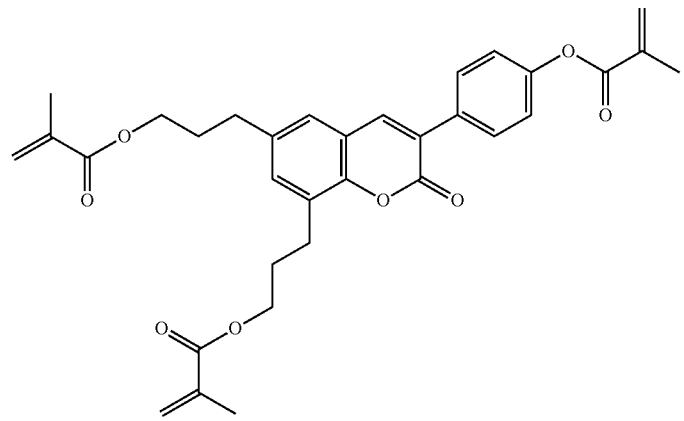 [SMILES: C=C(C)C(=O)OCCCc1cc(CCCOC(=O)C(=C)C)c2oc(=O)c(-c3ccc(OC(=O)C(=C)C)cc3)cc2c1]
RM-86
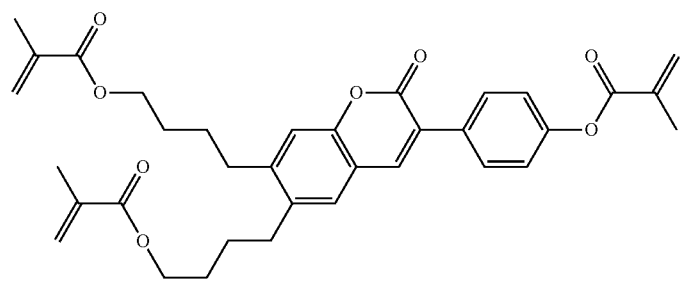 [SMILES: C=C(C)C(=O)OCCCCc1cc2cc(-c3ccc(OC(=O)C(=C)C)cc3)c(=O)oc2cc1CCCCOC(=O)C(=C)C]
RM-87
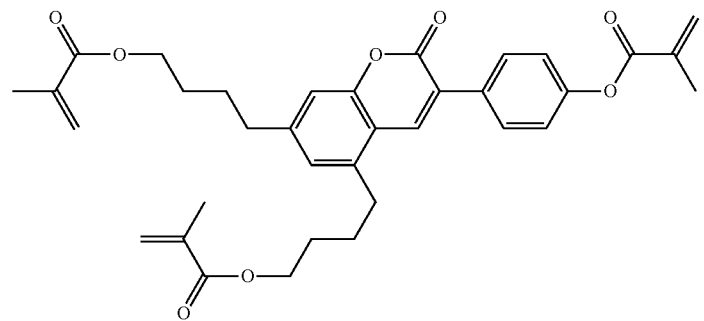 [SMILES: C=C(C)C(=O)OCCCCc1cc(CCCCOC(=O)C(=C)C)c2cc(-c3ccc(OC(=O)C(=C)C)cc3)c(=O)oc2c1]
RM-88
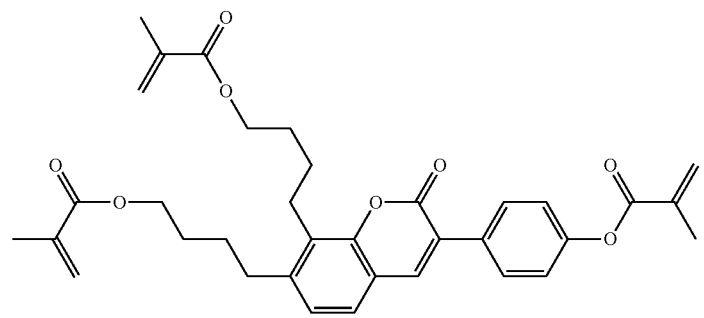 [SMILES: C=C(C)C(=O)OCCCCc1ccc2cc(-c3ccc(OC(=O)C(=C)C)cc3)c(=O)oc2c1CCCCOC(=O)C(=C)C]
RM-89
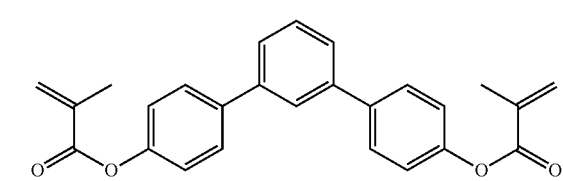 [SMILES: C=C(C)C(=O)Oc1ccc(-c2cccc(-c3ccc(OC(=O)C(=C)C)cc3)c2)cc1]
RM-90

TABLE D-continued
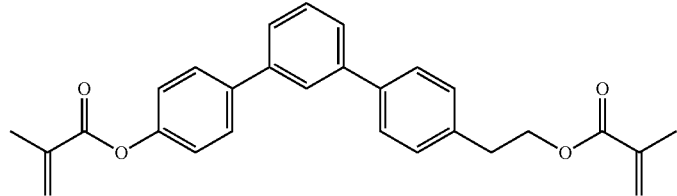 [SMILES: C=C(C)C(=O)OCCc1ccc(-c2cccc(-c3ccc(OC(=O)C(=C)C)cc3)c2)cc1]
RM-91
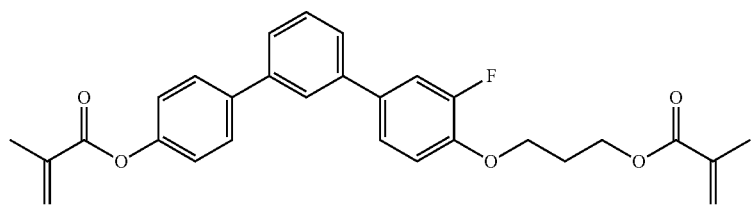 [SMILES: C=C(C)C(=O)OCCCOc1ccc(-c2cccc(-c3ccc(OC(=O)C(=C)C)cc3)c2)cc1F]
RM-92
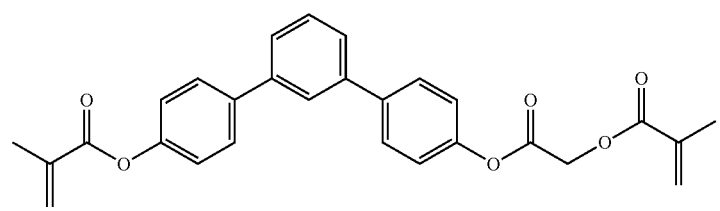 [SMILES: C=C(C)C(=O)OCC(=O)Oc1ccc(-c2cccc(-c3ccc(OC(=O)C(=C)C)cc3)c2)cc1]
RM-93
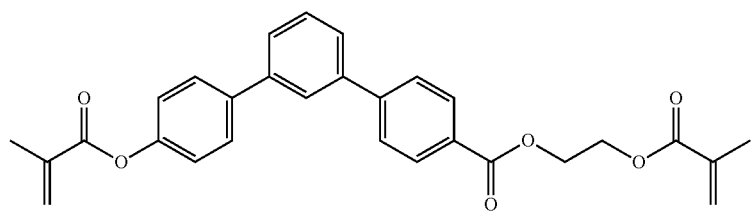 [SMILES: C=C(C)C(=O)OCCOC(=O)c1ccc(-c2cccc(-c3ccc(OC(=O)C(=C)C)cc3)c2)cc1]
RM-94
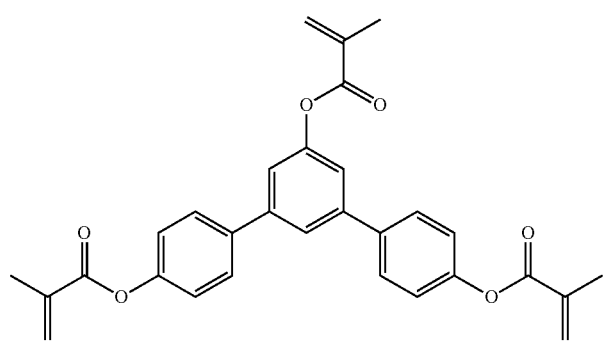 [SMILES: C=C(C)C(=O)Oc1ccc(-c2cc(OC(=O)C(=C)C)cc(-c3ccc(OC(=O)C(=C)C)cc3)c2)cc1]
RM-95
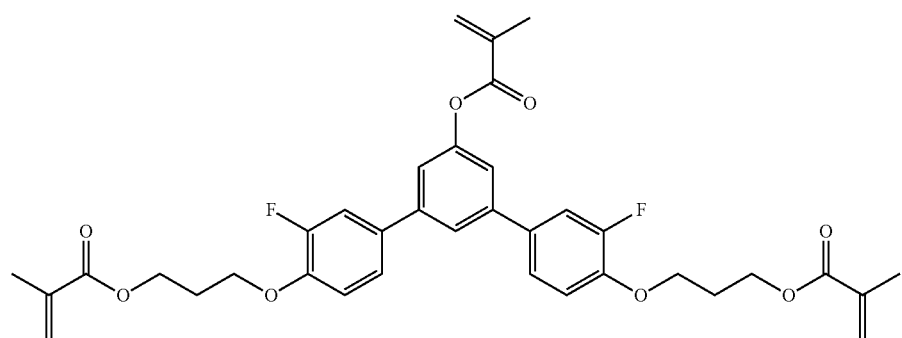 [SMILES: C=C(C)C(=O)OCCCOc1ccc(-c2cc(OC(=O)C(=C)C)cc(-c3ccc(OCCCOC(=O)C(=C)C)c(F)c3)c2)cc1F]
RM-96

TABLE D-continued
RM-97
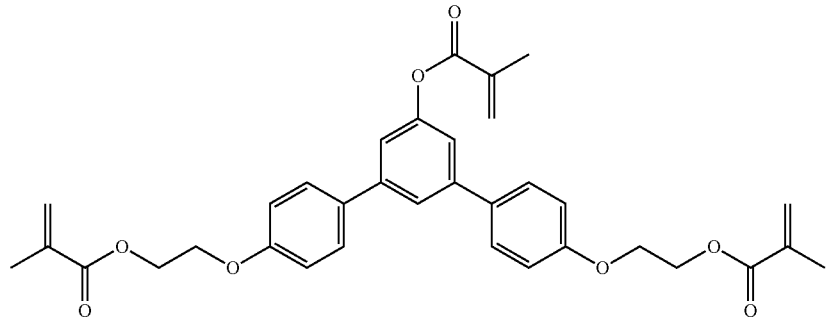 [SMILES: C=C(C)C(=O)OCCOc1ccc(-c2cc(OC(=O)C(=C)C)cc(-c3ccc(OCCOC(=O)C(=C)C)cc3)c2)cc1]
RM-98
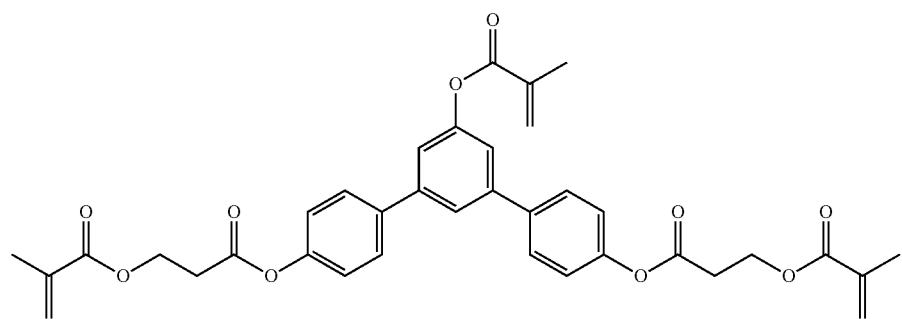 [SMILES: C=C(C)C(=O)OCCC(=O)Oc1ccc(-c2cc(OC(=O)C(=C)C)cc(-c3ccc(OC(=O)CCOC(=O)C(=C)C)cc3)c2)cc1]
RM-99
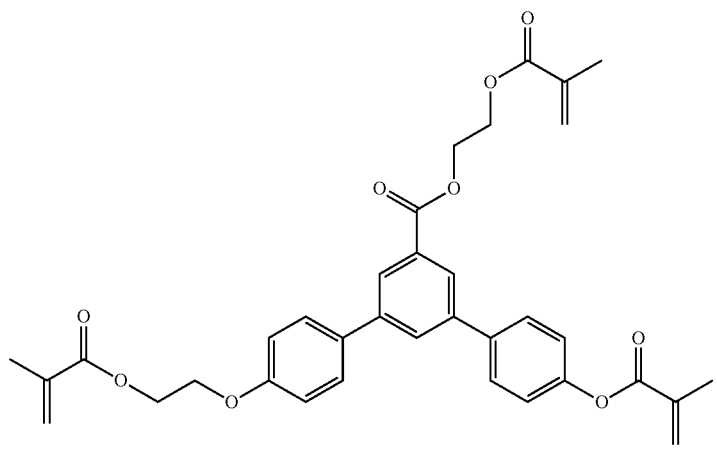 [SMILES: C=C(C)C(=O)OCCOC(=O)c1cc(-c2ccc(OCCOC(=O)C(=C)C)cc2)cc(-c2ccc(OC(=O)C(=C)C)cc2)c1]
RM-100
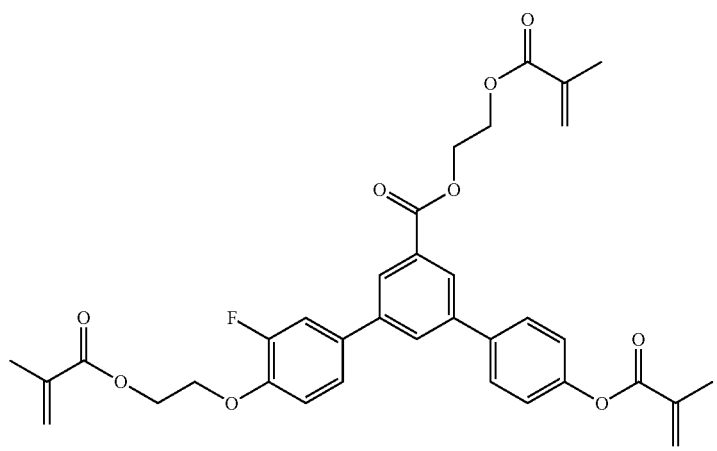 [SMILES: C=C(C)C(=O)OCCOC(=O)c1cc(-c2ccc(OC(=O)C(=C)C)cc2)cc(-c2ccc(OCCOC(=O)C(=C)C)c(F)c2)c1]

TABLE D-continued
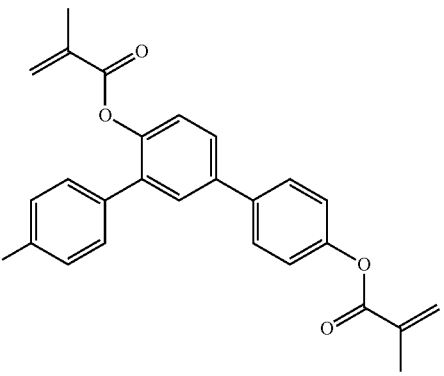
RM-101
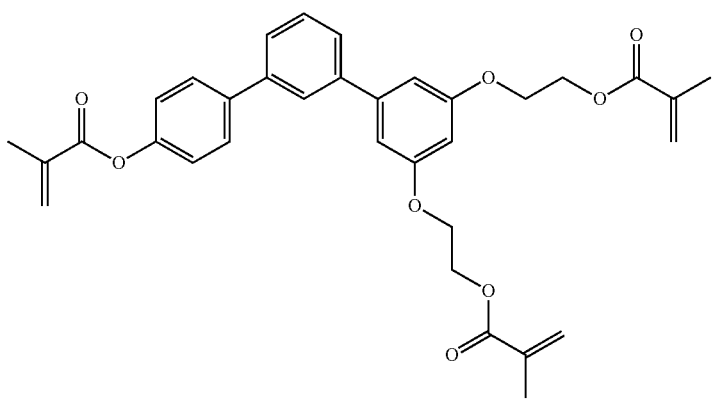 [SMILES: C=C(C)C(=O)OCCOc1cc(OCCOC(=O)C(=C)C)cc(-c2cccc(-c3ccc(OC(=O)C(=C)C)cc3)c2)c1]
RM-102
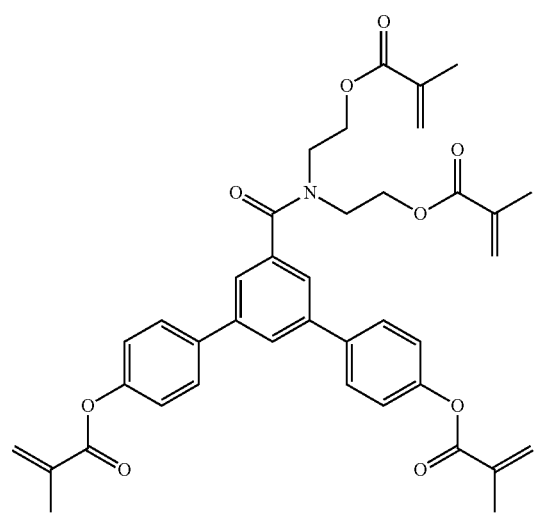 [SMILES: C=C(C)C(=O)OCCN(CCOC(=O)C(=C)C)C(=O)c1cc(-c2ccc(OC(=O)C(=C)C)cc2)cc(-c2ccc(OC(=O)C(=C)C)cc2)c1]
RM-103
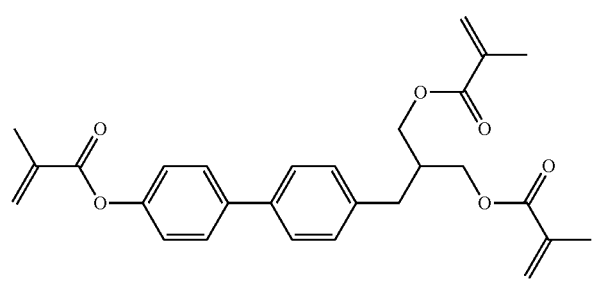 [SMILES: C=C(C)C(=O)OCC(COC(=O)C(=C)C)Cc1ccc(-c2ccc(OC(=O)C(=C)C)cc2)cc1]
RM-104

TABLE D-continued
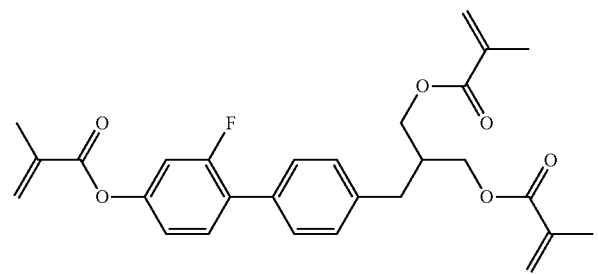 [SMILES: C=C(C)C(=O)OCC(COC(=O)C(=C)C)Cc1ccc(-c2ccc(OC(=O)C(=C)C)cc2F)cc1]
RM-105
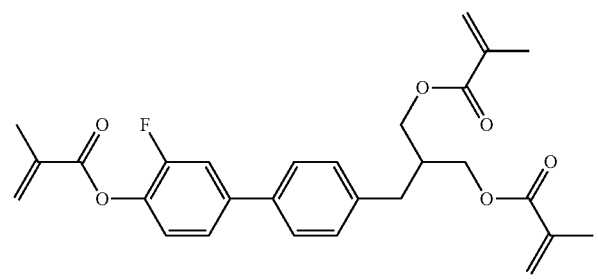 [SMILES: C=C(C)C(=O)OCC(COC(=O)C(=C)C)Cc1ccc(-c2ccc(OC(=O)C(=C)C)c(F)c2)cc1]
RM-106
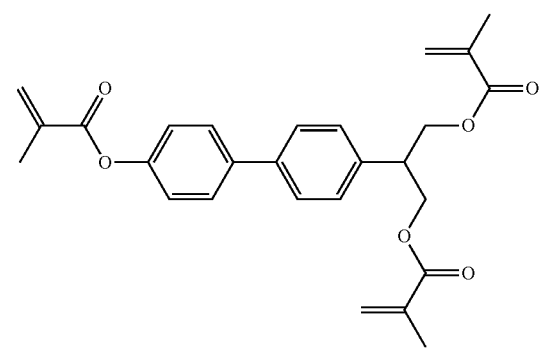
RM-107
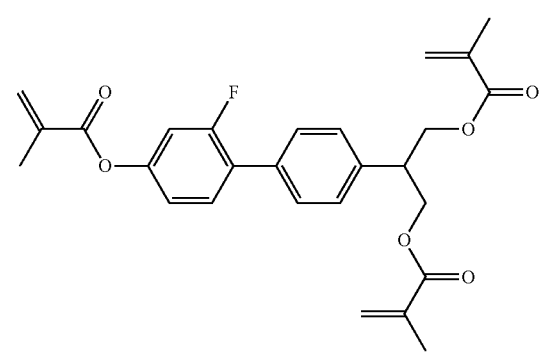 [SMILES: C=C(C)C(=O)OCC(COC(=O)C(=C)C)c1ccc(-c2ccc(OC(=O)C(=C)C)cc2)cc1]
RM-108
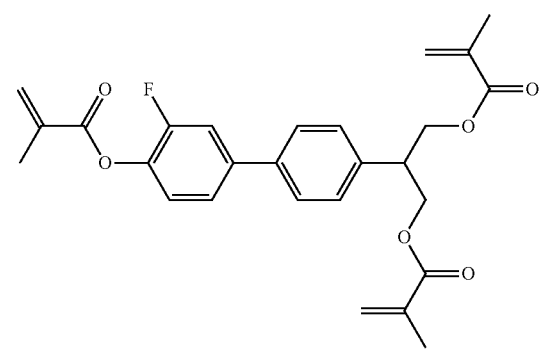
RM-109

TABLE D-continued
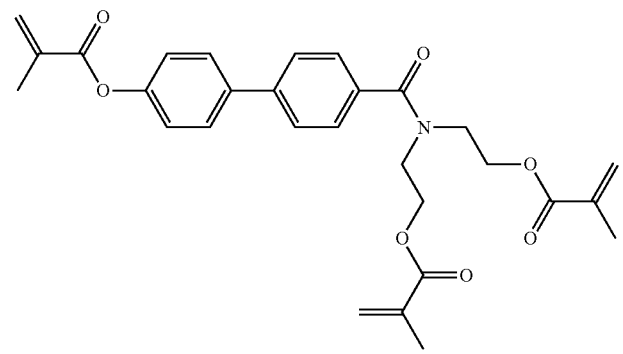 [SMILES: C=C(C)C(=O)OCCN(CCOC(=O)C(=C)C)C(=O)c1ccc(-c2ccc(OC(=O)C(=C)C)cc2)cc1]
RM-110
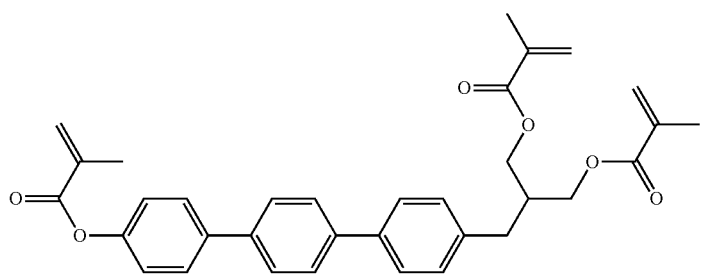 [SMILES: C=C(C)C(=O)OCC(COC(=O)C(=C)C)Cc1ccc(-c2ccc(-c3ccc(OC(=O)C(=C)C)cc3)cc2)cc1]
RM-111
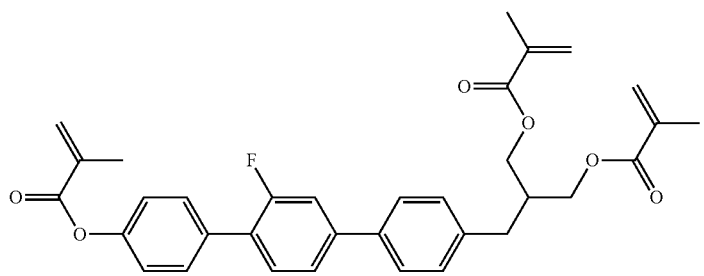 [SMILES: C=C(C)C(=O)OCC(COC(=O)C(=C)C)Cc1ccc(-c2ccc(-c3ccc(OC(=O)C(=C)C)cc3)c(F)c2)cc1]
RM-112
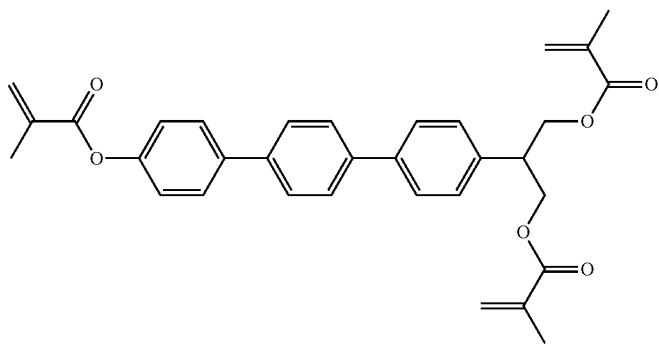 [SMILES: C=C(C)C(=O)OCC(COC(=O)C(=C)C)c1ccc(-c2ccc(-c3ccc(OC(=O)C(=C)C)cc3)cc2)cc1]
RM-113
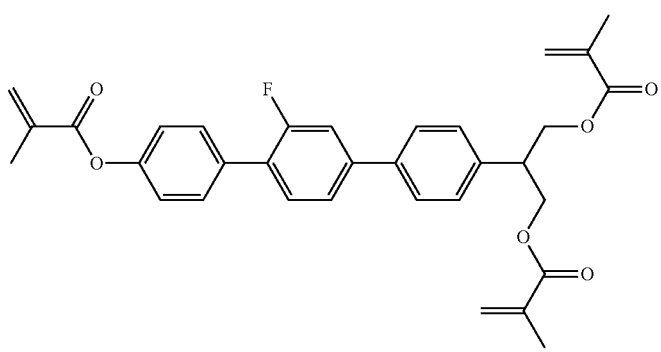 [SMILES: C=C(C)C(=O)OCC(COC(=O)C(=C)C)c1ccc(-c2ccc(-c3ccc(OC(=O)C(=C)C)cc3)c(F)c2)cc1]
RM-114

TABLE D-continued
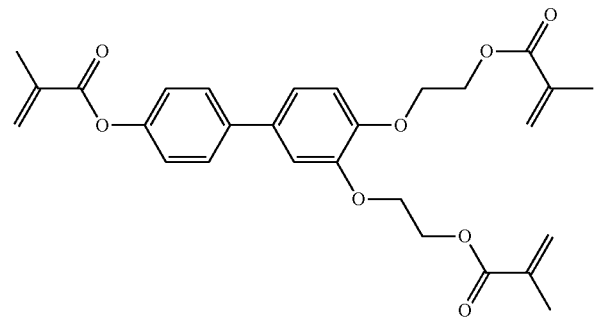 [SMILES: C=C(C)C(=O)OCCOc1ccc(-c2ccc(OC(=O)C(=C)C)cc2)cc1OCCOC(=O)C(=C)C]
RM-115
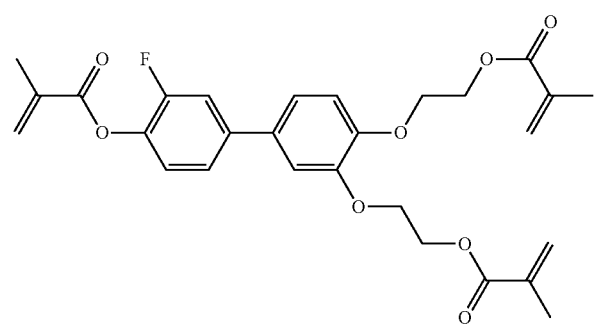 [SMILES: C=C(C)C(=O)OCCOc1ccc(-c2ccc(OC(=O)C(=C)C)c(F)c2)cc1OCCOC(=O)C(=C)C]
RM-116
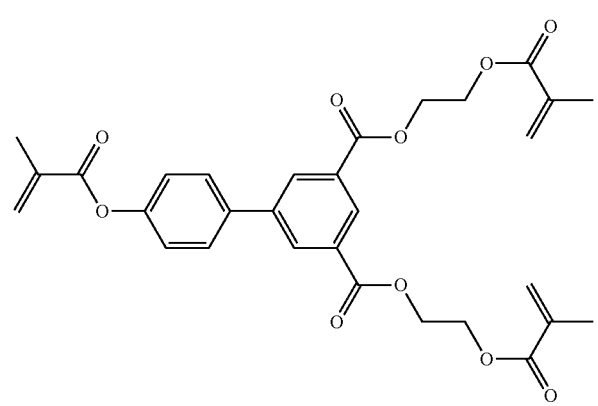 [SMILES: C=C(C)C(=O)OCCOC(=O)c1cc(C(=O)OCCOC(=O)C(=C)C)cc(-c2ccc(OC(=O)C(=C)C)cc2)c1]
RM-117
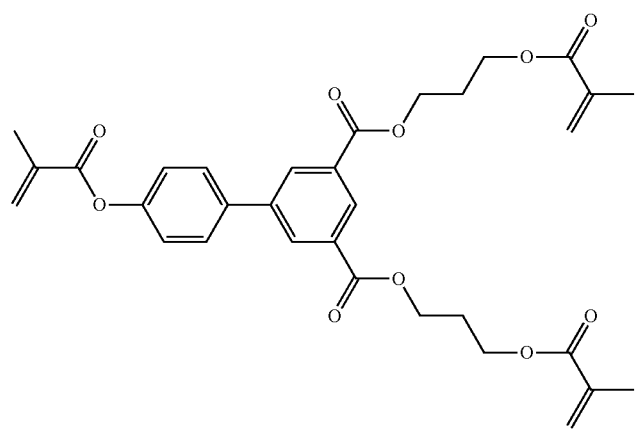 [SMILES: C=C(C)C(=O)OCCCOC(=O)c1cc(C(=O)OCCCOC(=O)C(=C)C)cc(-c2ccc(OC(=O)C(=C)C)cc2)c1]
RM-118

TABLE D-continued
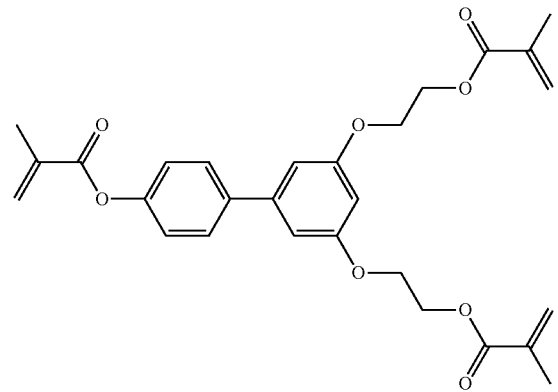 [SMILES: C=C(C)C(=O)OCCOc1cc(OCCOC(=O)C(=C)C)cc(-c2ccc(OC(=O)C(=C)C)cc2)c1]
RM-119
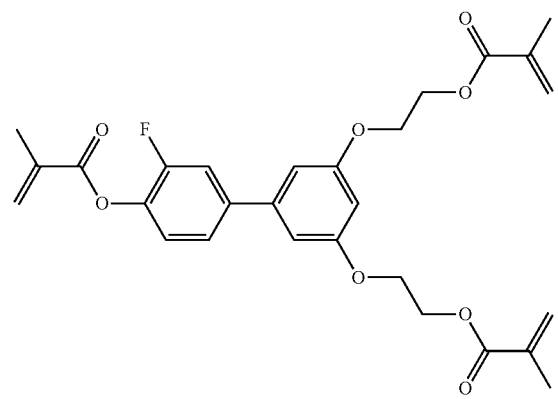 [SMILES: C=C(C)C(=O)OCCOc1cc(OCCOC(=O)C(=C)C)cc(-c2ccc(OC(=O)C(=C)C)c(F)c2)c1]
RM-120
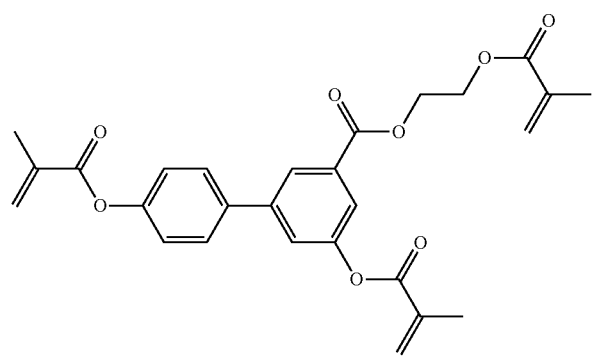 [SMILES: C=C(C)C(=O)OCCOC(=O)c1cc(OC(=O)C(=C)C)cc(-c2ccc(OC(=O)C(=C)C)cc2)c1]
RM-121
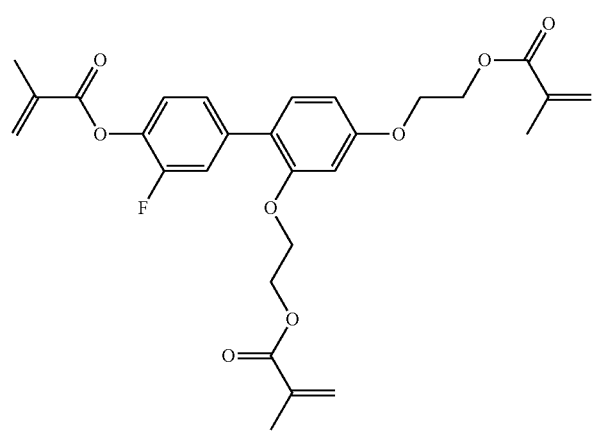 [SMILES: C=C(C)C(=O)OCCOc1ccc(-c2ccc(OC(=O)C(=C)C)c(F)c2)c(OCCOC(=O)C(=C)C)c1]
RM-122

TABLE D-continued
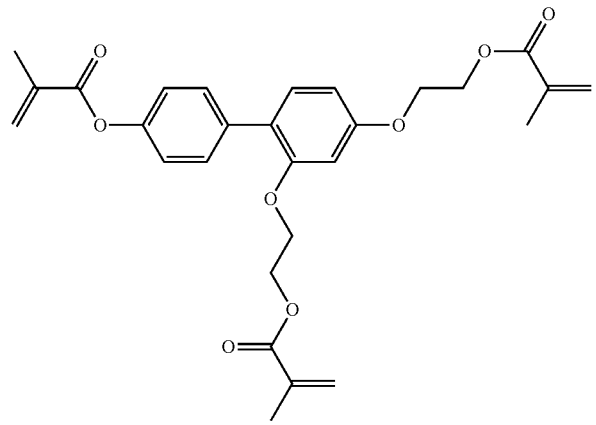 [SMILES: C=C(C)C(=O)OCCOc1ccc(-c2ccc(OC(=O)C(=C)C)cc2)c(OCCOC(=O)C(=C)C)c1]
RM-123
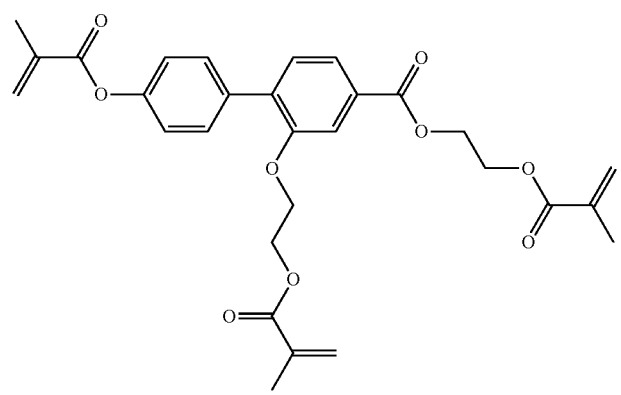 [SMILES: C=C(C)C(=O)OCCOC(=O)c1ccc(-c2ccc(OC(=O)C(=C)C)cc2)c(OCCOC(=O)C(=C)C)c1]
RM-124
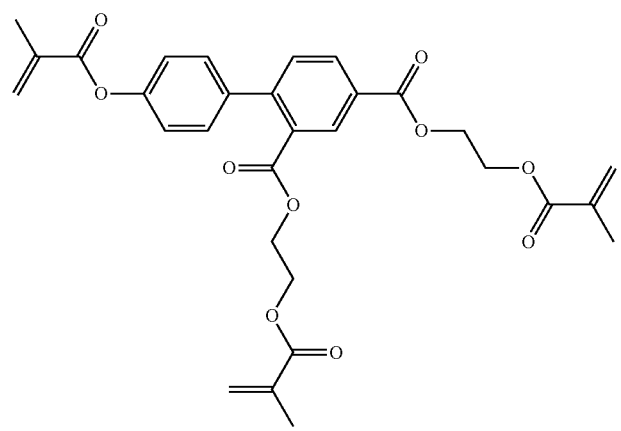 [SMILES: C=C(C)C(=O)OCCOC(=O)c1ccc(-c2ccc(OC(=O)C(=C)C)cc2)c(C(=O)OCCOC(=O)C(=C)C)c1]
RM-125
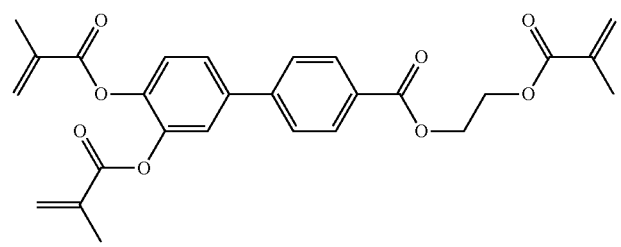 [SMILES: C=C(C)C(=O)OCCOC(=O)c1ccc(-c2ccc(OC(=O)C(=C)C)c(OC(=O)C(=C)C)c2)cc1]
RM-126

TABLE D-continued
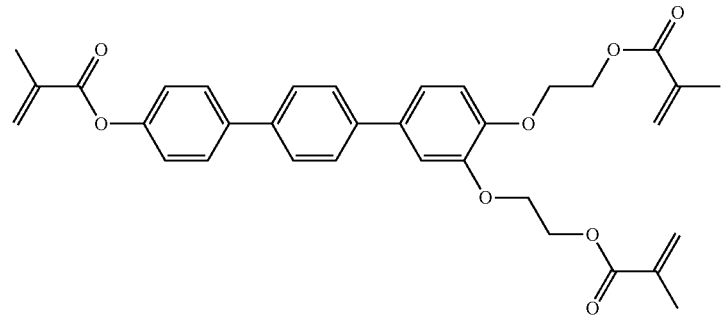 [SMILES: C=C(C)C(=O)OCCOc1ccc(-c2ccc(-c3ccc(OC(=O)C(=C)C)cc3)cc2)cc1OCCOC(=O)C(=C)C]
RM-127
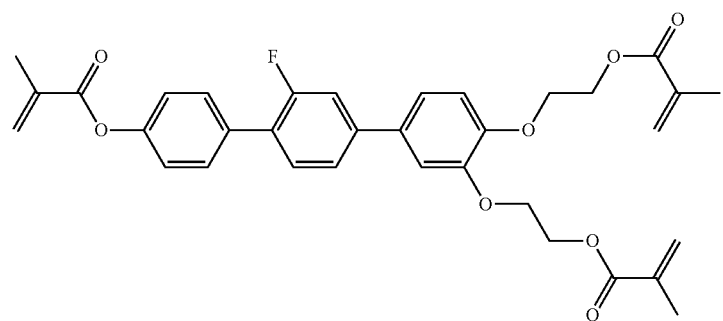 [SMILES: C=C(C)C(=O)OCCOc1ccc(-c2ccc(-c3ccc(OC(=O)C(=C)C)cc3)c(F)c2)cc1OCCOC(=O)C(=C)C]
RM-128
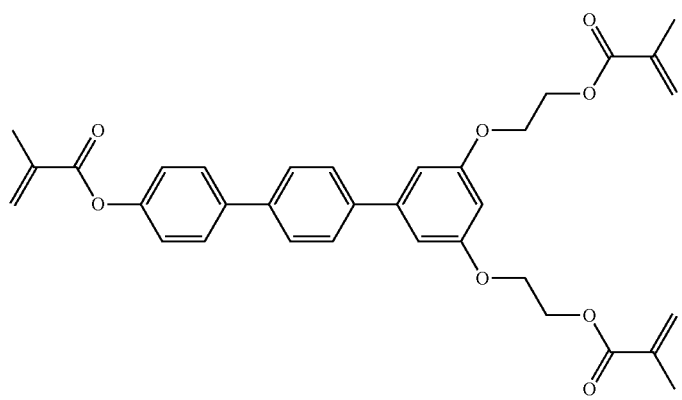 [SMILES: C=C(C)C(=O)OCCOc1cc(OCCOC(=O)C(=C)C)cc(-c2ccc(-c3ccc(OC(=O)C(=C)C)cc3)cc2)c1]
RM-129
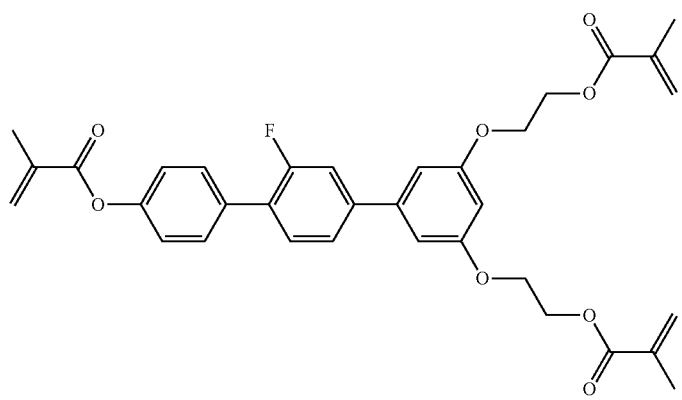 [SMILES: C=C(C)C(=O)OCCOc1cc(OCCOC(=O)C(=C)C)cc(-c2ccc(-c3ccc(OC(=O)C(=C)C)cc3)c(F)c2)c1]
RM-130

TABLE D-continued

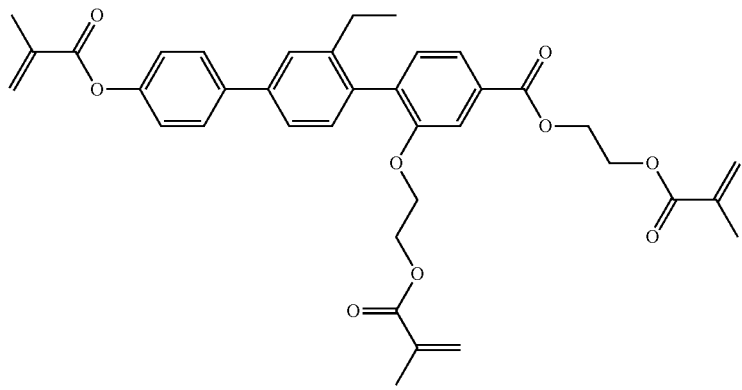 [SMILES: C=C(C)C(=O)OCCOC(=O)c1ccc(-c2ccc(-c3ccc(OC(=O)C(=C)C)cc3)cc2CC)c(OCCOC(=O)C(=C)C)c1]

RM-131

Table D shows illustrative reactive mesogenic compounds which can be used in the LC media in accordance with the present invention.

In a preferred embodiment, the mixtures according to the invention comprise one or more polymerizable compounds, preferably selected from the polymerizable compounds of the formulae RM-1 to RM-131. Of these, compounds RM-1, RM-4, RM-8, RM-17, RM-19, RM-35, RM-37, RM-43, RM-47, RM-49, RM-51, RM-59, RM-69, RM-71, RM-83, RM-97, RM-98, RM-104, RM-112, RM-115 and RM-116 are particularly preferred.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\epsilon_\perp$ dielectric permittivity perpendicular to the director at 20° C. and 1 kHz,
$\epsilon_\parallel$ dielectric permittivity parallel to the director at 20° C. and 1 kHz,
$\Delta\epsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application relate to the corresponding mixture as a whole, comprising all solid or liquid-crystalline components, without solvents. Unless explicitly noted otherwise, the expression "x % of compound Y are added to the mixture" means that the concentration of compound Y in the final mixture, i.e. after its addition, is x %.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status Nov. 1997, Merck KGaA, Germany, and apply for a temperature of 20° C., and $\Delta n$ is determined at 589 nm and $\Delta\epsilon$ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

Unless stated otherwise, the process of polymerizing the polymerizable compounds in the PSA displays as described above and below is carried out at a temperature where the LC medium exhibits a liquid crystal phase, preferably a nematic phase, and most preferably is carried out at room temperature.

Unless stated otherwise, methods of preparing test cells and measuring their electrooptical and other properties are carried out by the methods as described hereinafter or in analogy thereto.

The display used for measurement of the capacitive threshold voltage consists of two plane-parallel glass outer plates at a separation of 25 µm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 µm, each of which has on the inside an electrode layer and a polyimide alignment layer on top, where the two polyimide layers are rubbed antiparallel to one another and effect a homeotropic edge alignment of the liquid-crystal molecules.

The polymerizable compounds are polymerized in the display or test cell by irradiation with UV light of defined intensity for a prespecified time, with a voltage simultaneously being applied to the display (usually 10 V to 30 V alternating current, 1 kHz). In the examples, unless indicated otherwise, a metal halide lamp and an intensity of 100 mW/cm² is used for polymerization. The intensity is measured using a standard meter (Hoenle UV-meter high end with UV sensor).

The tilt angle is determined by crystal rotation experiment (Autronic-Melchers TBA-105). A low value (i.e. a large deviation from the 90° angle) corresponds to a large tilt here.

Unless stated otherwise, the term "tilt angle" means the angle between the LC director and the substrate, and "LC director" means in a layer of LC molecules with uniform orientation the preferred orientation direction of the optical main axis of the LC molecules, which corresponds, in case of calamitic, uniaxially positive birefringent LC molecules, to their molecular long axis.

The VHR value is measured as follows: 0.3% of a polymerizable monomeric compound is added to the LC host mixture, and the resultant mixture is introduced into VA-VHR test cells which comprise an unrubbed VA-polyimide alignment layer. The LC-layer thickness d is approx. 4 μm, unless stated othewise. The VHR value is determined after 5 min at 100° C. before and after UV exposure at 1 V, 60 Hz, 64 μs pulse (measuring instrument: Autronic-Melchers VHRM-105).

Example 1

Compound 1 is prepared as following.

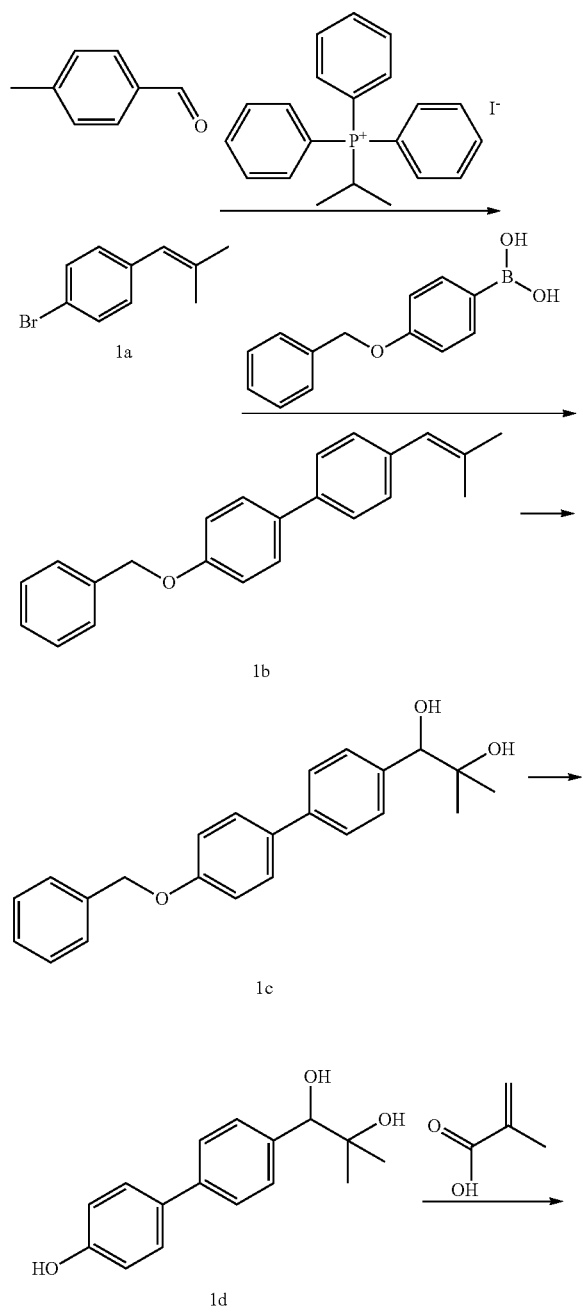

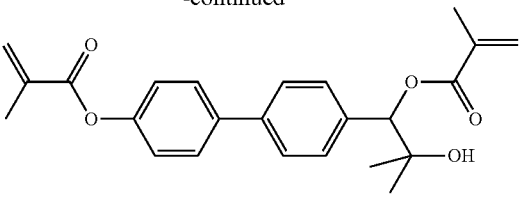

1a: To a solution of isopropyl-triphenylphosphonium iodide (87.4 g, 0.2 mol) in 120 ml THF is added the solution of potassium tert-butylate (22.8 g; 0.2 mol) at max. 10° C. After stirred for 1 h, the solution of 4-bormo-benzaldehyde (34.0 g, 0.18 mol) in 30 ml THF is added at max. 10° C. The reaction mixture is allowed to warm up to room temperature and stirred overnight. After carefully neutralized with 2 M HCl, the reactive mixture is extracted three time with heptane. The organic phase is combined, dried over anhydrous sodium sulfate, and filtrated through silica gel. After removing solvent in vacuo, 1a is obtained at colorless oil (35.0 g).

1b: To a solution of 1a (35.0 g, 0.16 mol) and 4-benzoxylphenyl boronic acid (37.8 g, 0.16 mol) in 200 ml THF was added 110 ml dist. water and potassium carbonate (14.0 g, 0.25 mol). The resulted suspension is degassed carefully with argon, tris(dibenzylideneacetone)dipalladium(0) (0.84 g, 0.9 mmol) and CataCium A (0.91 g, 2.5 mmol) are then added. The reaction mixture is heated to reflux and stirred for 3 hs. After cooling to room temperature, the reaction mixture is neutralized carefully with 2 M HCl acid. The aqueous phase is extracted with methyl t-butyl ether. The organic phase is combined and washed with sat. aq. NaCl solution, dried over sodium sulfate. After removing solvent, the solid residue recrystallized from ethylacetate to provide 1b as off-white solid (45.0 g).

1c: To the suspension of 1b (45.0 g, 0.14 mol), 4-methylmorpholine-4-oxide (26.8 g; 0.2 mol) in 700 ml aceton and 50 ml distilled water was added 4% aqueous solution of osmium tetraoxide (17 ml, 2.7 mmol) at room temperature. After stirred at RT for 48 hrs, 250 m ml water is added, the mixture is carefully neutralized with 2 M HCl acid. The precipitated crude product is recrystallized with ethyl acetate to provide 1c as off-white solid (27.0 g).

1d: A solution of 1c (27.0 g, 77.5 mmol) in 270 ml tetrahydrofuran is treated with palladium (5%) on activated charcoal (7.5 g) and submitted to hydrogenation for 12 hs. The catalyst is then filtered off, and the remaining solution is concentrated in vacuo. The residue is recrystallized from acetonitrile to provide 1d as white solid (16.0 g).

1: Methacrylic acid (12.0 ml, 0.14 mol) and 4-(dimethylamino)pyridine (0.75 g, 6.1 mmol) is added to a suspension of 1d (16.0 g, 62.0 mmol) in 400 ml dichloromethane. The reaction mixture is treated dropwise at 0° C. with a solution of N-(3-dimethylaminopropyl)-N'-ethylcarbodiimide (22.1 g, 0.14 mol) in dichloromethane (50 ml) and stirred for 20 h at room temperature. After removing solvent in vacuo, the oily residue is purified by silica gel chromatography with heptane/ethyl acetate 7:3 as eluent. The obtained product is recrystallized from heptane/ethanol solvent mixture to afford white crystals of 1 (14.0 g, mp. 111° C.).

Example 2

Compound 2 is prepared from the intermediate step 1c in the synthesis of Example 1 as following.

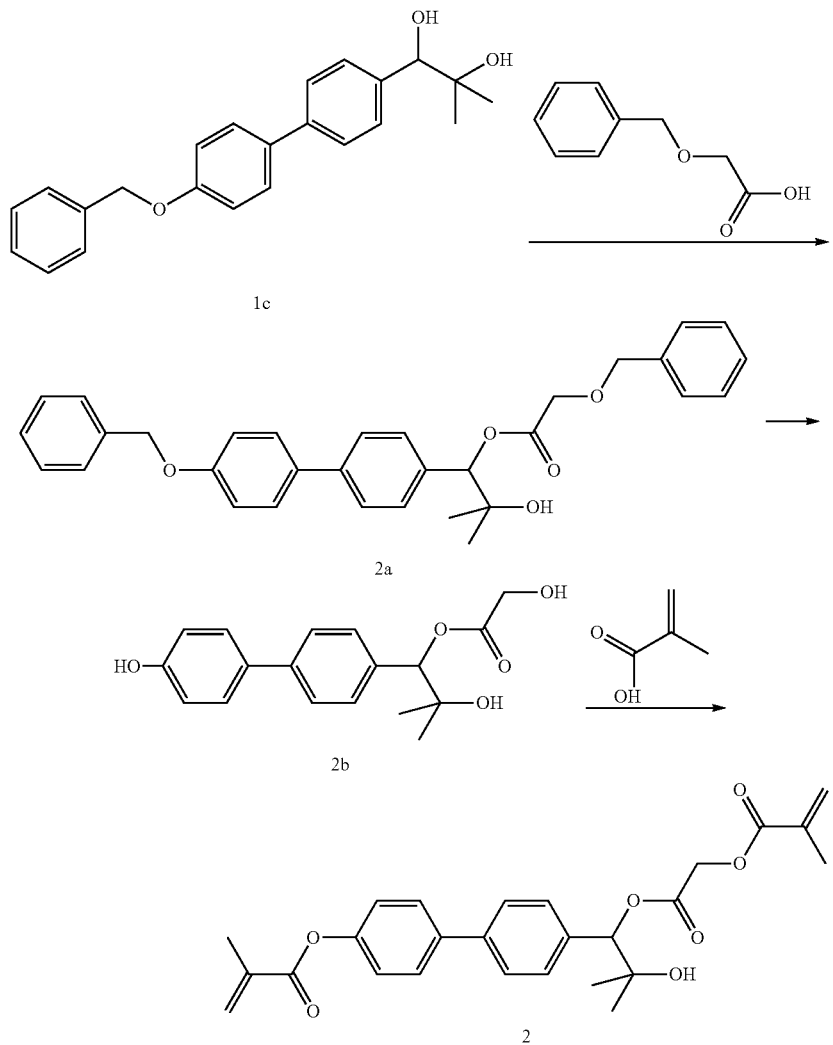

2a: To a solution of 1c (6.00 g, 17.2 mmol) in 80 ml dichloromethane are added 4-(dimethylamino)pyridine (0.16 g, 1.3 mmol) and N-(3-dimethylaminopropyl)-N'-ethylcarbodiimidhydrochlorid (DAPECI) (4.1 g, 21.3 mmol). The reaction mixture is stirred at room temperature overnight. 100 ml water is added. The aqueous phase is extracted with dichloromethane. The organic phase is combined and dried over anhydrous sodium sulfate. After removing solvent in vacuo, the solid residue is purified by column chromatography with dichloromethane as eluent to provide 2a as white solid (6.4 g).

2b: A suspension of 2a (6.4 g, 12.6 mmol) in 70 ml THF is treated with palladium (5%) on activated charcoal (1.5 g) and submitted to hydrogenation for 10 hs. The catalyst is then filtered off. After removing solvent, the crude product is recrystallized from heptane/toluene solvent mixture to provide 2b as white solid (3.9 g).

2: Methacrylic acid (1.6 g, 18 mmol) and 4-(dimethylamino)pyridine (0.10 g, 0.8 mmol) is added to a suspension of 5b (2.50 g, 7.9 mmol) in dichloromethane (50 ml). The reaction mixture is treated dropwise at 0° C. with a solution of N-(3-dimethylaminopropyl)-N'-ethylcarbodiimide (2.9 g, 18 mmol) in dichloromethane (10 ml) and stirred for 20 hs at room temperature. The reaction mixture is concentrated in vacuo, and the oily residue is purified by column chromatography on silica gel with heptane/ethyl acetate mixture as eluent. The obtained product is recrystallized from heptane/ methyl tert-butyl ether 3:1 solvent mixture to afford 2 as colorless solid (1.9 g, mp. 26° C.).

Example 3

Compound 3 is prepared as following.

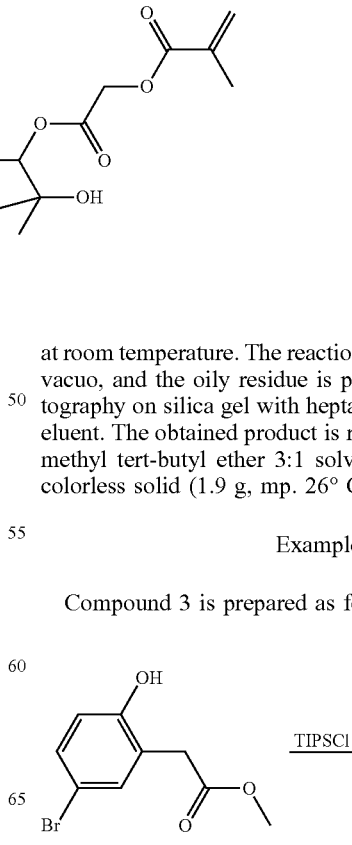

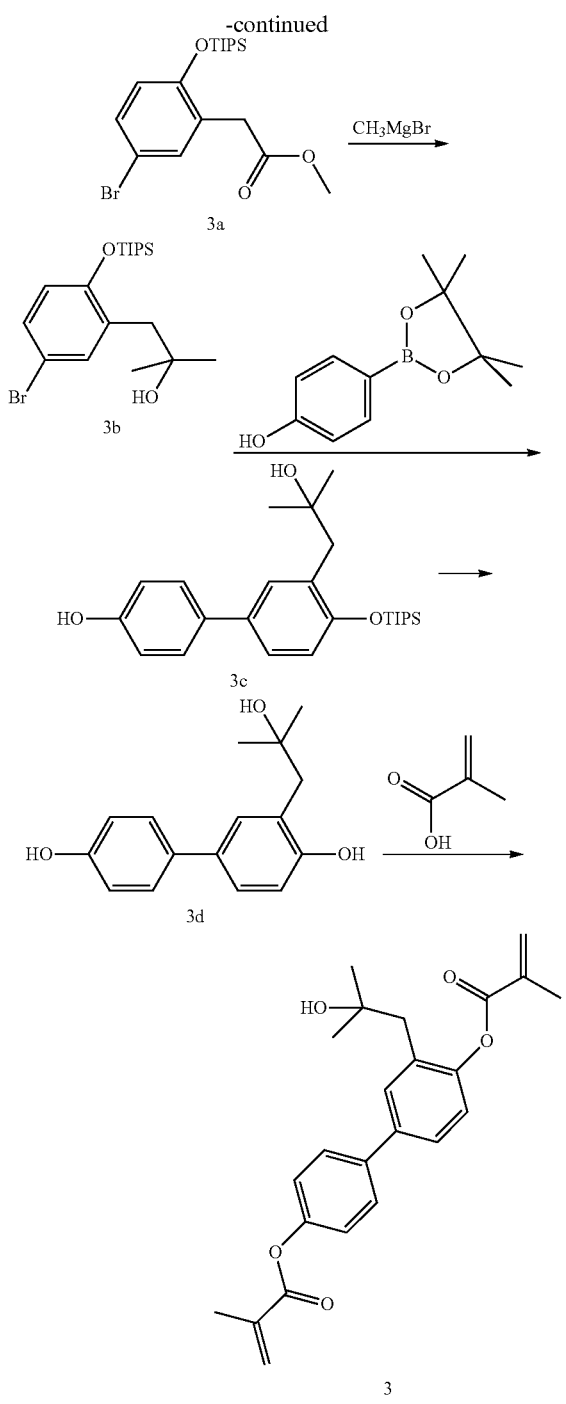

3a: To a solution of 5-bromo-2-hydroxyl-phenyl-acetic acid methyl ester (5.0 g, 20.4 mmol) in 50 ml DCM is added trimethylamine (3.4 ml, 24.4 mmol) and 4-dimethylaminopyridine (0.13 g, 1.08 mmol) at 0° C. A solution of chlorotriisopropylsilane (4.8 ml, 22.4 mmol) in 20 ml DCM is then added at max. 5° C. After stirring at RT for 4 hrs, 100 ml distilled water is added. The aqueous phase is extracted with DCM. The organic phase is combined and dried over anhydrous sodium sulfate. After removing solvent in vacuo, the solid residue is purified by column chromatography with heptane/chlorobutane as eluent to provide 3a as yellowish oil (7.3 g).

3b: To a solution of 3a (7.3 g, 18.2 mmol) in 90 ml anhydrous THF is added dropwise methyl magnesium iodide (21.9 ml, 66 mmol) at max. −5° C. After slowly warmed up to RT and stirred for 4 hrs, the reaction was quenched by carefully added into 1 L ice-water mixture. After neutralization with 2 M HCl acid, the aqueous phase is extracted with methyl tert-butyl ether. The organic phase is combined and dried over anhydrous sodium sulfate. After removing solvent in vacuo, the oily residue is purified by column chromatography with heptane/DCM mixture as eluent to provide 3b as colorless oil (6.1 g).

3c: To a solution of 3b (6.1 g, 15.2 mmol) and 4-hydroxyl phenyl bis(pinacolato)diboronic ester (3.2 g, 23.0 mmol) in 60 ml THF is added the solution of sodium metaborate (3.2 g, 23 mmol) in 60 ml distilled water. After thoroughly degassing with argon, bis(diphenylphosphino)ferrocene]dichloropalladium(II) (0.25 g, 0.3 mmol) is added. The reaction mixture is heated to reflux and stirred for 4 hrs. After cooling to room temperature, the aqueous phase is separated and extracted with ethyl acetate. The organic phase is combined and dried over anhydrous sodium sulfate, and filtrated through silica gel. After removing solvent in vacuo, the oily residue is purified by column chromatography on silica gel with chlorobutane/ethyl acetate mixture as eluent to afford 3c as colorless oil (5.8 g).

3d: To a solution of 6c (5.8 g, 14.0 mmol) in 70 ml anhydrous THF was added dropwise 1 M tetrabutylamonium fluoride solution in THF (17.5 ml, 17.5 mmol) at max. −5° C., and stirred for 1 h. The reaction is then quenched by carefully adding 100 ml distilled water at 0° C. The reaction mixture is extracted with ethyl acetate. The aqueous phase is extracted with ethylacetate. The organic phase is combined and washed with sat. aq. NaCl solution, dried over sodium sulfate. After removing solvent in vacuo, the solid residue is purified by recrystallized from dichloromethane to provide 3d as white solid (2.1 g).

3: Methacrylic acid (2.12 ml, 24.0 mmol) and 4-(dimethylamino)pyridine (0.10 g, 0.81 mmol) is added to a suspension of 3d (2.1 g, 8.1 mmol) in dichloromethane (60 ml). The reaction mixture is treated dropwise at 0° C. with a solution of N-(3-dimethylaminopropyl)-N'-ethylcarbodiimide (3.9 g, 25.0 mmol) in dichloromethane (20 ml) and stirred for 20 hs at room temperature. The reaction mixture is concentrated in vacuo, and the oily residue is purified by column chromatography on silica gel with heptane/ethyl acetate mixture as eluent. The obtained product is recrystallized from heptane/methyl tert-butyl ether mixture to afford white crystals of 3 (2.2 g, mp. 73° C.).

Examples 4-10

The following compounds are prepared in analogy to the methods described in Examples 1-3.

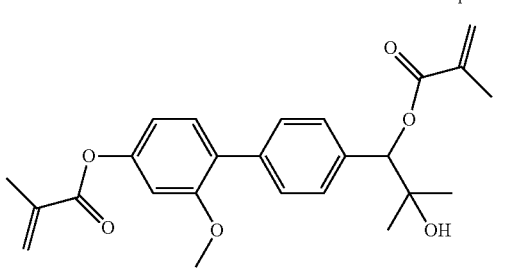

4 m.p. 138° C.

-continued 5 m.p. 144° C.

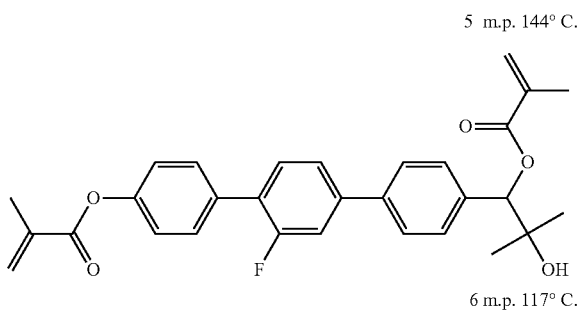

6 m.p. 117° C.

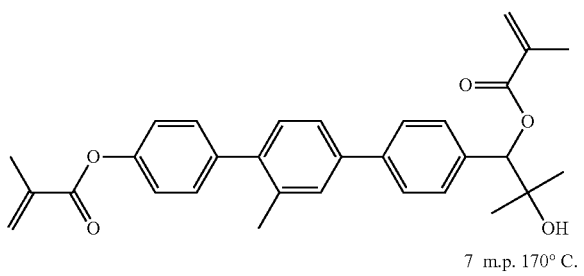

7 m.p. 170° C.

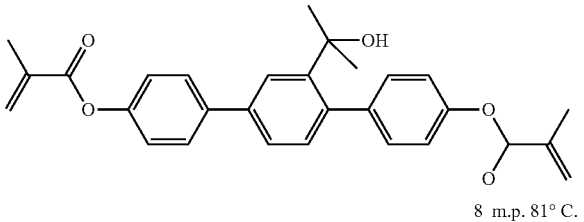

8 m.p. 81° C.

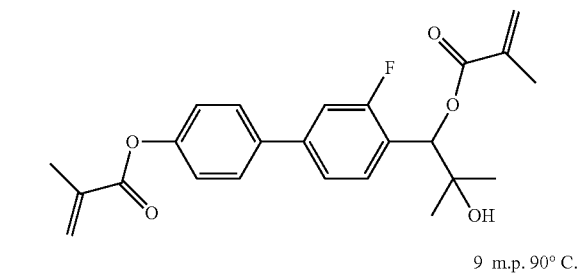

9 m.p. 90° C.

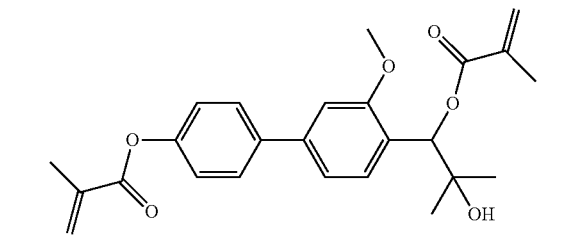

10 m.p. 161° C.

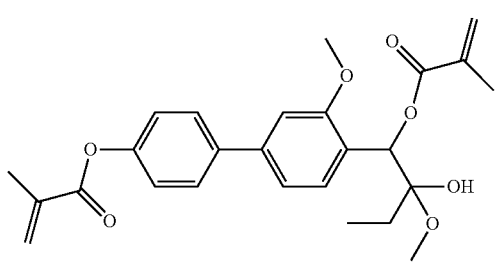

Mixture Example 1

The nematic LC host mixture N1 is formulated as follows.

| | | | |
|---|---|---|---|
| CCH-501 | 9.00% | cl.p. | 70.0° C. |
| CCH-35 | 14.00% | Δn | 0.0825 |
| PCH-53 | 8.00% | Δε | −3.5 |
| CY-3-O4 | 14.00% | ε$_{\parallel}$ | 3.5 |
| CY-5-O4 | 13.00% | K$_3$/K$_1$ | 1.00 |
| CCY-2-1 | 9.00% | γ$_1$ | 141 mPa s |
| CCY-3-1 | 9.00% | V$_0$ | 2.10 V |
| CCY-3-O2 | 8.00% | | |
| CCY-5-O2 | 8.00% | | |
| CPY-2-O2 | 8.00% | | |

Mixture Example 2

The nematic LC host mixture N2 is formulated as follows.

| | | | |
|---|---|---|---|
| CY-3-O2 | 18.00% | cl.p. | +74.5° C. |
| CPY-2-O2 | 10.00% | Δn | 0.1021 |
| CPY-3-O2 | 10.00% | Δε | −3.1 |
| CCY-3-O2 | 9.00% | ε$_{\parallel}$ | 3.5 |
| CCY-4-O2 | 4.00% | K$_3$/K$_1$ | 1.16 |
| PYP-23 | 9.00% | γ$_1$ | 86 mPa s |
| CC-3-V | 40.00% | V$_0$ | 2.29 V |

Polymerizable Mixture Examples

Polymerizable mixtures P11-P110 are prepared by adding one of polymerizable compounds 1 to 10, respectively, to nematic LC host mixture N1 at a concentration of 0.3% by weight.

Polymerizable mixtures P21-P210 are prepared by adding one of polymerizable compounds 1 to 10, respectively, to nematic LC host mixture N2 at a concentration of 0.3% by weight.

For comparison purposes polymerizable mixture C11 is prepared by adding polymerizable compound M1 of prior art to nematic LC host mixture N1 at a concentration of 0.3% by weight, and polymerizable mixture C21 is prepared by adding polymerizable compound M1 of prior art to nematic LC host mixture N2 at a concentration of 0.3% by weight.

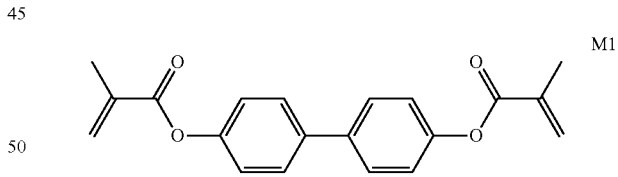

M1

Use Examples

Polymerizable mixtures C11 and C21, which contain M1 of prior art, are compared with polymerizable mixtures P11-P110 and P21-P210 which contain one of RMs 1-7 according to the invention with a hydroxy substituent.

Voltage Holding Ratio (VHR)

For measuring the VHR the polymerizable mixtures are inserted into electrooptic test cells. The test cells comprise two AF glass substrates with an ITO electrode layer of approx. 20 nm thickness and a VA-polyimide alignment layer (PI-4) of approx. 100 nm thickness. The LC layer thickness is approx. 4 μm. The VHR is measured at 100° C. with application of a voltage of 1 V/60 Hz. For the sun-test the test cells are irradiated at 20° C. for 2 h with light having an intensity of 750 W/m² using a Xenon lamp (Atlas Suntest CPS+). For the UV test the test cells are irradiated for 10 min with UV light having an intensity of 100 mW/cm² (Fe-doped Hg lamp with a 320 nm cut-off filter).

The results are shown in Table 1.

TABLE 1

VHR values

| Mixture | VHR (%) no illumination | 2 h Suntest |
|---|---|---|
| C11 | 98.2 | 97.6 |
| P11 | 98.8 | 98.8 |
| P12 | 98.7 | 98.7 |
| P13 | 99.1 | 98.8 |
| P14 | 99.1 | 99.0 |
| P15 | 98.7 | 98.7 |
| P16 | 98.9 | 99.0 |
| P17 | 98.3 | 98.6 |
| P18 | 98.6 | 98.8 |
| P19 | 98.6 | 98.8 |
| P110 | n.a. | n.a. |

| Mixture | VHR (%) no illumination | 2 h Suntest | 10 min UV |
|---|---|---|---|
| C21 | 98.3 | 85.6 | 74.8 |
| P21 | 98.3 | 95.4 | 95.0 |
| P22 | 98.0 | 93.1 | 92.2 |
| P23 | 98.8 | 92.3 | 85.2 |
| P24 | 98.7 | 95.1 | 92.8 |
| P25 | 98.1 | 90.8 | 86.3 |
| P26 | 98.1 | 96.0 | 94.7 |
| P27 | 98.0 | 77.7 | 85.0 |
| P28 | 98.0 | 95.3 | 93.8 |
| P29 | 97.8 | 95.5 | 93.6 |
| P210 | 96.0 | 79.1 | 78.1 |

It can be seen that polymerizable mixtures P11-P110 and P21-P210 containing hydroxy-substituted compounds 1-7 according to the present invention show a VHR value after suntest and/or UV test that is significantly higher than that of polymerizable mixtures C11 and C21 containing compound M1 of prior art.

Residual RM

The polymerization speed is measured by determining the residual content of residual, unpolymerized monomer (in % by weight) in the mixture after UV exposure at a given intensity and lamp spectrum.

For this purpose the polymerizable mixtures are inserted into electrooptic test cells. The test cells comprise two soda-lime glass substrates with an ITO electrode layer of approx. 200 nm thickness and a VA-polyimide alignment layer (JALS-2096-R1) of approx. 30 nm thickness. The LC layer thickness is approx. 25 µm.

The test cells are irradiated with UV light having an intensity of 100 mW/cm² (metal halide lamp with a 320 nm cut-off filter) for the time indicated, causing polymerization of the RM, while the temperature at the bottom side of the test cell is kept at 20° C.

The mixture is then rinsed out of the test cell using MEK (methyl ethyl ketone) and the residual amount of unreacted monomer is measured by HPLC. The results are shown in Table 2.

TABLE 2

Residual monomer content

| Mixture | Residual RM (%) after Exposure Time (min) | | | |
|---|---|---|---|---|
|  | 0 | 2 | 4 | 6 |
| C11 | 0.300 | 0.264 | 0.203 | 0.173 |
| P11 | 0.300 | 0.285 | 0.238 | 0.197 |
| P12 | 0.300 | 0.252 | 0.123 | 0.054 |
| P13 | 0.300 | 0.122 | 0.051 | 0.026 |
| P14 | 0.300 | 0.230 | 0.122 | 0.078 |
| P15 | 0.300 | 0.275 | 0.233 | 0.204 |
| P16 | 0.300 | 0.256 | 0.200 | 0.147 |
| P17 | 0.425 | 0.358 | 0.283 | 0.225 |
| P18 | 0.384 | 0.344 | 0.274 | 0.231 |
| P19 | 0.395 | 0.253 | 0.145 | 0.089 |
| P110 | 0.393 | 0.360 | 0.310 | 0.258 |

| Mixture | Residual RM (%) after Exposure Time (min) | | |
|---|---|---|---|
|  | 0 | 2 | 6 |
| C21 | 0.300 | 0.185 | 0.067 |
| P21 | 0.300 | 0.187 | 0.090 |
| P22 | 0.300 | 0.139 | 0.034 |
| P23 | 0.300 | 0.092 | 0.015 |
| P24 | 0.300 | 0.158 | 0.065 |
| P25 | 0.300 | 0.213 | 0.118 |
| P26 | 0.300 | 0.165 | 0.075 |
| P27 | 0.425 | 0.206 | 0.079 |
| P28 | 0.384 | 0.189 | 0.089 |
| P29 | 0.395 | 0.134 | 0.035 |
| P210 | 0.393 | 0.215 | 0.112 |

Tilt Angle Generation

For measuring the tilt angle generation the polymerizable mixtures are inserted into electrooptic test cells. The test cells comprise two soda-lime glass substrates with an ITO electrode layer of approx. 200 nm thickness and a VA-polyimide alignment layer (JALS-2096-R1) of approx. 30 nm thickness which is rubbed antiparallel. The LC-layer thickness d is approx. 4 µm.

The test cells are irradiated with UV light having an intensity of 100 mW/cm² (metal halide lamp with a 320 nm cut-off filter) for the time indicated, with application of a voltage of 24 $V_{RMS}$ (alternating current), causing polymerization of the RM.

The tilt angle is determined before and after UV irradiation by a crystal rotation experiment (Autronic-Melchers TBA-105). The results are shown in Table 3.

TABLE 3

Tilt angles

| Mixture | Tilt Angle (°) after Exposure Time (sec) | | | | | |
|---|---|---|---|---|---|---|
|  | 0 | 30 | 60 | 120 | 240 | 360 |
| C11 | 89.6 | 89.0 | 88.2 | 84.9 | 79.8 | 77.5 |
| P11 | 88.9 | 87.6 | 86.5 | 83.8 | 78.5 | 76.1 |
| P12 | 89.3 | 89.1 | 88.4 | 86.0 | 81.4 | 78.8 |
| P13 | 89.9 | 83.5 | 78.8 | 74.1 | 71.9 | 70.5 |
| P14 | 88.9 | 88.4 | 86.2 | 79.1 | 72.2 | 68.5 |
| P15 | 89.6 | 89.4 | 88.6 | 86.9 | 83.8 | 82.1 |
| P16 | 89.8 | 89.7 | 88.2 | 86.0 | 80.7 | 77.7 |
| P17 | 89.1 | 88.9 | 87.8 | 85.4 | 80.4 | 78.0 |
| P18 | 89.0 | 89.2 | 88.1 | 84.8 | 78.0 | 73.7 |
| P19 | 89.2 | 89.2 | 86.0 | 79.3 | 71.4 | 68.6 |
| P110 | 89.8 | 89.1 | 88.7 | 86.8 | 82.2 | 77.6 |

TABLE 3-continued

Tilt angles

| Mixture | Tilt Angle (°) after Exposure Time (sec) | | |
|---|---|---|---|
| | 0 | 120 | 360 |
| C21 | 88.8 | 77.2 | 70.3 |
| P21 | 88.9 | 78.7 | 74.4 |
| P22 | 89.8 | 77.2 | 74.7 |
| P23 | 89.9 | 76.3 | 75.0 |
| P24 | 89.7 | 78.3 | 75.2 |
| P25 | 89.4 | 83.2 | 79.7 |
| P26 | 89.6 | 81.7 | 76.9 |
| P27 | 87.9 | 78.8 | 73.9 |
| P28 | 88.9 | 78.1 | 72.3 |
| P29 | 89.1 | 72.1 | 66.7 |
| P210 | 89.0 | 79.8 | 72.1 |

The use examples demonstrate that the polymerizable compounds and polymerizable mixtures according to the present invention show in particular a quick polymerization with low amount of residual monomer, while maintaining sufficient pretilt angle generation and sufficient VHR values after suntest or UV exposure for display applications.

Stabilizer Examples

Examples S11-S27

To the nematic host mixture N1 or N2 one of the compounds of Examples 1-7 is added as stabilizer. The mixture compositions are shown in Table 4.

TABLE 4

Stabilized LC mixtures

| Example | LC Host Mixture | Compound | Compound conc./ppm |
|---|---|---|---|
| S11 | N1 | 1 | 300 |
| S12 | N1 | 2 | 300 |
| S13 | N1 | 3 | 300 |
| S14 | N1 | 4 | 500 |
| S21 | N2 | 1 | 300 |
| S23 | N2 | 3 | 300 |
| S24 | N2 | 4 | 500 |
| S25 | N2 | 5 | 500 |
| S26 | N2 | 6 | 500 |
| S27 | N2 | 7 | 500 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I $$P\text{-}Sp\text{-}A^1\text{-}(Z^1\text{-}A^2)_z\text{-}R \qquad I$$

wherein individual radicals, independently of each other and on each occurrence identically or differently, have the following meanings
P a polymerizable acrylate or methacrylate group,
Sp a spacer group that is optionally substituted by one or more groups P or $L^a$, or a single bond,
$\text{-}A^1\text{-}(Z^1\text{-}A^2)_z\text{-}$ is

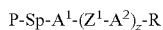 A1

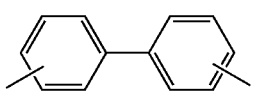 A2

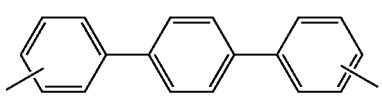 A3

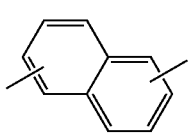 A4

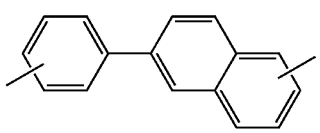 A5

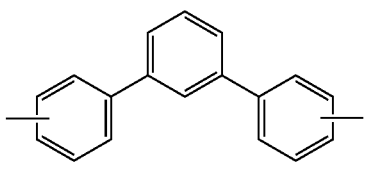 A6

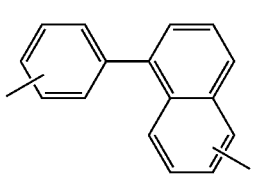 A7

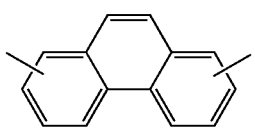 A8 or

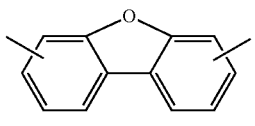 A9 wherein the benzene rings are optionally substituted by one or more groups L, P-Sp-, $L^a$ or $L^a$-Sp-
R P-Sp-,
L F, Cl, —CN, P-Sp-, $L^a$, $L^a$-Sp-, or straight chain alkyl having 1 to 25 C atoms or branched or cyclic alkyl having 3 to 25 C atoms, wherein one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by P, F, Cl or L$^a$-, L$^a$ —C(R$^{aa}$)(R$^{bb}$)OH, R$^{aa}$, R$^{bb}$ straight-chain alkyl with 1 to 20 C atoms, branched alkyl with 3 to 20 C atoms, or cyclic alkyl with 3 to 12 C atoms, or R$^{aa}$ and R$^{bb}$ together with the C atom to which they are attached form a cyclic alkyl group with 3 to 12 C atoms, wherein in R$^{aa}$ and R$^{bb}$ one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl, wherein the compound of formula I contains at least one group L$^a$ or L$^a$-Sp-.

2. The compound according to claim 1, wherein R$^{aa}$ and R$^{bb}$ denote straight-chain alkyl with 1 to 12 C atoms or branched alkyl with 3 to 12 C atoms, or R$^{aa}$ and R$^{bb}$ together with the C atom to which they are attached form a cyclic alkyl group with 3 to 12 C atoms.

3. The compound according to claim 1, wherein all groups P that are present in the compound have the same meaning.

4. The compound according to claim 1, containing a group P-Sp- of the following formulae

 SL1

 SL2

 SL3

 SL4 cc is 1, 2, 3, 4, 5 or 6 and
L$^a$ is as defined in claim 1.

5. The compound according to claim 1, wherein A$^1$-(Z$^1$-A$^2$)$_z$- is

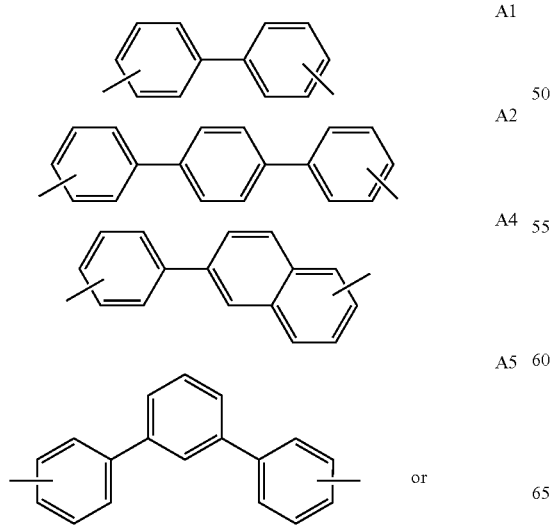

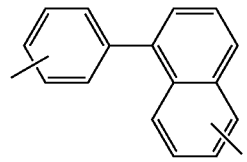

wherein the benzene rings are optionally substituted by one or more groups L, P-Sp-, L$^a$ or L$^a$-Sp-.

6. The compound according to claim 1, of the following subformulae:

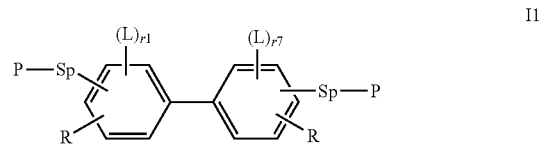

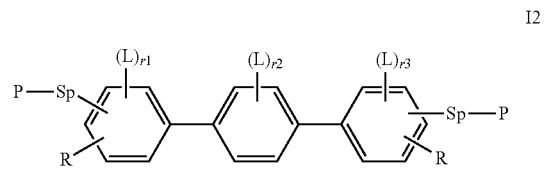

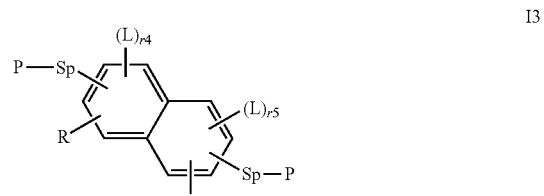

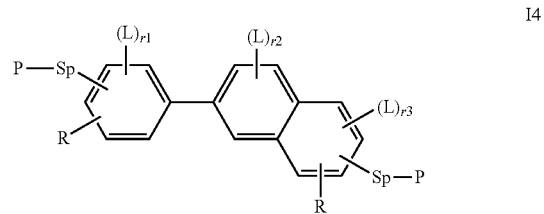

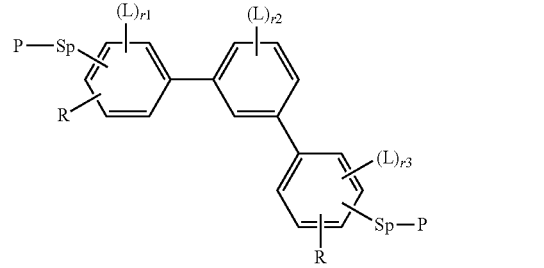

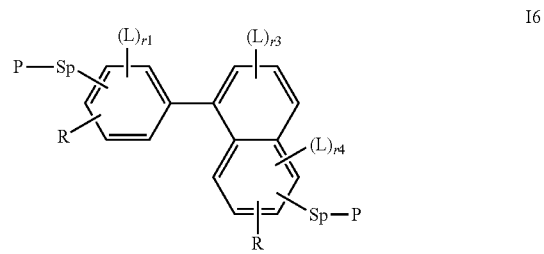

I7
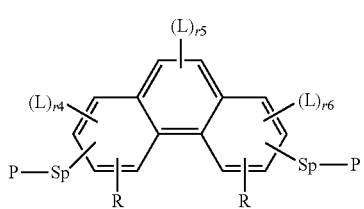
I8
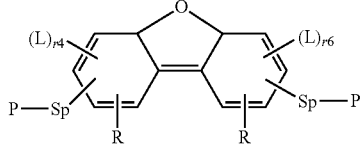
or
I9
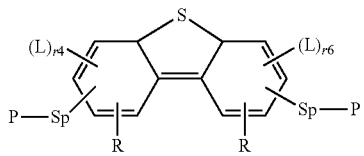
wherein
r1, r3, r7 are independently of each other 0, 1, 2 or 3,
r2 is 0, 1, 2, 3 or 4,
r4, r5, r6 are independently of each other 0, 1 or 2,
wherein r1+r7≥1, r1+r2+r3≥1, r4+r5≥1, r1+r3+r4≥1 and at least one of L denotes $L^a$ or $L^a$-Sp-, and/or
wherein the compounds contain at least one group Sp that is substituted by $L^a$.
7. A compound of the formula:
I1-1
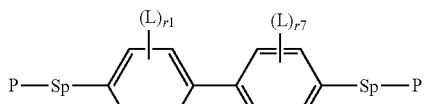
I1-2
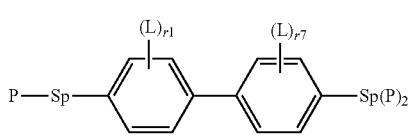
I1-3
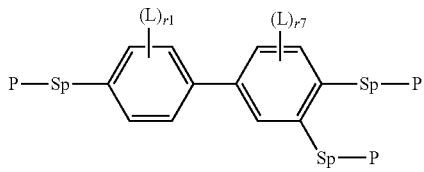
I1-4
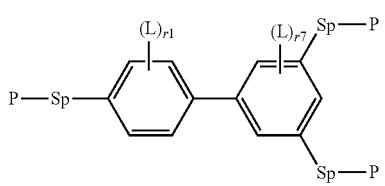
I2-1
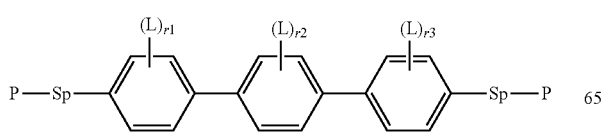
I2-2
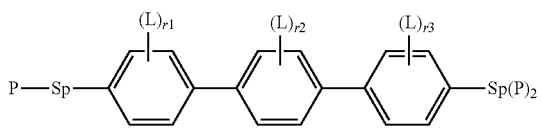
I2-3
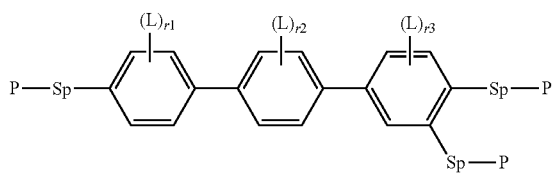
I2-4
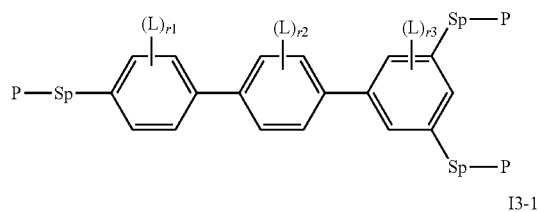
I3-1
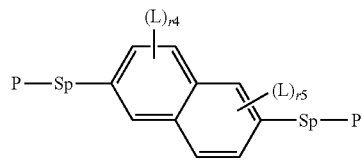
I3-2
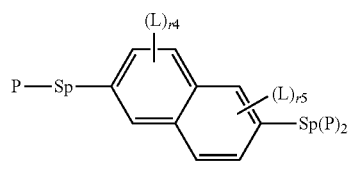
I3-3
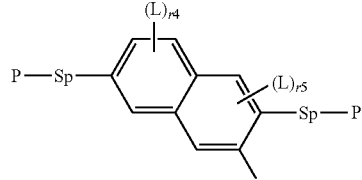
I3-4
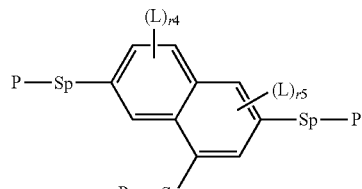
I4-1

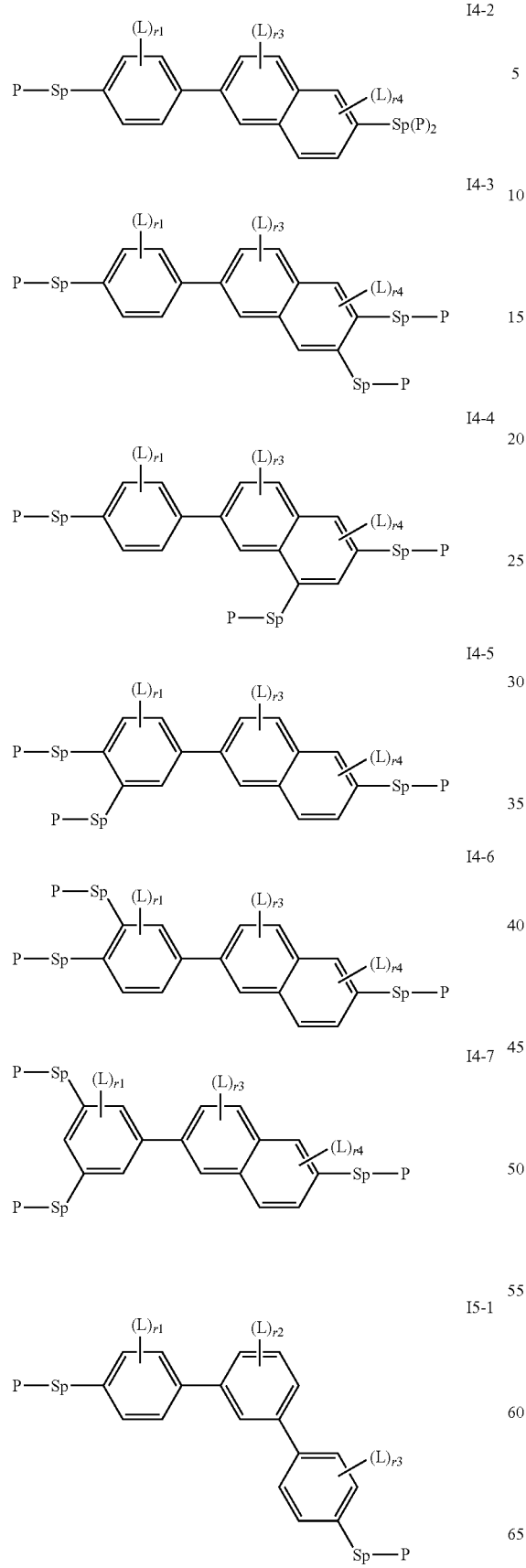
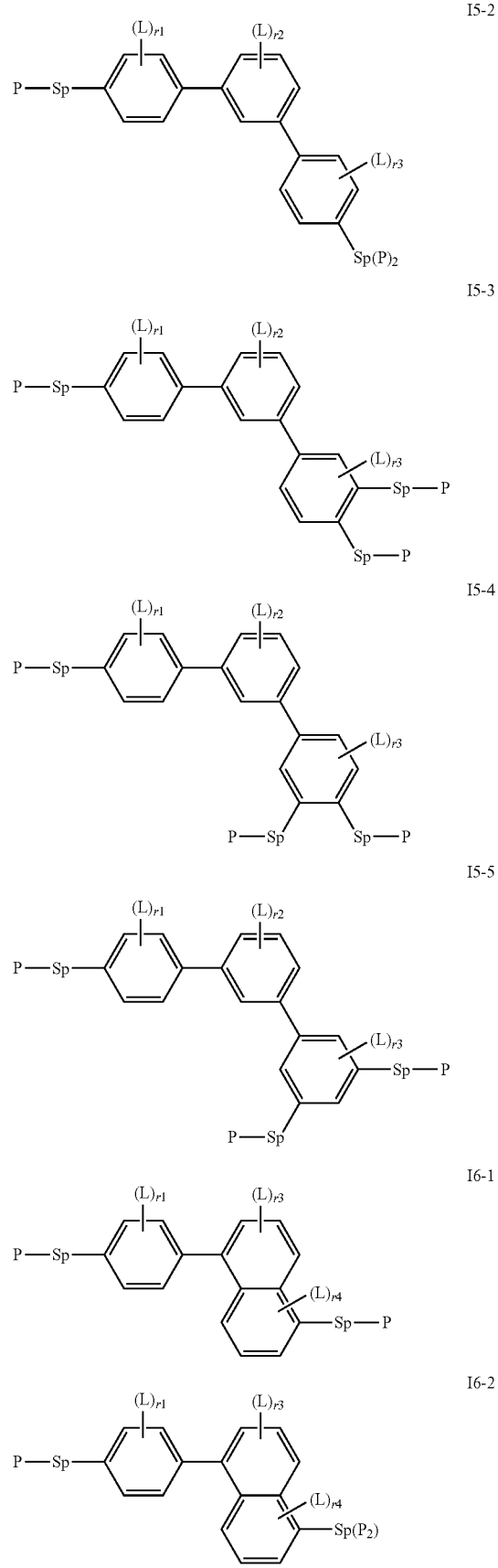

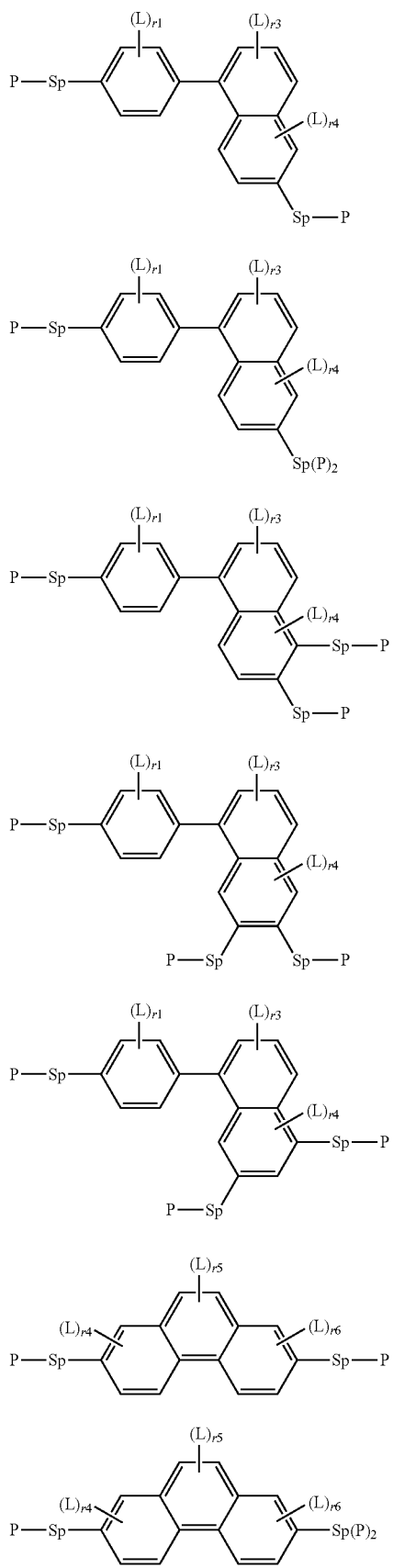
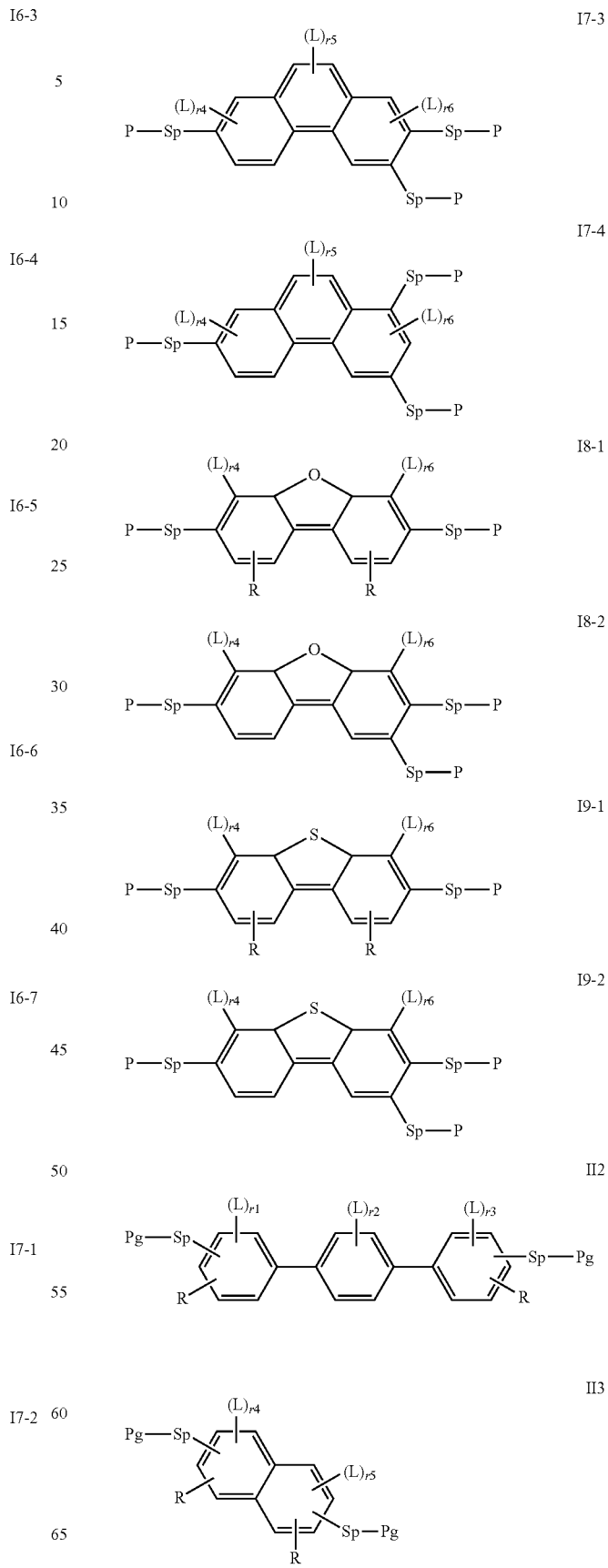

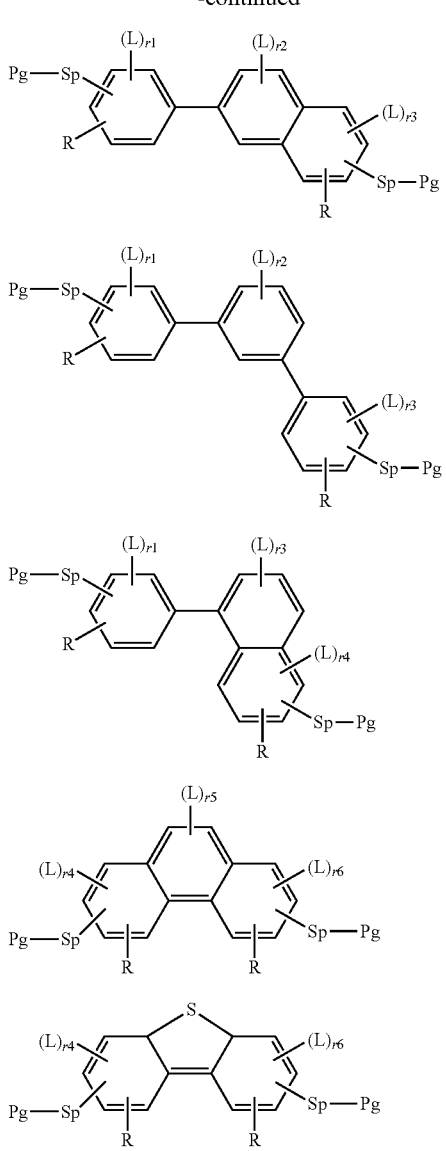

or a compound of formula I8-1 or I8-2 wherein P is replaced by Pg

Sp a spacer group that is optionally substituted by one or more groups P or $L^a$, or a single bond, P a polymerizable acrylate or methacrylate group, Pg is —OH, a protected hydroxy group or a masked hydroxy group, L F, Cl, —CN, P-Sp-, $L^a$, $L^a$-Sp-, or straight chain alkyl having 1 to 25 C atoms, or branched or cyclic alkyl having 3 to 25 C atoms, wherein one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by P, F, Cl or $L^a$-, $L^a$ —C($R^{aa}$)($R^{bb}$)OH, $R^{aa}$, $R^{bb}$ straight-chain alkyl with 1 to 20 C atoms, branched alkyl with 3 to 20 C atoms, or cyclic alkyl with 3 to 12 C atoms, or $R^{aa}$ and $R^{bb}$ together with the C atom to which they are attached form a cyclic alkyl group with 3 to 12 C atoms, wherein in $R^{aa}$ and $R^{bb}$ one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl, r1, r3, r7 are independently of each other 0, 1, 2 or 3, r2 is 0, 1, 2, 3 or 4, r4, r5, r6 are independently of each other 0, 1 or 2, wherein R denotes H or Pg-Sp, wherein r1+r7≥1, r1+r2+r3≥1, r4+r5≥1, r1+r3+r4≥1 and at least one of L denotes $L^a$ or $L^a$-Sp-, and/or wherein the compounds contain at least one group Sp that is substituted by $L^a$.

8. A liquid crystal (LC) medium comprising one or more compounds formula I as defined in claim 1.

9. The LC medium of claim 8, comprising
a polymerizable component A) comprising one or more compounds of formula I, and
a liquid-crystalline LC component B) comprising one or more mesogenic or liquid-crystalline compounds.

10. The LC medium of claim 9, wherein component B) comprises one or more compounds of formulae CY and/or PY:

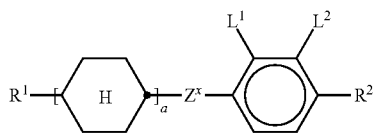

CY

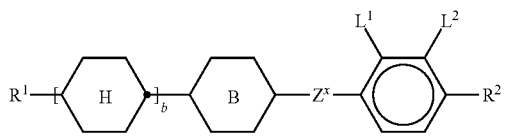

PY in which
a denotes 1 or 2,
b denotes 0 or 1,

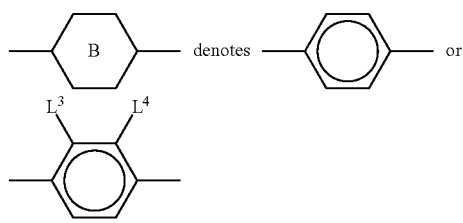

$R^1$ and $R^2$ each, independently of one another, denote alkyl having 1 to 12 C atoms, where, in addition, one or two non-adjacent CH$_2$ groups may be replaced by —O—, —CH=CH—, —CO—, —O—CO— or —CO—O— in such a way that O atoms are not linked directly to one another, $Z^x$ denotes —CH=CH—, —CH$_2$O—, —OCH$_2$—, —CF$_2$O—, —OCF$_2$—, —O—, —CH$_2$—, —CH$_2$CH$_2$— or a single bond, $L^{1-4}$ each, independently of one another, denote F, Cl, OCF$_3$, CF$_3$, CH$_3$, CH$_2$F, CHF$_2$.

11. The LC medium according to claim 9 wherein component B) comprises one or more compounds of the following formulae:

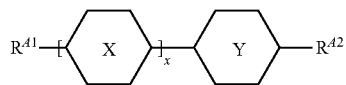

AN

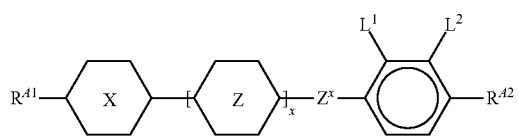

AY in which the individual radicals, on each occurrence identically or differently, each, independently of one another, have the following meaning:

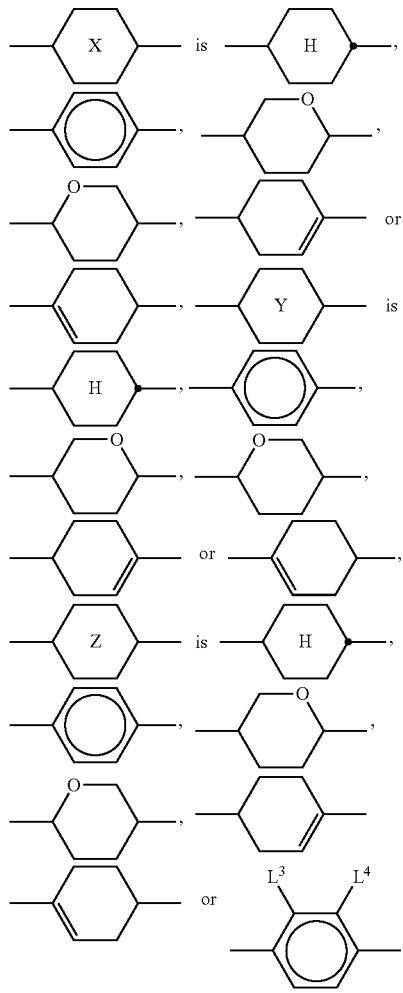

$R^{41}$ alkenyl having 2 to 9 C atoms or, if at least one of the rings X, Y and Z denotes cyclohexenyl, also one of the meanings of $R^{42}$, $R^{42}$ alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, $Z^x$ —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$—, or a single bond, $L^{1-4}$ each, independently of one another, H, F, Cl, $OCF_3$, $CF_3$, $CH_3$, $CH_2F$ or $CHF_2H$, x 1 or 2, z 0 or 1.

12. The LC medium according to claim 9, wherein component B) comprises one or more compounds of the following formula:

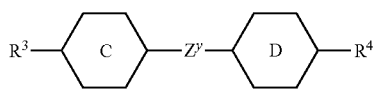

ZK in which the individual radicals have the following meanings:

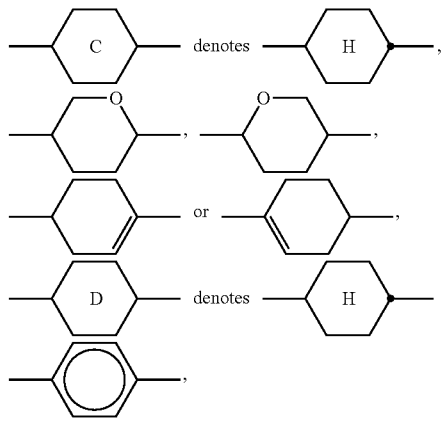

$R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another, $Z_y$ denotes —$CH_2CH_2$—, —CH=CH—, —$CF_2O$—, —$OCF_2$—, —$CH_2O$—, —$OCH_2$—, —COO—, —OCO—, —$C_2F_4$—, —CF=CF— or a single bond.

13. The LC medium according to claim 8, wherein the compounds of formula I are polymerized.

14. The LC medium according to claim 8, containing from 50 to 1000 ppm of one or more compounds of formula I.

15. A process of preparing an LC medium according to claim 8, comprising mixing one or more mesogenic or liquid-crystalline compounds, with one or more compounds of formula I and optionally with further liquid-crystalline compounds and/or additives.

16. An LC display comprising one or more compounds of formula I comprising an LC medium as defined in claim 8.

17. The LC display of claim 16, which is a VA, IPS, UB-FFS, TN, OCB, FFS or poli-VA display.

18. The LC display of claim 16, which is a PSA display.

19. The LC display of claim 18, which is a PS-VA, PS-OCB, PS-IPS, PS-FFS, PS-UB-FFS, PS-poli-VA or PS-TN display.

20. The LC display of claim 18, comprising two substrates, at least one which is transparent to light, an electrode provided on each substrate or two electrodes provided on only one of the substrates, and located between the substrates a layer of an LC medium, comprising one or more compounds of formula I and optionally one or more additional compounds that are polymerizable, wherein the compounds of formula I and the additional polymerizable compounds are polymerized between the substrates of the display.

21. A process for the production of an LC display according to claim 20, comprising providing an LC medium, comprising one or more compounds of formula I and optionally one or more additional compounds that are polymerizable, between the substrates of the display, and polymerizing the compounds of formula I and the additional polymerizable compounds.

22. A compound of the following formulae

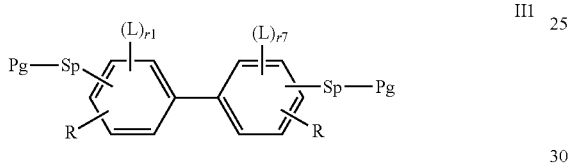

Sp a spacer group that is optionally substituted by one or more groups P or $L^a$, or a single bond, P is a polymerizable group, and at least one group Pg-Sp is a spacer group substituted by $L^a$, L F, Cl, —CN, P-Sp-, $L^a$, $L^a$-Sp-, or straight chain alkyl having 1 to 25 C atoms or branched or cyclic alkyl having 3 to 25 C atoms, wherein one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by P, F, Cl or $L^a$, $L^a$ —C($R^{aa}$)($R^{bb}$)OH, $R^{aa}$, $R^{bb}$ straight-chain alkyl with 1 to 20 C atoms, branched alkyl with 3 to 20 C atoms, or cyclic alkyl with 3 to 12 C atoms, or $R^{aa}$ and $R^{bb}$ together with the C atom to which they are attached form a cyclic alkyl group with 3 to 12 C atoms, wherein in $R^{aa}$ and $R^{bb}$ one or more non-adjacent CH$_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl, r1, r3, r7 are independently of each other 0, 1, 2 or 3, r2 is 0, 1, 2, 3 or 4, r4, r5, r6 are independently of each other 0, 1 or 2, wherein r1+r7≥1, r1+r2+r3≥1, r4+r5≥1, r1+r3+r4≥1, wherein R denotes H or Pg-Sp, and Pg denotes OH, a protected hydroxyl group or a masked hydroxyl group, wherein the compounds contain at least one group $L^a$ or $L^a$-Sp.

23. A process for preparing a compound of formula I of claim 1, by esterification of a compound

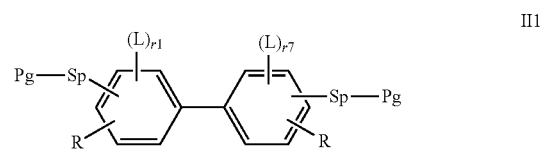

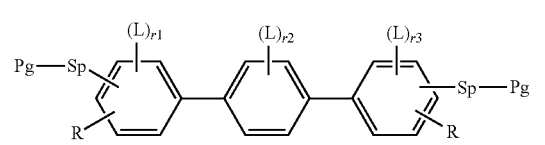

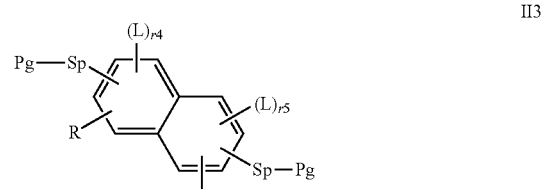

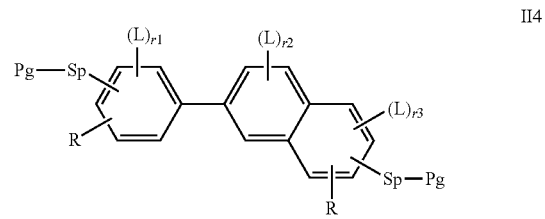

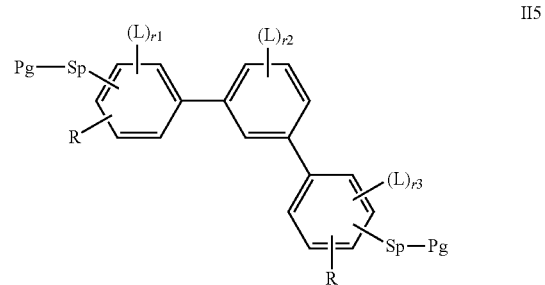

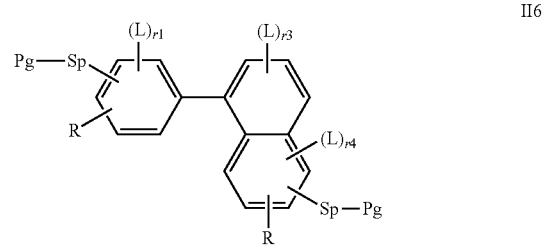

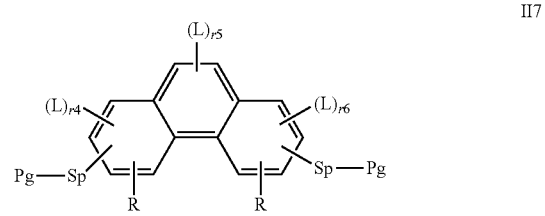

18-1

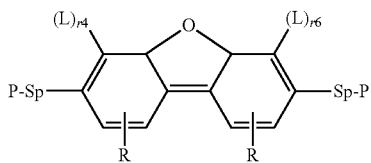

18-2

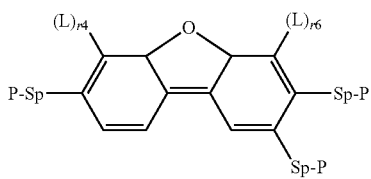

wherein P is replaced by Pg

119

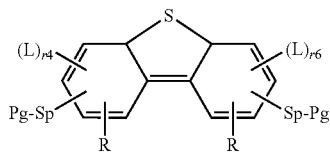

Sp a spacer group that is optionally substituted by one or more groups P or $L^a$, or a single bond, P is a polymerizable group, L  F, Cl, —CN, P-Sp-, $L^a$, $L^a$-Sp-, or straight chain alkyl having 1 to 25 carbon atoms or branched or cyclic alkyl having 3 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by P, F, Cl or $L^a$-, $L^a$ —$C(R^{aa})(R^{bb})$OH, $R^{aa}$, $R^{bb}$ straight-chain alkyl with 1 to 20 C atoms, branched alkyl with 3 to 20 C atoms, or cyclic alkyl with 3 to 12 C atoms, or $R^{aa}$ and $R^{bb}$ together with the C atom to which they are attached form a cyclic alkyl group with 3 to 12 C atoms, wherein in $R^{aa}$ and $R^{bb}$ one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl, r1, r3, r7 are independently of each other 0, 1, 2 or 3, r2 is 0, 1, 2, 3 or 4, r4, r5, r6 are independently of each other 0, 1 or 2, wherein r1+r7≥1, r1+r2+r3≥1, r4+r5≥1, r1+r3+r4≥1, wherein R denotes H or Pg-Sp, and wherein Pg denotes OH, using corresponding acids, acid derivatives, or halogenated compounds containing a group P, in the presence of a dehydrating reagent, and the compounds 111-119 contain at least one group $L^a$ or $L^a$-Sp.

* * * * *